US008609090B2

(12) United States Patent
Burgess et al.

(10) Patent No.: US 8,609,090 B2
(45) Date of Patent: Dec. 17, 2013

(54) SPECIFIC BINDING AGENTS TO HEPATOCYTE GROWTH FACTOR

(75) Inventors: Teresa L. Burgess, Ventura, CA (US); Angela Coxon, Moorpark, CA (US); Larry L. Green, San Francisco, CA (US); Ke Zhang, Bethesda, MD (US)

(73) Assignees: Amgen Inc., Thousand Oaks, CA (US); Amgen Fremont Inc., Thousand Oaks, CA (US)

( * ) Notice: Subject to any disclaimer, the term of this patent is extended or adjusted under 35 U.S.C. 154(b) by 1620 days.

(21) Appl. No.: 10/893,576

(22) Filed: Jul. 16, 2004

(65) Prior Publication Data

US 2005/0118643 A1 Jun. 2, 2005

Related U.S. Application Data

(60) Provisional application No. 60/488,681, filed on Jul. 18, 2003.

(51) Int. Cl.
*C12P 21/08* (2006.01)
*C07K 16/22* (2006.01)
*A61K 38/17* (2006.01)
*A61K 39/395* (2006.01)

(52) U.S. Cl.
USPC .......... 424/132.1; 424/133.1; 424/139.1; 424/141.1; 424/142.1; 424/145.1; 424/152.1; 424/158.1; 424/172.1; 424/177.1; 424/185.1; 530/324; 530/387.3; 530/387.9; 530/388.1; 530/388.15; 530/388.24

(58) Field of Classification Search
None
See application file for complete search history.

(56) References Cited

U.S. PATENT DOCUMENTS

| 5,268,384 | A | 12/1993 | Galardy |
|---|---|---|---|
| 5,284,827 | A | 2/1994 | Maione et al. |
| 5,362,716 | A | 11/1994 | Kmiecik et al. |
| 5,429,746 | A | 7/1995 | Shadle et al. |
| 5,520,914 | A | 5/1996 | Fett et al. |
| 5,684,136 | A | 11/1997 | Godowski |
| 5,707,624 | A | 1/1998 | Nickoloff et al. |
| 5,807,711 | A | 9/1998 | Hara et al. |
| 5,821,223 | A | 10/1998 | Rubin et al. |
| 5,821,337 | A | 10/1998 | Carter et al. |
| 5,827,673 | A | 10/1998 | Matsumori |
| 5,837,676 | A | 11/1998 | Goldberg et al. |
| 5,871,959 | A | 2/1999 | Rong et al. |
| 5,888,965 | A | 3/1999 | Kmiecik et al. |
| 5,919,759 | A | 7/1999 | Goldberg et al. |
| 5,965,523 | A | 10/1999 | Goldberg et al. |
| 5,997,868 | A | 12/1999 | Goldberg et al. |
| 6,011,009 | A | 1/2000 | Goldberg et al. |
| 6,013,624 | A | 1/2000 | Goldberg et al. |
| 6,090,382 | A | 7/2000 | Salfeld et al. |
| 6,171,586 | B1 | 1/2001 | Lam et al. |
| 6,207,152 | B1 | 3/2001 | Schwall et al. |
| 6,214,344 | B1 | 4/2001 | Schwall et al. |
| 6,225,088 | B1 | 5/2001 | Rubin et al. |
| 6,232,456 | B1 | 5/2001 | Cohen et al. |
| 6,416,958 | B2 | 7/2002 | Vidovic et al. |
| 6,417,335 | B1 | 7/2002 | Basey et al. |
| 6,432,406 | B1 | 8/2002 | Goldberg et al. |
| 6,468,529 | B1 | 10/2002 | Schwall et al. |
| 6,498,144 | B1 | 12/2002 | Rosen et al. |
| 6,803,039 | B2 | 10/2004 | Tsuji et al. |
| 6,902,734 | B2 | 6/2005 | Giles-Komar et al. |
| 7,220,410 | B2 | 5/2007 | Kim et al. |
| 7,494,650 | B2 | 2/2009 | Kim et al. |
| 7,687,063 | B2 | 3/2010 | Kim et al. |
| 2002/0058791 | A1* | 5/2002 | Goldschneider et al. ..... 530/351 |
| 2002/0123091 | A1 | 9/2002 | Gurney et al. |
| 2003/0124123 | A1 | 7/2003 | Giles-Komar et al. |
| 2003/0190317 | A1* | 10/2003 | Baca et al. ................. 424/142.1 |
| 2004/0208876 | A1 | 10/2004 | Kim et al. |
| 2005/0019327 | A1 | 1/2005 | Kim et al. |
| 2005/0037431 | A1 | 2/2005 | Kirchhofer et al. |
| 2006/0035278 | A9 | 2/2006 | Kirchhofer et al. |
| 2007/0129301 | A1 | 6/2007 | Kirchhofer et al. |
| 2010/0040634 | A1 | 2/2010 | Kirchhofer et al. |
| 2011/0177058 | A1 | 7/2011 | Kirchhofer et al. |

FOREIGN PATENT DOCUMENTS

| AR | 030134 B1 | 11/2008 |
|---|---|---|
| EP | 0239400 B1 | 8/1994 |
| EP | 0451216 B1 | 1/1996 |
| EP | 0 805 203 A1 | 5/1997 |
| EP | 0461560 B1 | 11/1998 |
| EP | 0478101 B1 | 8/2001 |
| EP | 0865448 B1 | 10/2003 |
| EP | 1636593 B9 | 3/2009 |
| EP | 2093570 A1 | 8/2009 |
| EP | 1734995 B1 | 7/2010 |
| EP | 2367008 A2 | 9/2011 |
| JP | SHO64-27491 | 1/1989 |

(Continued)

OTHER PUBLICATIONS

Rucikoff et al (PNAS, 1982, vol. 79, pp. 1979-1983).*
Panka et al (PNAS, 1988, vol. 85, p. 3080-3084).*
MacCallum et al (Journal of Molecular Biology, 1996, vol. 262, pp. 732-745).*
Pascalis et al (journal of Immunology, 2002, pp. 3076-3084).*
Casset et al (Biochemical and Biophysical Research Communications, 2003, vol. 307, pp. 198-205).*
Vajdos et al (Journal of Molecular biology, 2002, vol. 320, pp. 415-428).*

(Continued)

*Primary Examiner* — Karen Canella
(74) *Attorney, Agent, or Firm* — Scott L. Ausenhus; Melissa A. Shaw

(57) ABSTRACT

Specific binding agents that interact with hepatocyte growth factor (HGF) are described. Methods of treating cancer by administering a pharmaceutically effective amount of a specific binding agent to HGF are described. Methods of detecting the amount of HGF in a sample using a specific binding agent to HGF are described.

36 Claims, 40 Drawing Sheets

(56) References Cited

FOREIGN PATENT DOCUMENTS

| | | | |
|---|---|---|---|
| JP | 02240100 | * | 9/1990 |
| JP | 02288899 | * | 11/1990 |
| JP | 11-505523 | | 5/1999 |
| JP | 11-505523 A | | 5/1999 |
| WO | WO90/07861 A1 | | 7/1990 |
| WO | WO91/09967 | * | 7/1991 |
| WO | 91/12272 A1 | | 8/1991 |
| WO | WO91/16928 A1 | | 11/1991 |
| WO | WO 92/10210 | | 6/1992 |
| WO | 94/06909 | | 3/1994 |
| WO | WO96/33735 A1 | | 10/1996 |
| WO | WO 98/19696 | | 5/1998 |
| WO | WO 99/46291 | | 9/1999 |
| WO | WO 99/48537 | | 9/1999 |
| WO | WO 01/34650 A1 | | 5/2001 |
| WO | WO01/34650 A1 | | 5/2001 |
| WO | WO 01/59100 A2 | | 8/2001 |
| WO | WO 01/68707 A1 | | 9/2001 |
| WO | 01/75140 | | 10/2001 |
| WO | WO02/02593 A2 | | 1/2002 |
| WO | WO 02/02593 A2 | | 1/2002 |
| WO | WO03/057155 A2 | | 7/2003 |
| WO | WO2005/001486 | * | 1/2005 |
| WO | WO2005/001486 A1 | | 1/2005 |
| WO | WO2005/017107 A2 | | 2/2005 |
| WO | PCT50/2006 | | 1/2006 |
| WO | WO2007/115049 A2 | | 10/2007 |
| WO | 2007/143090 A2 | | 12/2007 |

OTHER PUBLICATIONS

Holm et al (Molecular Immunology, 2007, vol. 44, pp. 1075-1084).*
Chen et al. (Journal of Molecular Biology, 1999, vol. 293, pp. 865-881).*
Wu et al. (Journal of Molecular Biology, 1999, vol. 294, pp. 151-162).*
Gillis et al (Journal of Cell Science, 1999, vol. 112, pp. 2049-2057).*
Dgene Abstract Accession No. AAY17836, 2008.*
Dgene Abstract Accession No. AAR10144, 2008.*
Miyazawa et al (Biochemical and Biophysical Research Communications, 1989, vol. 163, pp. 967-973).*
Lai et al (Journal of Immunology, 2001, vol. 167, pp. 3550-3554).*
Notification of Transmittal of the International Search Report and the Written Opinion of the International Searching Authority, or the Declaration, issued in International Application No. PCT/US04/18936, mailed on Dec. 28, 2006 (9 pages).
Behrens et al., 1991, "The role of E-cadherin and scatter factor in tumor invasion and cell motility." Cell Motility Factors, ed. by I.D. Goldberg, Birkhauser Verlag: Basel, Switzerland, p. 109-126.
Bhargava et al., Jan. 1992, "Scatter Factor and Hepatocyte Growth Factor: Activities, Properties, and Mechanism." Cell Growth & Differentiation 3: 11-20.
Folkman, J., Nov. 18, 1971, "Tumor Angiogenesis: Therapeutic Implications." New Eng. J. Med. 285: 1182-1186.
Iwasaki et al., Aug. 2003, "Predicting Treatment Responses and Disease Progression in Myeloma using Serum Vascular Endothelial Growth Factor and Hepatocyte Growth Factor Levels." Leukemia and Lymphoma 44: 1275-1279.
Rosen et al., 1990, "Purified Scatter Factor Stimulates Epithelial and Vascular Endothelial Cell Migration." Proc. Soc. Exper. Biol. and Med. 195: 34-43.
O. Arrieta et al., Jun. 15, 2002, "Hepatocyte Growth Factor Is Associated with Poor Prognosis of Malignant Gliomas and Is a Predictor for Recurrence of Meningioma." Cancer 94: 3210-3218.
C. Birchmeier et al., Dec. 2003, "Met, metastasis, motility and more." Nature Reviews/Molecular Cell Biology 4: 915-925.
F. Bussolino et al., Nov. 1992, "Hepatocyte Growth Factor Is a Potent Angiogenic Factor Which Stimulates Endothelial Cell Motility and Growth." The Journal of Cell Biology 119: 629-641.
A. Cantón et al., 2000, "Hepatocyte growth factor in vitreous and serum from patients with proliferative diabetic retinopathy." Br. J. Ophthalmol. 84: 732-735 (2000).
B. Cao et al., Jun. 19, 2001, "Neutralizing monoclonal antibodies to hepatocyte growth factor/scatter factor (HGF/SF) display antitumor activity in animal models." Proc. Natl. Acad. Sci. 98: 7443-7448.
M. Carrolo et al., Nov. 2003, Epub Oct. 12, 2003, "Hepatocyte growth factor and its receptor are required for malaria infection." Nature Medicine 9:1363-1369.
G. Dong et al., Aug. 1, 2001, "Hepatocyte Growth Factor/Scatter Factor-induced Activation of MEK and PI3K Signal Pathways Contributes to Expression of Proangiogenic Cytokines Interleukin-8 and Vascular Endothelial Growth Factor in Head and Neck Squamous Cell Carcinoma." Cancer Research 61: 5911-5918.
D. Grant et al., Mar. 1993, "Scatter factor induces blood vessel formation in vivo." Proc. Natl. Acad. Sci. USA 90: 1937-1941.
Y. Liu et al., Nov. 16, 1993, "Molecular cloning and characterization of cDNA encoding mouse hepatocyte growth factor." Biochim. Biophys. Acta 1216: 299-300.
G. Maulik et al., 2002, "Role of the hepatocyte growth factor receptor, c-Met, in oncogenesis and potential for therapeutic inhibition." Cytokine & Growth Factor Reviews 13: 41-59.
R. Montesano et al., Nov. 29, 1991, "Identification of a Fibroblast-Derived Epithelial Morphogen as Hepatocyte Growth Factor." Cell 67: 901-908.
T. Nakamura et al., Nov. 23, 1989, "Molecular cloning and expression of human hepatocyte growth factor." Nature 342: 440-443.
R. Samudrala et al., 1999, "Ab Initio Protein Structure Prediction Using a Combined Hierarchical Approach." Proteins: Structure, Function, and Genetics Suppl. 3: 194-198.
K. Weidner et al., Nov. 1990, "Scatter Factor: Molecular Characteristics and Effect on the Invasiveness of Epithelial Cells." The Journal of Cell Biology 111: 2097-2108.
Communication from European Patent Office pursuant to Article 94(3) EPC dated Dec. 23, 2008.
Zaccolo et al., "Dimerization of Fab fragments enables ready screening of phage antibodies that affect hepatocyte growth factor/scatter factor activity on target cells," Eur. J. Immunol. 27:618-623 (1997).
Official Decision from Egyptian Patent Office in Patent Application No. PCT 50/2006, with English translation.
Notice of Rejection (with translation), mailed Apr. 20, 2010, for Japanese Patent Application No. 2006-520171 (8 pages).
Substantive Examination Adverse Report (section 30(1)/30(2), mailed Jun. 20, 2008, for Malaysian Patent Application No. PI 20042873 (5 pages).
Translation of Notification on the Necessity of Submitting Additional Materials, mailed Sep. 29, 2009, for Eurasian Patent Application No. 200600233/28 (2 pages).
Notification on the Necessity of Submitting Additional Materials (with translation), mailed Oct. 29, 2008, for Eurasian Patent Application No. 200600233/28 (6 pages).
First Office Action (with translation), mailed Dec. 4, 2009, for Chinese Patent Application No. 200480026298.8 (13 pages).
Notification of Defects in Patent Application No. 172,906 (with translation), mailed Jan. 5, 2009, for Israeli Patent Application No. 172,906 (6 pages).
Notification of Defects in Patent Application No. 172,906 (with translation), mailed Nov. 1, 2009, for Israeli Patent Application No. 172,906(3 pages).
Examiner's First Report, mailed Feb. 19, 2010, for Australian Patent Application No. 2004265595 (2 pages).
Communication pursuant to Article 94(3) EPC, mailed Dec. 22, 2009, for European Patent Application No. 04776560.7 (4 pages).
Examination Report, mailed Oct. 12, 2007, for New Zealand Patent Application No. 544797 (2 pages).
Examination Report, mailed Apr. 29, 2009, for New Zealand Patent Application No. 544797 (3 pages).
Examination Report, mailed May 1, 2009, for New Zealand Patent Application No. 544797 (3 pages).
Examination Report, mailed Sep. 10, 2009, for New Zealand Patent Application No. 544797 (2 pages).
Examination Report, mailed Sep. 14, 2009, for New Zealand Patent Application No. 544797 (2 pages).
Examination Report, mailed May 6, 2010, for New Zealand Patent Application No. 544797 (2 pages).

(56) References Cited

OTHER PUBLICATIONS

Invitation to Respond to Written Opinion, Singapore Written Opinion, and Singapore Search Report, mailed Jul. 22, 2009, for Singaporean Patent Application No. 200702945-7 (17 pages).
Search and Examination Report, mailed Jun. 3, 2010, for Singaporean Patent Application No. 200702945-7 (11 pages).
Examiner's report No. 2, mailed Nov. 18, 2011, for Australian Patent Application No. 2004265595, 1 page.
Office Action, mailed Nov. 8, 2011, for Canadian Patent Application No. 2,532,027, 3 pages.
Second Office Action. mailed Jul. 21, 2011, for Chinese Patent Application No. 200480026298.8, 5 pages.
Second Office Action, mailed Mar. 29, 2011, for Japanese Patent Application No. 2006-52171, 2 pages.
Office Action, mailed Jun. 9, 2011, for Mexican Patent Application No. PA/a/2006/000508, 1 page.
Office Action, mailed Mar. 30, 2011, for European Patent Application No. 04 776 560.7, 6 pages.
EPO Communication, Extended Search Report for European Patent Application EP 10 016 059.7, mailed Jun. 1, 2011, 6 pages.
Office Action, mailed Apr. 14, 2011, for Israeli Patent Application No. 172,906, 1 page.
Office Action, mailed Aug. 14, 2011, for Taiwanese Patent Application 093121107, 3 pages.
Office Action, mailed Dec. 24, 2010 for Taiwanese Patent Application 093121407, 9 pages.
File history of U.S. Patent No. 7,494,650, issued Feb. 24, 2009, 1090 pages.
File history of U.S. Patent No. 7,687,063, issued Mar. 30, 2010, 1253 pages.
File history of European Patent Application EP 1734995, filed Aug. 13, 2004, 1762 pages.
Opposition proceedings, complete history with references, Submission No. 1400089, Patent No. EP 1731995, Nov. 16, 2011, 1436 pages.
Amgen Notice of opposition to a European patent, patent opposed EP 1734995 B1, Proprietor, Galaxy Biotech, LLC, Opponent, Amgen Inc., Apr. 14, 2011, 386 pages.
Glaxo Notice of Opposition to European Patent No. EP 1 734 995 B1, Facts and arguments presented in support of the opposition, filed by Glaxo Group (Opponent), Apr. 13, 2011, 783 pages.
Response by Galaxy Biotech to Notices of Opposition against EP1734995B1, Nov. 16, 2011, 255 pages.
Email from Technical Correspondent from R&D Systems dated Mar. 25, 2011, from Submission in opposition proceedings, Submission No. 140089, Application No. EP04781281.3, p. 678.
"Anti-human hepatocyte growth factor (HGF) developed in goat, affinity isolated antibody," Sigma-Aldrich Material Data Sheet, H7157, revision date Nov. 4, 2011, print date Jan. 12, 2012, 1 page.
Burr, et al., "Anti-hepatocyte growth factor antibody inhibits hepatocyte proliferation during liver regeneration," *Journal of Pathology*, Chichester, Sussex, GB, vol. 185, Jul. 1998, pp. 298-302.
Crestani et al., Differential role of neutrophils and alveolar . . . fibrosis, *Laboratory Investigation*, 82:8, Aug. 2002, pp. 1015-1022.
DiNicola et al., "Human bone marrow stromal cells suppress T-lymphocyte proliferation induced by cellular or nonspecific mitogenic stimuli," *Blood*, W.B. Saunders Company, Orlando, FL, US, vol. 99, No. 10, May 15, 2002, pp. 3838-3843.
Feagan et al., "Treatment of ulcerative colitis with a humanized antibody to the $\alpha_4\beta_7$ integrin," *The New England Journal of Medicine*, Jun. 16, 2005, pp. 2499-2507.
Grenier et al., "Presence of a mobilizable intracellular pool of hepatocyte growth factor . . . ," *Blood*, 99:8, Apr. 15, 2002, pp. 2997-3004.
Kuus-Reichel et al., "Will immunogenicity limit the use, efficacy, and future development of . . . antibodies," *Clin. Diag. Lab. Immunol.*, 1:4, Jul. 1994, pp. 365-372.
Hwang et al., "Immunogenicity of engineered antibodies," *Methods*, 36, 2005, pp. 3-10.
Yamamoto et al., "Modulation of motility and proliferation of glioma cells . . . ," *Jpn. J. Cancer Res.*, 88, Jun. 1997, pp. 564-577.
Nishimura et al., Prostate stromal cell-derived hepatocyte growth factor induces invasion of prostate cancer cell line DU145 . . . , *Prostate*, vol. 41, No. 3, Nov. 1999, pp. 145-153.
Monoclonal Anti-human HGF antibody, brochure rev date Jul. 12, 2011 by R & D Systems, downloaded from WWW.rndsystems.com/pdf/MAB284.pdf.
Human HGF antibody, brochure rev date Sep. 23, 2010 by R & D Systems, downloaded from WWW.rndsystems.com/pdf/MAB294.pdf.
Human HGF antibody, brochure by R & D Systems, MAB294, rev date Nov. 11, 2008, 1 page.
Human HGF antibody, brochure by R & D Systems, MAB694, rev date Apr. 23, 2010, 1 page.
DiRenzo et al., "Expression of the Met/HGF receptor in normal and neoplastic human tissues," Oncogene 6:1997-2003, 1991.
Gherardi and Stoker, "Hepatocyte growth factor-scatter factor: mitogen, motogen, and Met," Cancer Cells, 3(6):227-232, 1991.
Higashio and Shima, "Tumor cytotoxic activity of HGF-SF," In Hepatocyte growth factor-scatter factor (HGF-SF) and the C-met receptor, by I.D. Goldberg and E.M. Rosen, eds., Birkhauser Verlag, pp. 351-368, 1993.
Jeffers et al., "Hepatocyte growth factor/scatter factor-Met signaling in tumorigenicity and invasion/metastasis," J Mol Med 74:505-513, 1996.
Jeffers et al., "Autocrine hepatocyte growth factor/scatter factor-Met signaling induces transformation and the invasive/metastastic phenotype in C127 cells," Oncogene 13:853-861, 1996.
Kuba et al., "HGF/NK4, a four-kringle antagonist of hepatocyte growth factor, is an angiogenesis inhibitor that suppresses tumor growth and metastasis in mice," Cancer Res 60:6737-6743, 2000.
Lamszus et al., "Scatter factor promotes motility of human glioma and neuromicrovascular endothelial cells," Int J Cancer 75:19-28, 1998.
Laterra et al., "Scatter factor/hepatocyte growth factor expression enhances human glioblastoma tumorigenicity and growth," Biochem Biophyis Res Commun 235:743-747, 1997.
Laterra et al., "Scatter factor/hepatocyte growth factor gene transfer enhances glioma growth and angiogenesis in vivo," Lab Invest 76(4):565-577, 1997.
Moriyama et al., "Comparative analysis of expression of hepatocyte growth factor and its receptor, c-met, in gliomas, meningiomas and schwannomas in humans," Cancer Lett 124:149-155, 1998.
Rong et al., "Met expression and sarcoma tumorigenicity," Cancer Res 53:5355-5360, 1993.
Rosen et al., "Scatter factor expression and regulation in human glial tumors," Int J Cancer 67:248-255, 1996.
Siegfried et al., "Association of immunoreactive hepatocyte growth factor with poor survival in resectable non-small cell lung cancer," Cancer Res 57:433-439, 1997.
Takayama et al., "Diverse tumorigenesis associated with aberrant development in mice overexpressing hepatocyte growth factor/scatter factor," Proc Natl Acad Sci USA 94:701-706, 1997.
Wang et al., "Potent and selective inhibitors of the Met [hepatocyte growth factor/scatter factor (HGF-SF) receptor] tyrosine kinase block HGF/SF-induced tumor cell growth and invasion," Mol Cancer Ther 2:1085-1092, 2003.
Galaxy Biotech's Further Submission and Auxiliary Requests, filed Jul. 20, 2012, in Opposition to European Patent EP1734995.
Third Party Observations Regarding Proprietor's Submission, filed Aug. 6, 2012, in Opposition to European Patent EP1734995.
Amgen's Response to Galaxy Biotech's Submission, filed Aug. 29, 2012, in Opposition to European Patent EP1734995.
Galaxy Biotech's Agument Against Third Party Observations, filed Sep. 5, 2012, in Opposition to European Patent EP1734995.
Burgess et al., "Fully human monoclonal antibodies to hepatocyte growth factor with therapeutic potential against hepatocyte growth factor/c-Met-dependent human tumors," Cancer Res 66(3):1721-1729, 2006.
Michieli et al., "Targeting the tumor and its microenvironment by a dual-function decoy Met receptor," Cancer Cell 6:61-73, 2004.

(56) References Cited

OTHER PUBLICATIONS

Beilmann et al., "Human primary co-culture angiogenesis assay reveals additive stimulation and different angiogenic properties of VEGF and HGF," Cytokine 26:178-185, 2004.
Cavallaro et al., "FGF-2 stimulates migration of Kaposi's sarcoma-like vascular cells by HGF-dependent relocalization of the urokinase receptor," FASEB J 12:1027-1034, 1998.
DiNicola et al., "Human bone marrow stromal cells suppress T-lymphocyte proliferation induced by cellular or nonspecific mitogenic stimuli," Blood 99:3838-3843, 2002.
Dokras et al., "Regulation of human cytotrophoblast morphogenesis by hepatocyte growth factor/scatter factor," Biol Reprod 65:1278-1288, 2001.
Glenjen et al., "In vitro effects of native human acute myelogenous leukemia blasts on fibroblasts and osteoblasts," Int J Cancer 111:858-867, 2004.
Lewis et al., "Tumour-derived TGF-β1 modulates myofibroblast differentiation and promotes HGF/SF-dependent invasion of squamous carcinoma cells," B J Cancer 90:822-832, 2004.
Sherman, "Role of CD44 in malignant peripheral nerve sheath tumor growth and metastasis," Final Progress Report prepared for U.S. Army Medical Research and Material Command, Fort Detrick, MD, Sep. 2003 (49pp).
Shinomiya et al., "Suppression of met expression: a possible cancer treatment," Clin Cancer Res 9:5085-5090, 2003.
Sowter et al., "Hepatocyte growth factor (HGF) in ovarian epithelial tumour fluids stimulates the migration of ovarian carcinoma cells," Int J Cancer 83:476-480, 1999.
Third Party Observation, filed May 24, 2012, in Opposition to European Patent EP1734995.
Adamczyk et al., "Complete sequencing of anti-vancomycin fab fragment by liquid chromatography-electrospray ion trap mass spectrometry with a combination of database searching and manual interpretation of the MS/MS spectra," J Immunol Methods 260:235-249, 2002.
Adamczyk et al., "Sequence of anti-thyroxine monoclonal antibodies Fab fragment by ion trap mass spectrometry," Rapid Commun Mass Spectrom 14:999-1007, 2000.
Cacciotti et al., "SV40 replication in human mesothelial cells induces HGF/Met receptor activation: A model for viral-related carcinogenesis of human malignant mesothelioma," Proc Natl Acad Sci USA 98(21):12032-12037, 2001.
Carter et al., "Humanization of an anti-p185HER2 antibody for human cancer therapy," Proc Natl Acad Sci USA 89:4285-4289, 1992.
Declaration of May Han, Ph.D. (May 23, 2012).
Goldstein et al., "Biological efficacy of a chimeric antibody to the epidermal growth factor receptor in a human tumor xenograft model," Clin Cancer Res 1:1311-1318, 1995.
Goodrich & Kugel, "Binding and Kinetics for Molecular Biologists," Cold Spring Harbor Laboratory Press, pp. 19-20, 2007.
Information Sheet, Product Information Sheet from a 2002 R&D Systems Catalog for MAB294.
Information Sheet, Product Information Sheet from a 1998 R&D Systems Catalog for MAB294.
Jiang & Harding, "Enhancement of wound tissue expansion and angiogenesis by matrix-embedded fibroblast (Dermagraft), a role of hepatocyte growth factor/scatter factor," Int J Mol Med 2:203-210, 1998.
Johnson et al., "Development of a humanized monoclonal antibody (MEDI-493) with potent In vitro and In vivo activity against respiratory syncytial virus," J Infect Dis 76:1215-1224, 1997.
Khachigian et al., "Platelet-derived growth factor A-chain synthetic peptide inhibits human glioma xenograft proliferation in nude mice," Anticancer Res 15:337-341, 1995.
Klabunde et al., "The amino acid sequence of the red kidney bean Fe(III)-Zn(II) purple acid phosphatase: Determination of the amino acid sequence by a combination of matrix-assisted laser desorption/ionization mass spectrometry and automated Edman sequencing," Eur J Biochem 226:369-375, 1994.
Klominek et al., "Hepatocyte growth factor/scatter factor stimulates chemotaxis and growth of malignant mesothelioma cells through c-met receptor," Int J Cancer 76:240-249, 1998.
Knight et al., "Construction and initial characterization of a mouse human chimeric anti-TNF antibody," Mol Immunol 30:1443-1453, 1993.
Koochekpour et al., "Met and hepatocyte growth factor/scatter factor expression in human gliomas," 1997, Cancer Res 57:5391-5398, 1997.
NCBI Genebank Accession No. AAG53460.1, Jan. 24, 2001.
Presta et al., "Humanization of an antibody directed against IgE," J Immunol 151(5):2623-2632, 1993.
Presta et al., "Humanization of an anti-vascular endothelial growth factor monoclonal antibody for the therapy of solid tumors and other disorders," Cancer Res 57:4593-4599, 1997.
Queen et al., "A humanized antibody that binds to the interleukin 2 receptor," Proc Natl Acad Sci USA 86:10029-10033, 1989.
Reff et al., "Depletion of B cells In vivo by a chimeric mouse human monoclonal antibody to CD20," Blood 83:435-445, 1994.
Reichert,"Monoclonal antibodies in the clinic," Nature 19:819-822, 2001.
Studnicka et al., "Human-engineered monoclonal antibodies retain full specific binding activity by preserving non-CDR complementarity-modulating residues," Protein Eng 7:805-814, 1994.
Verhoeyen et al., "Construction of a reshaped HMFG1 antibody and comparison of its fine specificity with that of the parent mouse antibody," Immunology 78:364-370, 1993.
Waldmann, "Immunotherapy: past, present and future," Nat Med 9:269-277, 2003.
Weiner & Adam, "New approaches to antibody therapy," Oncogene 19:6144-6151, 2000.
Werther et al., "Humanization of an anti-lymphocyte function-associated antigen (LFA)-1 monoclonal antibody and reengineering of the humanized antibody for binding to rhesus LFA-1," J Immunol 157(11):4986-4995, 1996.
Summons to Attend Oral Hearing and Summary of Facts and Submissions from Opposition Division, mailed Mar. 8, 2012, in Opposition to European Patent EP1734995.
Amgen's Response to Summons, filed Jul. 20, 2012, in Opposition to European Patent EP1734995.
Statement from R&D Systems regarding 1994 release date of MAB294, dated Jul. 12, 2012.
Declaration of Dr. Angela Coxon, Jul. 12, 2012.
Schmidt et al., "Levels of vascular endothelial growth factor, hepatocyte growth factor/scatter factor and basic fibroblast growth factor in human gliomas and their relation to angiogenesis," Int J Cancer (Pred Oncol) 84:10-18, 1999.
Tokunou et al., "c-MET expression in myofibroblasts. Role in autocrine Aactivation and prognostic significance in lung adenocarcinoma," Am J Pathol 158(4):1451-1463, 2001.
Christensen et al., "A selective small molecule inhibitor of c-Met kinase inhibits c-Met-dependent phenotypes in vitro and exhibits cytoreductive antitumor activity in vivo," Cancer Res. 63:7345-7355, 2003.
Declaration of Dr. Robert Radinsky with curriculum vitae and list of reviewed documents, Jul. 10, 2012.

\* cited by examiner

```
                                              CDR 1                                Section 1
                                                                                   CDR 2
                       1        10        20        30        40        50
HGF 2.4.4 VK4-B3   (1) DIVMTQSPDSLAVSLGERATINCKSSQSVLFSSNNKNYLAWYQQKPGQPPKLLIYWASTR   (Seq ID No.: 173)
HGF 1.29.1 VK4-B3  (1) DIVMTQSPDSLAVSLGERATINCKSSQSVLFSSNNKNYLAWYQQKPGQPPKLLIYWASTR   (Seq ID No.: 174)
HGF 1.75.1 VK1-A30 (1) DIQMTQSPSSLSASVGDRVTITCRASQG------IRNDLGWFQQKPGKAPKRLIYAASSL   (Seq ID No.: 175)
HGF 2.40.1 VK1-A30 (1) DIQMTQSPSSLSASVGDRVTITCRASQG------IRNDLGWYQQKPGKAPKRLIYVASSL   (Seq ID No.: 176)
HGF 1.24.1 VK1-L15 (1) DIQMTQSPSSVSASVGDRVTITCRASQG------ISSWLAWYQQKPGKAPNLLIYEASSL   (Seq ID No.: 177)
HGF 1.60.1 VK1-A20 (1) DIQMTQSPSSLSASVGDRVTITCRASQG------ISSYLAWYQQKPGKVPKLLIYVASTL   (Seq ID No.: 178)
HGF 1.74.3 VK1-O12/O2 (1) DIQMTQSPSSLSASVGDRVTITCRASQS------INSDLNWYQQKPGKVPKLLIYVASSL (Seq ID No.: 179)
HGF 1.61.3 VK1-O18/O8 (1) DIQMTQSPSSLSASVGDRVTITCQASQD------ISNYLNWYQQKPGTAPKLLIYGASDL (Seq ID No.: 180)
HGF 2.12.1 VK3-L2/L16 (1) EIVMTQSPATLSVSPGERATLSCRASQS------VDSNLAWYRQKPGQAPRLLIYGASTR (Seq ID No.: 181)
HGF 3.10.1 VK3-L2/L16 (1) EIVMTQSPATLSVSPGERATLSCRASQS------VSSNLAWYQQKPGQAPRLLMYGASTR (Seq ID No.: 182)
Consensus          (1) DIQMTQSPSSLS  SVGDRVTITCRASQS       I    LAWYQQKPGKAPKLLIY ASTL
                                                                                   Section 2
                                                                  CDR 3
                       61        70        80        90        100       114
HGF 2.4.4 VK4-B3  (61) ESGVPDRFSGSGSGTDFTLTISSLQAEDVAVYYCQQYFSPP-WTFGQGTKVEIK   (Seq ID No.: 173)
HGF 1.29.1 VK4-B3 (61) ESGVPDRFSGSGSGTDFTLTISSLQAEDVAVYYCQQYYSTP-WTFGQGTKVEIK   (Seq ID No.: 174)
HGF 1.75.1 VK1-A30 (55) QSGVPSRFSGSGSGTEFTLTISSLQPEDFATYYCLQHDSYP-LTFGGGTKVEIK  (Seq ID No.: 175)
HGF 2.40.1 VK1-A30 (55) QSGVPSRFSGSGSGTEFTLTISSLQPEDFATYYCLQHNSYP-LTFGGGTKVEIK  (Seq ID No.: 176)
HGF 1.24.1 VK1-L15 (55) QSGVPSRFSGSGSGTDFTLTISSLQPEDVATYYCQQANGFP-WTFGQGTKVEIK  (Seq ID No.: 177)
HGF 1.60.1 VK1-A20 (55) QNGVPSRFSGSGSGTDFTLTISSLQPEDFATYYCQNYNSDP-LTFGGGTKVEIK  (Seq ID No.: 178)
HGF 1.74.3 VK1-O12/O2 (55) ETGVPSRFSGSGSGTDFTLTISSLQPEDFATYYCQRSYSTP-PTFGPGTKVDIK (Seq ID No.: 179)
HGF 1.61.3 VK1-O18/O8 (55) ATGIPARFSGSGSGTDFTFAISSLQPEDIATYYCQQYDNLP-YNFGQGTKRLEIK (Seq ID No.: 180)
HGF 2.12.1 VK3-L2/L16 (55) ATGIPARFSGSGSGTDFTLTISSLQSEDFAVYYCQQYINWPPITFGQGTRLEIK (Seq ID No.: 181)
HGF 3.10.1 VK3-L2/L16 (55) QSGVPSRFSGSGSGTDFTLTISSLQPEDFATYYCQQY  S P  TFGQGTKVEIK (Seq ID No.: 183)
Consensus         (61) QSGVPSRFSGSGSGTDFTLTISSLQPEDFATYYCQQY  S P  TFGQGTKVEIK
```

|                         |       | 1          10         20         30 CDR1 40         50 CDR2    62 |
|-------------------------|-------|---------------------------------------------------------------------|
| HGF 1.74.3 VG 1-02      | (1)   | QVQLVQSGAEVKKPGASVKVSCKASGYTFT--GYYIHWVRQAPGQGLEWMGWINPNSGGTNY       |
| HGF 1.60.1 VG 1-02      | (1)   | QVQLVQSGAEVKKPGASVKVSCKASGYTFT--GYYINWVRQAPGQGLEWMGWINPNSGGTNY       |
| HGF 1.24.1 VG 3-11      | (1)   | QVQLVESGGGLVKPGGSLRLSCAASGFTFS--DYYMSWIRQAPGKGLEWVSYISSSGSTIYY       |
| HGF 1.29.1 VG 3-33      | (1)   | QVQLVESGGGVVQPGRSLRLSCAASGFTFS--SYGMHWVRQAPGKGLEWVAVIWYDGSDKYY       |
| HGF 1.61.3 VG 4-31      | (1)   | QVQLQESGPGLVKPSQTLSLTCTVSGGSISSDGYYWSWIRQHPGKGLEWIGYIYYSG-STYY       |
| HGF 2.40.1 VG 4-31      | (1)   | QVQLQESGPGLVKPSQTLSLTCTVSGGSISSGGYYWSWIRQHPGKGLEWIGNIYYSG-ITYY       |
| HGF 1.75.1 VG 4-31      | (1)   | QVQLQESGPGLVKPSQTLSLTCTVSGGSISSGGYYWSWIRQHPGKGLEWIGYIYYSG-STYY       |
| HGF 2.4.4 VG 4-31       | (1)   | QVQLKESGPGLVKPSQTLSLTCTVSGGSISSGVYYWSWIRQHPGKGLEWIGYFYYSG-NTYH       |
| HGF 3.10.1 VG 4-34      | (1)   | QVQLQQWGAGLLKPSETLSLTCAVYGGSFS--TYYWSWIRQPPGKGLEWIGEINHSG-STNY       |
| HGF 2.12.1 VG 4-59      | (1)   | QVQLQESGPGLVKPSETLSLTCTVSGGSIS--IYYWSWIRQPPGKGLEWIGYVYYSG-STNY       |
| Consensus               | (1)   | QVQLQESGPGLVKPS TLSLTCTVSGGSIS   GYYWSWIRQ PGKGLEWIGYIYYSG STYY      |

|                         |       | 63 CDR2 70         80         90        100 CDR3  124              |
|-------------------------|-------|--------------------------------------------------------------------|
| HGF 1.74.3 VG 1-02      | (61)  | AQKFQGRVTMTRDTSISTAYMELSRLRSDDTAVYYCARELELR--------YYG-MDVWGQG      |
| HGF 1.60.1 VG 1-02      | (61)  | AQKFQGRVTMTRDTSITTAYMELSRLRADDTAVYYCARELELR--------YYG-MDVWGQG      |
| HGF 1.24.1 VG 3-11      | (61)  | ADSVKGRFTISRDNAKNSLYLQMNSLRAEDTAVYYCARDEYNSGW-------YVLFDYWGQG      |
| HGF 1.29.1 VG 3-33      | (61)  | ADSVKGRFTISRDNSKNTLYLQMNSLRAEDTAVYYCAREDYGEG-----------FDYWGQG      |
| HGF 1.61.3 VG 4-31      | (62)  | NPSLKSRVTISVDTSKNQFSLKLSSVTAADTAVYYCARSHLHY-YDSSGYYYGGAPDIWGQG      |
| HGF 2.40.1 VG 4-31      | (62)  | NPSLKSRVTMSVDTSKNQFSLKLSSVTAADTAVYYCARDPLYG---------DYGFDPWGQG      |
| HGF 1.75.1 VG 4-31      | (62)  | NPSLKSRVTISVDTSKNQFSLKVSSVTAADTAVYYCARDPLWFG-----EFDYYGMDVWGQG      |
| HGF 2.4.4 VG 4-31       | (62)  | NPSLKSRVTISVDTSKNQFSLKLSSVTAADTAVYYCAR-------DRSGYDHPDAPDIWGQG      |
| HGF 3.10.1 VG 4-34      | (60)  | NPSLKSRVTISVDTSKNQFSLKLSSVTAADTAVYYCARGG--------YDFWSGYFDYWGQG      |
| HGF 2.12.1 VG 4-59      | (60)  | NPSLKSRVTISVDTSKNQFSLKLNSVTAADTAVYYCARGG--------YDFWSGYFDYWGQG      |
| Consensus               | (63)  | NPSLKSRVTISVDTSKNQFSLKLSSVTAADTAVYYCARD          Y G FDVWGQG       |

|                        |       | 125 129              |
|------------------------|-------|----------------------|
| HGF 1.74.3 VG 1-02     | (114) | TTVTV (Seq ID No.: 184) |
| HGF 1.60.1 VG 1-02     | (114) | TTVTV (Seq ID No.: 185) |
| HGF 1.24.1 VG 3-11     | (116) | TLVTV (Seq ID No.: 186) |
| HGF 1.29.1 VG 3-33     | (112) | TLVTV (Seq ID No.: 187) |
| HGF 1.61.3 VG 4-31     | (123) | TMVTV (Seq ID No.: 188) |
| HGF 2.40.1 VG 4-31     | (115) | TLVTV (Seq ID No.: 189) |
| HGF 1.75.1 VG 4-31     | (119) | TTVTV (Seq ID No.: 190) |
| HGF 2.4.4 VG 4-31      | (117) | TMVTV (Seq ID No.: 191) |
| HGF 3.10.1 VG 4-34     | (114) | TLVTV (Seq ID No.: 192) |
| HGF 2.12.1 VG 4-59     | (114) | TLV-- (Seq ID No.: 193) |
| Consensus              | (125) | TLVTV (Seq ID No.: 194) |

HGF 1.24.1 Light chain V region (Vk, 1-L15)
ATGGACATGAGGGTGCCCGCTCAGCTCCTGGGGCTCCTGCTGCTCTGGTTCCC
AGGTTCCAGATGCGACATCCAGATGACCCAGTCTCCATCTTCCGTGTCTGCAT
CTGTAGGAGACAGAGTCACCATCACTTGTCGGGCGAGTCAGGGTATTAGCAG
CTGGTTAGCCTGGTATCAGCAGAAACCAGGGAAAGCCCCTAACCTCCTGATC
TATGAAGCATCCAGTTTGCAAAGTGGGGTCCCATCAAGGTTCGGCGGCAGTG
GATCTGGGACAGATTTCACTCTCACCATCAGCAGCCTGCAGCCTGAAGATTTT
GCAACTTACTATTGTCAACAGGCTAACGGTTTCCCGTGGACGTTCGGCCAAG
GGACCAAGGTGGAAATCAAA   (SEQ ID NO: 01)

HGF 1.24.1 Heavy chain V region (Vh, H3-11)-huIgG2 C region)
ATGGAGTTTGGGCTGAGCTGGGTTTTCCTTGTTGCTATTATAAAAGGTGTCCA
GTGTCAGGTGCAGCTGGTGGAGTCTGGGGGAGGCTTGGTCAAGCCTGGAGGG
TCCCTGAGACTCTCCTGTGCAGCCTCTGGATTCACCTTCAGTGACTACTACAT
GAGCTGGATCCGCCAGGCTCCAGGGAAGGGGCTGGAGTGGGTTTCATACATT
AGTAGTAGTGGTAGTACCATATACTACGCAGACTCTGTGAAGGGCCGATTCA
CCATCTCCAGGGACAACGCCAAGAACTCACTGTATCTGCAAATGAACAGCCT
GAGAGCCGAGGACACGGCCGTGTATTACTGTGCGAGAGATGAGTATAACAGT
GGCTGGTACGTCCTCTTTGACTACTGGGGCCAGGGAACCCTGGTCACCGTCTC
TAGT (SEQ ID NO: 02)

HGF 1.29.1 Light chain V region (Vk, 4-B3)
ATGGTGTTGCAGACCCAGGTCTTCATTTCTCTGTTGCTCTGGATCTCTGATGCC
TACGGAGACATCGTGATGACCCAGTCTCCAGACTCCCTGGCTGTGTCTCTGGG
CGAGAGGGCCACCATCAACTGCAAGTCCAGCCAGAGTATTTTTTACAGCTCC
ACCAATAAGAACTACTTAGCTTGGTATCAGAAGAAACCGGGACAGCCTCCTA
AGCTGCTCATTTACTGGGCATCTACCCGGGAATCCGGGGTCCCTGACCGGTTC
AGTGGCAGCGGGTCTGGGACAGATTTCACTCTCACCATCAGCAGCCTGCAGG
CTGAAGATGTGGCAGTTTATTACTGTCAGCAATATTATAGTACTCCGTGGACG
TTCGGCCAAGGGACCAAGGTGGAAATCAAA (SEQ ID NO: 03)

HGF 1.29.1 Heavy chain V region (Vh, 3-33)- huIgG2 C region
ATGGAGTTTGGGCTGAACTGGGTTTTCCTCGTTGCTCTTTTAAGAGGTGTCCA
GTGTCAGGTGCAGCTGGTGGAGTCTGGGGGAGGCGTGGTCCAGCCTGGGAGG
TCCCTGAGACTCTCCTGTGCAGCGTCTGGATTCACCTTCAGTAGCTATGGCAT
GCACTGGGTCCGCCAGGCTCCGGGCAAGGGACTGGAGTGGGTGGCAGTTATA
TGGTATGATGGAAGTGATAAATACTATGCAGACTCCGTGAAGGGCCGATTCA
CCATCTCCAGAGACAATTCCAAGAACACGCTGTATCTGCAAATGAACAGCCT
GAGAGCCGAGGACACGGCTGTGTATTACTGTGCGAGAGAGGACTACGGCGA
GGGTTTTGACTACTGGGGCCAGGGAACCCTGGTCACCGTCTCTAGT      (SEQ
ID NO: 04)

HGF 1.60.1 Light chain V region (Vk, 1-A20)
ATGGACATGAGGGTGCCCGCTCAGCTCCTGGGACTCCTGCTGCTCTGGCTCCC
AGATACCAGATGTGACATCCAGATGACCCAGTCTCCATCCTCCCTGTCTGTAT
CTGTCGGAGACAGAGTCACCATCACTTGCCGGGCGAGTCAGGGCATTAGCAG
TTATTTAGCCTGGTATCAGCAGAAACCAGGGAAAGTTCCTAAGCTCCTGATCT
ATGTTGCATCCACTTTGCAATCAGGGGTCCCGTCTCGGTTCAGTGGCAGTGGA
TCTGGGACAGATTTCACTCTCACCATCAGCAGCCTGCAGCCTGAAGATGTTGC
AACTTATTACTGTCAAACTATAACAGTGACCCGCTCACTTTCGGCGGCGGG
ACCAAGGTGGAGATCAAA      (SEQ ID NO: 05)

FIG. 3A

HGF 1.60.1 Heavy chain V region (Vh, H1-02)- huIgG2 C region
<u>ATGGACTGGACCTGGAGGATCCTCTTCTTGGTGGCAGCAGCCACAGGAGCCC</u>
<u>ACTCCC</u>AGGTGCAGCTGGTGCAGTCTGGGGCTGAGGTGAAGAAGCCTGGGGC
CTCAGTGAAGGTCTCCTGCAAGGCTTCTGGATACACCTTCACCGGCTACTATA
TAAACTGGGTGCGACAGGCCCCTGGACAAGGGCTTGAGTGGATGGGATGGAT
CAACCCTAACAGTGGTGGCACAAACTATGCACAGAAGTTTCAGGGCAGGGTC
ACCATGACCAGGGACACGTCCATCACCACAGCCTACATGGAGCTGAGCAGGC
TGAGAGCTGACGACACGGCCGTGTACTACTGTGCGAGAGAACTGGAACTACG
CTACTACGGTATGGACGTCTGGGGCCAAGGGACCACGGTCACCGTCTCTAGT
 (SEQ ID NO: 06)

HGF 1.61.3 Light chain V region (Vk, 1-O18/08)
<u>ATGGACATGAGGGTGCCCGCTCAGCTCCTGGGGCTCCTGCTGCTCTGGCTCTC</u>
<u>AGGTGCCAGATGT</u>GACATCCAGATGACCCAGTCTCCATCCTCCCTGTCTGCAT
CTGTAGGAGACAGAGTCACCATCACTTGCCAGGCGAGTCAGGACATTAGCAA
CTATTTAAATTGGTATCAGCAGAAACCAGGGACAGCCCCTAAACTCCTGATC
TACGGTGCATCCGATTTGGAAACGGGGGTCCCATCAAGGTTCAGTGGAAGTG
GATCTGGGACAGATTTTACTTTCGCCATCAGCAGCCTGCAGCCTGAAGATATT
GCAACATATTACTGTCAACAGTATGATAATCTCCCGTACAATTTTGGCCAGGG
GACCAAGCTGGAGATCAAA   (SEQ ID NO: 07)

HGF 1.61.3 Heavy chain V region (Vh, 4-31)- huIgG2 C region
<u>ATGAAACACCTGTGGTTCTTCCTCCTGCTGGTGGCAGCTCCCAGATGGGTCCT</u>
<u>GTCCC</u>AGGTGCAGCTGCAGGAGTCGGGCCCAGGACTGGTGAAGCCTTCACAG
ACCCTGTCCCTCACCTGCACTGTCTCTGGTGGCTCCATCAGCAGTGATGGTTA
CTACTGGAGCTGGATCCGCCAGCACCCAGGGAAGGGCCTGGAGTGGATTGGG
TACATCTATTACAGTGGGAGCACCTACTACAACCCGTCCCTCAAGAGTCGAG
TCACCATATCAGTAGACACGTCTAAGAACCAGTTCTCCCTGAAGCTGAGCTCT
GTGACTGCCGCGGACACGGCCGTCTATTACTGTGCGAGATCCCACCTTCATTA
CTATGATAGTAGTGGTTATTACTACGGCGGTGCTTTTGATATCTGGGGCCAAG
GGACAATGGTCACCGTCTCTAGT   (SEQ ID NO: 08)

HGF 1.74.3 Light chain V region (Vk, 1-012/02)
<u>ATGGACATGAGGGTGCCCGCTCAGCTCCTGGGGCTCCTGCTACTCTGGCTCCG</u>
<u>AGGTGCCAGATGT</u>GACATCCAGATGACCCAGTCTCCATCCTCCCTGTCTGCAT
CTGTAGGAGACAGAGTCACCATCACTTGCCGGGCAAGTCAGAGCATTAACAG
CGATTTAAATTGGTATCAGCAGAAACCAGGGAAAGTCCCTAAGCTCCTGATC
TATGTTGCATCCAGTTTGCAAAATGGGGTCCCATCAAGGTTCAGTGGCAGTG
GATCTGGGACAGATTTCACTCTCACCATCAGCAGTCTGCAACCTGAAGATTTT
GCAACTTACTACTGTCAACGGAGTTACAGTACCCCTCCCACTTTCGGCCCTGG
GACCAAAGTGGATATCAAA   (SEQ ID NO: 09)

HGF 1.74.3 Heavy chain V region (Vh, VG1-02)- huIgG2 C region
<u>ATGGACTGGACCTGGAGGATCCTCTTCTTGGTGGCAGCAGCCACAGGAGCCC</u>
<u>ACTCCC</u>AGGTGCAGCTGGTGCAGTCTGGGGCTGAGGTGAAGAAGCCTGGGGC
CTCAGTGAAGGTCTCCTGCAAGGCTTCTGGATACACCTTCACCGGCTACTATA
TACACTGGGTGCGACAGGCCCCTGGACAAGGGCTTGAGTGGATGGGATGGAT
CAACCCTAACAGTGGTGGCACAAACTATGCACAGAAGTTTCAGGGCAGGGTC
ACCATGACCAGGGACACGTCCATCAGCACAGCCTACATGGAGCTGAGCAGGC
TGAGATCTGACGACACGGCCGTGTATTACTGTGCGAGAGAACTGGAACTACG
CTACTACGGTATGGACGTCTGGGGCCAAGGGACCACGGTCACCGTCTCTAGT
 (SEQ ID NO: 10)

FIG. 3B

HGF 1.75.1 Light chain V region (Vk, 1-A30)
ATGGACATGAGGGTGCCCGCTCAGCTCCTGGGGCTCCTGCTGCTCTGGTTCCC
AGGTGCCAGGTGTGACATCCAGATGACCCAGTCTCCATCCTCCCTGTCTGCAT
CTGTAGGAGACAGAGTCACCATCACTTGCCGGGCAAGTCAGGGCATTAGAAA
TGATTTAGGCTGGTTTCAGCAGAAACCAGGGAAAGCCCCTAAGCGCCTGATC
TATGCTGCATCCAGTTTGCAAAGTGGGGTCCCATCAAGGTTCAGCGGCAGTG
GATCTGGGACAGAATTCACTCTCACAATCAGCAGCCTGCAGCCTGAAGATTT
TGCAACTTATTACTGTCTACAGCATGATAGTTACCCGCTCACTTTCGGCGGAG
GGACCAAGGTGGAGATCAAA  (SEQ ID NO: 11)

HGF 1.75.1 Heavy chain V region (Vh, VG4-31)- huIgG2 C region
ATGAAACACCTGTGGTTCTTCCTCCTGCTGGTGGCAGCTCCCAGATGGGTCCT
GTCCCAGGTGCAGCTGCAGGAGTCGGGCCCAGGACTGGTGAAGCCTTCACAG
ACCCTGTCCCTCACCTGCACTGTCTCTGGTGGCTCCATCAGCAGTGGTGGTTA
CTACTGGAGCTGGATCCGCCAGCACCCAGGGAAGGGCCTGGAGTGGATTGGG
TACATCTATTACAGTGGGAGCACCTACTACAACCCGTCCCTCAAGAGTCGAG
TTACCATATCAGTAGACACGTCTAAGAACCAGTTCTCCCTGAAGGTGAGCTCT
GTGACTGCCGCGGACACGGCCGTGTATTACTGTGCGAGAGACCCACTATGGT
TCGGGGAGTTCGACTACTACGGTATGGACGTCTGGGGCCAAGGGACCACGGT
CACCGTCTCTAGT (SEQ ID NO: 12)

HGF 2.4.4 Light chain V region (Vk, 4-B3)
ATGGTGTTGCAGACCCAGGTCTTCATTTCTCTGTTGCTCTGGATCTCTGGTGCC
TACGGGGACATCGTGATGACCCAGTCTCCAGACTCCCTGGCTGTGTCTCTGGG
CGAGAGGGCCACCATCAACTGCAAGTCCAGCCAGAGTGTTTTATTCAGCTCC
AACAATAAGAATTACTTAGCTTGGTATCAGCAGAAACCAGGACAGCCTCCTA
AGTTGCTCATTTACTGGGCATCTACCCGGGAATCCGGGGTCCCTGACCGATTC
AGTGGCAGCGGGTCTGGGACAGATTTCACTCTCACCATCAGCAGCCTGCAGG
CTGAAGATGTGGCAGTTTATTACTGTCAGCAATATTTTAGTCCTCCGTGGACG
TTCGGCCAAGGGACCAAGGTGGAAATCAAA (SEQ ID NO: 13)

HGF 2.4.4 Heavy chain V region (Vh, VG 4-31)- huIgG2 C region
ATGAAACACCTGTGGTTCTTCCTCCTGCTGGTGGCAGCTCCCAGATGGATCCT
GTCCCAGGTGCAGCTGAAGGAGTCGGGCCCAGGACTGGTGAAGCCTTCACAG
ACCCTGTCCCTCACCTGCACTGTCTCTGGTGGCTCCATCAGCAGTGGTGTTTA
CTACTGGAGCTGGATCCGCCAGCACCCAGGGAAGGGCCTGGAGTGGATTGGG
TACTTCTATTATAGTGGGAACACCTACCACAACCCGTCCCTCAAGAGTCGAGT
GACCATATCAGTAGACACGTCTAAGAACCAGTTCTCCCTGAAGCTGAGCTCT
GTGACTGCCGCGGACACGGCCGTGTATTACTGTGCGAGAGATCGTAGTGGCT
ACGATCACCCTGATGCTTTTGATATCTGGGGCCAAGGGACAATGGTCACCGT
CTCTAGT   (SEQ ID NO: 14)

HGF 2.12.1 Light chain V region (Vk, 3-L2/L16)
ATGGAAGCCCCAGCTCAGCTTCTCTTCCTCCTGCTACTCTGGCTCCCAGATAC
CACTGGAGAAATAGTGATGACGCAGTCTCCAGCCACCCTGTCTGTGTCTCCA
GGGGAAAGAGCCACCCTCTCCTGCAGGGCCAGTCAGAGTGTTGACAGCAACT
TAGCCTGGTACCGGCAGAAACCTGGCCAGGCTCCCAGGCTCCTCATCTATGG
TGCATCCACCAGGGCCACTGGTATCCCAGCCAGGTTCAGTGGCAGTGGGTCT
GGGACTGAGTTCACTCTCACCATCAGCAGCCTGCAGTCTGAAGATTTTGCAGT
TTATTACTGTCAGCAGTATATTAACTGGCCTCCGATCACCTTCGGCCAAGGGA
CACGACTGGAGATTAAA (SEQ ID NO: 15)

FIG. 3C

HGF 2.12.1 Heavy chain V region (Vh4-59)- huIgG2 C region
ATGAAACACCTGTGGTTCTTCCTTCTCCTGGTGGCAGCTCCCAGATGGGTCCT
GTCCCAGGTGCAGCTGCAGGAGTCGGGCCCAGGACTGGTGAAGCCTTCGGAG
ACCCTGTCCCTCACCTGCACTGTCTCTGGTGGCTCCATCAGTATTTACTACTG
GAGCTGGATCCGGCAGCCCCAGGGAAGGGACTGGAGTGGATTGGGTATGTC
TATTACAGTGGGAGCACCAATTACAACCCCTCCCTCAAGAGTCGAGTCACCA
TATCAGTAGACACGTCCAAGAACCAGTTCTCCCTGAAGCTGAACTCTGTGAC
CGCTGCGGACACGGCCGTGTATTACTGTGCGAGAGGGGGATACGATTTTGG
AGTGGTTATTTTGACTACTGGGGCCAGGGAACCCTGGTCACCGTCTCTAGT
  (SEQ ID NO: 16)

HGF 2.40.1 Light chain V region (Vk, 1A20)
ATGGACATGAGGGTGCCCGCTCAGCTCCTGGGGCTCCTGCTGCTCTGGTTCCC
AGGTGCCAGGTGTGACATCCAGATGACCCAGTCTCCATCCTCCCTGTCTGCAT
CTGTAGGAGACAGAGTCACCATCACTTGCCGGGCAAGTCAGGGCATTAGAAA
TGATTTAGGCTGGTATCAGCAGAAACCAGGGAAAGCCCCTAAGCGCCTGATC
TATGTTGCATCCAGTTTGCAAAGTGGGGTCCCATCAAGGTTCAGCGGCAGTG
GATCTGGGACAGAATTCACTCTCACAATCAGCAGCCTGCAGCCTGAAGATTT
TGCAACTTATTACTGTCTACAACATAATAGTTACCCGCTCACTTTCGGCGGAG
GGACCAAGGTGGAGATCAAA (SEQ ID NO: 17)

HGF 2.40.1 Heavy chain V region (Vh, VG 4-31)- huIgG2 C region
ATGAAACACCTGTGGTTCTTCCTCCTGCTGGTGGCAGCTCCCAGATGGGTCCT
GTCCCAGGTGCAGCTGCAGGAGTCGGGCCCAGGACTGGTGAAGCCTTCACAG
ACCCTGTCCCTCACCTGCACTGTCTCTGGTGGCTCCATCAGCAGTGGTGGTTA
CTACTGGAGCTGGATCCGTCAGCACCCAGGGAAGGGCCTGGAGTGGATTGGG
AACATCTATTACAGTGGGATCACCTACTACAACCCGTCCCTCAAGAGTCGAG
TTACCATGTCAGTAGACACGTCTAAGAACCAGTTCTCCCTGAAGCTGAGTTCT
GTGACTGCCGCGGACACGGCCGTGTATTACTGTGCGAGAGATCCCCTCTACG
GTGACTACGGGTTCGACCCCTGGGGCCAGGGAACCCTGGTCACCGTCTCTAG
T (SEQ ID NO: 18)

HGF 3.10.1 Light chain V region (Vk, 3-L2/L16)
ATGGAAGCCCCAGCTCAGCTTCTCTTCCTCCTGCTACTCTGGCTCCCAGATAC
CACTGGAGAAATAGTGATGACGCAGTCTCCAGCCACCCTGTCTGTGTCTCCTG
GGGAAAGAGCCACCCTCTCCTGCAGGGCCAGTCAGAGTGTTAGCAGCAACTT
AGCCTGGTACCAGCAGAAACCTGGCCAGGCTCCCAGGCTCCTCATGTATGGT
GCATCCACCAGGGCCACTGGTATCCCAGCCAGGTTCAGTGGCAGTGGGTCTG
GGACAGAGTTCACTCTCACCATCAGCAGCCTGCAGTCTGAAGATTTTGCAGTT
TATTACTGTCAGCAGTATAATAACTGGCCTCCGATCACCTTCGGCCAAGGGAC
ACGACTGGAGATTAAA (SEQ ID NO: 19)

HGF 3.10.1 Heavy chain V region (Vh, VG 4-34)- huIgG1 C region
ATGAAACACCTGTGGTTCTTCCTCCTCCTGGTGGCAGCTCCCAGATGGGTCCT
GTCCCAGGTGCAGCTACAGCAGTGGGGCGCAGGACTGTTGAAGCCTTCGGAG
ACCCTGTCCCTCACCTGCGCTGTCTATGGTGGGTCCTTCAGTACTTACTACTG
GAGCTGGATCCGCCAGCCCCAGGGAAGGGGCTGGAGTGGATTGGGGAAAT
CAATCATAGTGGAAGCACCAACTACAACCCGTCCCTCAAGAGTCGAGTCACC
ATATCAGTAGACACGTCCAAGAACCAGTTCTCCCTGAAGCTGAGCTCTGTGA
CCGCCGCGGACACGGCTGTGTATTACTGTGCGAGAGGGGGGTACGATTTTTG
GAGTGGTTATTATGACTACTGGGGCCAGGGAACCCTGGTCACCGTCTCTAGT
  (SEQ ID NO: 20)

FIG. 3D

Human Kappa Constant Region
CGAACTGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAGCAG
GACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTCA
CAAAGAGCTTCAACAGGGGAGAGTGTTGA (SEQ ID NO: 21)

Human IgG1 Constant Region
GCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACCCTGCCCCCA
TCCCGGGATGAGCTGACCAAGAACCAGGTCAGCCTGACCTGCCTGGTCAAAGGCTTCTA
TCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTATAGCAAGCTCACCGTG
GACAAGAGCAGGTGGCAGCAGGGGAACGTCTTCTCATGCTCCGTGATGCATGAGGCTCT
GCACAACCACTACACGCAGAAGAGCCTCTCCCTGTCTCCGGGTAAATGA
(SEQ ID NO: 22)

Human IgG2 Constant Region
GCCTCCACCAAGGGCCCATCGGTCTTCCCCCTGGCGCCCTGCTCCAGGAGCACCTCCGA
GAGCACAGCGGCCCTGGGCTGCCTGGTCAAGGACTACTTCCCCGAACCGGTGACGGTGT
CGTGGAACTCAGGCGCTCTGACCAGCGGCGTGCACACCTTCCCAGCTGTCCTACAGTCC
TCAGGACTCTACTCCCTCAGCAGCGTGGTGACCGTGCCCTCCAGCAACTTCGGCACCCA
GACCTACACCTGCAACGTAGATCACAAGCCCAGCAACACCAAGGTGGACAAGACAGTTG
AGCGCAAATGTTGTGTCGAGTGCCCACCGTGCCCAGCACCACCTGTGGCAGGACCGTCA
GTCTTCCTCTTCCCCCCAAAACCCAAGGACACCCTCATGATCTCCCGGACCCCTGAGGT
CACGTGCGTGGTGGTGGACGTGAGCCACGAAGACCCCGAGGTCCAGTTCAACTGGTACG
TGGACGGCGTGGAGGTGCATAATGCCAAGACAAAGCCACGGGAGGAGCAGTTCAACAGC
ACGTTCCGTGTGGTCAGCGTCCTCACCGTTGTGCACCAGGACTGGCTGAACGGCAAGGA
GTACAAGTGCAAGGTCTCCAACAAAGGCCTCCCAGCCCCCATCGAGAAAACCATCTCCA
AAACCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTACCCCAGCGACAT
CGCCGTGGAGTGGGAGAGCAATGGGCAGCCGGAGAACAACTACAAGACCACACCTCCCA
TGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTA
CACGCAGAAGAGCCTCTCCCTGTCTCCGGGTAAATGA (SEQ ID NO: 23)

FIG. 3E

HGF 1.24.1 Light chain V region (Vk, 1-L15)
MDMRVPAQLLGLLLLWFPGSRCDIQMTQSPSSVSASVGDRVTITCRASQGISSWL
AWYQQKPGKAPNLLIYEASSLQSGVPSRFGGSGSGTDFTLTISSLQPEDFATYYC
QQANGFPWTFGQGTKVEIK    (SEQ ID NO: 24)

HGF 1.24.1 Heavy chain V region (Vh, H3-11)-huIgG2 C region
MEFGLSWVFLVAIIKGVQCQVQLVESGGGLVKPGGSLRLSCAASGFTFSDYYMS
WIRQAPGKGLEWVSYISSSGSTIYYADSVKGRFTISRDNAKNSLYLQMNSLRAED
TAVYYCARDEYNSGWYVLFDYWGQGTLVTVSS    (SEQ ID NO: 25)

HGF 1.29.1 Light chain V region (Vk, 4-B3)
MVLQTQVFISLLLWISDAYGDIVMTQSPDSLAVSLGERATINCKSSQSIFYSSTNK
NYLAWYQKKPGQPPKLLIYWASTRESGVPDRFSGSGSGTDFTLTISSLQAEDVAV
YYCQQYYSTPWTFGQGTKVEIK    (SEQ ID NO: 26)

HGF 1.29.1 Heavy chain V region (Vh, 3-33)- huIgG2 C region
MEFGLNWVFLVALLRGVQCQVQLVESGGGVVQPGRSLRLSCAASGFTFSSYGM
HWVRQAPGKGLEWVAVIWYDGSDKYYADSVKGRFTISRDNSKNTLYLQMNSL
RAEDTAVYYCAREDYGEGFDYWGQGTLVTVSS    (SEQ ID NO: 27)

HGF 1.60.1 Light chain V region (Vk, 1-A20)
MDMRVPAQLLGLLLLWLPDTRCDIQMTQSPSSLSVSVGDRVTITCRASQGISSYL
AWYQQKPGKVPKLLIYVASTLQSGVPSRFSGSGSGTDFTLTISSLQPEDVATYYC
QNYNSDPLTFGGGTKVEIK    (SEQ ID NO: 28)

HGF 1.60.1 Heavy chain V region (Vh, H1-02)- huIgG2 C region
MDWTWRILFLVAAATGAHSQVQLVQSGAEVKKPGASVKVSCKASGYTFTGYYI
NWVRQAPGQGLEWMGWINPNSGGTNYAQKFQGRVTMTRDTSITTAYMELSRL
RADDTAVYYCARELELRYYGMDVWGQGTTVTVSS    (SEQ ID NO: 29)

HGF 1.61.3 Light chain V region (Vk, 1-O18/08)
MDMRVPAQLLGLLLLWLSGARCDIQMTQSPSSLSASVGDRVTITCQASQDISNY
LNWYQQKPGTAPKLLIYGASDLETGVPSRFSGSGSGTDFTFAISSLQPEDIATYYC
QQYDNLPYNFGQGTKLEIK    (SEQ ID NO: 30)

HGF 1.61.3 Heavy chain V region (Vg, 4-31)- huIgG2 C region
MKHLWFFLLLVAAPRWVLSQVQLQESGPGLVKPSQTLSLTCTVSGGSISSDGYY
WSWIRQHPGKGLEWIGYIYYSGSTYYNPSLKSRVTISVDTSKNQFSLKLSSVTAA
DTAVYYCARSHLHYYDSSGYYYGGAFDIWGQGTMVTVSS    (SEQ ID NO: 31)

HGF 1.74.3 Light chain V region (Vk, 1-O12/02)
MDMRVPAQLLGLLLLWLRGARCDIQMTQSPSSLSASVGDRVTITCRASQSINSDL
NWYQQKPGKVPKLLIYVASSLQNGVPSRFSGSGSGTDFTLTISSLQPEDFATYYC
QRSYSTPPTFGPGTKVDIK    (SEQ ID NO: 32)

HGF 1.74.3 Heavy chain V region(Vh, VG1-02)-huIgG2 C region
MDWTWRILFLVAAATGAHSQVQLVQSGAEVKKPGASVKVSCKASGYTFTGYYI
HWVRQAPGQGLEWMGWINPNSGGTNYAQKFQGRVTMTRDTSISTAYMELSRL
RSDDTAVYYCARELELRYYGMDVWGQGTTVTVSS    (SEQ ID NO: 33)

FIG. 4A

HGF 1.75.1 Light chain V region (Vk, 1-A30)
MDMRVPAQLLGLLLLWFPGARCDIQMTQSPSSLSASVGDRVTITCRASQGIRND
LGWFQQKPGKAPKRLIYAASSLQSGVPSRFSGSGSGTEFTLTISSLQPEDFATYYC
LQHDSYPLTFGGGTKVEIK     (SEQ ID NO: 34)

HGF 1.75.1 Heavy chain V region (Vh, VG4-31)-huIgG2 C region
MKHLWFFLLLVAAPRWVLSQVQLQESGPGLVKPSQTLSLTCTVSGGSISSGGYY
WSWIRQHPGKGLEWIGYIYYSGSTYYNPSLKSRVTISVDTSKNQFSLKVSSVTAA
DTAVYYCARDPLWFGEFDYYGMDVWGQGTTVTVSS     (SEQ ID NO: 35)

HGF 2.4.4 Light chain V region (Vk, 4-B3)
MVLQTQVFISLLLWISGAYGDIVMTQSPDSLAVSLGERATINCKSSQSVLFSSNNK
NYLAWYQQKPGQPPKLLIYWASTRESGVPDRFSGSGSGTDFTLTISSLQAEDVAV
YYCQQYFSPPWTFGQGTKVEIK     (SEQ ID NO: 36)

HGF 2.4.4 Heavy chain V region (Vh, VG 4-31)-huIgG2 C region
MKHLWFFLLLVAAPRWILSQVQLKESGPGLVKPSQTLSLTCTVSGGSISSGVYY
WSWIRQHPGKGLEWIGYFYYSGNTYHNPSLKSRVTISVDTSKNQFSLKLSSVTAA
DTAVYYCARDRSGYDHPDAFDIWGQGTMVTVSS     (SEQ ID NO: 37)

HGF 2.12.1 Light chain V region (Vk, 3-L2/L16)
MEAPAQLLFLLLLWLPDTTGEIVMTQSPATLSVSPGERATLSCRASQSVDSNLAW
YRQKPGQAPRLLIYGASTRATGIPARFSGSGSGTEFTLTISSLQSEDFAVYYCQQYI
NWPPITFGQGTRLEIK     (SEQ ID NO: 38)

HGF 2.12.1 Heavy chain V region (Vg, 4-59)- huIgG2 C region
MKHLWFFLLLVAAPRWVLSQVQLQESGPGLVKPSETLSLTCTVSGGSISIYYWS
WIRQPPGKGLEWIGYVYYSGSTNYNPSLKSRVTISVDTSKNQFSLKLNSVTAADT
AVYYCARGGYDFWSGYFDYWGQGTLVTVSS     (SEQ ID NO: 39)

HGF 2.40.1 Light chain V region (Vk, 1A20)
MDMRVPAQLLGLLLLWFPGARCDIQMTQSPSSLSASVGDRVTITCRASQGIRND
LGWYQQKPGKAPKRLIYVASSLQSGVPSRFSGSGSGTEFTLTISSLQPEDFATYYC
LQHNSYPLTFGGGTKVEIK     (SEQ ID NO: 40)

HGF 2.40.1 Heavy chain V region (Vh, VG 4-31)-huIgG2 C region
MKHLWFFLLLVAAPRWVLSQVQLQESGPGLVKPSQTLSLTCTVSGGSISSGGYY
WSWIRQHPGKGLEWIGNIYYSGITYYNPSLKSRVTMSVDTSKNQFSLKLSSVTAA
DTAVYYCARDPLYGDYGFDPWGQGTLVTVSS     (SEQ ID NO: 41)

HGF 3.10.1 Light chain V region (Vk, 3-L2/L16)
MEAPAQLLFLLLLWLPDTTGEIVMTQSPATLSVSPGERATLSCRASQSVSSNLAW
YQQKPGQAPRLLMYGASTRATGIPARFSGSGSGTEFTLTISSLQSEDFAVYYCQQ
YNNWPPITFGQGTRLEIK     (SEQ ID NO: 42)

HGF 3.10.1 Heavy chain V region (Vh, VG 4-34)-huIgG1 C region
MKHLWFFLLLVAAPRWVLSQVQLQQWGAGLLKPSETLSLTCAVYGGSFSTYYW
SWIRQPPGKGLEWIGEINHSGSTNYNPSLKSRVTISVDTSKNQFSLKLSSVTAADT
AVYYCARGGYDFWSGYYDYWGQGTLVTVSS     (SEQ ID NO: 43)

FIG. 4B

Human Kappa Constant Region
RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC
    (SEQ ID NO: 44)

Human IgG1 Constant Region
ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLS
PGK   (SEQ ID NO: 45)

Human IgG2 Constant Region
ASTKGPSVFPLAPCSRSTSESTAALGCLVKDYFPEPVTVSWNSGALTSGVHTFPA
VLQSSGLYSLSSVVTVPSSNFGTQTYTCNVDHKPSNTKVDKTVERKCCVECPPCP
APPVAGPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPENNYKT
TPPMLDSDGSFFLYSKLTVDKSRWQQGNVFSCSVMHEALHNHYTQKSLSLSPGK
    (SEQ ID NO: 46)

FIG. 4C

Light Chain Variable Region Amino Acid Sequences for CDR1, CDR2, and CDR3

| Antibody | CDR1 | CDR2 | CDR3 |
|---|---|---|---|
| 1.24.1 | RASQGISSWLA (SEQ ID NO. 60) | EASSLQS (SEQ ID NO. 70) | QQANGFPWT (SEQ ID NO. 80) |
| 1.29.1 | KSSQSIFYSSTNKNYLA (SEQ ID NO. 61) | WASTRES (SEQ ID NO. 71) | QQYYSTPWT (SEQ ID NO. 81) |
| 1.60.1 | RASQGISSYLA (SEQ ID NO. 62) | VASTLQS (SEQ ID NO. 72) | QNYNSDPLT (SEQ ID NO. 82) |
| 1.61.3 | QASQDISNYLN (SEQ ID NO. 63) | GASDLET (SEQ ID NO. 73) | QQYDNLPYN (SEQ ID NO. 83) |
| 1.74.3 | RASQSINSDLN (SEQ ID NO. 64) | VASSLQN (SEQ ID NO. 74) | QRSYSTPPT (SEQ ID NO. 84) |
| 1.75.1 | RASQGIRNDLG (SEQ ID NO. 65) | AASSLQS (SEQ ID NO. 75) | LQHDSYPLT (SEQ ID NO. 85) |
| 2.4.4 | KSSQSVLFSSNNKNYLA (SEQ ID NO. 66) | WASTRES (SEQ ID NO. 76) | QQYFSPPWT (SEQ ID NO. 86) |
| 2.12.1 | RASQSVDSNLA (SEQ ID NO. 67) | GASTRAT (SEQ ID NO. 77) | QQYINWPPIT (SEQ ID NO. 87) |
| 2.40.1 | RASQGIRNDLG (SEQ ID NO. 68) | VASSLQS (SEQ ID NO. 78) | LQHNSYPLT (SEQ ID NO. 88) |
| 3.10.1 | RASQSVSSNLA (SEQ ID NO. 69) | GASTRAT (SEQ ID NO. 79) | QQYNNWPPIT (SEQ ID NO. 89) |

Light chain CDR1 consensus sequence (CDR1a) (SEQ ID NO: 166): a b c d e f g h i j k l m n o p q, where wherein amino acid a is selected from lysine, arginine, or glutamine; amino acid b is selected from serine or alanine; amino acid c is serine, amino acid d is glutamine; amino acid e is selected from serine, glycine, or aspartic acid; amino acid f is selected from valine or isoleucine or is not present; amino acid g is selected from leucine or phenylalanine or is not present; amino acid h is selected from phenylalanine or tyrosine or is not present; amino acid i is serine or not present; amino acid j is serine or not present; amino acid k is selected from asparagine, threonine, or not present; amino acid l is selected from asparagine, isoleucine, or valine; amino acid m is selected from lysine, arginine, serine, asparagine, or aspartic acid; amino acid n is selected from asparagine or serine; amino acid o is selected from tyrosine, aspartic acid, tryptophan, or asparagine; amino acid p is leucine; and amino acid q is selected from alanine, glycine, or asparagine

Light chain CDR2 consensus sequence (CDR2a) (SEQ ID NO: 167) r s t u v w x, wherein amino acid r is selected from tryptophan, alanine, valine, glutamic acid, or glycine; amino acid s is alanine, amino acid t is serine, amino acid u is selected from threonine, serine, or aspartic acid, amino acid v is selected from arginine or leucine; amino acid w is selected from glutamic acid, glutamine, or alanine; amino acid x is selected from serine, asparagine, or threonine

Light chain CDR3 consensus sequence (CDR3a) (SEQ ID NO: 168) y z a' b' c' d' e' f' g' h', wherein amino acid y is selected from glutamine or leucine; amino acid z is selected from glutamine, asparagine, or arginine; amino acid a' is selected from tyrosine, histidine, alanine, or serine; amino acid b' is selected from phenylalanine, tyrosine, aspartic acid, asparagine, or isoleucine; amino acid c' is selected from serine, glycine, or asparagine; amino acid d' is selected from proline, tyrosine, threonine, phenylalanine, aspartic acid, leucine, or tryptophan; amino acid e' is proline; amino acid f' is proline or is not present; amino acid g' is tryptophan, leucine, proline, tyrosine, or isoleucine; and amino acid h' is threonine or asparagine

FIG. 5A

Heavy Chain Variable Region Amino Acid Sequences for CDR1, CDR2, and CDR3

| Antibody | CDR1 | CDR2 | CDR3 |
|---|---|---|---|
| 1.24.1 | DYYMS (SEQ ID NO. 90) | YISSSGSTIYYADSVKG (SEQ ID NO. 100) | DEYNSGWYVLFDY (SEQ ID NO. 110) |
| 1.29.1 | SYGMH (SEQ ID NO. 91) | VIWYDGSDKYYADSVKG (SEQ ID NO. 101) | EDYGEGFDY (SEQ ID NO. 111) |
| 1.60.1 | GYYIN (SEQ ID NO. 92) | WINPNSGGTNYAQKFQG (SEQ ID NO. 102) | ELELRYYGMDV (SEQ ID NO. 112) |
| 1.61.3 | SDGYYWS (SEQ ID NO. 93) | YIYYSGSTYYNPSLKS (SEQ ID NO. 103) | SHLHYYDSSGYYYGGAFDI (SEQ ID NO. 113) |
| 1.74.3 | GYYIH (SEQ ID NO. 94) | WINPNSGGTNYAQKFQG (SEQ ID NO. 104) | ELELRYYGMDV (SEQ ID NO. 114) |
| 1.75.1 | SGGYYWS (SEQ ID NO. 95) | YIYYSGSTYYNPSLKS (SEQ ID NO. 105) | DPLWFGEFDYYGMDV (SEQ ID NO. 115) |
| 2.4.4 | SGVYYWS (SEQ ID NO. 96) | YFYYSGNTYHNPSLKS (SEQ ID NO. 106) | DRSGYDHPDAFDI (SEQ ID NO. 116) |
| 2.12.1 | IYYWS (SEQ ID NO. 97) | YVYYSGSTNYNPSLKS (SEQ ID NO. 107) | GGYDFWSGYFDY (SEQ ID NO. 117) |
| 2.40.1 | SGGYYWS (SEQ ID NO. 98) | NIYYSGITYYNPSLKS (SEQ ID NO. 108) | DPLYGDYGFDP (SEQ ID NO. 118) |
| 3.10.1 | TYYWS (SEQ ID NO. 99) | EINHSGSTNYNPSLKS (SEQ ID NO. 109) | GGYDFWSGYYDY (SEQ ID NO. 119) |

Heavy chain CDR1 consensus sequence (CDR1b) (SEQ ID NO: 169): a b c d e f g, wherein amino acid a is serine or is not present; amino acid b is selected from aspartic acid or glycine, or is not present; amino acid c is selected from aspartic acid, glycine, serine, valine, threonine, or isoleucine; amino acid d is tyrosine; amino acid e is selected from tyrosine or glycine; amino acid f is selected from isoleucine, methionine, or tryptophan; and amino acid g is selected from histidine, asparagine, or serine

Heavy chain CDR2 consensus sequence (CDR2b) (SEQ ID NO: 170) h i j k l m n o p q r s t u v w x, wherein amino acid h is selected from tryptophan, tyrosine, valine, asparagine, or glutamic acid; amino acid i is selected from isoleucine, phenylalanine, or valine; amino acid j is selected from asparagine, serine, tryptophan, or tyrosine; amino acid k is selected from proline, serine, tyrosine, or histidine; amino acid l is selected from asparagine, serine, or aspartic acid; amino acid m is selected from serine or glycine; amino acid n is selected from glycine or serine, or is not present; amino acid o is selected from glycine, threonine, aspartic acid, serine, isoleucine, or asparagine; amino acid p is selected from threonine, isoleucine, or lysine; amino acid q is selected from asparagine or tyrosine; amino acid r is selected from tyrosine or histidine; amino acid s is selected from alanine or asparagine; amino acid t is selected from glutamine, aspartic acid, or proline; amino acid u is selected from lysine or serine; amino acid v is selected from phenylalanine, valine, or leucine; amino acid w is selected from glutamine or lysine, and amino acid x is selected from glycine or serine

Heavy chain CDR3 consensus sequence (CDR3b) (SEQ ID NO: 171) y z a' b' c' d' e' f' g' h' i' j' k' l' m' n' o' p' q' r', wherein amino acid y is selected from glutamic acid, aspartic acid, serine, or glycine, or is not present; amino acid z is selected from leucine, glutamic acid, aspartic acid, histidine, proline, or glycine, or is not present; amino acid a' is selected from glutamic acid, tyrosine, or leucine, or is not present; amino acid b' is selected from leucine, asparagine, glycine, histidine, tyrosine, or tryptophan, or is not present; amino acid c' is selected from arginine, serine, glutamic acid, tyrosine, glycine, or phenylalanine, or is not present; amino acid d' is glycine or is not present; amino acid e' is selected from tryptophan or tyrosine, or is not present; amino acid f' is aspartic acid or is not present; amino acid g' is selected from serine or arginine, or is not present; amino acid h' is serine or is not present; amino acid i' is selected from glycine or tyrosine, or is not present; amino acid j' is selected from tyrosine, glutamic acid, or aspartic acid, or is not present; amino acid k' is selected from tyrosine, phenylalanine, or aspartic acid, or is not present; amino acid l' is selected from tyrosine, aspartic acid, histidine, or tryptophan, or is not present; amino acid m' is selected from tyrosine, glycine, aspartic acid, proline, or serine, or is not present; amino acid n' is selected from glycine, valine, tyrosine, or aspartic acid, or is not present; amino acid o' is selected from leucine, alanine, glycine, or tyrosine, or is not present; amino acid p' is selected from methionine, phenylalanine, or tyrosine; amino acid q' is aspartic acid, and amino acid r' is selected from valine, tyrosine, isoleucine, or proline

FIG. 5B

| ID | ~$K_D$ (M) | ka (1/Ms) | kd (1/s) |
|---|---|---|---|
| 3.10.1 | 4.7E-10 | 6.5E+04 | 3.0E-05 |
| 2.4.4 | 9.9E-11 | 2.7E+05 | 2.7E-05 |
| 2.12.1 | 2.2E-10 | 1.3E+05 | 2.8E-05 |
| 1.29.1 | 7.9E-10 | 6.2E+04 | 4.8E-05 |
| 1.75.1 | 7.8E-10 | 3.6E+04 | 2.8E-05 |
| 1.74.3 | 3.6E-10 | 1.3E+05 | 4.7E-05 |

FIG. 6A

| ID | $K_D$ (pM) |
|---|---|
| 2.4.4 | < 10 |
| 1.29.1 | 34 +/- 15 |
| 1.74.2 | 41 +/- 13 |
| 2.12.1 | 54 +/- 7 |

FIG. 6B

FIG. 7B
1.74.1 (IgG2)
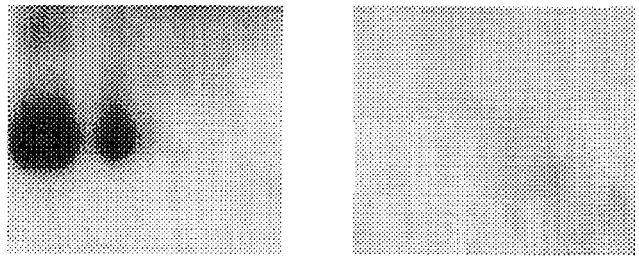
1.29.1 (IgG2)
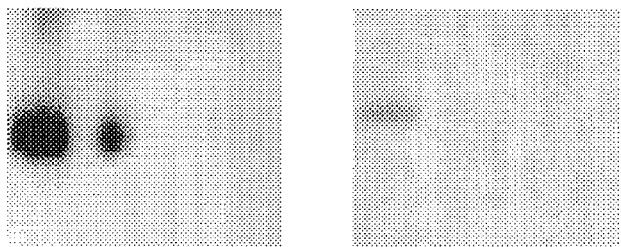
1.24.1 (IgG2)
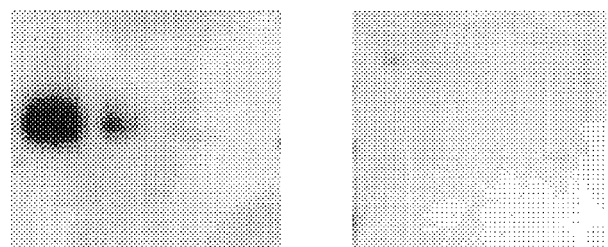
1.61.3 (IgG2)
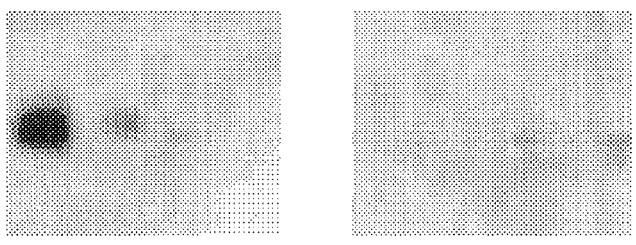
2.4.4 (IgG2)
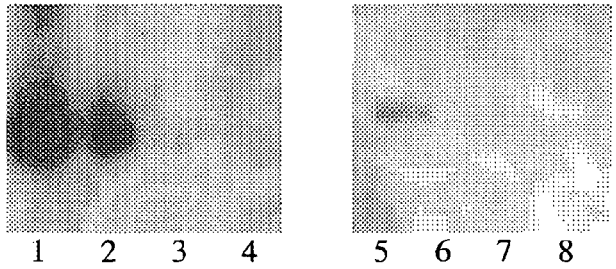
1  2  3  4     5  6  7  8

Abgenix1.75.1
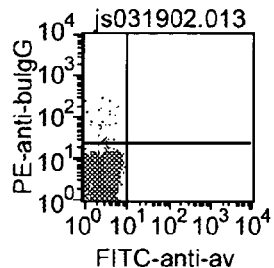 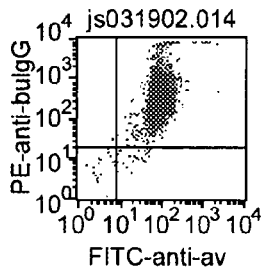 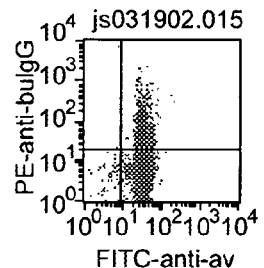 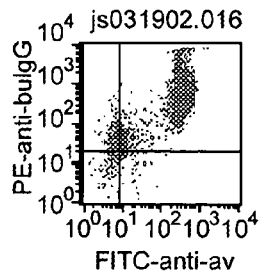
Abgenix3.10.1
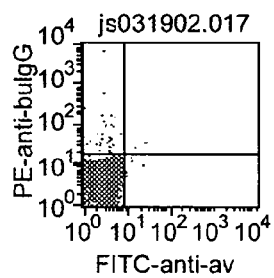 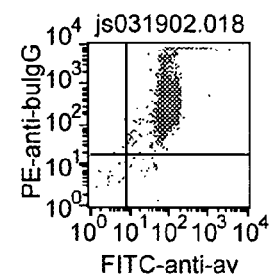 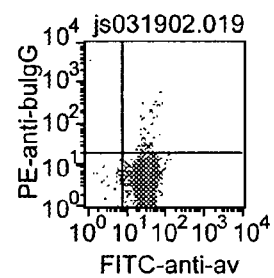 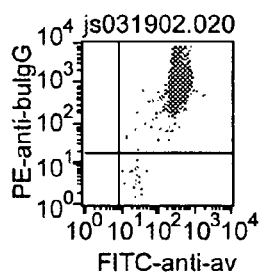
Abgenix2.12.1
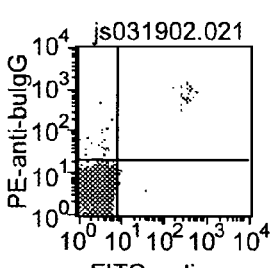 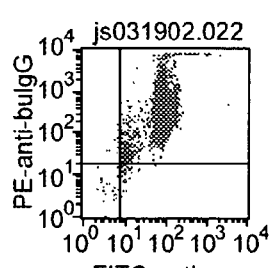 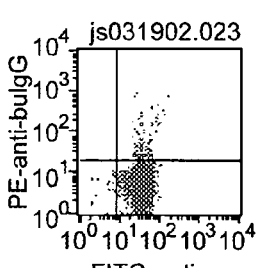 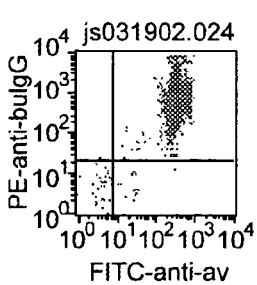
control     huHGF     muHGF     huHGFd5
FIG. 8B

```
CCCCACCATGGTGCACGCAACCTCCCCGCTGCTGCTGCTGCTGCTGCTCAGCCTGGCTCT
---------+---------+---------+---------+---------+---------+
GGGGTGGTACCACGTGCGTTGGAGGGGCGACGACGACGACGACGACGAGTCGGACCGAGA
   P  T  M  V  H  A  T  S  P  L  L  L  L  L  L  L  S  L  A  L
GGTGGCTCCCGGCCTCTCTGCCAGAAAGTGCTCGCTGACTGGGAAATGGACCAACGATCT
---------+---------+---------+---------+---------+---------+
CCACCGAGGGCCGGAGAGACGGTCTTTCACGAGCGACTGACCCTTTACCTGGTTGCTAGA
  V  A  P  G  L  S  A  R  K  C  S  L  T  G  K  W  T  N  D  L
                                                  EcoRI
                                                    |
GGGCTCCAACATGACCATCGGGGCTGTGAACAGCAAAGGTGAATTCACAGGCACCTACAC
---------+---------+---------+---------+---------+---------+
CCCGAGGTTGTACTGGTAGCCCCGACACTTGTCGTTTCCACTTAAGTGTCCGTGGATGTG
   G  S  N  M  T  I  G  A  V  N  S  K  G  E  F  T  G  T  Y  T
CACAGCCGTAACAGCCACATCAAATGAGATCAAAGAGTCACCACTGCATGGGACACAAAA
---------+---------+---------+---------+---------+---------+
GTGTCGGCATTGTCGGTGTAGTTTACTCTAGTTTCTCAGTGGTGACGTACCCTGTGTTTT
   T  A  V  T  A  T  S  N  E  I  K  E  S  P  L  H  G  T  Q  N
CACCATCAACAAGAGGACCCAGCCCACCTTTGGCTTCACTGTCAATTGGAAGTTTTCAGA
---------+---------+---------+---------+---------+---------+
GTGGTAGTTGTTCTCCTGGGTCGGGTGGAAACCGAAGTGACAGTTAACCTTCAAAAGTCT
   T  I  N  K  R  T  Q  P  T  F  G  F  T  V  N  W  K  F  S  E
GTCCACCACTGTCTTCACGGGCCAGTGCTTCATAGACAGGAACGGGAAGGAGGTCCTGAA
---------+---------+---------+---------+---------+---------+
CAGGTGGTGACAGAAGTGCCCGGTCACGAAGTATCTGTCCTTGCCCTTCCTCCAGGACTT
   S  T  T  V  F  T  G  Q  C  F  I  D  R  N  G  K  E  V  L  K
GACCATGTGGCTGCTGCGGTCAAGTGTTAATGACATTGGTGATGACTGGAAAGCTACCAG
---------+---------+---------+---------+---------+---------+
CTGGTACACCGACGACGCCAGTTCACAATTACTGTAACCACTACTGACCTTTCGATGGTC
   T  M  W  L  L  R  S  S  V  N  D  I  G  D  D  W  K  A  T  R
                                                        HindIII
                                                  NheI     |
                                            PvuII   |      |
                                              |     |      |
GGTCGGCATCAACATCTTCACTCGCCTGCGCACACAGAAGGAGCAGCTGCTAGCAAGCTT
---------+---------+---------+---------+---------+---------+
CCAGCCGTAGTTGTAGAAGTGAGCGGACGCGTGTGTCTTCCTCGTCGACGATCGTTCGAA
   V  G  I  N  I  F  T  R  L  R  T  Q  K  E  Q  L  L  A  S  L
NheI NotI XhoI            BamHI
  |    |   |                |
GCTAGCGGCCGCTCGAGGCCGGCAAGGCCGGATCCAGACATGATAAGATACATTGATGAG
(SEQ ID NO: 57)
---------+---------+---------+---------+---------+---------+
CGATCGCCGGCGAGCTCCGGCCGTTCCGGCCTAGGTCTGTACTATTCTATGTAACTACTC
(SEQ ID NO: 58)
  L  A  A  A  R  G  R  Q  G  R  I  Q  T  *   *  (SEQ ID NO: 59)
```

FIG. 9B

```
                451                                                          500
human HGF (450) PWCYTGNPLIPWDYCPISRCEGDTTPTIVNLDHPVISCAKTKQLRVVNGI
mouse HGF (451) PWCYTGNPLIPWDYCPISRCEGDTTPTIVNLDHPVISCAKTKQLRVVNGI
Consensus (451) PWCYTGNPLIPWDYCPISRCEGDTTPTIVNLDHPVISCAKTKQLRVVNGI
                501                                                          550
human HGF (500) PTRTNIGWMVSLRYRNKHICGGSLIKESWVLTARQCFPSR--DLKDYEAW
mouse HGF (501) PTQTTVGWMVSLKYRNKHICGGSLIKESWVLTARQCFPARNKDLKDYEAW
Consensus (501) PT T  GWMVSLKYRNKHICGGSLIKESWVLTARQCFPAR  DLKDYEAW
                551                                                          600
human HGF (548) LGIHDVHGRGDEKCKQVLNVSQLVYGPEGSDLVMKLARPAVLDDFVSTI
mouse HGF (551) LGIHDVHERGEEKRKQILNISQLVYGPEGSDLVLLKLARPAILDNFVSTI
Consensus (551) LGIHDVH  RGDEK KQILNISQLVYGPEGSDLVLLKLARPAILD FVSTI
                601                                                          650
human HGF (598) DLPNYGCTIPEKTSCSVYGWGYTGLINYDGLLRVAHLYIMGNEKCSQHHR
mouse HGF (601) DLPSYGCTIPEKTTCSIYGWGYTGLINADGLLRVAHLYIMGNEKCSQHHQ
Consensus (601) DLP YGCTIPEKTSCSIYGWGYTGLIN DGLLRVAHLYIMGNEKCSQHH
                651                                                          700
human HGF (648) GKVTLNESEICAGAEKIGSGPCEGDYGGPLVCEQHKMRMVLGVIVPGRGC
mouse HGF (651) GKVTLNESELCAGAEKIGSGPCEGDYGGPLICEQHKMRMVLGVIVPGRGC
Consensus (651) GKVTLNESEICAGAEKIGSGPCEGDYGGPLICEQHKMRMVLGVIVPGRGC
                701                                 731
human HGF (698) AIPNRPGIFVRVAYYAKWIHKIILTYKVPQS   (SEQ ID NO. 120)
mouse HGF (701) AIPNRPGIFVRVAYYAKWIHKVILTYKL---   (SEQ ID NO. 121)
Consensus (701) AIPNRPGIFVRVAYYAKWIHKIILTYKL      (SEQ ID NO. 122)
```

FIG. 10D

T38.6 = V V N G I P T R ———————— H G R (calc. mass=7152)    obs. mass=7165   (SEQ ID NO. 161)

G I P T R T ———————— H G R (calc. mass=6840)    obs mass= ~6878   (SEQ ID NO. 162)

T33 = V N T L D Q ———————— ?   (SEQ ID NO. 163)

Predicted protected peptides from peak T38.6:

VVNGIPTRTNIGWMVSLRYRNKHICGGSLIKESWVLTARQCFPSRDLKDYEAWLGIHDVHGR
(SEQ ID NO. 164)

GIPTRTNIGWMVSLRYRNKHICGGSLIKESWVLTARQCFPSRDLKDYEAWLGIHDVHGR
(SEQ ID NO. 165)

FIG. 11C

| ID | IC50 IP (nM) | ID | IC50 IP (nM) |
|---|---|---|---|
| 3.10.1 | 0.9 | 3.10.1 | 0.37 |
| 2.40.1 | 1.0 | 2.12.1 | 0.52 |
| 1.75.1 | 1.0 | 1.75.1 | 0.72 |
| 2.12.1 | 2.1 | 1.29.1 | 1.93 |
| 1.24.1 | 2.6 | 1.74.1 | 2.31 |
| 1.29.1 | 3.2 | 1.61.3 | 2.59 |
| 1.74.1 | 3.7 | 1.24.1 | 9.36 |
| 1.60.2 | 4.5 | | |
| 2.4.4 | 5.1 | | |

FIG. 13

| Experiment #1 | | Experiment #2 | |
|---|---|---|---|
| ID | IC50 IP (nM) | ID | IC50 IP (nM) |
| 1.75.1 | 0.34 | 1.61.3 | 0.28 |
| 2.12.1 | 0.49 | 1.24.1 | 0.40 |
| 2.40.1 | 0.51 | 1.75.1 | 0.59 |
| 3.10.1 | 0.64 | 1.29.1 | 0.88 |
| 1.24.1 | 0.64 | 1.60.1 | 1.06 |
| 1.29.1 | 1.18 | 1.74.1 | 2.17 |
| 2.4.4 | 1.24 | | |
| 1.74.1 | 1.25 | | |

FIG. 14

| Experiment #1 | | Experiment #2 | |
| --- | --- | --- | --- |
| ID | IC50 IP (nM) | ID | IC50 IP (nM) |
| 1.24.1 | 15 | 2.4.4 | 8 |
| 1.60.1 | 15 | 1.61.3 | 17 |
| 1.29.1 | 23 | 1.29.1 | 21 |
| 2.4.4 | 33 | 2.12.1 | 34 |
| 2.12.1 | 57 | 2.40.1 | 59 |
| 3.10.1 | 137 | 3.10.1 | 133 |
| | | 1.60.1 | 215 |
| | | 1.74.1 | >666 |
| | | 1.75.1 | >666 |

FIG. 15

SPECIFIC BINDING AGENTS TO HEPATOCYTE GROWTH FACTOR

This application claims the benefit of U.S. Provisional Application No. 60/488,681, filed Jul. 18, 2003, which is incorporated herein by reference for any purpose.

FIELD OF THE INVENTION

The present invention relates to specific binding agents that bind to hepatocyte growth factor (HGF). Compositions, methods of producing said compositions, and methods for the treatment of various disorders, such as certain types of cancer, including, but not limited to, solid tumors and hematologic malignancies are also described.

BACKGROUND OF THE INVENTION

Hepatocyte Growth Factor (HGF) has been identified as a potent mitogen for hepatocytes. HGF was also identified as a secretory protein of fibroblasts and smooth muscle that induces motility of epithelial cells. HGF is also referred to in the literature as Scatter Factor (SF).

HGF is a multifunctional heterodimeric polypeptide produced predominantly by mesenchymal cells, which acts as a ligand for the Met receptor tyrosine kinase (Met). The human Met receptor is also known as "c-met." Signaling through the Met receptor tyrosine kinase-HGF (Met-HGF) pathway has been shown to lead to an array of cellular responses, including, but not limited to proliferation (mitosis), scattering (motility), stimulation of cell movement through a matrix (invasion), and branching morphogenesis. In vivo, the Met-HGF signaling pathway (Met-HGF) plays a role in, e.g., neural induction, liver regeneration, wound healing, angiogenesis, growth, invasion, morphologic differentiation, and normal embryological development. In addition to these functions, the Met-HGF pair may also play a role in human cancers. Aberrant Met-HGF signaling has been shown to be involved in tumorigenesis, particularly in the development of the invasive and metastatic phenotypes. Certain pathogens, such as malaria, have also been found to exploit aberrant Met-HGF signaling. See Carrolo et al., Nat Med. 2003 9(11):1363-9 (Oct. 12, 2003), the contents of which are hereby incorporated by reference for any purpose.

Further, some groups have reported that HGF may play a role in angiogenesis and in angiogenesis-mediated disease, such as proliferative diabetic reinopathy or macular degeneration. See e.g., Grant, D. S. et al., Proc. Nat. Acad. Sci. U.S.A. 90(5) 1937-41 (1993); Bussolino et al., J. Cell Biol., 119(3):629-641 (1992); Montesano et al., Cell, 67:901-908 (1991); Canon et al., Br. J. Ophthalmol. 84(7):732-5 (2000). HGF may also play a role in apoptosis or programmed cell death. Tumors can arise when normal regulatory mechanisms fail to maintain a balance between proliferation and apoptosis, such that cells accumulate in excess numbers. HGF can effect both proliferation and apoptosis, depending on the biological context.

Because HGF is involved in many physiological processes, in certain instances, it may be useful to have molecules that can regulate its activity. For example, in certain instances, such molecules may be useful for treating a variety of different types of cancer.

SUMMARY OF THE INVENTION

In certain embodiments, the invention provides an isolated polypeptide comprising at least one complementarity determining region (CDR) selected from CDR1a, CDR2a, and CDR3a wherein CDR1a comprises the amino acid sequence a b c d e f g h i j k l m n o p q, wherein amino acid a is selected from lysine, arginine, or glutamine; amino acid b is selected from serine or alanine; amino acid c is serine, amino acid d is glutamine; amino acid e is selected from serine, glycine, or aspartic acid; amino acid f is selected from valine or isoleucine or is not present; amino acid g is selected from leucine or phenylalanine or is not present; amino acid h is selected from phenylalanine or tyrosine or is not present; amino acid i is serine or not present; amino acid j is serine or not present; amino acid k is selected from asparagine, threonine, or not present; amino acid l is selected from asparagine, isoleucine, or valine; amino acid m is selected from lysine, arginine, serine, asparagine, or aspartic acid; amino acid n is selected from asparagine or serine; amino acid o is selected from tyrosine, aspartic acid, tryptophan, or asparagine; amino acid p is leucine; and amino acid q is selected from alanine, glycine, or asparagine;

wherein CDR2a comprises the amino acid sequence r s t u v w x, wherein amino acid r is selected from tryptophan, alanine, valine, glutamic acid, or glycine; amino acid s is alanine, amino acid t is serine, amino acid u is selected from threonine, serine, or aspartic acid; amino acid v is selected from arginine or leucine; amino acid w is selected from glutamic acid, glutamine, or alanine; and amino acid x is selected from serine, asparagine, or threonine;

wherein CDR3a comprises the amino acid sequence y z a' b' c' d' e' f' g' h', wherein amino acid y is selected from glutamine or leucine; amino acid z is selected from glutamine, asparagine, or arginine; amino acid a' is selected from tyrosine, histidine, alanine, or serine; amino acid b' is selected from phenylalanine, tyrosine, aspartic acid, asparagine, or isoleucine; amino acid c' is selected from serine, glycine, or asparagine; amino acid d' is selected from proline, tyrosine, threonine, phenylalanine, aspartic acid, leucine, or tryptophan; amino acid e' is proline; amino acid f' is proline or is not present; amino acid g' is tryptophan, leucine, proline, tyrosine, or isoleucine; and amino acid h' is threonine or asparagine; and wherein the polypeptide, in association with an antibody heavy chain, is capable of binding hepatocyte growth factor (HGF).

In certain embodiments, the invention provides an isolated polypeptide comprising at least one complementarity determining region (CDR) selected from CDR1b, CDR2b, and CDR3b wherein CDR1b comprises the amino acid sequence a b c d e f g, wherein amino acid a is serine or is not present; amino acid b is selected from aspartic acid or glycine, or is not present; amino acid c is selected from aspartic acid, glycine, serine, valine, threonine, or isoleucine; amino acid d is tyrosine; amino acid e is selected from tyrosine or glycine; amino acid f is selected from isoleucine, methionine, or tryptophan; and amino acid g is selected from histidine, asparagine, or serine;

wherein CDR2b comprises the amino acid sequence h i j k l m n o p q r s t u v w x, wherein amino acid h is selected from tryptophan, tyrosine, valine, asparagine, or glutamic acid; amino acid i is selected from isoleucine, phenylalanine, or valine; amino acid j is selected from asparagine, serine, tryptophan, or tyrosine; amino acid k is selected from proline, serine, tyrosine, or histidine; amino acid l is selected from asparagine, serine, or aspartic acid; amino acid m is selected from serine or glycine; amino acid n is selected from glycine or serine, or is not present; amino acid o is selected from glycine, threonine, aspartic acid, serine, isoleucine, or asparagine; amino acid p is selected from threonine, isoleucine, or lysine; amino acid q is selected from asparagine or tyrosine; amino acid r is selected from tyrosine or histidine; amino acid s is selected from alanine or asparagine; amino acid t is selected from glutamine, aspartic acid, or proline; amino acid u is selected from lysine or serine; amino acid v is selected from phenylalanine, valine, or leucine; amino acid w is selected from glutamine or lysine, and amino acid x is selected from glycine or serine;

wherein CDR3b comprises the amino acid sequence y z a' b' c' d' e' f' g' h' i' j' k' l' m' n' o' p' q' r', wherein amino acid y is selected from glutamic acid, aspartic acid, serine, or glycine, or is not present; amino acid z is selected from leucine, glutamic acid, aspartic acid, histidine, proline, or glycine, or is not present; amino acid a' is selected from glutamic acid, tyrosine, or leucine, or is not present; amino acid b' is selected from leucine, asparagine, glycine, histidine, tyrosine, or tryptophan, or is not present; amino acid c' is selected from arginine, serine, glutamic acid, tyrosine, glycine, or phenylalanine, or is not present; amino acid d' is glycine or is not present; amino acid e' is selected from tryptophan or tyrosine, or is not present; amino acid f' is aspartic acid or is not present; amino acid g' is selected from serine or arginine, or is not present; amino acid h' is serine or is not present; amino acid i' is selected from glycine or tyrosine, or is not present; amino acid j' is selected from tyrosine, glutamic acid, or aspartic acid, or is not present; amino acid k' is selected from tyrosine, phenylalanine, or aspartic acid, or is not present; amino acid l' is selected from tyrosine, aspartic acid, histidine, or tryptophan, or is not present; amino acid m' is selected from tyrosine, glycine, aspartic acid, proline, or serine, or is not present; amino acid n' is selected from glycine, valine, tyrosine, or aspartic acid, or is not present; amino acid o' is selected from leucine, alanine, glycine, or tyrosine, or is not present; amino acid p' is selected from methionine, phenylalanine, or tyrosine; amino acid q' is aspartic acid, and amino acid r' is selected from valine, tyrosine, isoleucine, or proline; and wherein the polypeptide, in association with an antibody light chain is capable of binding HGF.

In certain embodiments, the invention provides an isolated specific binding agent, wherein the specific binding agent comprises:

(i) a first polypeptide comprising at least one complementarity determining region (CDR) selected from CDR1a, CDR2a, and CDR3a wherein CDR1a comprises the amino acid sequence a b c d e f g h i j k l m n o p q, wherein amino acid a is selected from lysine, arginine, or glutamine; amino acid b is selected from serine or alanine; amino acid c is serine, amino acid d is glutamine; amino acid e is selected from serine, glycine, or aspartic acid; amino acid f is selected from valine or isoleucine or is not present; amino acid g is selected from leucine or phenylalanine or is not present; amino acid h is selected from phenylalanine or tyrosine or is not present; amino acid i is serine or not present; amino acid j is serine or not present; amino acid k is selected from asparagine, threonine, or not present; amino acid l is selected from asparagine, isoleucine, or valine; amino acid m is selected from lysine, arginine, serine, asparagine, or aspartic acid; amino acid n is selected from asparagine or serine; amino acid o is selected from tyrosine, aspartic acid, tryptophan, or asparagine; amino acid p is leucine; and amino acid q is selected from alanine, glycine, or asparagine;

wherein CDR2a comprises the amino acid sequence r s t u v w x, wherein amino acid r is selected from tryptophan, alanine, valine, glutamic acid, or glycine; amino acid s is alanine, amino acid t is serine, amino acid u is selected from threonine, serine, or aspartic acid; amino acid v is selected from arginine or leucine; amino acid w is selected from glutamic acid, glutamine, or alanine; and amino acid x is selected from serine, asparagine, or threonine;

wherein CDR3a comprises the amino acid sequence y z a' b' c' d' e' f g' h', wherein amino acid y is selected from glutamine or leucine; amino acid z is selected from glutamine, asparagine, or arginine; amino acid a' is selected from tyrosine, histidine, alanine, or serine; amino acid b' is selected from phenylalanine, tyrosine, aspartic acid, asparagine, or isoleucine; amino acid c' is selected from serine, glycine, or asparagine; amino acid d' is selected from proline, tyrosine, threonine, phenylalanine, aspartic acid, leucine, or tryptophan; amino acid e' is proline; amino acid f' is proline or is not present; amino acid g' is tryptophan, leucine, proline, tyrosine, or isoleucine; and amino acid h' is threonine or asparagine; and wherein the first polypeptide, in association with an antibody heavy chain, is capable of binding hepatocyte growth factor (HGF); and (ii) a second polypeptide comprising at least one complementarity determining region (CDR) selected from CDR1b, CDR2b, or CDR3b wherein CDR1b comprises the amino acid sequence a b c d e f g, wherein amino acid a is serine or is not present; amino acid b is selected from aspartic acid or glycine, or is not present; amino acid c is selected from aspartic acid, glycine, serine, valine, threonine, or isoleucine; amino acid d is tyrosine; amino acid e is selected from tyrosine or glycine; amino acid f is selected from isoleucine, methionine, or tryptophan; and amino acid g is selected from histidine, asparagine, or serine;

wherein CDR2b comprises the amino acid sequence h i j k l m n o p q r s t u v w x, wherein amino acid h is selected from tryptophan, tyrosine, valine, asparagine, or glutamic acid; amino acid i is selected from isoleucine, phenylalanine, or valine; amino acid j is selected from asparagine, serine, tryptophan, or tyrosine; amino acid k is selected from proline, serine, tyrosine, or histidine; amino acid l is selected from asparagine, serine, or aspartic acid; amino acid m is selected from serine or glycine; amino acid n is selected from glycine or serine, or is not present; amino acid o is selected from glycine, threonine, aspartic acid, serine, isoleucine, or asparagine; amino acid p is selected from threonine, isoleucine, or lysine; amino acid q is selected from asparagine or tyrosine; amino acid r is selected from tyrosine or histidine; amino acid s is selected from alanine or asparagine; amino acid t is selected from glutamine, aspartic acid, or proline; amino acid u is selected from lysine or serine; amino acid v is selected from phenylalanine, valine, or leucine; amino acid w is selected from glutamine or lysine, and amino acid x is selected from glycine or serine;

wherein CDR3b comprises the amino acid sequence y z a' b' c' d' e' f' g' h' i' j' k' l' n' o' p' q' r', wherein amino acid y is selected from glutamic acid, aspartic acid, serine, or glycine, or is not present; amino acid z is selected from leucine, glutamic acid, aspartic acid, histidine, proline, or glycine, or is not present; amino acid a' is selected from glutamic acid, tyrosine, or leucine, or is not present; amino acid b' is selected from leucine, asparagine, glycine, histidine, tyrosine, or tryptophan, or is not present; amino acid c' is selected from arginine, serine, glutamic acid, tyrosine, glycine, or phenylalanine, or is not present; amino acid d' is glycine or is not present; amino acid e' is selected from tryptophan or tyrosine, or is not present; amino acid f' is aspartic acid or is not present; amino acid g' is selected from serine or arginine, or is not present; amino acid h' is serine or is not present; amino acid I' is selected from glycine or tyrosine, or is not present; amino acid j' is selected from tyrosine, glutamic acid, or aspartic acid, or is not present; amino acid k' is selected from tyrosine, phenylalanine, or aspartic acid, or is not present; amino acid l' is selected from tyrosine, aspartic acid, histidine, or tryptophan, or is not present; amino acid m' is selected from tyrosine, glycine, aspartic acid, proline, or serine, or is not present; amino acid n' is selected from glycine, valine, tyrosine, or aspartic acid, or is not present; amino acid o' is selected from leucine, alanine, glycine, or tyrosine, or is not present; amino acid p' is selected from methionine, phenylalanine, or tyrosine; amino acid q' is aspartic acid, and amino acid r' is selected from valine, tyrosine, isoleucine, or proline; and wherein the second polypeptide, in association with an antibody light chain, is capable of binding HGF.

In certain embodiments, the invention provides an isolated polypeptide comprising at least one amino acid sequence selected from SEQ ID NO: 24, 26, 28, 30, 32, 34, 36, 38, 40, and 42.

In certain embodiments, the invention provides an isolated polypeptide comprising at least one amino acid sequence selected from SEQ ID NO: 25, 27, 29, 31, 33, 35, 37, 39, 41, and 43.

In certain embodiments, the invention provides an isolated nucleic acid molecule comprising at least one nucleotide sequence selected from SEQ ID NO: 1, 3, 5, 7, 9, 11, 13, 15, 17, and 19.

In certain embodiments, the invention provides an isolated nucleic acid molecule comprising at least one nucleotide sequence selected from SEQ ID NO: 2, 4, 6, 8, 10, 12, 14, 16, 18, and 20.

In certain embodiments, the invention provides an isolated nucleic acid molecule that encodes a polypeptide comprising at least one complementarity determining region (CDR) selected from CDR1a, CDR2a, and CDR3a wherein CDR1a comprises the amino acid sequence a b c d e f g h i j k l m n o p q, wherein amino acid a is selected from lysine, arginine, or glutamine; amino acid b is selected from serine or alanine; amino acid c is serine, amino acid d is glutamine; amino acid e is selected from serine, glycine, or aspartic acid; amino acid f is selected from valine or isoleucine or is not present; amino acid g is selected from leucine or phenylalanine or is not present; amino acid h is selected from phenylalanine or tyrosine or is not present; amino acid i is serine or not present; amino acid j is serine or not present; amino acid k is selected from asparagine, threonine, or not present; amino acid l is selected from asparagine, isoleucine, or valine; amino acid m is selected from lysine, arginine, serine, asparagine, or aspartic acid; amino acid n is selected from asparagine or serine; amino acid o is selected from tyrosine, aspartic acid, tryptophan, or asparagine; amino acid p is leucine; and amino acid q is selected from alanine, glycine, or asparagine;

wherein CDR2a comprises the amino acid sequence r s t u v w x, wherein amino acid r is selected from tryptophan, alanine, valine, glutamic acid, or glycine; amino acid s is alanine, amino acid t is serine, amino acid u is selected from threonine, serine, or aspartic acid; amino acid v is selected from arginine or leucine; amino acid w is selected from glutamic acid, glutamine, or alanine; and amino acid x is selected from serine, asparagine, or threonine;

wherein CDR3a comprises the amino acid sequence y z a' b' c' d' e' f g' h', wherein amino acid y is selected from glutamine or leucine; amino acid z is selected from glutamine, asparagine, or arginine; amino acid a' is selected from tyrosine, histidine, alanine, or serine; amino acid b' is selected from phenylalanine, tyrosine, aspartic acid, asparagine, or isoleucine; amino acid c' is selected from serine, glycine, or asparagine; amino acid d' is selected from proline, tyrosine, threonine, phenylalanine, aspartic acid, leucine, or tryptophan; amino acid e' is proline; amino acid f' is proline or is not present; amino acid g' is tryptophan, leucine, proline, tyrosine, or isoleucine; and amino acid h' is threonine or asparagine; and wherein the polypeptide, in association with an antibody heavy chain, is capable of binding hepatocyte growth factor (HGF).

In certain embodiments, the invention provides an isolated nucleic acid molecule that encodes a polypeptide comprising at least one complementarity determining region (CDR) selected from CDR1b, CDR2b, and CDR3b wherein CDR1b comprises the amino acid sequence a b c d e f g, wherein amino acid a is serine or is not present; amino acid b is selected from aspartic acid or glycine, or is not present; amino acid c is selected from aspartic acid, glycine, serine, valine, threonine, or isoleucine; amino acid d is tyrosine; amino acid e is selected from tyrosine or glycine; amino acid f is selected from isoleucine, methionine, or tryptophan; and amino acid g is selected from histidine, asparagine, or serine;

wherein CDR2b comprises the amino acid sequence h i j k l m n o p q r s t u v w x, wherein amino acid h is selected from tryptophan, tyrosine, valine, asparagine, or glutamic acid; amino acid i is selected from isoleucine, phenylalanine, or valine; amino acid j is selected from asparagine, serine, tryptophan, or tyrosine; amino acid k is selected from proline, serine, tyrosine, or histidine; amino acid l is selected from asparagine, serine, or aspartic acid; amino acid m is selected from serine or glycine; amino acid n is selected from glycine or serine, or is not present; amino acid o is selected from glycine, threonine, aspartic acid, serine, isoleucine, or asparagine; amino acid p is selected from threonine, isoleucine, or lysine; amino acid q is selected from asparagine or tyrosine; amino acid r is selected from tyrosine or histidine; amino acid s is selected from alanine or asparagine; amino acid t is selected from glutamine, aspartic acid, or proline; amino acid u is selected from lysine or serine; amino acid v is selected from phenylalanine, valine, or leucine; amino acid w is selected from glutamine or lysine, and amino acid x is selected from glycine or serine;

wherein CDR3b comprises the amino acid sequence y z a' b' c' d' e' f' g' h' i' j' k' l' m' n' o' p' q' r', wherein amino acid y is selected from glutamic acid, aspartic acid, serine, or glycine, or is not present; amino acid z is selected from leucine, glutamic acid, aspartic acid, histidine, proline, or glycine, or is not present; amino acid a' is selected from glutamic acid, tyrosine, or leucine, or is not present; amino acid b' is selected from leucine, asparagine, glycine, histidine, tyrosine, or tryptophan, or is not present; amino acid c' is selected from arginine, serine, glutamic acid, tyrosine, glycine, or phenylalanine, or is not present; amino acid d' is glycine or is not present; amino acid e' is selected from tryptophan or tyrosine, or is not present; amino acid f' is aspartic acid or is not present; amino acid g' is selected from serine or arginine, or is not present; amino acid h' is serine or is not present; amino acid i' is selected from glycine or tyrosine, or is not present; amino acid j' is selected from tyrosine, glutamic acid, or aspartic acid, or is not present; amino acid k' is selected from tyrosine, phenylalanine, or aspartic acid, or is not present; amino acid l' is selected from tyrosine, aspartic acid, histidine, or tryptophan, or is not present; amino acid m' is selected from tyrosine, glycine, aspartic acid, proline, or serine, or is not present; amino acid n' is selected from glycine, valine, tyrosine, or aspartic acid, or is not present; amino acid o' is selected from leucine, alanine, glycine, or tyrosine, or is not present; amino acid p' is selected from methionine, phenylalanine, or tyrosine; amino acid q' is aspartic acid, and amino acid r' is selected from valine, tyrosine, isoleucine, or proline; and wherein the polypeptide, in association with an antibody light chain, is capable of binding HGF.

In certain embodiments, the invention provides an isolated cell line that produces an antibody selected from 1.24.1, 1.29.1, 1.60.1, 1.61.3, 1.74.3, 1.75.1, 2.4.4, 2.12.1, 2.40.1, and 3.10.1.

In certain embodiments, the invention provides a method of inhibiting binding of HGF to Met comprising administering a specific binding agent to HGF.

In certain embodiments, the invention provides a polypeptide comprising at least one amino acid sequence selected from SEQ ID NO: 164 and 165.

In certain embodiments, the invention provides a polypeptide consisting essentially of at least one amino acid sequence selected from SEQ ID NO: 164 and 165.

In certain embodiments, the invention provides a specific binding agent which is capable of binding at least one amino acid sequence selected from SEQ ID NO: 164 and 165.

In certain embodiments, the invention provides an antibody or antigen binding domain which is capable of binding at least one amino acid sequence selected from SEQ ID NO: 164 and 165.

In certain embodiments, the invention provides a method of obtaining an antibody capable of binding hepatocyte growth factor (HGF) comprising administering at least one polypeptide selected from SEQ ID NO: 164 and 165 to an animal and obtaining an antibody capable of binding HGF from the animal.

In certain embodiments, the invention provides a method of decreasing or preventing binding of a specific binding agent to hepatocyte growth factor (HGF) by administering a polypeptide comprising at least one amino acid sequence selected from SEQ ID NO: 164 and 165.

In certain embodiments, the invention provides a method of decreasing or preventing binding of a specific binding agent to hepatocyte growth factor (HGF) by administering a polypeptide consisting of at least one amino acid sequence selected from SEQ ID NO: 164 and 165.

Other embodiments of this invention will be readily apparent from the disclosure provided herewith.

BRIEF DESCRIPTION OF THE FIGURES

FIG. 1A shows a dendrogram of kappa light chains of certain antibodies to HGF showing their germ line relationships. Germ line gene identifications are indicated to the right of the antibody designation. FIG. 1B shows an amino acid sequence alignment of kappa light chain variable regions of certain antibodies to HGF. Germ line gene identifications are indicated at the left. The CDR regions are indicated as bold lines above the aligned sequences.

FIG. 2A shows a dendrogram of gamma heavy chains of certain antibodies to HGF showing their germ line relationships. Germ line gene identifications are indicated to the right of the antibody designation. FIG. 2B shows an amino acid sequence alignment of gamma heavy chain variable regions of certain antibodies to HGF. Germ line gene identifications are indicated at the left. The CDR regions are indicated as bold lines above the aligned sequences.

FIGS. 3A to 3E show DNA sequences encoding variable regions from both the light and the heavy chains of certain antibodies to HGF. Antibody name, germ line designation, and sequence ID are indicated for each sequence. The natural signal peptide sequence is underlined. The DNA sequences of the human Kappa, IgG1, and IgG2 constant regions are also shown.

FIGS. 4A to 4C show amino acid sequences of variable regions of the light and the heavy chains of certain antibodies to HGF. Antibody name, germ-line designation, and sequence ID are indicated for each sequence. The natural signal peptide sequence is underlined. The amino acid sequences of the human Kappa, IgG1, and IgG2 constant regions are also shown.

FIG. 5 shows amino acid sequences of complementarity determining regions (CDRs) of the light and heavy chains of certain antibodies to HGF. Antibody name and sequence ID are indicated for each sequence. FIG. 5A shows amino acid sequences of CDRs of the light chain of certain antibodies to HGF. FIG. 5B show amino acid sequence of CDRs of the heavy chain of certain antibodies to HGF.

FIG. 6 shows results of $K_D$ determination of certain antibodies to HGF, discussed in Example 8. FIG. 6A shows data from a kinetic method. FIG. 6B shows data from an equilibrium/solution method.

FIGS. 7A and 7B show autoradiograms from Western blots discussed in Example 8 testing the ability of certain antibodies to bind to human HGF and to mouse HGF. Panels on the left (lanes 1-4) show autoradiograms from experiments performed under non-reducing conditions. Panels on the right (lanes 5-8) show autoradiograms from experiments performed under reducing conditions.

FIGS. 8A and 8B show Fluorescence Activated Cell Sorter (FACS) data from experiments discussed in Example 8, assessing binding of certain antibodies to certain targets. The top of FIG. 8A shows FACS data from control samples lacking a specific binding agent. Panels 1 and 2 (from the left) show data from control samples lacking target incubated with FITC and PE, respectively. Panels 3 and 4 show data from control samples comprising FITC and PE labeled d5 HGF, respectively, but lacking a specific binding agent. Panels below the solid line on FIG. 8A and panels on FIG. 8B show FACS data from experiments testing five antibodies to HGF. For each antibody, the first panel (from the left) shows data from control samples lacking target, the second through fourth panels show data from experiments in which the target was: human HGF, mouse HGF, and human d5 HGF, respectively.

FIG. 9A shows a schematic of a plasmid encoding avidin adjacent to a multiple cloning site which was used to generate fusion proteins comprising avidin and target protein as is discussed in Example 8. FIG. 9B shows the sequence of chicken avidin.

FIGS. 10A and 10B show schematic representations of certain fusion proteins and results from binding assays, discussed in Examples 8C and 8D, using those fusion proteins. FIG. 10C shows a schematic representation of certain fusion proteins having point mutations, insertions, or deletions. FIG. 10D shows the amino acid sequences of human and mouse HGF in the region of amino acids 451-731 (SEQ ID NO. 120 and 121, respectively), with the corresponding consensus sequence indicated (SEQ ID NO. 122).

FIG. 11C shows the amino acid sequences of peptides protected from proteolytic digestion by binding to antibody 2.12.1 in that work.

FIG. 13 shows IC50 data from neutralization assays discussed in Example 9.

FIG. 14 shows data from neutralization assays in PC3 cells discussed in Example 10.

FIG. 15 shows data from inhibition assays in U-87 cells discussed in Example 10.

Figure 1A:
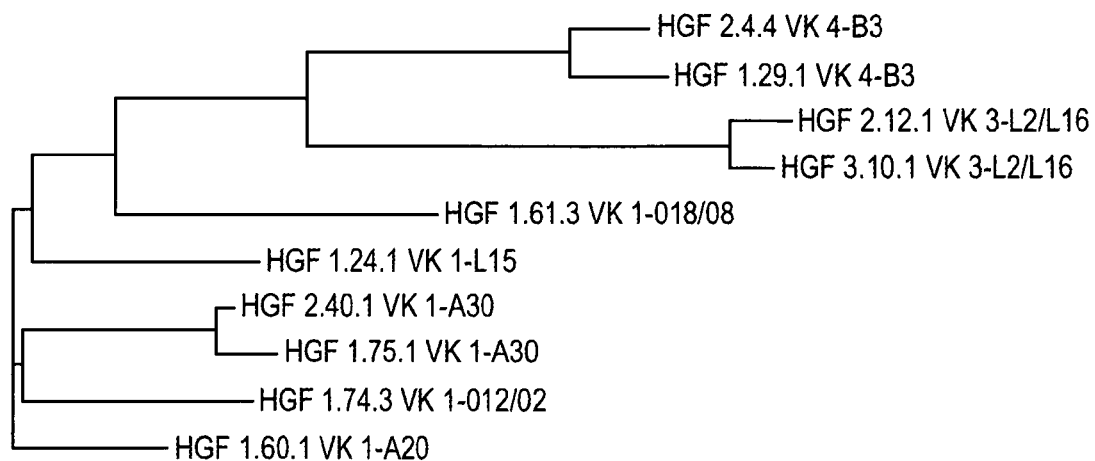

FIG. 16 shows results from experiments discussed in Example 11 assessing the effect of certain antibodies to HGF on U-87 MG xenograft tumors in mice. FIG. 16A shows dose-response data for antibody 2.4.4 on U-87 MG xenograft tumor growth in the minimal residual disease model. FIG. 16B shows the dose-response data for antibody 2.4.4 on U-87 xenograft tumor growth in an established disease model. FIGS. 16C, 16D, 16E, and 16F show data from head-to-head experiments testing antibodies to HGF in a U-87 minimal residual disease model (16C and 16D) or in a U-87 established disease model (16E and 16F).

DETAILED DESCRIPTION OF CERTAIN EXEMPLARY EMBODIMENTS

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "hepatocyte growth factor" or "HGF" refers to a polypeptide as set forth in Nakamura et al., Nature 342: 440-443 (1989) or fragments thereof, as well as related polypeptides, which include, but are not limited to, allelic variants, splice variants, derivative variants, substitution variants, deletion variants, and/or insertion variants, fusion polypeptides, and interspecies homologs. In certain embodiments, an HGF polypeptide includes terminal residues, such as, but not limited to, leader sequence residues, targeting residues, amino terminal methionine residues, lysine residues, tag residues and/or fusion protein residues.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region.

The term "specific binding agent to HGF" refers to a specific binding agent that specifically binds any portion of HGF. In certain embodiments, a specific binding agent to HGF is an antibody to HGF. In certain embodiments, a specific binding agent is an antigen binding region.

The term "polyclonal antibody" refers to a heterogeneous mixture of antibodies that bind to different epitopes of the same antigen.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

The term "chimeric antibody" refers to an antibody in which a portion of the antibody is homologous to a sequence of a particular species or a particular antibody class, while another portion of the antibody is homologous to a sequence of a different species or antibody class. See, e.g., U.S. Pat. No. 4,816,567 and Morrison et al., *Proc Natl Acad Sci* (USA), 81:6851-6855 (1985).

The term "CDR grafted antibody" refers to an antibody in which the CDR from one antibody is inserted into the framework of another antibody. In certain embodiments, the antibody from which the CDR is derived and the antibody from which the framework is derived are of different species. In certain embodiments, the antibody from which the CDR is derived and the antibody from which the framework is derived are of different isotypes.

The term "multi-specific antibody" refers to an antibody wherein two or more variable regions bind to different epitopes. The epitopes may be on the same or different targets. In certain embodiments, a multi-specific antibody is a "bi-specific antibody," which recognizes two different epitopes on the same or different antigens.

The term "catalytic antibody" refers to an antibody in which one or more catalytic moieties is attached. In certain embodiments, a catalytic antibody is a cytotoxic antibody, which comprise a cytotoxic moiety.

The term "humanized antibody" refers to an antibody in which all or part of an antibody framework region is derived from a human, but all or part of one or more CDR regions is derived from another species, for example a mouse.

The term "fully human antibody" refers to an antibody in which both the CDR and the framework comprise substantially human sequences. In certain embodiments, fully human antibodies are produced in non-human mammals, including, but not limited to, mice, rats, and lagomorphs. In certain embodiments, fully human antibodies are produced in hybridoma cells. In certain embodiments, fully human antibodies are produced recombinantly.

The term "anti-idiotype antibody" refers to an antibody that specifically binds to another antibody.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method.

The term "epitope" refers to a portion of a molecule capable of being bound by a specific binding agent. In certain embodiments, epitopes typically comprise chemically active surface groupings of molecules, such as, for example, amino acids or carbohydrate side chains, and have specific three-dimensional structural characteristics as well as specific charge characteristics. Epitopes may be contiguous or non-contiguous. In certain embodiments, epitopes may be mimetic in that they comprise a three dimensional structure that is similar to an epitope used to generate the antibody, yet comprise none or only some of the amino acid residues found in that epitope used to generate the antibody.

The term "inhibiting and/or neutralizing epitope" refers to an epitope, which when bound by a specific binding agent results in a decrease in a biological activity in vivo, in vitro, and/or in situ. In certain embodiments, a neutralizing epitope is located on or is associated with a biologically active region of a target.

The term "activating epitope" refers to an epitope, which when bound by a specific binding agent results in activation or maintenance of a biological activity in vivo, in vitro, and/or in situ. In certain embodiments, an activating epitope is located on or is associated with a biologically active region of a target.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The term "isolated protein" referred to herein means a protein encoded by cDNA, recombinant RNA, or synthetic origin or some combination thereof, which (1) is free of at least some proteins with which it would normally be found, (2) is essentially free of other proteins from the same source, e.g., from the same species, (3) is expressed by a cell from a different species, or (4) does not occur in nature.

The term "polypeptide" is used herein as a generic term to refer to native proteins, or modifications of such proteins that have deletions, additions, and/or substitutions of one or more amino acids of the native sequence. In certain embodiments, polypeptide have deletions, additions, and/or substitutions of at least one but not more than 50, 30, 20, 15, 10, 8, 5, or 3 amino acids of the native sequence.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to components that are in a relationship permitting them to function in their intended manner. For example, a control sequence "operably linked" to a coding sequence is ligated in such a way that expression of the coding sequence is achieved under conditions compatible with the control sequences.

The term "control sequence" as used herein refers to polynucleotide sequences which may effect the expression and processing of coding sequences to which they are ligated. The nature of such control sequences may differ depending upon the host organism. According to certain embodiments, control sequences for prokaryotes may include promoter, ribosomal binding site, and transcription termination sequence. According to certain embodiments, control sequences for eukaryotes may include promoters, one or more enhancers and transcription termination sequence. In certain embodiments, "control sequences" can include leader sequences and/or fusion partner sequences.

The term "polynucleotide" as referred to herein means a polymeric form of nucleotides of at least 10 bases in length. In certain embodiments, the bases may be ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset generally comprising a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides may be sense or antisense oligonucleotides.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. Nucl. Acids Res. 14:9081 (1986); Stec et al.

J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990), the disclosures of which are hereby incorporated by reference for any purpose. In certain embodiments, an oligonucleotide can include a label for detection.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Certain methods to determine identity are designed to give the largest match between the sequences tested. Methods to determine identity are described in publicly available computer programs. Computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3)(1978) for the PAM 250 comparison matrix; Henikoff et al., *Proc. Natl. Acad. Sci USA*, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, a specific binding agent comprises a heavy chain comprising a variable region comprising an amino acid sequence at least 90% identical to an amino acid sequence selected from SEQ ID NO: 25, 27, 29, 31, 33, 35, 37, 39, 41, and 43. In certain embodiments, a specific binding agent comprises a heavy chain comprising a variable region comprising an amino acid sequence at least 95% identical to an amino acid sequence selected from SEQ ID NO: 25, 27, 29, 31, 33, 35, 37, 39, 41, and 43. In certain embodiments, a specific binding agent comprises a heavy chain comprising a variable region comprising an amino acid sequence at least 99% identical to an amino acid sequence selected from SEQ ID NO: 25, 27, 29, 31, 33, 35, 37, 39, 41, and 43.

In certain embodiments, a specific binding agent comprises a light chain comprising a variable region comprising an amino acid sequence at least 90% identical to an amino acid sequence selected from SEQ ID NO: 24, 26, 28, 30, 32, 34, 36, 38, 40, and 42. In certain embodiments, a specific binding agent comprises a light chain comprising a variable region comprising an amino acid sequence at least 95% identical to an amino acid sequence selected from SEQ ID NO: 24, 26, 28, 30, 32, 34, 36, 38, 40, and 42. In certain embodiments, a specific binding agent comprises a light chain comprising a variable region comprising an amino acid sequence at least 99% identical to an amino acid sequence selected from SEQ ID NO: 24, 26, 28, 30, 32, 34, 36, 38, 40, and 42.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., Science, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, specific binding agent variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiocochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The term "derivative" refers to a molecule that includes a chemical modification other than an insertion, deletion, or substitution of amino acids. In certain embodiments, derivatives comprise covalent modifications, including, but not limited to, chemical bonding with polymers, lipids, or other organic or inorganic moieties. In certain embodiments, a chemically modified specific binding agent may have greater circulating half-life than a specific binding agent that is not chemically modified. In certain embodiments, a chemically modified specific binding agent may have improved targeting capacity for desired cells, tissues, and/or organs. In certain embodiments, a derivative specific binding agent is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative specific binding agent comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for a specific binding agent. In certain embodiments, PEG is used to improve the therapeutic capacity for a humanized antibody. Certain such methods are discussed, for example, in U.S. Pat. No. 6,133,426, which is hereby incorporated by reference for any purpose.

The term "polypeptide fragment" as used herein refers to a polypeptide that has an amino-terminal and/or carboxy-terminal deletion. In certain embodiments, fragments are at least 5 to 478 amino acids long. It will be appreciated that in certain embodiments, fragments are at least 5, 6, 8, 10, 14, 20, 50, 70, 100, 150, 200, 250, 300, 350, 400, or 450 amino acids long.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987), which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference for any purpose); for example, by adding internal cysteine residues capable of forming intramolecular disulfide bridges which cyclize the peptide.

The terms "antibody" or "antibody peptide(s)" refer to an intact antibody, or a binding fragment thereof that competes with the intact antibody for specific binding. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')2, Fv, and single-chain antibodies.

The term "heavy chain" includes any polypeptide having sufficient variable region sequence to confer specificity for a target. The term "light chain" includes any polypeptide having sufficient variable region sequence to confer specificity for a target. A full-length heavy chain includes a variable region domain, V$_H$, and three constant region domains, C$_H$1, C$_H$2, and C$_H$3. The V$_H$ domain is at the amino-terminus of the polypeptide, and the C$_H$3 domain is at the carboxy-terminus. The term "heavy chain", as used herein, encompasses a full-length heavy chain and fragments thereof. A full-length light chain includes a variable region domain, V$_L$, and a constant region domain, C$_L$. Like the heavy chain, the variable region domain of the light chain is at the amino-terminus of the polypeptide. The term "light chain", as used herein, encompasses a full-length light chain and fragments thereof. A Fab fragment is comprised of one light chain and the C$_H$1 and variable regions of one heavy chain. The heavy chain of a Fab molecule cannot form a disulfide bond with another heavy chain molecule. A Fab' fragment contains one light chain and one heavy chain that contains more of the constant region, between the C$_H$1 and C$_H$2 domains, such that an interchain disulfide bond can be formed between two heavy chains to form a F(ab')2 molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain which forms an antigen-binding region. Single chain antibodies are discussed in detail in e.g., WO 88/01649 and U.S. Pat. Nos. 4,946,778 and 5,260,203.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target The term "immunologically functional immunoglobulin fragment" refers to a polypeptide fragment comprising at least the variable domains of an immunoglobulin heavy chain and an immunoglobulin light chain. In certain embodiments, an immunologically functional immunoglobulin fragment is capable of binding to a ligand, preventing binding of the ligand to its receptor, and thereby interrupting a biological response resulting from ligand binding to the receptor. In certain embodiments, an immunologically functional immunoglobulin fragment is capable of binding to a receptor, preventing binding of the ligand to its receptor, and thereby interrupting a biological response resulting from ligand binding to the receptor. In certain embodiments, an immunologically functional immunoglobulin fragment is capable of binding a receptor and activating or inactivating that receptor.

A bivalent antibody other than a "multispecific" or "multifunctional" antibody, in certain embodiments, typically is understood to have each of its binding sites identical.

A specific binding agent substantially inhibits adhesion of a ligand to a receptor when an excess of specific binding agent reduces the quantity of receptor bound to counterreceptor by at least about 20%, 40%, 60%, 80%, 85%, or more (as measured in an in vitro competitive binding assay).

The term "target" refers to a molecule or a portion of a molecule capable of being bound by a specific binding agent. In certain embodiments, a target may have one or more epitopes. In certain embodiments, a target is an antigen.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the dissociation constant is ≤1 µM, in certain embodiments, when the dissociation constant is ≤100 nM, and in certain embodiments, when the dissociation constant is ≤10 n M.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or calorimetric methods). In certain embodiments, the label or marker can also be therapeutic. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 13 I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "cancer" includes, but is not limited to solid tumors and hematologic malignancies. Exemplary cancers include, but are not limited to, breast cancer, colorectal cancer, gastric carcinoma, glioma, head and neck squamous cell carcinoma, hereditary and sporadic papillary renal carcinoma, leukemia, lymphoma, Li-Fraumeni syndrome, malignant pleural mesothelioma, melanoma, multiple myeloma, non-small cell lung carcinoma, osteosarcoma, ovarian cancer, pancreatic cancer, prostate cancer, small cell lung cancer, synovial sarcoma, thyroid carcinoma, and transitional cell carcinoma of urinary bladder.

The term "HGF activity" includes any biological effect of HGF. In certain embodiments, HGF activity is Met-HGF activity. In certain embodiments, HGF activity is Met independent HGF activity.

The term "Met-HGF signaling" includes the interaction of HGF with a Met receptor.

The term "Met-HGF activity" includes any biological activity resulting from Met-HGF signaling. Exemplary activities include, but are not limited to, neural induction, liver regeneration, wound healing, growth, invasion, morphologic differentiation, embryological development, scattering, proliferation, apoptosis, cell motility, metastisis, migration, cell adhesion, integrin clustering, phosphorylation of paxillin, formation of focal adhesions, and cancer resulting from aberrant Met-HGF signaling.

The term "aberrant Met-HGF signaling" includes any circumstance in which Met-HGF signaling fails to stimulate any Met-HGF activity when normally signaling would result in such activity. Aberrant Met-HGF signaling also includes any circumstance in which Met-HGF signaling results in less Met-HGF activity than would occur with normal signaling. Aberrant activity also includes any circumstance in which Met-HGF signaling results in greater Met-HGF activity than would occur with normal signaling. Aberrant Met-HGF signaling can result, for example, in certain cancers.

The term "Met independent HGF activity" refers to any biological activity affected by HGF that does not depend on binding of HGF to a Met receptor. Such activity includes, but is not limited to, biological activity affected by HGF interaction with other receptors and biological activity affected by HGF through other pathways, e.g., Ron or met/ron heterodimers.

The term "aberrant HGF activity" refers to any circumstance in which HGF activity is either higher or lower than it should be. In certain circumstances, aberrant HGF activity results from aberrant HGF signaling. In certain circumstances, aberrant HGF activity results from a concentration of HGF that is higher than it should be. In certain embodiments, aberrant HGF activity results from a concentration of HGF that is lower than it should be.

The term "pharmaceutical agent or drug" as used herein refers to a chemical compound or composition capable of inducing a desired therapeutic effect when properly administered to a patient.

The term "modulator," as used herein, is a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO01/83525).

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term patient includes human and animal subjects.
Certain Exemplary Specific Binding Agents In certain instances, HGF binds a Met receptor to induce Met phosphorylation. In certain instances, normal HGF-induced Met phosphorylation regulates a variety of cellular processes. In certain instances, aberrant Met-HGF activity correlates with a number of human disease states. For example, in certain instances, too much HGF activity correlates with certain cancers. Therefore, in certain instances, modulating HGF activity may be therapeutically useful. In certain embodiments, specific binding agents to HGF are used to decrease the amount of HGF activity from an abnormally high level. In certain embodiments, decreasing HGF activity from an abnormally high level decreases tumorigenic activity and reduces the severity of cancer. According to certain embodiments, specific binding agents to HGF are used to treat cancer. In certain embodiments, specific binding agents to HGF are used to prevent cancer.

In certain embodiments, a specific binding agent to HGF is used to treat cancers in which HGF activity is normal. In such cancers, for example, reduction of HGF activity to below normal may provide a therapeutic effect.

In certain embodiments, a specific binding agent to HGF is used to modulate at least one Met-HGF activity. In certain embodiments, a specific binding agent to HGF is used to modulate at least one Met independent HGF activity. In certain embodiments, more than one specific binding agent to HGF is used to modulate HGF activity.

In certain embodiments, specific binding agents to HGF are fully human monoclonal antibodies. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments a hybridoma cell line is selected from at least one of 1.24.1, 1.29.1, 1.60.1, 1.61.3, 1.74.3. 1.75.1, 2.4.4, 2.12.1, 2.40.1, and 3.10.1. In certain embodiments, a purified human monoclonal antibody to human HGF is provided.

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy may provide a source for production of fully human monoclonal antibodies (Mabs). In certain embodiments, fully human antibodies are expected to minimize the immunogenic and allergic responses intrinsic to mouse or mouse-derivatized Mabs, and thus, in certain embodiments, increase the efficacy and safety of the administered antibodies. In certain embodiments, fully human antibodies may be used in the treatment of chronic or recurring human diseases, such as cancer, malaria, or proliferative diabetic retinopathy, which may involve repeated antibody administrations.

One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity fully human antibodies against any antigen of interest, including human antigens. Using the hybridoma technology, antigen-specific human MAbs with the desired specificity may be produced and selected. Certain exemplary methods are described in WO 98/24893, U.S. Pat. No. 5,545,807, EP 546073B1, and EP 546073A1.

In certain embodiments, one may use constant regions from species other than human along with the human variable region(s).

Naturally Occurring Antibody Structure

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson and Wu, *Nucleic Acids Res,* 28: 214-8 (2000). The Chothia definition is similar to the Kabat definition, but the Chothia definition takes into account positions of certain structural loop regions. See, e.g., Chothia et al., *J Mol Biol,* 196: 901-17 (1986); Chothia et al., *Nature,* 342: 877-83 (1989). The AbM definition uses an integrated suite of computer programs produced by Oxford Molecular Group that model antibody structure. See, e.g., Martin et al., *Proc Natl Acad Sci* (USA) 86:9268-9272 (1989); AbM™, a computer program for modeling variable regions of antibodies, Oxford, UK; Oxford Molecular, Ltd. The AbM definition models the tertiary structure of an antibody from primary sequence using a combination of knowledge databases and ab initio methods, such as those described in Samudrala et al., *Ab Initio Protein Structure Prediction Using a Combined Hierarchical Approach*, PROTEINS, Structure, Function and Genetics Suppl. 3:194-198 (1999). The contact definition is based on an analysis of the available complex crystal structures. See, e.g., MacCallum et al., *J Mol Biol*, 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

Bispecific or Bifunctional Antibodies

A bispecific or bifunctional antibody typically is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai et al., Clin. Exp. Immunol. 79: 315-321 (1990); Kostelny et al., J. Immunol. 148:1547-1553 (1992).

Preparation of Antibodies

According to certain embodiments, certain antibodies specifically binding to HGF are encompassed by the invention. In certain embodiments, antibodies are produced by immunization with an antigen. The term "antigen" refers to a molecule used in an animal to produce antibodies capable of binding to that antigen and/or another target. In certain embodiments, antibodies may be produced by immunization with full-length HGF, a soluble form of HGF, a splice variant form of HGF, or a fragment thereof. In certain embodiments, the antibodies of the invention may be polyclonal or monoclonal, and/or may be recombinant antibodies. In certain embodiments, antibodies of the invention are human antibodies prepared, for example, by immunization of transgenic animals capable of producing human antibodies (see, for example, PCT Published Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See, e.g., Hudson, *Curr Opin Biotech*, 9:395-402 (1999) and references therein.

In certain embodiments, smaller and more effectively screened libraries of antibody variants are produced by restricting random or site-directed mutagenesis to hyper-mutation sites in the CDRs, which are sites that correspond to areas prone to mutation during the somatic affinity maturation process. See, e.g., Chowdhury and Pastan, *Nature Biotech*, 17: 568-572 (1999) and references therein. In certain embodiments, certain types of DNA elements may be used to identify hyper-mutation sites including, but not limited to, certain direct and inverted repeats, certain consensus sequences, certain secondary structures, and certain palindromes. For example, such DNA elements that may be used to identify hyper-mutation sites include, but are not limited to, a tetra-base sequence comprising a purine (A or G), followed by guainine (G), followed by a pyrimidine (C or T), followed by either adenosine or tyrosine (A or T) (i.e., A/G-G-C/T-A/T). Another example of a DNA element that may be used to identify hyper-mutation sites is the serine codon; A-G-C/T.

In certain embodiments, antibodies are humanized. In certain embodiments, a humanized antibody is substantially non-immunogenic in humans. In certain embodiments, a humuanized antibody has substantially the same affinity for a target as an antibody from another species from which the humanized antibody is derived. See, e.g., U.S. Pat. No. 5,530, 101, U.S. Pat. No. 5,693,761; U.S. Pat. No. 5,693,762; U.S. Pat. No. 5,585,089.

In certain embodiments, amino acids of an antibody variable domain that may be modified without diminishing the native affinity of the antigen binding domain while reducing its immunogenicity are identified. See, e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See, e.g., Co et al., *Mol Immunol* 30:1361-1367 (1993). In certain embodiments, techniques such as "reshaping," "hyperchimerization," or "veneering/resurfacing" are used to produce humanized antibodies. See, e.g., Vaswami et al., *Annals of Allergy, Asthma, & Immunol* 81:105 (1998); Roguska et al., *Prot Engineer* 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., *J Immunol* 62(6): 3663-71 (1999).

In certain instances, humanizing antibodies results in a loss of antigen binding capacity. In certain embodiments, humanized antibodies are "back mutated." In certain such embodiments, the humanized antibody is mutated to include one or more of the amino acid residues found in the donor antibody. See, e.g., Saldanha et al., *Mol Immunol* 36:709-19 (1999).

In certain embodiments the complementarity determining regions (CDRS) of the light and heavy chain variable regions of an antibody to HGF may be grafted to framework regions (FRs) from the same, or another, species. In certain embodiments, the CDRs of the light and heavy chain variable regions of an antibody to HGF may be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to HGF heavy chain or light chain are replaced with the FRs from a different heavy chain or light chain. In certain embodiments, rare amino acids in the FRs of the heavy and light chains of an antibody to HGF are not replaced, while the rest of the FR amino acids are replaced. Rare amino acids are specific amino acids that are in positions in which they are not usually found in FRs. In certain embodiments, the grafted variable regions from an antibody to HGF may be used with a constant region that is different from the constant region of an antibody to HGF. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., *Nature* 321: 522-525 (1986); Riechmann et al., *Nature*, 332: 323-327 (1988); Verhoeyen et al., *Science* 239:1534-1536 (1988), Winter, *FEBS Letts* 430:92-94 (1998), which are hereby incorporated by reference for any purpose.

In certain embodiments, a phage display technique is used to generate monoclonal antibodies. In certain embodiments, such techniques produce fully human monoclonal antibodies. In certain embodiments, a polynucleotide encoding a single Fab or Fv antibody fragment is expressed on the surface of a phage particle. See, e.g., Hoogenboom et al., *J Mol Biol* 227: 381 (1991); Marks et al., *J Mol Biol* 222: 581 (1991); U.S. Pat. No. 5,885,793. In certain embodiments, phage are "screened" to identify those antibody fragments having affinity for target. Thus, certain such processes mimic immune selection through the display of antibody fragment repertoires on the surface of filamentous bacteriophage, and subsequent selection of phage by their binding to target. In certain such procedures, high affinity functional agonistic antibody fragments are isolated. In certain such embodiments, a complete repertoire of human antibody genes is created by cloning naturally rearranged human V genes from peripheral blood lymphocytes. See, e.g., Mullinax et al., *Proc Nat Acad Sci* (USA) 87: 8095-8099 (1990).

According to certain embodiments, antibodies of the invention are prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving this result are disclosed in the patents, applications and references disclosed in the specification, herein. In certain embodiments, one may employ methods such as those disclosed in PCT Published Application No. WO 98/24893 or in Mendez et al, Nature Genetics 15:146-156 (1997), which are hereby incorporated by reference for any purpose.

According to certain embodiments, fully human monoclonal antibodies specific for HGF are produced as follows. Transgenic mice containing human immunoglobulin genes are immunized with the antigen of interest, e.g. HGF, lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to HGF is provided.

In certain embodiments, fully human antibodies are produced by the expression of recombinant DNA in host cells or by expression in hybridoma cells. In certain embodiments, antibodies are produced using the phage display technique described above.

In certain embodiments, fully human antibodies are produced by exposing human splenocytes (B or T cells) to an antigen in vitro, and then reconstituting the exposed cells in an immunocompromised mouse, e.g. SCID or nod/SCID. See, e.g., Brams et al., *J Immunol,* 160: 2051-2058 (1998); Carballido et al., *Nat Med,* 6: 103-106 (2000). In certain such approaches, engraftment of human fetal tissue into SCID mice (SCID-hu) results in long-term hematopoiesis and human T-cell development. See, e.g., McCune et al., *Science* 241:1532-1639 (1988); Ifversen et al., *Sem Immunol* 8:243-248 (1996). In certain instances, humoral immune response in such chimeric mice is dependent on co-development of human T-cells in the animals. See, e.g., Martensson et al., *Immunol* 83:1271-179 (1994). In certain approaches, human peripheral blood lymphocytes are transplanted into SCID mice. See, e.g., Mosier et al., *Nature* 335:256-259 (1988). In certain such embodiments, when such transplanted cells are treated either with a priming agent, such as Staphylococcal Enterotoxin A (SEA), or with anti-human CD40 monoclonal antibodies, higher levels of B cell production is detected. See, e.g., Martensson et al., *Immunol* 84: 224-230 (1995); Murphy et al., *Blood* 86:1946-1953 (1995).

In certain embodiments, antibodies of the invention are produced by at least one of the following hybridomas: 1.24.1, 1.29.1, 1.60.1, 1.61.1, 1.74.1, 1.75.1, 2.4.4, 2.12.1, 2.40.1, and 3.10.1. In certain embodiments, specific binding agents bind to HGF with a $K_D$ of $10^{-8}$, $10^{-9}$, or $10^{-10}$M. In certain embodiments, specific binding agents bind to HGF with a dissociation constant ($K_D$) of between approximately 0.099 and 0.79 nM as measured by the kinetic method (FIG. 6A). In certain embodiments, specific binding agents bind to HGF with a $K_D$ of less than 10 pM to approximately 54 pM, as measured by the equilibrium/solution method (FIG. 6B).

In certain embodiments, specific binding agents comprise an immunoglobulin molecule of at least one of the IgG1, IgG2, IgG3, IgG4, IgE, IgA, IgD, and IgM isotype. In certain embodiments, specific binding agents comprise a human kappa light chain and/or a human heavy chain. In certain embodiments, the heavy chain is of the IgG1, IgG2, IgG3, IgG4, IgE, IgA, IgD, or IgM isotype. In certain embodiments, specific binding agents have been cloned for expression in mammalian cells. In certain embodiments, specific binding agents comprise a constant region other than any of the constant regions of the IgG1, IgG2, IgG3, IgG4, IgE, IgA, IgD, and IgM isotype.

In certain embodiments, specific binding agents comprise a human kappa light chain and a human IgG1 heavy chain. In certain embodiments, specific binding agents comprise a human kappa light chain and a human IgG2 heavy chain. In certain embodiments, specific binding agents comprise a human kappa light chain and a human IgG3, IgG4, IgE, IgA, IgD or IgM heavy chain. In certain embodiments, specific binding agents comprise variable regions of antibodies ligated to a constant region that is neither the constant region for the IgG1 isotype, nor the constant region for the IgG2 isotype. In certain embodiments, specific binding agents have been cloned for expression in mammalian cells.

In certain embodiments, conservative modifications to the heavy and light chains of antibodies from at least one of the hybridoma lines: 1.24.1, 1.29.1, 1.60.1, 1.61.1, 1.74.1, 1.75.1, 2.4.4, 2.12.1, 2.40.1, and 3.10.1 (and corresponding modifications to the encoding nucleotides) will produce antibodies to HGF having functional and chemical characteristics similar to those of the antibodies from the hybridoma lines: 1.24.1, 1.29.1, 1.60.1, 1.61.1, 1.74.1, 1.75.1, 2.4.4, 2.12.1, 2.40.1, and 3.10.1. In contrast, in certain embodiments, substantial modifications in the functional and/or chemical characteristics of antibodies to HGF may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to HGF, or to increase or decrease the affinity of the antibodies to HGF described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used may depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and produce antibodies with constitutive HGF binding properties. Appropriate expression vectors for mammalian host cells are well known.

In certain embodiments, specific binding agents comprise one or more polypeptides. In certain embodiments, any of a variety of expression vector/host systems may be utilized to express polynucleotide molecules encoding polypeptides. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide is recombinantly expressed in yeast. Certain such embodiments use commercially available expression systems, e.g., the Pichia Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia larvae*. See, e.g., Smith et al., *J Virol* 46: 584 (1983); Engelhard et al., *Proc Nat Acad Sci* (USA) 91: 3224-7 (1994).

In certain embodiments, polypeptides made in bacterial cells are produced as insoluble inclusion bodies in the bacteria. In certain embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (See, e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxylapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps may be changed or certain steps may be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide is partially purified. In certain embodiments, partial purification may be accomplished by using fewer purification steps or by utilizing different forms of the same general purification scheme. For example, in certain embodiments, a cation-exchange column chromatography performed utilizing an HPLC apparatus will generally result in a greater "fold purification" than the same technique utilizing a low-pressure chromatography system. In certain embodiments, methods resulting in a lower degree of purification may have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al., *Biochem Biophys\Res Comm*, 76: 425 (1977). It will be appreciated that under different electrophoresis conditions, the apparent molecular weights of purified or partially purified polypeptide may be different.

Certain Exemplary Epitopes

Figure 10A:
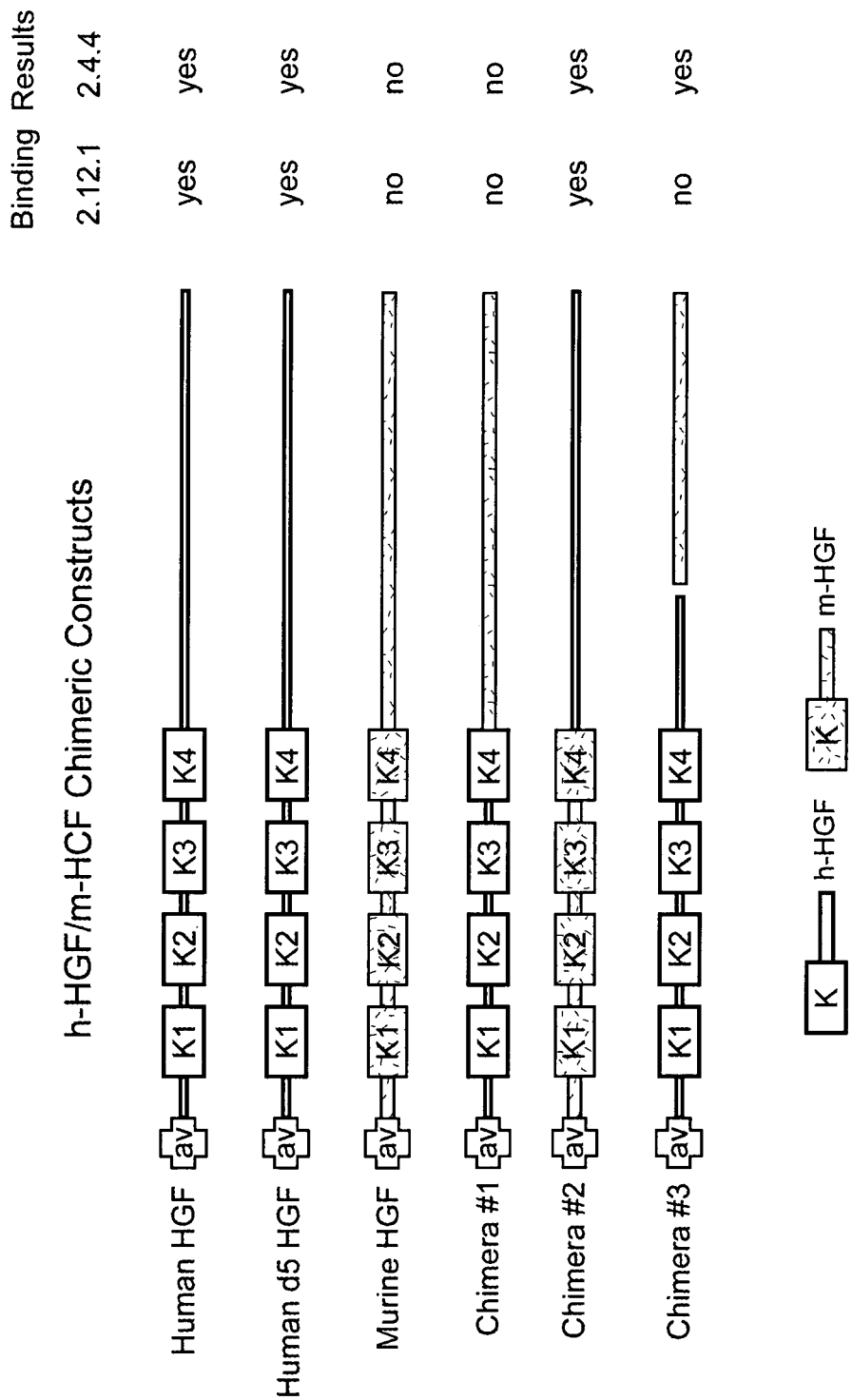
Figure 10B:
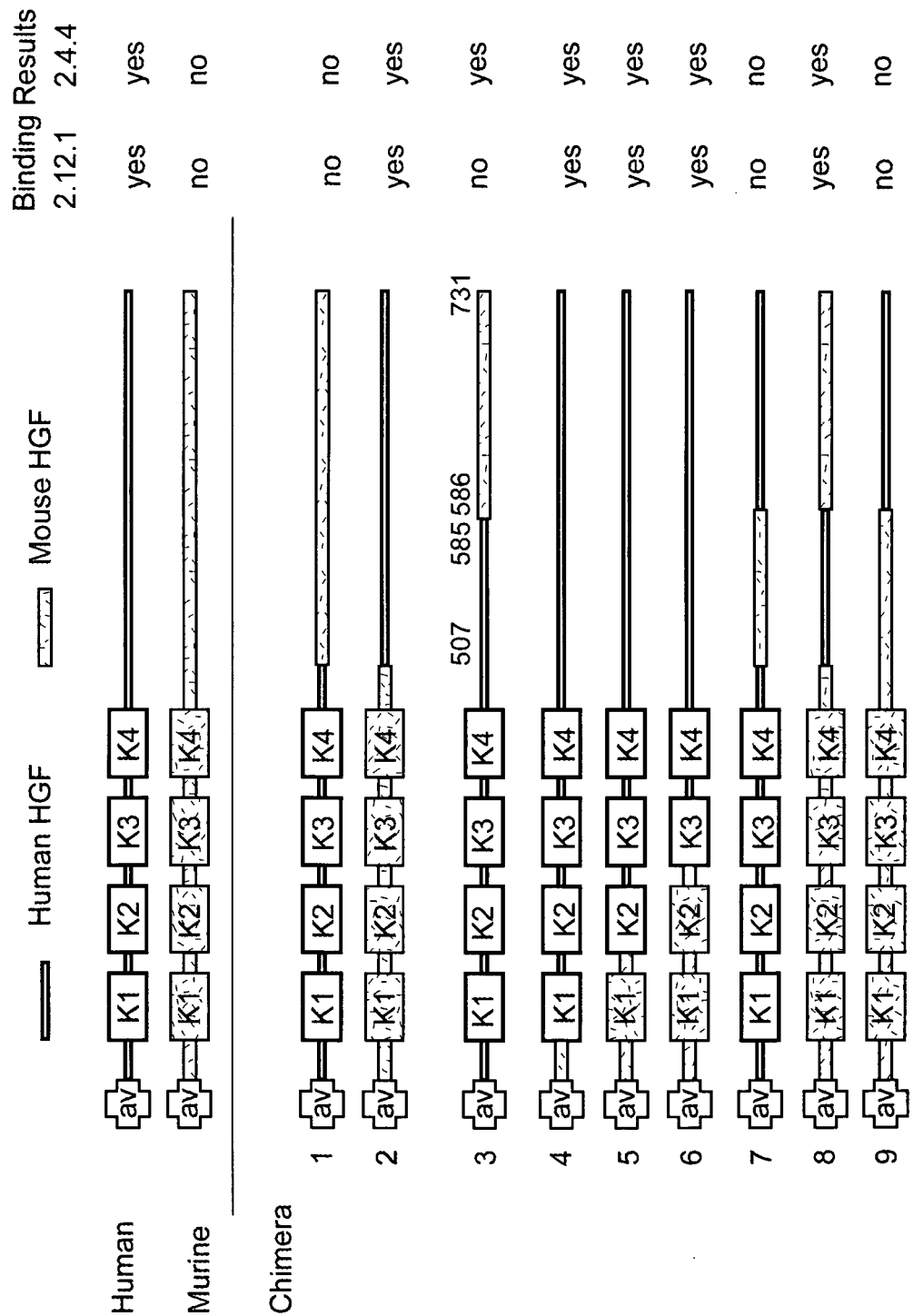
Figure 10C:
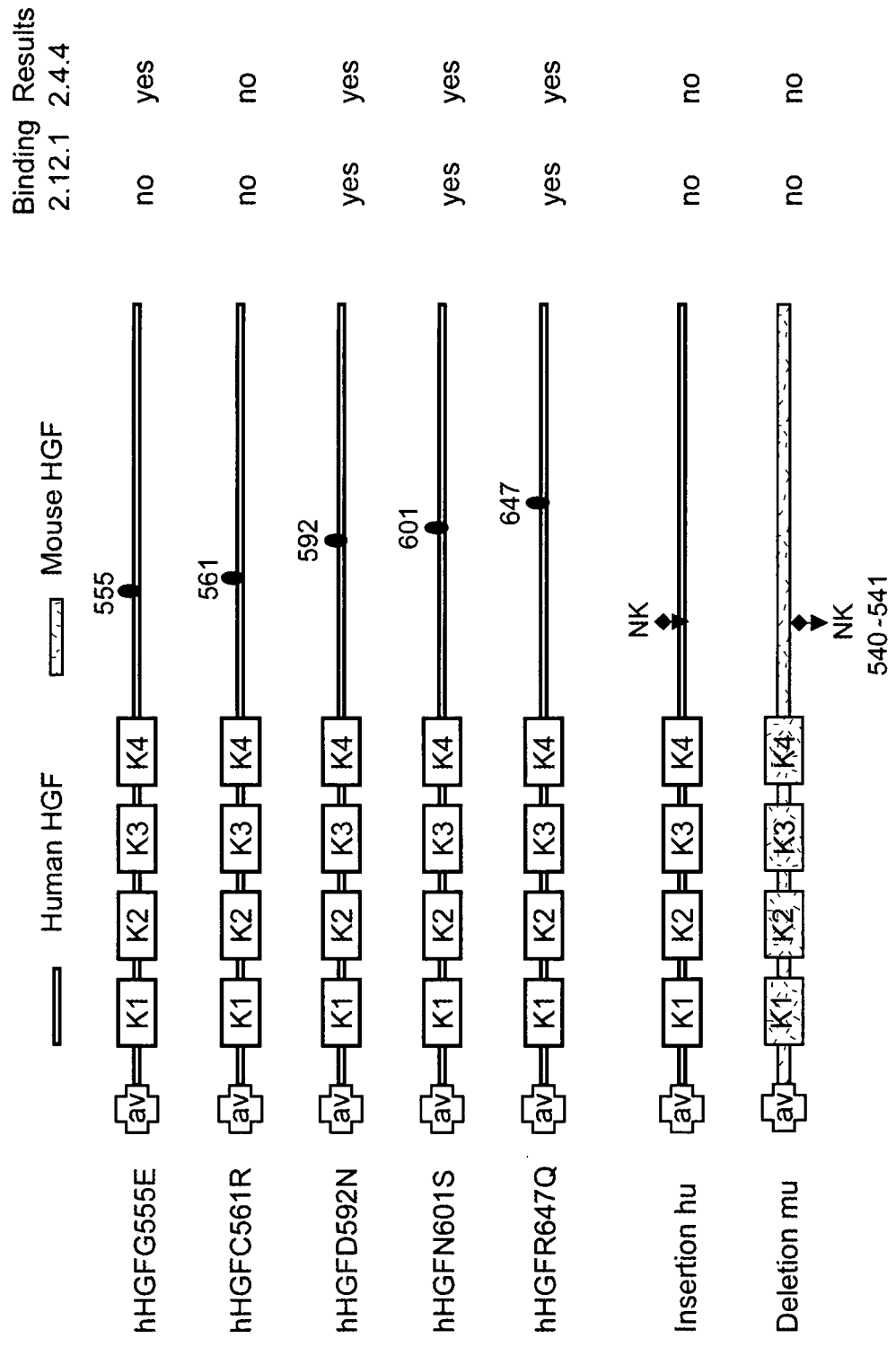
Figure 11A:
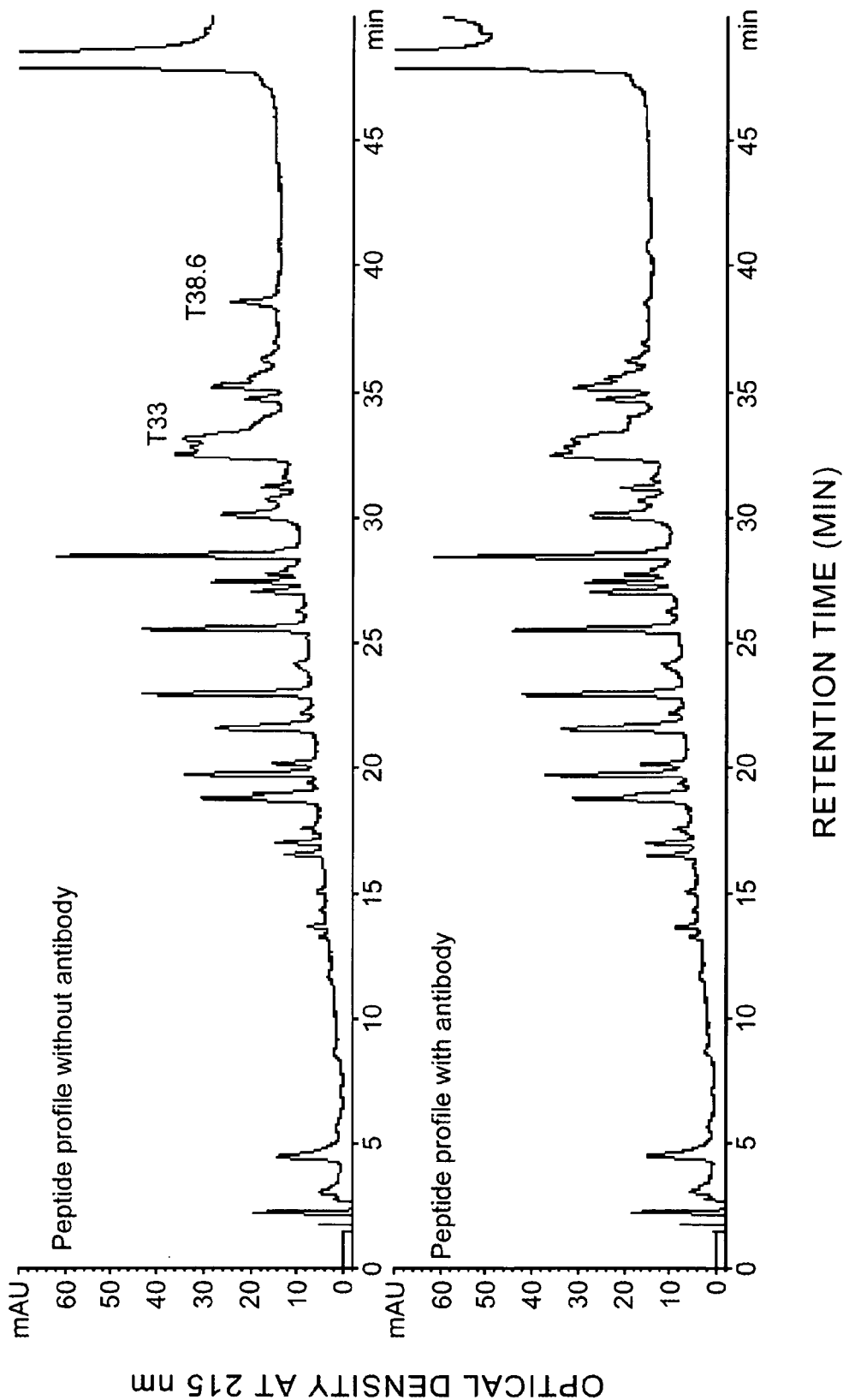
FIGS. 11A and 11B show HPLC analyses of protease protection experiments on human HGF as discussed in Example 8E.
Figure 11B:
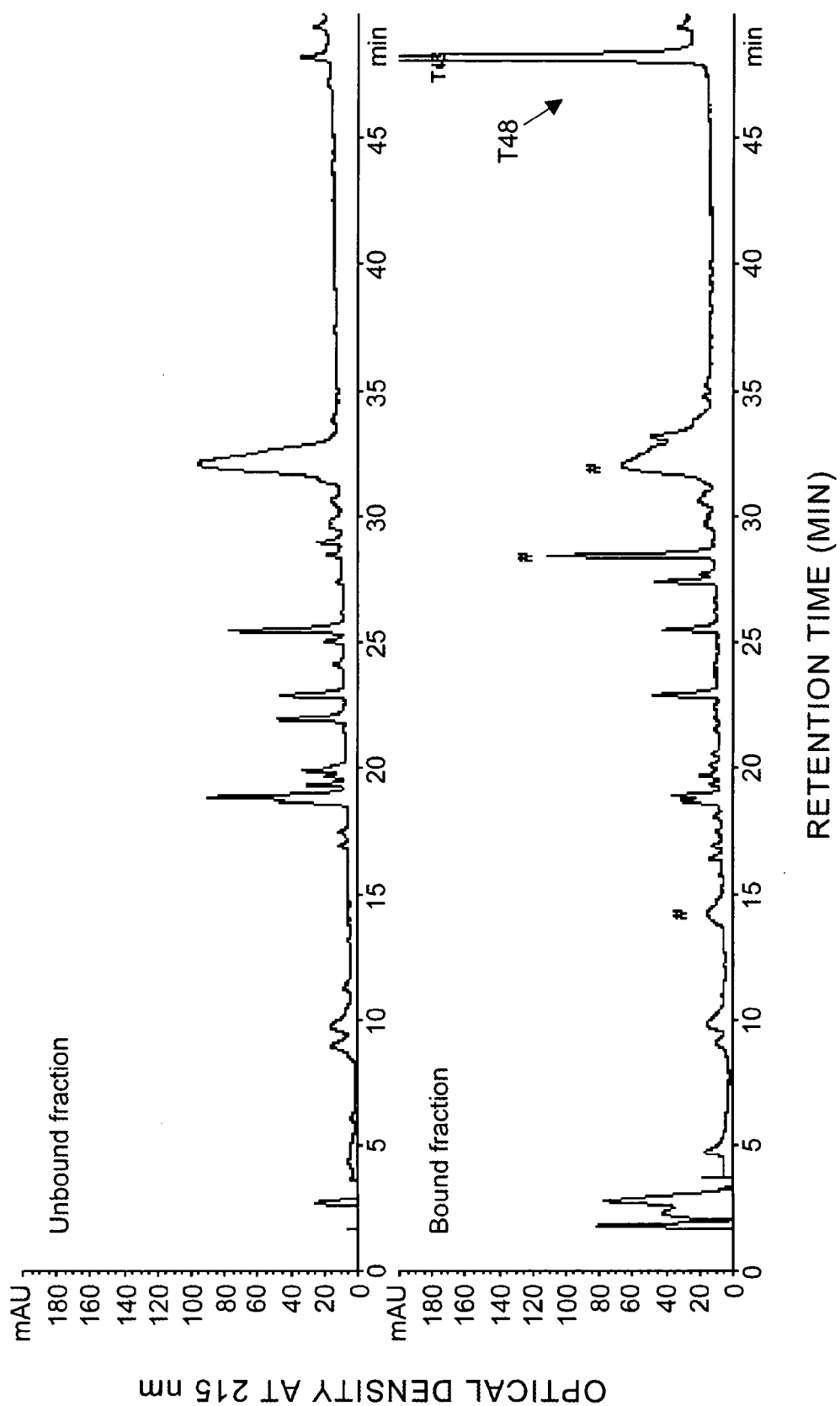
Figure 12A:
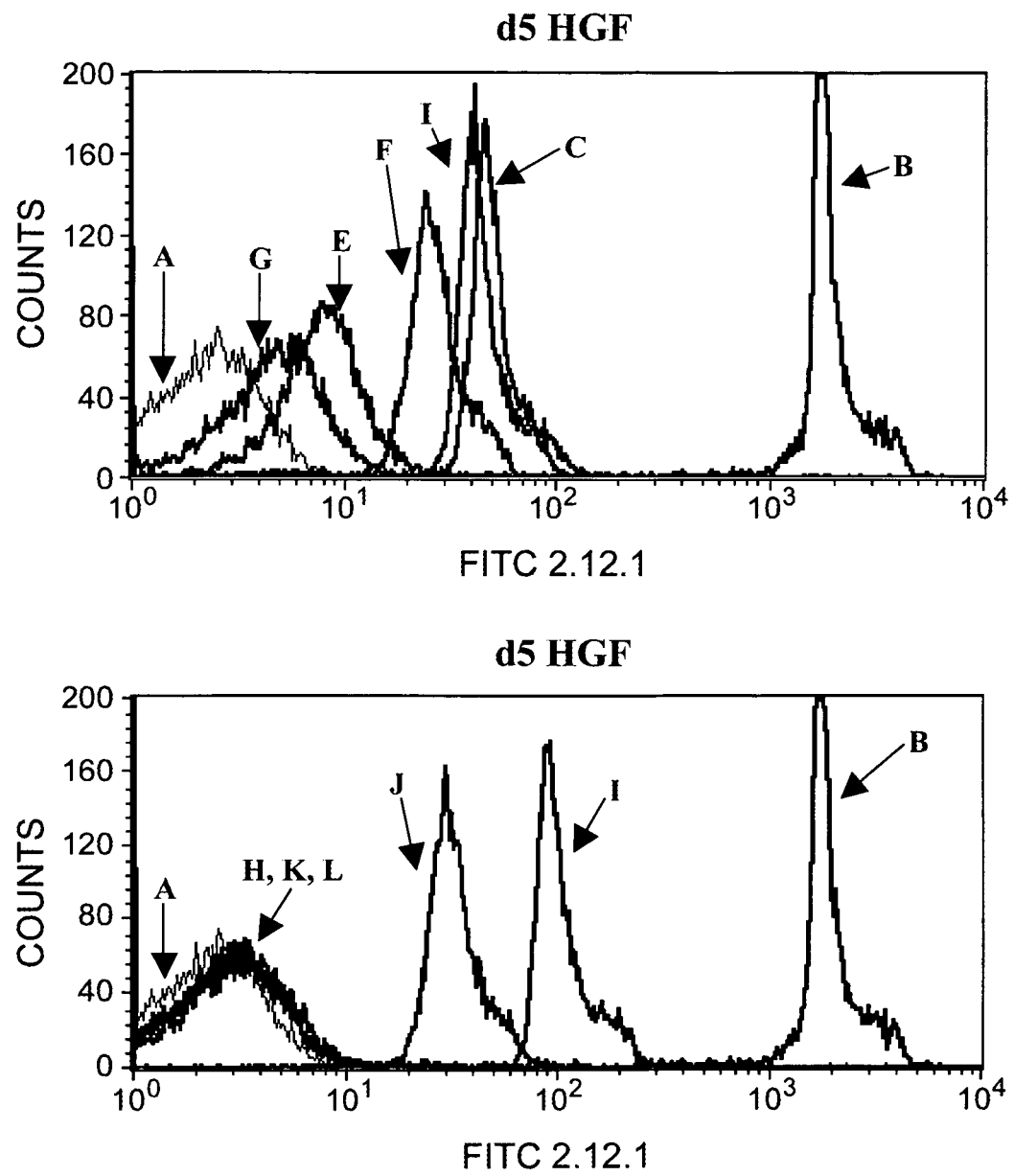
FIGS. 12A-12D show results from competitive binding assays discussed in Example 8.
Figure 12B:
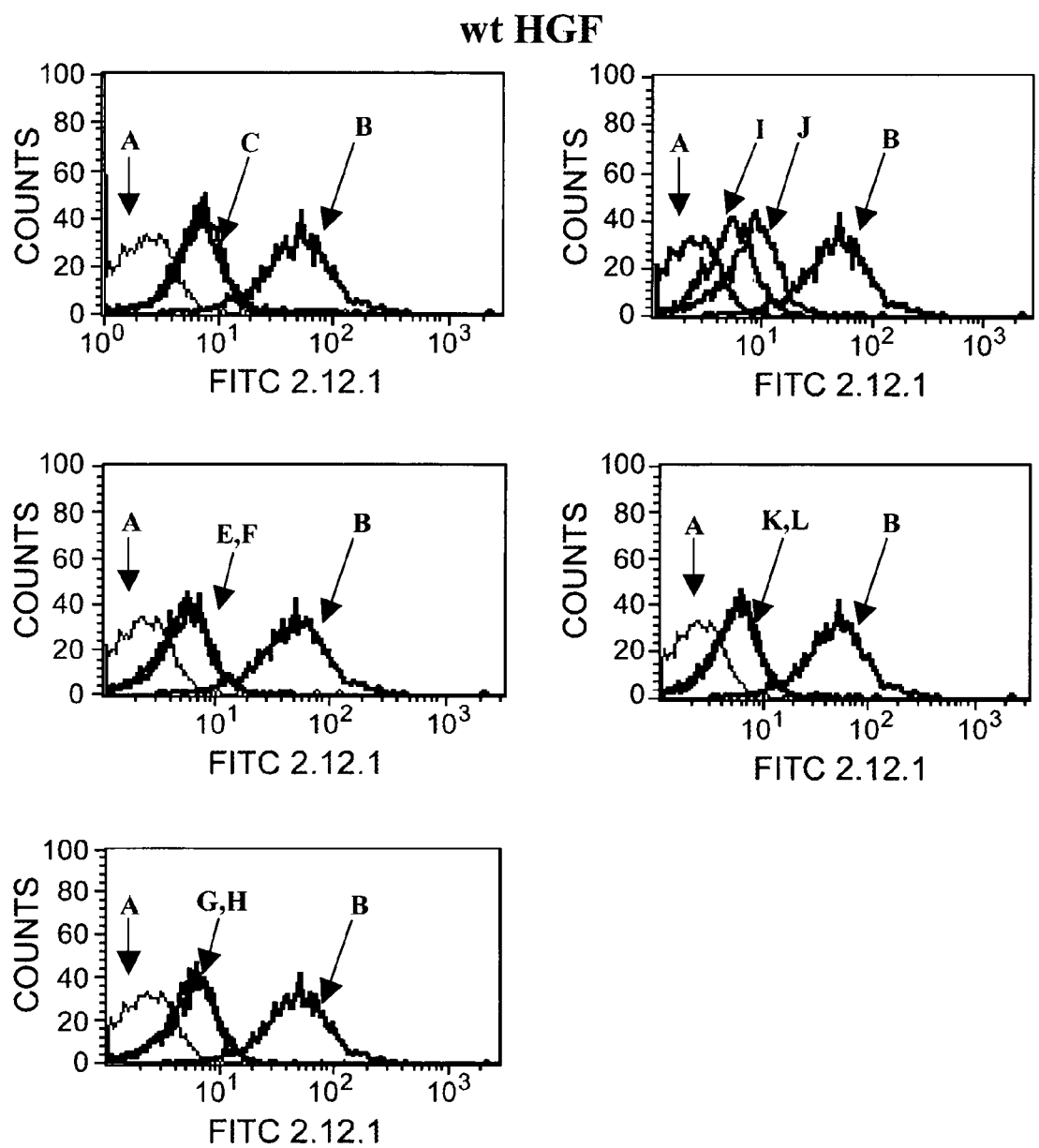
Figure 12C:
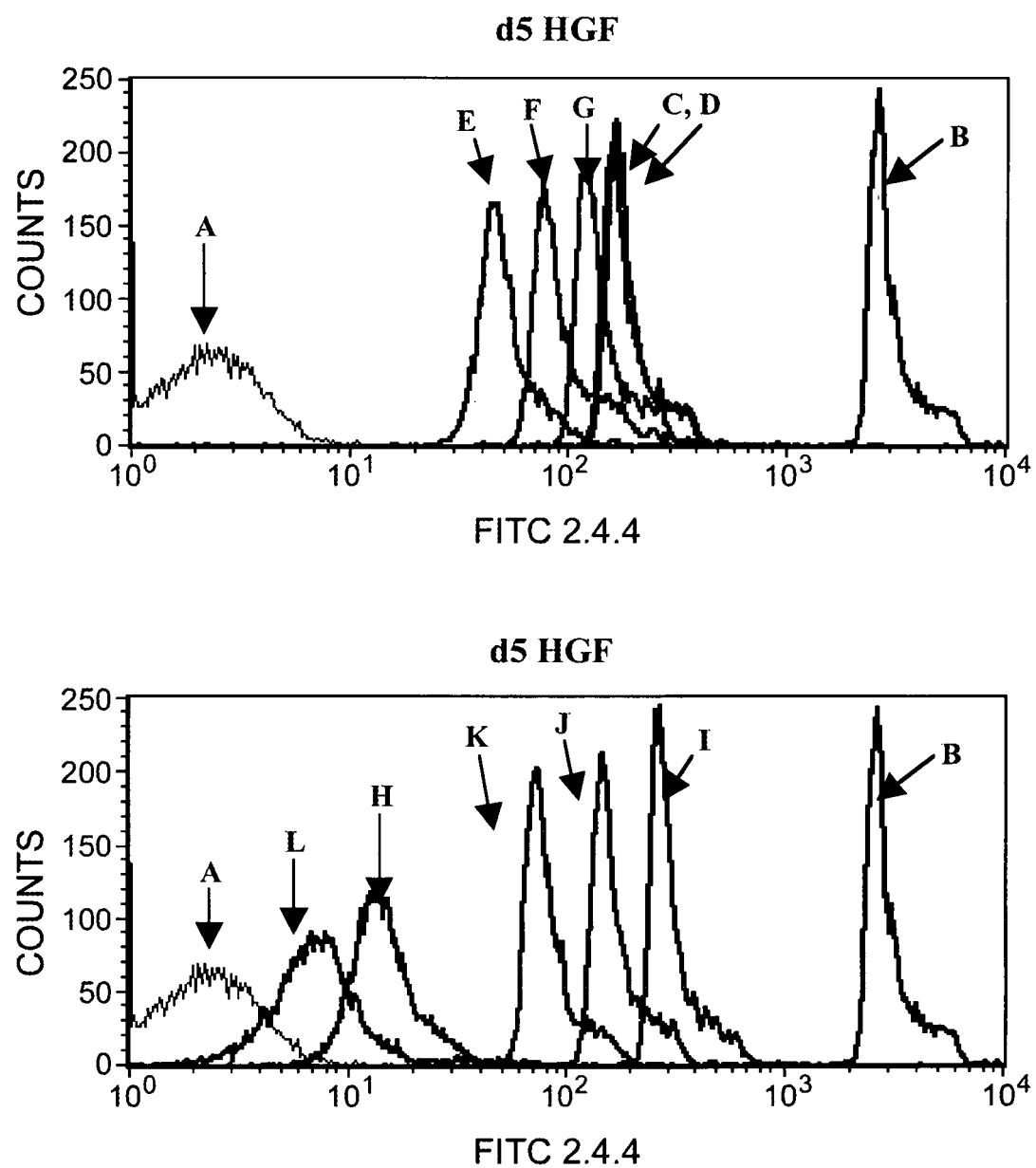
Figure 12D:
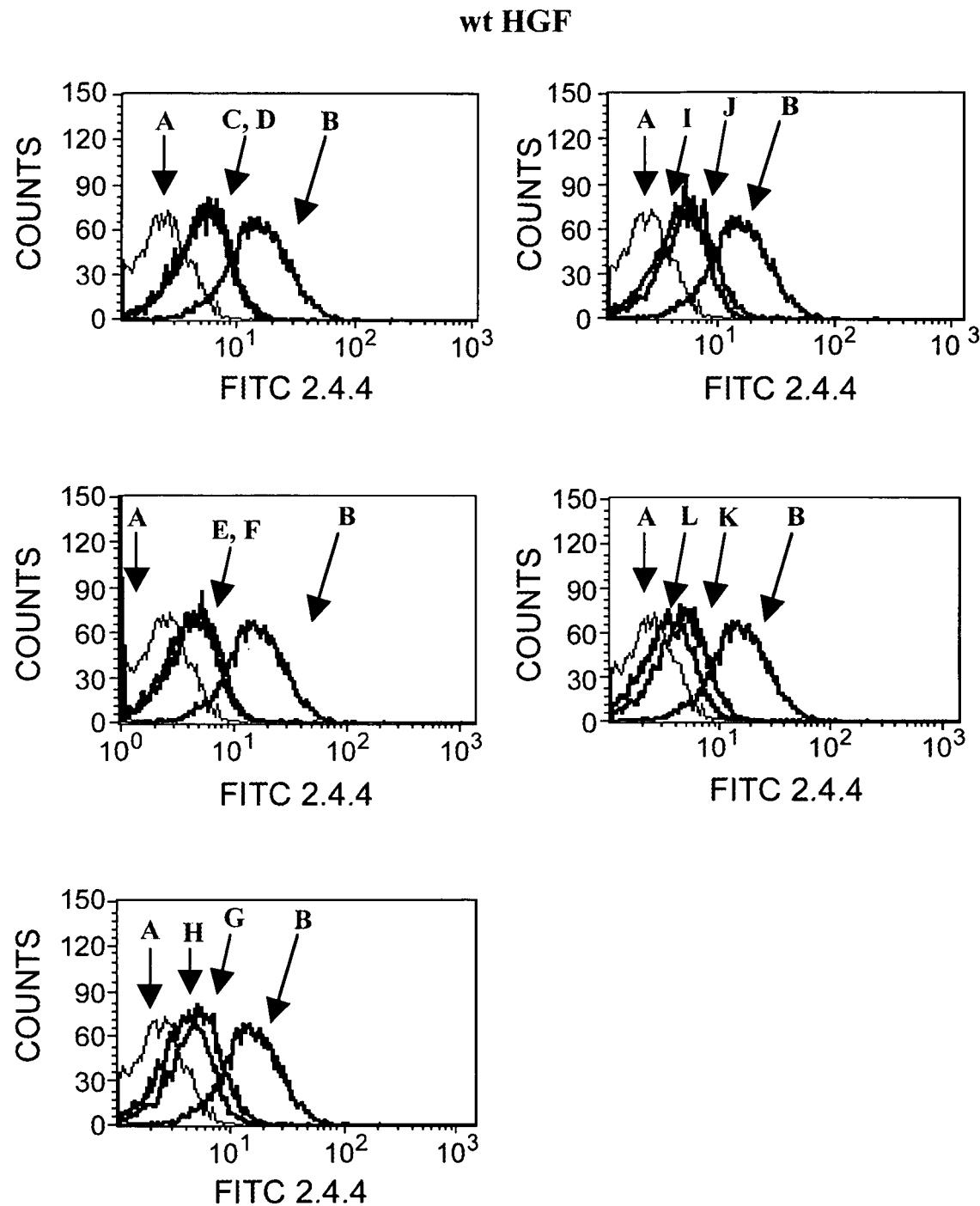

In certain embodiments, epitopes to which anti-HGF antibodies bind are provided (see, e.g., Example 8, FIGS. 10 and 11, and SEQ ID NO. 164 and 165). In certain embodiments, an HGF epitope may be utilized to prevent binding of an anti-HGF antibody or specific binding agent to HGF. In certain embodiments, an HGF epitope may be utilized to decrease binding of an anti-HGF antibody or specific binding agent to HGF. In certain embodiments, an HGF epitope may be utilized to substantially inhibit binding of an anti-HGF antibody or specific binding agent to HGF. An epitope substantially inhibits binding of an anti-HGF antibody or specific binding agent to HGF when an excess of epitope reduces the quantity of anti-HGF antibody or specific binding agent bound to HGF by at least about 20%, 40%, 60%, 80%, 85%, or more. In certain embodiments, an HGF epitope may be utilized to bind anti-HGF antibody or specific binding agent. In certain embodiments, an HGF epitope may be utilized to identify antibodies or specific binding agents which bind to HGF. In certain embodiments, an HGF epitope may be utilized to isolate antibodies or specific binding agents which bind to HGF. In certain embodiments, an HGF epitope may be utilized to generate antibodies or specific binding agents which bind to HGF. In certain embodiments, an HGF epitope may be utilized as an immunogen to generate antibodies or specific binding agents which bind to HGF. In certain embodiments, an HGF epitope may be administered to an animal, and antibodies which bind to HGF may subsequently be obtained from the animal. In certain embodiments, an HGF epitope may be utilized to interfere with normal HGF-Met signaling.

Certain Therapeutic Uses

In certain embodiments, methods are provided of treating a cancer comprising administering a therapeutically effective amount of one or more specific binding agents to HGF. In certain embodiments, methods are provided of treating cancer comprising administering a therapeutically effective amount of one or more specific binding agents to HGF and another therapeutic agent.

In certain embodiments, methods are provided of treating or preventing malaria comprising administering a therapeutically effective amount of one or more specific binding agents to HGF. In certain embodiments, methods are provided of treating or preventing malaria comprising administering a therapeutically effective amount of one or more specific binding agents to HGF and another therapeutic agent.

In certain embodiments, methods are provided of treating or preventing proliferative diabetic retinopathy comprising administering a therapeutically effective amount of one or more specific binding agents to HGF. In certain embodiments, methods are provided of treating or preventing proliferative diabetic retinopathy comprising administering a therapeutically effective amount of one or more specific binding agents to HGF and another therapeutic agent.

In certain embodiments, a specific binding agent to HGF is administered alone. In certain embodiments, a specific binding agent to HGF is administered prior to the administration of at least one other therapeutic agent. In certain embodiments, a specific binding agent to HGF is administered concurrent with the administration of at least one other therapeutic agent. In certain embodiments, a specific binding agent to HGF is administered subsequent to the administration of at least one other therapeutic agent. Therapeutic agents, include, but are not limited to, at least one other cancer therapy agent. Exemplary cancer therapy agents include, but are not limited to, radiation therapy and chemotherapy.

Pharmaceutical compositions of the invention can be administered in combination therapy, i.e., combined with other agents. In certain embodiments, the combination therapy comprises a specific binding agent capable of binding HGF, in combination with at least one anti-angiogenic agent. Agents include, but are not limited to, in vitro synthetically prepared chemical compositions, antibodies, antigen binding regions, radionuclides, and combinations and conjugates thereof. In certain embodiments, an agent may act as an agonist, antagonist, alllosteric modulator, or toxin. In certain embodiments, an agent may act to inhibit or stimulate its target (e.g., receptor or enzyme activation or inhibition), and thereby promote cell death or arrest cell growth.

Chemotherapy treatments include, but are not limited to anti-neoplastic agents including, but not limited to, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Cancer therapies, which may be administered with a specific binding agent to HGF, also include, but are not limited to, targeted therapies. Examples of targeted therapies include, but are not limited to, use of therapeutic antibodies. Exemplary therapeutic antibodies, include, but are not limited to, mouse, mouse-human chimeric, CDR-grafted, humanized and fully human antibodies, and synthetic antibodies, including, but not limited to, those selected by screening antibody libraries. Exemplary antibodies include, but are not limited to, those which bind to cell surface proteins Her2, CDC20, CDC33, mucin-like glycoprotein, and epidermal growth factor receptor (EGFR) present on tumor cells, and optionally induce a cytostatic and/or cytotoxic effect on tumor cells displaying these proteins. Exemplary antibodies also include HERCEPTIN® (trastuzumab), which may be used to treat breast cancer and other forms of cancer, and RITUXAN® (rituximab), ZEVALIN® (ibritumomab tiuxetan), GLEEVEC®, and LYMPHOCIDE® (epratuzumab), which may be used to treat non-Hodgkin's lymphoma and other forms of cancer. Certain exemplary antibodies also include ERBITUX® (IMC-C225); ertinolib (Iressa); BEXXAR® (iodine 131 tositumomab); KDR (kinase domain receptor) inhibitors; anti VEGF antibodies and antagonists (e.g., Avastin® (bevacizumab) and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; and Campath® (Alemtuzumab). In certain embodiments, cancer therapy agents are polypeptides which selectively induce apoptosis in tumor cells, including, but not limited to, the TNF-related polypeptide TRAIL.

In certain embodiments, cancer therapy agents are anti-angiogenic agents which decrease angiogenesis. Certain such agents include, but are not limited to, IL-8; Campath, B-FGF; FGF antagonists; Tek antagonists (Cerretti et al., U.S. Publication No. 2003/0162712; Cerretti et al., U.S. Pat. No. 6,413,932, and Cerretti et al., U.S. Pat. No. 6,521,424, each of which is incorporated herein by reference for any purpose); anti-TWEAK agents (which include, but are not limited to, antibodies and antigen binding regions); soluble TWEAK receptor antagonists (Wiley, U.S. Pat. No. 6,727,225); an ADAM distintegrin domain to antagonize the binding of integrin to its ligands (Fanslow et al., U.S. Publication No. 2002/0042368); anti-eph receptor and anti-ephrin antibodies; antigen binding regions, or antagonists (U.S. Pat. Nos. 5,981,245; 5,728,813; 5,969,110; 6,596,852; 6,232,447; 6,057,124 and patent family members thereof); anti-VEGF agents (e.g., antibodies or antigen binding regions that specifically bind VEGF, or soluble VEGF receptors or a ligand binding regions thereof) such as Avastin™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as panitumumab, IRESSA™ (gefitinib), TARCEVA™ (erlotinib), anti-Ang-1 and anti-Ang-2 agents (e.g., antibodies or antigen binding regions specifically binding thereto or to their receptors, e.g., Tie-2/TEK), and anti-Tie-2 kinase inhibitory agents (e.g., antibodies or antigen binding regions that specifically bind and inhibit the activity of growth factors, such as antagonists of hepatocyte growth factor (HGF, also known as Scatter Factor), and antibodies or antigen binding regions that specifically bind its receptor "c-met"; anti-PDGF-BB antagonists; antibodies and antigen binding regions to PDGF-BB ligands; and PDGFR kinase inhibitors.

In certain embodiments, cancer therapy agents are angiogenesis inhibitors. Certain such inhibitors include, but are not limited to, SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); semaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin 1, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (PINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); ML 993, (Novartis, Switzerland); VEGI, (Proteom Tech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); thrombospondin 1 inhibitor, (Allegheny Health, Education and Research Foundation, USA); 2-Benzenesulfonamide, 4-(5-(4-chlorophenyl)-3-(trifluoromethyl)-1H-pyrazol-1-yl)-; Arriva; and C-Met. AVE 8062 ((2S)-2-amino-3-hydroxy-N-[2-methoxy-5-[(1Z)-2-(3,4,5-trimethoxyphenyl) ethenyl]phenyl]propanamide monohydrochloride); metelimumab (pINN)(immunoglobulin G4, anti-(human transforming growth factor .beta.1 (human monoclonal CAT 192.gamma.4-chain)), disulfide with human monoclonal CAT 192.kappa.-chain dimer); Flt3 ligand; CD40 ligand; interleukin-2; interleukin-12; 4-1BB ligand; anti-4-1BB antibodies; TNF antagonists and TNF receptor antagonists including TNFR/Fc, TWEAK antagonists and TWEAK-R antagonists including TWEAK-R/Fc; TRAIL; VEGF antagonists including anti-VEGF antibodies; VEGF receptor (including VEGF-R1 and VEGF-R2, also known as Flt1 and Flk1 or KDR) antagonists; CD148 (also referred to as DEP-1, ECRTP, and PTPRJ, see Takahashi et al., J. Am. Soc. Nephrol. 10: 213545 (1999), hereby incorporated by reference for any purpose) agonists; thrombospondin 1 inhibitor, and inhibitors of one or both of Tie-2 or Tie-2 ligands (such as Ang-2). A number of inhibitors of Ang-2 are known in the art, including anti-Ang-2 antibodies described in published U.S. Patent Application No. 20030124129 (corresponding to PCT Application No. WO03/030833), and U.S. Pat. No. 6,166, 185, the contents of which are hereby incorporated by reference in their entirety. Additionally, Ang-2 peptibodies are also known in the art, and can be found in, for example, published U.S. Patent Application No. 20030229023 (corresponding to PCT Application No. WO03/057134), and published U.S. Patent Application No. 20030236193, the contents of which are hereby incorporated by reference in their entirety.

Certain cancer therapy agents include, but are not limited to: thalidomide and thalidomide analogues (N-(2,6-dioxo-3-piperidyl)phthalimide); tecogalan sodium (sulfated polysaccharide peptidoglycan); TAN 1120 (8-acetyl-7,8,9,10-tetrahydro-6,8,11-trihydroxy-1-methoxy-10-[[octahydro-5-hydroxy-2-(2-hydroxypropyl)-4,10-dimethylpyrano[3,4-d]-1,3,6-dioxazocin-8-yl]oxy]-5,12-naphthacenedione); suradista (7,7'-[carbonylbis[imino(1-methyl-1H-pyrrole-4,2-diyl)carbonylimino(1-methyl-1H-pyrrole-4,2-diyl)carbonylimino]]bis-1,3-naphthalenedisulfonic acid tetrasodium salt); SU 302; SU 301; SU 1498 ((E)-2-cyano-3-[4-hydroxy-3,5-bis(1-methylethyl)phenyl]-N-(3-phenylpropyl)-2-propenamide); SU 1433 (4-(6,7-dimethyl-2-quinoxalinyl)-1,2-benzenediol); ST 1514; SR 25989; soluble Tie-2; SERM derivatives, Pharmos; semaxanib (pINN)(3-[(3,5-dimethyl-1H-pyrrol-2-yl)methylene]-1,3-dihydro-2H-indol-2-one); S 836; RG 8803; RESTIN; R 440 (3-(1-methyl-1H-indol-3-yl)-4-(1-methyl-6-nitro-1H-indol-3-yl)-1H-pyrrole-2,5-dione); R 123942 (1-[6-(1,2,4-thiadiazol-5-yl)-3-pyridazinyl]-N-[3-(trifluoromethyl)phenyl]-4-piperidinamine); prolyl hydroxylase inhibitor; progression elevated genes; prinomastat (INN) ((S)-2,2-dimethyl-4-[[p-(4-pyridyloxy)phenyl]sulphonyl]-3-thiomorpholinecarbohydroxamic acid); NV 1030; NM 3 (8-hydroxy-6-methoxy-alpha-methyl-1-oxo-1H-2-benzopyran-3-acetic acid); NF 681; NF 050; MIG; METH 2; METH 1; manassantin B (alpha-[1-[4-[5-[4-[2-(3,4-dimethoxyphenyl)-2-hydroxy-1-methylethoxy]-3-methoxyphenyl]tetrahydro-3,4-dimethyl-2-furanyl]-2-methoxyphenoxy]ethyl]-1,3-benzodioxole-5-methanol); KDR monoclonal antibody; alpha5beta3 integrin monoclonal antibody; LY 290293 (2-amino-4-(3-pyridinyl)-4H-naphtho[1,2-b]pyran-3-carbonitrile); KP 0201448; KM 2550; integrin-specific peptides; INGN 401; GYKI 66475; GYKI 66462; greenstatin (101-354-plasminogen (human)); gene therapy for rheumatoid arthritis, prostate cancer, ovarian cancer, glioma, endostatin, colorectal cancer, ATF BTPI, antiangiogenesis genes, angiogenesis inhibitor, or angiogenesis; gelatinase inhibitor, FR 111142 (4,5-dihydroxy-2-hexenoic acid 5-methoxy-4-[2-methyl-3-(3-methyl-2-butenyl)oxiranyl]-1-oxaspiro[2.5] oct-6-yl ester); forfenimex (PINN) (S)-alpha-amino-3-hydroxy-4-(hydroxymethyl)benzeneacetic acid); fibronectin antagonist (1-acetyl-L-prolyl-L-histidyl-L-seryl-L-cysteinyl-L-aspartamide); fibroblast growth factor receptor inhibitor; fibroblast growth factor antagonist; FCE 27164 (7,7'-[carbonylbis[imino(1-methyl-1H-pyrrole-4,2-diyl)carbonylimino(1-methyl-1H-pyrrole-4,2-diyl)carbonylimino]] bis-1,3,5-naphthalenetrisulfonic acid hexasodium salt); FCE 26752 (8,8'-[carbonylbis[imino(1-methyl-1H-pyrrole-4,2-diyl)carbonylimino(1-methyl-1H-pyrrole-4,2-diyl)carbonylimino]]bis-1,3,6-naphthalenetrisulfonic acid); endothelial monocyte activating polypeptide II; VEGFR antisense oligonucleotide; anti-angiogenic and trophic factors; ANCHOR angiostatic agent; endostatin; Del-1 angiogenic protein; CT 3577; contortrostatin; CM 101; chondroitinase AC; CDP 845; CanStatin; BST 2002; BST 2001; BLS 0597; BIBF 1000; ARRESTIN; apomigren (1304-1388-type XV collagen (human gene COL15A1 alpha1-chain precursor)); angioinhibin; aaATIII; A 36; 9alpha-fluoromedroxyprogesterone acetate ((6-alpha)-17-(acetyloxy)-9-fluoro-6-methyl-pregn-4-ene-3, 20-dione); 2-methyl-2-phthalimidino-glutaric acid (2-(1,3-dihydro-1-oxo-2H-isoindol-2-yl)-2-methylpentanedioic acid); Yttrium 90 labelled monoclonal antibody BC-1; Semaxanib (3-(4,5-Dimethylpyrrol-2-ylmethylene)indolin-2-one)(C15 H14 N2 O); PI 88 (phosphomannopentaose sulfate); Alvocidib (4H-1-Benzopyran-4-one, 2-(2-chlorophenyl)-5,7-dihydroxy-8-(3-hydroxy-1-methyl-4-piperidinyl)-cis-(−)-) (C21-H20 Cl N O5); E 7820; SU 11248 (5-[3-Fluoro-2-oxo-1,2-dihydroindol-(3Z)-ylidenemethyl]-2,4-dimethyl-1H-pyrrole-3-carboxylic acid (2-diethylaminoethyl)amide) (C22 H27 F N4 O2); Squalamine (Cholestane-7,24-diol, 3-[[3-[(4-aminobutyl)aminopropyl]amino]-, 24-(hydrogen sulfate), (3.beta.,5.alpha.,7.alpha.)-) (C34 H65 N3 O5 S); Eriochrome Black T; AGM 1470 (Carbamic acid, (chloroacetyl)-, 5-methoxy-4-[2-methyl-3-(3-methyl-2-butenyl)oxiranyl]-1-oxaspiro[2,5] oct-6-yl ester, [3R-[3alpha, 4alpha(2R,3R), 5beta, 6beta]]) (C19 H28 Cl N O6); AZD 9935; BIBF 1000; AZD 2171; ABT 828; KS-interleukin-2; Uteroglobin; A 6; NSC 639366 (1-[3-(Diethylamino)-2-hydroxypropylamino]-4-(oxyran-2-ylmethylamino)anthraquinone fumerate) (C24 H29 N3 O4. C4 H4 O4); ISV 616; anti-ED-B fusion proteins; HUI 77; Troponin I; BC-1 monoclonal antibody; SPV 5.2; ER 68203; CKD 731 (3-(3,4,5-Trimethoxyphenyl)-2(E)-propenoic acid (3R, 4S,5S,6R)-4-[2(R)-methyl-3(R)-(3-methyl-2-butenyl)oxiran-2-yl]-5-methoxy-1-oxaspiro[2.5]oct-6-yl ester) (C28 H38 O8); IMC-1C11; aaATIII; SC 7; CM 101; Angiocol; Kringle 5; CKD 732 (3-[4-[2-(Dimethylamino)ethoxy]phenyl]-2(E)-propenoic acid)(C29 H41 N O6); U 995; Canstatin; SQ 885; CT 2584 (1-[11-(Dodecylamino)-10-hydroxyundecyl]-3,7-dimethylxanthine)(C30 H55 N5 O3); Salmosin; EMAP II; TX 1920 (1-(4-Methylpiperazino)-2-(2-nitro-1H-1-imidazoyl)-1-ethanone) (C10 H15 N5 O3); Alpha-v Beta-x inhibitor; CHIR 11509 (N-(1-Propynyl)glycyl-[N-(2-naphthyl)]glycyl-[N-(carbamoylmethyl)]glycine bis(4-methoxyphenyl)methylamide)(C36 H37 N5 O6); BST 2002; BST 2001; B 0829; FR 111142; 4,5-Dihydroxy-2(E)-hexenoic acid (3R,4S,5S,6R)-4-[1(R),2(R)-epoxy-1,5-dimethyl-4-hexenyl]-5-methoxy-1-oxaspiro[2.5]octan-6-yl ester (C22 H34 O7); and kinase inhibitors including, but not limited to, N-(4-chlorophenyl)-4-(4-pyridinylmethyl)-1-phthalazinamine; 4-[4-[[[[4-chloro-3-(trifluoromethyl)phenyl]amino] carbonyl]amino]phenoxy]-N-methyl-2-pyridinecarboxamide; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; 3-[(4-bromo-2,6-difluorophenyl)methoxy]-5-[[[[4-(1-pyrrolidinyl)butyl]amino]carbonyl]amino]-4-isothiazolecarboxamide; N-(4-bromo-2-fluorophenyl)-6-methoxy-7-[(1-methyl-4-piperidinyl)methoxy]-4-quinazolinamine; 3-[5,6,7,13-tetrahydro-9-[(1-methylethoxy)methyl]-5-oxo-12H-indeno[2,1-a]pyrrolo[3, 4-c]carbazol-12-yl]propyl ester N,N-dimethyl-glycine; N-[5-[[[5-(1,1-dimethylethyl)-2-oxazolyl]methyl]thio]-2-thiazolyl]-4-piperidinecarboxamide; N-[3-chloro-4-[(3-fluorophenyl)methoxy]phenyl]-6-[5-[[[2-(methylsulfonyl) ethyl]amino]methyl]-2-furanyl]4-quinazolinamine; 4-[(4-Methyl-1-piperazinyl)methyl]-N-[4-methyl-3-[[4-(3-pyridinyl)-2-pyrimidinyl]amino]-phenyl]benzamide; N-(3-chloro-4-fluorophenyl)-7-methoxy-6-[3-(4-morpholinyl) propoxy]-4-quinazolinamine; N-(3-ethynylphenyl)-6,7-bis (2-methoxyethoxy)-4-quinazolinamine; N-(3-((((2R)-1-methyl-2-pyrrolidinyl)methyl)oxy)-5-(trifluoromethyl) phenyl)-2-((3-(1,3-oxazol-5-yl)phenyl)amino)-3-pyridinecarboxamide; 2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide; N-[3-(Azetidin-3-ylmethoxy)-5-trifluoromethyl-phenyl]-2-(4- fluoro-benzylamino)-nicotinamide; 6-fluoro-N-(4-(1-methylethyl)phenyl)-2-((4-pyridinylmethyl)amino)-3-pyridinecarboxamide; 2-((4-pyridinylmethyl)amino)-N-(3-(((2S)-2-pyrrolidinylmethyl)oxy)-5-(trifluoromethyl)phenyl)-3-pyridinecarboxamide; N-(3-(1,1-dimethylethyl)-1H-pyrazol-5-yl)-2-((4-pyridinylmethyl)amino)-3-pyridinecarboxamide; N-(3,3-dimethyl-2,3-dihydro-1-benzofuran-6-yl)-2-((4-pyridinylmethyl)amino)-3-pyridinecarboxamide; N-(3-((((2S)-1-methyl-2-pyrrolidinyl)methyl)oxy)-5-(trifluoromethyl)phenyl)-2-((4-pyridinylmethyl)amino)-3-pyridinecarboxamide; 2-((4-pyridinylmethyl)amino)-N-(3-((2-(1-pyrrolidinyl)ethyl)oxy)-4-(trifluoromethyl)phenyl)-3-pyridinecarboxamide; N-(3,3-dimethyl-2,3-dihydro-1H-indol-6-yl)-2-((4-pyridinylmethyl)amino)-3-pyridinecarboxamide; N-(4-(pentafluoroethyl)-3-(((2S)-2-pyrrolidinylmethyl)oxy)phenyl)-2-((4-pyridinylmethyl)amino)-3-pyridinecarboxamide; N-(3-((3-azetidinylmethyl)oxy)-5-(trifluoromethyl)phenyl)-2-((4-pyridinylmethyl)amino)-3-pyridinecarboxamide; N-(3-(4-piperidinyloxy)-5-(trifluoromethyl)phenyl)-2-((2-(3-pyridinyl)ethyl)amino)-3-pyridinecarboxamide; N-(4,4-dimethyl-1,2,3,4-tetrahydro-isoquinolin-7-yl)-2-(1H-indazol-6-ylamino)-nicotinamide; 2-(1H-indazol-6-ylamino)-N-[3-(1-methylpyrrolidin-2-ylmethoxy)-5-trifluoromethyl-phenyl]-nicotinamide; N-[1-(2-dimethylamino-acetyl)-3,3-dimethyl-2,3-dihydro-1H-indol-6-yl]-2-(1H-indazol-6-ylamino)-nicotinamide; 2-(1H-indazol-6-ylamino)-N-[3-(pyrrolidin-2-ylmethoxy)-5-trifluoromethyl-phenyl]-nicotinamide; N-(1-acetyl-3,3-dimethyl-2,3-dihydro-1H-indol-6-yl)-2-(1H-indazol-6-ylamino)-nicotinamide; N-(4,4-dimethyl-1-oxo-1,2,3,4-tetrahydro-isoquinolin-7-yl)-2-(1H-indazol-6-ylamino)-nicotinamide; N-[4-(tert-butyl)-3-(3-piperidylpropyl)phenyl][2-(1H-indazol-6-ylamino)(3-pyridyl)]carboxamide; N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide, and kinase inhibitors disclosed in U.S. Pat. Nos. 6,258,812; 6,235,764; 6,630,500; 6,515,004; 6,713,485; 5,521,184; 5,770,599; 5,747,498; 5,990,141; U.S. Publication No. U.S. 20030105091; and Patent Cooperation Treaty publication nos. WO01/37820; WO01/32651; WO02/68406; WO02/66470; WO02/55501; WO04/05279; WO04/07481; WO04/07458; WO04/09784; WO02/59110; WO99/45009; WO98/35958; WO00/59509; WO99/61422; WO00/12089; and WO00/02871, each of which publications are hereby incorporated by reference for any purpose.

In certain embodiments, a specific binding agent to HGF may be administered prior to, concurrent with, and subsequent to treatment with a cancer therapy agent. In certain embodiments, a specific binding agent to HGF may be administered prophylactially to prevent or mitigate the onset of bone loss by metastatic cancer. In certain embodiments, a specific binding agent to HGF may be administered for the treatment of an existing condition of bone loss due to metastasis.

Exemplary cancers include, but are not limited to, breast cancer, colorectal cancer, gastric carcinoma, glioma, head and neck squamous cell carcinoma, hereditary and sporadic papillary renal carcinoma, leukemia, lymphoma, Li-Fraumeni syndrome, malignant pleural mesothelioma, melanoma, multiple myeloma, non-small cell lung carcinoma, osteosarcoma, ovarian cancer, pancreatic cancer, prostate cancer, small cell lung cancer, synovial sarcoma, thyroid carcinoma, and transitional cell carcinoma of urinary bladder.

In certain embodiments, a specific binding agent to HGF may be used alone or with at least one additional therapeutic agents for the treatment of cancer. In certain embodiments, a specific binding agent to HGF is used in conjunction with a therapeutically effective amount of an additional therapeutic agent. Exemplary therapeutic agents that may be administered with a specific binding agent to HGF include, but are not limited to, a member of the geldanamycin family of anisamycin antibiotics; a Pro-HGF; NK2; a c-Met peptide inhibitor; an antagonist of Grb2 Src homology 2; a Gab1 modulator; dominant-negative Src; a von-Hippel-Lindau inhibitor, including, but not limited to, wortmannin; P13 kinase inhibitors, other anti-receptor therapies, anti EGFR, a COX-2 inhibitor, Celebrex®, Vioxx®; a vascular endothelial growth factor (VEGF), a VEGF modulator, a fibroblast growth factor (FGF), an FGF modulator, an epidermal growth factor (EGF); an EGF modulator; a keratinocyte growth factor (KGF), a KGF-related molecule, a KGF modulator; a matrix metalloproteinase (MMP) modulator.

In certain embodiments, a specific binding agent to HGF is used with particular therapeutic agents to treat various cancers. In certain embodiments, a specific binding agent to HGF is used with particular therapeutic agents to treat or prevent malaria. In certain embodiments, a specific binding agent to HGF is used with particular therapeutic agents to treat or prevent proliferative diabetic retinopathy. In certain embodiments, in view of the condition and the desired level of treatment, two, three, or more agents may be administered. In certain embodiments, such agents may be provided together by inclusion in the same formulation. In certain embodiments, such agents and a specific binding agent to HGF may be provided together by inclusion in the same formulation. In certain embodiments, such agents may be formulated separately and provided together by inclusion in a treatment kit. In certain embodiments, such agents and a specific binding agent to HGF may be formulated separately and provided together by inclusion in a treatment kit. In certain embodiments, such agents may be provided separately. In certain embodiments, when administered by gene therapy, the genes encoding protein agents and/or a specific binding agent to HGF may be included in the same vector. In certain embodiments, the genes encoding protein agents and/or a specific binding agent to HGF may be under the control of the same promoter region. In certain embodiments, the genes encoding protein agents and/or a specific binding agent to HGF may be in separate vectors.

In certain embodiments, the invention provides for pharmaceutical compositions comprising a specific binding agent to HGF together with a pharmaceutically acceptable diluent, carrier, solubilizer, emulsifier, preservative and/or adjuvant.

In certain embodiments, the invention provides for pharmaceutical compositions comprising a specific binding agent to HGF and a therapeutically effective amount of at least one additional therapeutic agent, together with a pharmaceutically acceptable diluent, carrier, solubilizer, emulsifier, preservative and/or adjuvant.

In certain embodiments, the present invention is directed to therapies comprising a specific binding agent to HGF and at least one serine protease inhibitor, and methods of treatment using such therapies. In certain embodiments, a therapy comprises a specific binding agent to HGF and a serine protease inhibitor and at least one additional molecule described herein.

In certain instances, a disturbance of the protease/protease inhibitor balance can lead to protease-mediated tissue destruction, including, but not limited to, tumor invasion of normal tissue leading to metastasis.

In certain embodiments, a specific binding agent to HGF may be used with at least one therapeutic agent for inflammation. In certain embodiments, an a specific binding agent to HGF may be used with at least one therapeutic agent for an immune disorder. Exemplary therapeutic agents for inflammation and immune disorders include, but are not limited to cyclooxygenase type 1 (COX-1) and cyclooxygenase type 2 (COX-2) inhibitors small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and Ick. Certain exemplary therapeutic agents for inflammation are described, e.g., in C. A. Dinarello and L. L. Moldawer *Proinflammatory and Anti-Inflammatory Cytokines in Rheumatoid Arthritis: A Primer for Clinicians* Third Edition (2001) Amgen Inc. Thousand Oaks, Calif.

In certain embodiments, pharmaceutical compositions will include more than one different a specific binding agent to HGF. In certain embodiments, pharmaceutical compositions will include more than one a specific binding agent to HGF wherein the specific binding agents to HGF bind more than one epitope.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1990).

In certain embodiments, a specific binding agent to HGF and/or a therapeutic molecule is linked to a half-life extending vehicle known in the art. Such vehicles include, but are not limited to, polyethylene glycol, and dextran. Such vehicles are described, e.g., in U.S. application Ser. No. 09/428,082 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefore. In certain embodiments, a composition comprising a specific binding agent to HGF, with or without at least one additional therapeutic agents, may be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising a specific binding agent to HGF, with or without at least one additional therapeutic agents, may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition may be in the form of a pyrogen-free, parenterally acceptable aqueous solution comprising a desired specific binding agent to HGF, with or without additional therapeutic agents, in a pharmaceutically acceptable vehicle. In certain embodiments, a vehicle for parenteral injection is sterile distilled water in which a specific binding agent to HGF, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, a specific binding agent to HGF, with or without at least one additional therapeutic agent, may be formulated as a dry powder for inhalation. In certain embodiments, an inhalation solution comprising a specific binding agent to HGF, with or without at least one additional therapeutic agent, may be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments, a specific binding agent to HGF, with or without at least one additional therapeutic agents, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of a specific binding agent to HGF and/or any additional therapeutic agents. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of a specific binding agent to HGF, with or without at least one additional therapeutic agents, in a mixture with non-toxic excipients which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving specific binding agents to HGF, with or without at least one additional therapeutic agents, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058, 481), copolymers of L-glutamic acid and gamma ethyl-L-glutamate (Sidman et al., *Biopolymers,* 22:547-556 (1983)), poly(2-hydroxyethyl-methacrylate) (Langer et al., *J. Biomed. Mater. Res.,* 15:167-277 (1981) and Langer, *Chem. Tech.,* 12:98-105 (1982)), ethylene vinyl acetate (Langer et al., supra) or poly-D(−)-3-hydroxybutyric acid (EP 133,988). In certain embodiments, sustained release compositions may also include liposomes, which can be prepared by any of several methods known in the art. See, e.g., Eppstein et al., *Proc. Nat. Acad. Sci. USA,* 82:3688-3692 (1985); EP 036, 676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, the present invention is directed to kits for producing a single-dose administration unit. In certain embodiments, the kits may each contain both a first container having a dried protein and a second container having an aqueous formulation. In certain embodiments of this invention, kits containing single and multi-chambered pre-filled syringes (e.g., liquid syringes and lyosyringes) are included.

In certain embodiments, the effective amount of a pharmaceutical composition comprising a specific binding agent to HGF, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a specific binding agent to HGF, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of a specific binding agent to HGF and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising a specific binding agent to HGF, with or without at least one additional therapeutic agent, in an ex vivo manner. In such instances, cells, tissues and/or organs that have been removed from the patient are exposed to a pharmaceutical composition comprising a specific binding agent to HGF, with or without at least one additional therapeutic agent, after which the cells, tissues and/or organs are subsequently implanted back into the patient.

In certain embodiments, a specific binding agent to HGF and/or any additional therapeutic agents can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved, are provided for illustrative purposes only and are not to be construed as limiting the present invention.

Example 1

Generation of Anti-HGF Hybridomas

Antibodies to HGF were raised in XenoMouse® mice (Abgenix, Fremont, Calif.), which are mice containing human immunoglobulin genes. Three groups of XenoMouse® mice, groups 1a, 1b, and 2, were used to produce antibodies to HGF and are summarized in Table 1. Group 1a consisted of mice of the XenoMouse® strain XMG2, which produces fully human $IgG2_\kappa$ antibodies. Group 1a mice were immunized with HGF. HGF was prepared using standard recombinant techniques using the sequence in Nakamura et al., *Nature* 342: 440-443 (1989).

Group 1b also consisted of mice of the XenoMouse® strain XMG2, but Group 1b mice were immunized with HGF that had been chemically conjugated to a T-cell epitope (TCE) having the sequence: Gln Tyr Ile Lys Ala Asn Ser Lys Phe Ile Gly Ile Thr Glu Leu Lys Lys Cys (SEQ ID NO. 47). The TCE was conjugated to HGF by cross-linking through the C-terminal cysteine of TCE to the N-terminus of HGF using Sulpho-SMCC (Pierce, cat#22322) and dithiothreiotol (Fisher Scientific). The resulting conjugated TCE-HGF was separated from unconjugated peptide using a Centricon® column (Amicon).

Group 2 consisted of mice of the XenoMouse® strain XMG1, which produce fully human $IgG1_\kappa$ antibodies. Group 2 mice were immunized with the conjugated TCE-HGF described above.

The mice of all three groups were injected with antigen (either HGF or TCE-HGF) eight times, according to the schedule in Table 1. In the initial immunizations, each mouse was injected with a total of 10 µg of antigen in the hind footpads (5 µg per footpad). Those injections contained the adjuvant TiterMax® Gold (Sigma, Cat # T2684). In injections 2 through 7, each mouse was injected with a total of 5 µg of antigen in the adjuvant alum gel (aluminum phosphate gel adjuvant; Superfos Biosector a/s, distributed by E. M. Sargent Pulp and Chemical Co., Clifton N.J., cat #1452-250). The final injection contained a total of 10 µg of antigen per mouse and did not contain an adjuvant.

TABLE 1

| Immunization of Mice | | | |
|---|---|---|---|
| | Group 1a | Group 1b | Group 2 |
| Strain | XMG2 | XMG2 | XMG1 |
| # of mice | 8 | 8 | 10 |
| Antigen | HGF | HGF-TCE | HGF-TCE |
| 1st Injection (day 1) | 10 µg/mouse in TiterMax Gold | 10 µg/mouse in TiterMax Gold | 10 µg/mouse in TiterMax Gold |
| 2nd boost (day 7) | 5 µg/mouse in Alum Gel | 5 µg/mouse in Alum Gel | 5 µg/mouse in Alum Gel |
| 3rd boost (day 9) | 5 µg/mouse in Alum Gel | 5 µg/mouse in Alum Gel | 5 µg/mouse in Alum Gel |
| 4th boost (day 13) | 5 µg/mouse in Alum Gel | 5 µg/mouse in Alum Gel | 5 µg/mouse in Alum Gel |
| 5th boost (day 16) | 5 µg/mouse in Alum Gel | 5 µg/mouse in Alum Gel | 5 µg/mouse in Alum Gel |
| 6th boost (day 20) | 5 µg/mouse in Alum Gel | 5 µg/mouse in Alum Gel | 5 µg/mouse in Alum Gel |
| Bleed (day 22) | | | |
| 7th boost (day 24) | 5 µg/mouse in Alum Gel | 5 µg/mouse in Alum Gel | 5 µg/mouse in Alum Gel |
| 8th boost (day 27) | 5 µg/mouse in D-PBS | 5 µg/mouse in D-PBS | 5 µg/mouse in D-PBS |

Each mouse was bled two days after the sixth injection. Blood samples from those bleeds were assayed by ELISA to determine the titer of antibodies to HGF. In those ELISA assays, 96-well plates (Fisher Scientific cat. #12-565-136) were coated with HGF in 0.1 M carbonate buffer (pH 9.6). The blood samples were added and the plates were incubated for two hours at room temperature. After incubation, the plates were washed three times with washing solution (0.05% Tween 20 in PBS) and 100 µl/well of secondary antibody was added. The secondary antibody was goat anti-human IgGFc antibody conjugated with horse radish peroxidase (Southern Biotech cat. #9060-05). After incubation for 1 hour at room temperature, the plates were washed and 100 µl/well of TMB developing solution (BioFX Lab Cat. # TMSK-0100-01) was added. After 10 minutes, 50 µl/well of TMB stop solution (BioFX Lab Cat. # STPR-0100-01) was added. The plates were read on an ELISA plate reader at wavelength 450 nm.

Four days after the final injection, the mice were sacrificed and their draining lymph nodes were harvested and the lymphocytes were recovered. Lymphocytes from the mice of each of the three groups were separately pooled. To enrich the lymphocyte samples for B-cells, T-cells were depleted by adding anti-CD90 magnetic beads (Miltenyi Biotech cat. #491-01) and then passing the lymphoscytes through an $LS^+$ column (Miltenyi Biotech cat. #424-01).

Each of the three samples of B-cell enriched lymphocytes was then fused with P3 myeloma cells using an electrocell fusion device (Genetronic, Inc., Model ECM 2001) to create hybridomas. The three groups of fused hybridoma lines were then plated in 96-well plates at a density of $1\times10^6$ input B-cell enriched lymphocytes per well in hybridoma media (for components see Table 2) containing hypoxantinine-azaserine (Sigma). The hybridoma lines were cultured for 14 days at 37° C., in 15% $CO_2$.

After 14 days, culture supernatants were assayed by ELISA to detect the presence of human IgG antibodies to HGF using the same protocol as was used to assay the blood samples, described above. Culture supernatants that tested positive in that ELISA were tested for the presence of human kappa chain in a second ELISA. In that second ELISA, the conditions were identical to the first ELISA, except that the secondary antibody was a goat anti-human kappa chain antibody conjugated to horseradish peroxidase. Hybridomas that tested positive in both ELISA assays were further expanded to produce 5 ml of supernatant for in vitro functional testing, which is discussed in Examples 8 and 9. Supernatants from 82 clones corresponding to mice from group 1a, 42 clones corresponding to mice from group 1b, and 176 clones corresponding to mice from group 2 were tested.

Based on the results of those functional assays, several hybridoma lines were identified as producing antibodies to HGF. Limiting dilution was used to isolate three to six clones from each line. The clones were designated by hybridoma line number (e.g. 1.24) and clone number (e.g. 1.24.1). No difference among the different clones of a particular line have been detected by the functional assays discussed in Examples 8 and 9. Those isolated clones were each expanded in 50-100 ml of hybridoma media and allowed to grow to exhaustion, (i.e., less than about 10% cell viability). The concentration and potency of the antibodies to HGF in the supernatants of those cultures were determined by ELISA and by in vitro functional testing, as discussed in Examples 8 and 9. The ten hybridomas with the highest titer of Antibodies to HGF were identified. Those hybridomas were designated 1.24.1, 1.29.1, 1.60.1, 1.61.3, 1.74.3, 1.75.1, 2.4.4, 2.12.1, 2.40.1, and 3.10.1.

TABLE 2

| Component | Source |
|---|---|
| Composition of Media | |
| Hybridoma Media | |
| DMEM | Gibco |
| 15% Fetal Bovine Serum | Hyclone, cat # SH 30070.03 |
| 1% 200 mM L-glutamine | Sigma, cat # G2150 |
| 1% 100X non-essential amino acids | Sigma cat # M 7145 |
| 1% 100X pen/strep | Sigma Cat# P 7539 (10,000 U/ml penicillin/10 mg/ml streptomycin) |
| 10 U/ml IL-6 | Boehringer Mannheim, cat. # 1299972 |
| 1 vial/L OPI media Supplement (oxaloacetate, pyruvate, bovine insulin) | Sigma, cat # O 5003 |
| HSFM MEDIA | |
| HSFM | Gibco, Cat # 12045-076 |
| 10% Ultra Low IgG serum | Gibco Cat# 16250-078 |
| 2 mmol/L L-glutamine | JRH 200 mM Cat# 59202 |
| 1% 100X non-essential amino acids | JRH 100X Cat# 58572 |
| 1% 100X pen/strep | Gemini Cat# 400-109 |
| INTEGRA MEDIA | |
| HSFM | Gibco, Cat # 12045-076 |
| 10% Ultra Low IgG serum | Gibco Cat# 16250-078 |
| 2 mmol/L L-glutamine | JRH 200 mM Cat# 59202 |
| 1% NEAA | JRH 100X Cat# 58572 |
| 4 g/L glucose | JT Baker Cat # 1920-07 |

Example 2

Production of Antibodies from the Hybridomas

Antibodies were prepared from the ten hybridomas discussed in Example 1 using one of two different systems: Integra flasks and sparged spinners.

Integra Flasks

Seven hybridoma lines, 2.12.1, 1.24.2, 1.29.1, 1.74.1, 1.75.1, 1.60.2, and 2.40.1, were each separately grown in T75 flasks in 20 ml of HSFM media (see Table 2 for media components). When the hybridomas were nearly confluent in the T75 flasks, they were transferred to Integra flasks (Integra Biosciences, Integra CL1000, cat#90 005).

The Integra flask is a cell culture flask that is divided by a membrane into two chambers, a small chamber and a large chamber. A volume of 20-30 ml Hybridoma cells at a minimum cell density of $1\times10^6$ cells per ml from each of the seven hybridoma lines were placed into the small chamber of seven Integra flasks in Integra media (see Table 2 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber.

After one week, media was removed from both chambers of each of the seven Integra flasks and was replaced with fresh Integra media. The collected media from the seven small chambers were separately retained. After a second week of growth, the media from the small chambers was again collected. The collected media from week 1 from each hybridoma line was combined with the collected media from week 2 from the same hybridoma line. The resulting seven collected media samples from the seven hybridoma lines were spun to remove cells and debris (15 minutes at 3000 rpm) and the resulting supernatants were filtered (0.22 um).

Sparged Spinner Flasks (3 L)

Three hybridoma lines, 3.10.1, 2.4.4, and 2.12.1 were separately grown in T75 flasks in 20 ml of HSFM medium. When the hybridomas reached sufficient cell density, they were transferred to T175 flasks. Likewise, when the hybridomas reached sufficient cell density in the T175 flasks, they were transferred to 100 ml spinner flasks and then to 500 ml spinner flasks, and then to 1 L spinner flasks. When the cells reached sufficient cell density in the 1 L spinner flasks, they were transferred to 3 L sparged spinner flasks (Bellco Biotechnology, cat #1965-300, with sidearm fitting, cat #1965-30003).

The 3 L sparged spinner flask is a glass vessel where cultures are mixed with an impeller controlled by a magnetic platform. The spinner is connected to gas line to provide 5% $CO_2$ and air.

Hybridoma 3.10.1

Two 3 L sparged spinner flasks were seeded with hybridoma cells from hybridoma line 3.10.1 in HSFM media with the additions noted in Table 3, which summarizes the growth conditions for those two sparged flasks.

TABLE 3

| Conditions for Growing Hybridoma 3.10.1. | | |
| --- | --- | --- |
| Conditions | Spinner 1 | Spinner 2 |
| Seeding density (10E6 cells/ml) | 0.46 | 0.46 |
| HSFM (Gibco cat# 12045-076) | X | X |
| Ultra low IgG serum (Gibco cat# 16250-078) | 5% | 5% |
| L glutamine (JRH cat# 59202-500M) | 8 mmol/L | 2 mmol/L |
| P/S (Gemini cat# 400-109) | 1% | 1% |
| NEAA (JRH cat# 58572-77P) | 1% | 1% |
| Peptone (Difco, cat # 211693) | 1 g/L | 1 g/L |
| 2M glucose (JT Baker, cat # 1920-07) | 8 g/L | 2 g/L |

TABLE 3-continued

| Conditions for Growing Hybridoma 3.10.1. | | |
| --- | --- | --- |
| Conditions | Spinner 1 | Spinner 2 |
| Antifoam C (Sigma cat # A-8011) | 2 ml/L | 2 ml/L |
| Productivity (μg/ml) | 24 | 34 |

The cultures were grown for 15 days and were harvested when the viability was below 20%, as determined by trypan blue exclusion. Harvesting consisted of centrifugation for 15 minutes at 700 rpm and subsequent filtration of the resulting supernatant through a 0.22 μm filter. Productivity was determined by measuring the amount of protein present in the final harvested samples by protein A HPLC and is reported in Table 3.

Hybridoma 2.4.4

Five 3 L sparged spinner flasks were seeded with hybridoma cells from hybridoma line 2.4.4 in HSFM media with the additions noted in Table 4, which summarizes the growth conditions for those five sparged flasks.

TABLE 4

| Conditions for Growing Hybridoma 2.4.4. | | | | | |
| --- | --- | --- | --- | --- | --- |
| Conditions | Spinner 1 | Spinner 2 | Spinner 3 | Spinner 4 | Spinner 5 |
| Seeding density (10E6 cells/ml) | 0.3 | 0.3 | 0.18 | 0.18 | 0.4 |
| HSFM (Gibco cat# 12045-076) | X | X | X | X | X |
| Ultra low IgG serum (Gibco cat# 16250-078) | 5% | 5% | 5% | 5% | 5% |
| L glutamine (JRH cat# 59202-500M) | 8 mmol/L | 2 mmol/L | 2 mmol/L | 8 mmol/L | 4 mmol/L |
| P/S (Gemini cat# 400-109) | 1% | 1% | 1% | 1% | 1% |
| NEAA (JRH cat# 58572-77P) | 1% | 1% | 1% | 1% | 1% |
| Peptone | 1 g/L | 1 g/L | 1 g/L | 1 g/L | 1 g/L |
| 2M glucose | 8 g/L | 2 g/L | 2 g/L | 8 g/L | 4 g/L |
| Antifoam C | 2 ml/L | 2 ml/L | 2 ml/L | 2 ml/L | 2 ml/L |
| Productivity (ug/ml) | 41 | 82 | 38 | 45 | 79 |
| Culture duration (days) | 10 | 10 | 7 | 7 | 8 |

The cultures were grown for 7, 8, or 10 days as indicated in Table 4, and harvested when cell viability was below 20%, as described above.

Hybridoma 2.12.1

Six 3 L sparged spinner flasks were seeded with hybridoma cells from hybridoma line 2.12.1 in HSFM media with the additions noted in Table 5, which summarizes the growth conditions for those six sparged spinner flasks.

TABLE 5

| Conditions for Growing Hybridoma 2.12.1. | | | | | | |
| --- | --- | --- | --- | --- | --- | --- |
| Conditions | Spinner 1 | Spinner 2 | Spinner 3 | Spinner 4 | Spinner 5 | Spinner 6 |
| Seeding density (10E6 cells/ml) | 0.2 | 0.2 | 0.4 | 0.4 | 0.4 | 0.4 |
| HSFM (Gibco cat# 12045-076) | X | X | X | X | X | X |
| Ultra low IgG serum (Gibco cat# 16250-078) | 5% | 5% | 5% | 5% | 5% | 5% |
| L glutamine (JRH cat# 59202-500M) | 2 mmol/L | 8 mmol/L | 4 mmol/L | 4 mmol/L | 4 mmol/L | 4 mmol/L |
| P/S (Gemini cat# 400-109) | 1% | 1% | 1% | 1% | 1% | 1% |
| NEAA (JRH cat# 58572-77P) | 1% | 1% | 1% | 1% | 1% | 1% |
| Peptone | 1 g/L | 1 g/L | 1 g/L | 1 g/L | 1 g/L | 1 g/L |
| 2M glucose | 2 g/L | 8 g/L | 4 g/L | 4 g/L | 4 g/L | 4 g/L |
| Antifoam C | 2 ml/L | 2 ml/L | 2 ml/L | 2 ml/L | 2 ml/L | 2 ml/L |
| Productivity (μg/ml) | 44 | 49 | 65 | 65 | 65 | 65 |
| Culture duration (days) | 7 | 7 | 11 | 11 | 11 | 11 |

Cultures were grown for 7 or 11 days, as indicated in Table 5, and were harvested when the viability was below 20%, as described above.

Example 3

Cloning and Sequence Analysis of Antibody Heavy and Light Chains

A. Cloning of Light Chains

Ten hybridomas (1.24.1, 1.29.1, 1.60.1, 1.61.3, 1.74.3, 1.75.1, 2.4.4, 2.12.1, 2.40.1, and 3.10.1) were identified as expressing monoclonal antibodies to HGF, as discussed in Example 1. Total RNA was isolated from each of those ten hybridomas using TRIzol® reagent (Invitrogen, Carlsbad, Calif.). The 5'-ends of those ten total RNA preparations were adapted for 5' Rapid Amplification of cDNA Ends (RACE) using the GeneRacer® Kit (Invitrogen). Those ten 5'-modified RNA preparations were then used in ten separate RACE reactions, each using a random primer with an extension adapter (5'-GGC CGG ATA GGC CTC CAN NNN NNT-3') (SEQ ID NO: 48), to generate ten cDNA molecules.

The ten cDNA molecules were then amplified in separate polymerase chain reactions (PCR) to generate ten amplified kappa light chain sequences. For each of those reactions, the forward primer was the forward GeneRacer™ nested primer (5' GGA CAC TGA CAT GGA CTG MG GAG TA-3') (SEQ ID NO: 49). The reverse primer (5'-GGG GTC AGG CTG GAA CTG AGG-3') (SEQ ID NO 50) was designed to bind to the sequence complementary to the kappa light chain.

Each of the ten amplified kappa light chain sequences was then separately ligated into separate pCR4-TOPO plasmids (Invitrogen). The ten resulting plasmids, each containing one of the ten kappa light chain sequences, were then separately amplified in bacteria and several clones of each were sequenced. Those sequences were used to design PCR primers to amplify the ten kappa light chain open reading frame sequences from the cloned plasmids as follows.

The primer sets for each of the ten PCRs comprised a 5'-primer and a 3'-primer. Each 5'-primer comprised a portion complementary to the sequence of the amino terminus of the particular kappa light chain sequence, an optimized Kozak sequence, and one or more restriction sites. For example, the sequence of the 5'-primer used in the reaction with the plasmid ultimately derived from hybridoma 3.10.1 was:

```
5'- ACA ACA AAG CTT CTA GAC CAC CAT    (SEQ ID: 51)
             XbaI    Kozak

GGA AGC CCC AGC TCA GCT TCT CTT -3'
```

The 3'-primer for each of the PCRs comprised a portion complementary to the carboxyl terminus of the sequence of the particular kappa light chain sequence, including the termination codon and a restriction site. For example, the sequence of the 3'-primer used in the reaction with the plasmid ultimately derived from hybridoma 3.10.1 was:

```
5'- CTT GTC GAC TCA ACA CTC TCC   (SEQ ID NO: 52)
        SalI    *

CCT GTT GAA GCT C -3'
```

Separate primer sets were used in separate PCR reactions with the corresponding cloned plasmids to amplify the ten kappa light chain coding region sequences. The ten amplification products from those reactions were separately gel isolated and purified using a QIAquick® Gel Extraction kit (Catalog No. 28704, Qiagen, Valencia, Calif.). Those purified products were then each cut with the appropriate restriction enzymes to obtain the kappa light chain coding region sequences free from the plasmid. For example, the purified product corresponding to hybridoma 3.10.1 was cut with XbaI and SalI, the sites which were introduced by the primers during PCR amplification of that cloned plasmid, as discussed above. The resulting restriction digested kappa light chain coding region sequences were again separately gel isolated and purified using a QIAquick® Gel Extraction kit (Catalog No. 28704, Qiagen, Valencia, Calif.).

Those ten purified restriction digested kappa light chain coding region sequences were then each separately ligated into mammalian expression vector, pDSRα20 (WO 90/14363), to create ten separate kappa light chain expression vectors corresponding to the ten original hybridomas. The ten kappa light chain expression vector inserts were then sequenced. The pDSRα20 expression vector containing the kappa light chain coding region ultimately derived from hybridoma 3.10.1 (pDSRα20:3.10.1) was confirmed to comprise 5473 base pairs including a 719 base pair PCR fragment, which encoded the 235 amino acid residues (including the 20 amino acid kappa chain signal sequence) of the 3.10.1 kappa light chain. That expression vector comprised seven functional regions, as described in Table 6.

TABLE 6

Expression Vector pDSRα20:3.10.1kappa

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, *Nucleic Acids Res.* 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U.S.A.* 79: 6522-6; Nunberg et al., 1980, *Cell* 19: 355-64; Setzer et al., 1982, *J. Biol. Chem.* 257: 5143-7; McGrogan et al., 1985, *J. Biol. Chem.* 260: 2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, *Mol. Cell Biol.* 8: 466-72, Genbank Accession Number J02400) |
| 4299 to 4565 | A translational enhancer element from the HTLV-1 LTR domain (Seiki et al., 1983, *Proc. Natl. Acad. Sci. U.S.A.* 80: 3618-22, Genbank Accession Number J02029) |
| 4574 to 4730 | An intron from the SV40 16S, 19S splice donor/acceptor signals (Okayama and Berg, 1983. *Mol. Cell Biol.* 3: 280-9, Genbank Accession Number J02400) |
| 4755 to 5473 | The 3.10.1 kappa light chain cDNA between the XbaI and Sa/1 sites |

B. Cloning of the Heavy Chains

The variable region of the heavy chains of the antibodies to HGF from the ten hybridomas were cloned using the same methods as those used for the light chains discussed above in Example 3A. Total RNA from each of the ten hybridomas was isolated, 5'-modified for RACE, and used to generate cDNA molecules as described above in Example 3A.

Those ten cDNA molecules were amplified in separate PCR reactions as discussed for the light chains in Example 3A, except the reverse primer (5'-GGA CAC TGA CAT GGA CTG MG GAG TA-3' (SEQ ID NO: 53)) was designed to bind to the complementary sequence of the heavy chain variable region. The forward primer was again the forward GeneRacer™ nested primer (5' GGA CAC TGA CAT GGA CTG MG GAG TA-3') (SEQ ID NO: 49).

Each of the ten amplified heavy chain variable region sequences were separately ligated into separate pCR4-TOPO plasmids. The ten resulting plasmids, each containing one of the ten heavy chain variable region sequences, were then separately amplified in bacteria and several clones of each were sequenced as described above for the light chains in Example 3A. Those sequences were used to design PCR primers for amplifying each of the heavy chain variable regions from the cloned plasmids as follows.

The primer sets for each of the ten PCRs were designed using the same strategy as used for the light chains, discussed above in Example 3A. Each 5'-primer comprised a portion complementary to the sequence of the amino terminus of the particular heavy chain variable region sequence, an optimized Kozak sequence, and one or more restriction sites. For example, the sequence of the 5'-primer used for amplifying the heavy chain variable region ultimately derived from hybridoma 3.10.1 was:

5'- AGC AGA AGC <u>TTC TAG ACC ACC</u>   (SEQ ID NO: 54)
             XbaI    Kozak

ATG AAA CAC CTG TGG TTC TTC CTC

CTC -3'

The 3'-primer for each of the ten PCRs comprised a portion complementary to the carboxyl terminus of the consensus sequence of the particular heavy chain variable region sequence, including a termination codon and a restriction site. For example the sequence of the 3'-primer used for amplifying the heavy chain variable region ultimately derived from hybridoma 3.10.1 was:

5'- GTG GAG GCA CTA <u>GAG ACG GTG</u>   (SEQ ID NO: 55)
                      BsmBI

ACC AGG GTT CC -3'

Separate primer sets were used in separate PCR reactions with the corresponding cloned plasmids to amplify the ten heavy chain variable region sequences. The ten amplification products from those reactions were separately gel isolated and purified using a QUIAquick Gel Extraction kit and cut with the appropriate restriction enzymes as described for the light chains in Example 3A. The resulting restriction digested heavy chain variable region sequences were again separately gel isolated and purified using a QUIAquick Gel Extraction kit as described in Example 3A.

Three of those ten purified restriction digested heavy chain variable region sequences, those ultimately derived from hybridoma 3.10.1, 1.24.1, and 2.4.4, were then separately ligated into mammalian expression vector pDSRα20:hIgGC$_H$ to create three heavy chain IgG1 expression vectors. The pDSRα20:hIgGC$_H$ expression vector is the same as pDSRα20 except that it also contains the IgG1 constant region sequence. The pDSRα20:hIgGC$_H$ expression vector is summarized in Table 7.

TABLE 7

Expression Vector pDSRα20:hIgGC$_H$

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, Nucleic Acids Res. 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, Proc. Natl. Acad. Sci. U.S.A. 79: 6522-6; Nunberg et al., 1980, Cell 19: 355-64; Setzer et al., 1982, J. Biol. Chem. 257: 5143-7; McGrogan et al., 1985, J. Biol. Chem. 260: 2307-14) |
| 2031 to 3947 | pBR322 sequences containing the ampicillin resistance marker gene and the origin for replication of the plasmid in E. coli (Genbank Accession Number J01749) |
| 3949 to 4292 | An SV40 early promoter, enhancer and origin of replication (Takebe et al.,1988, Mol. Cell Biol. 8: 466-72, Genbank Accession Number J02400) |
| 4299 to 4565 | A translational enhancer element from the HTLV-1 LTR domain (Seiki et al., 1983, Proc. Natl. Acad. Sci. U.S.A. 80: 3618-22, Genbank Accession Number J02029) |
| 4574 to 4730 | An intron from the SV40 16S, 19S splice donor/acceptor signals (Okayama and Berg, 1983. Mol. Cell Biol. 3: 280-9, Genbank Accession Number J02400) |
| 4755 to 5791 | The p1/hCh1 heavy chain cDNA between the XbaI and SalI sites. The sequences of which follows:<br>  XbaI                                      BsmBI<br>TCTAGACCACCGCCATGGGTGAAAATTGAATCGTCTCTA<br>GTGCCTCCACCAAGGGCCCA TCGGTCTTCC CCCTGGCACC<br>CTCCTCCAAG AGCACCTCTGGGGGCACAGC |

TABLE 7-continued

Expression Vector pDSRα20:hIgGC<sub>H</sub>

Plasmid Base Pair Number:

```
            GGCCCTGGGC TGCCTGGTCA AGGACTACTT
            CCCCGAACCG GTGACGGTGT CGTGGAACTC
            AGGCGCCCTG ACCAGCGGCG TGCACACCTT
            CCCGGCTGTC CTACAGTCCT CAGGACTCTA CTCCCTCAGC
            AGCGTGGTGACCGTGCCCTC CAGCAGCTTG GGCACCCAGA
            CCTACATCTG CAACGTGAATCACAAGCCCA GCAACACCAA
            GGTGGACAAG AAAGTTGAGC CCAAATCTTG TGACAAAACT
            CACACATGCC CACCGTGCCC AGCACCTGAA
            CTCCTGGGGG GACCGTCAGT CTTCCTCTTC CCCCCAAAAC
            CCAAGGACAC CCTCATGATC TCCCGGACCC CTGAGGTCAC
            ATGCGTGGTG GTGGACGTGA GCCACGAAGACCCTGAGGTC
            AAGTTCAACT GGTACGTGGA CGGCGTGGAG GTGCATAATG
            CCAAGACAAA GCCGCGGGAG GAGCAGTACA
            ACAGCACGTA CCGTGTGGTC AGCGTCCTCA CCGTCCTGCA
            CCAGGACTGG CTGAATGGCA AGGAGTACAAGTGCAAGGTC
            TCCAACAAAG CCCTCCCAGC CCCCATCGAG
            AAAACCATCTCCAAAGCCAA AGGGCAGCCC CGAGAACCAC
            AGGTGTACAC CCTGCCCCCA TCCCGGGATG AGCTGACCAA
            GAACCAGGTC AGCCTGACCT GCCTGGTCAA AGGCTTCTAT
            CCCAGCGACA TCGCCGTGGA GTGGGAGAGC
            AATGGGCAGCCGGAGAACAA CTACAAGACC ACGCCTCCCG
            TGCTGGACTC CGACGGCTCC TTCTTCCTCT ATAGCAAGCT
            CACCGTGGAC AAGAGCAGGT GGCAGCAGGG
            GAACGTCTTC TCATGCTCCG TGATGCATGA GGCTCTGCAC
            AACCACTACA CGCAGAAGAG CCTCTCCCTG TCTCCGGGTA
                       SalI
            AATGATAAGT CGAC (SEQ ID NO: 56)
```

The heavy chain variable regions of the three IgG1 expression vector inserts were sequenced. The pDSRα20:hIgGC<sub>H</sub> expression vector containing the heavy chain variable region ultimately derived from hybridoma 3.10.1 (pDSRα20:hIg-GC<sub>H</sub>:3.10.1) is summarized in Table 8.

TABLE 8

Expression Vector pDSRα20:hIgGC<sub>H</sub>:3.10.1

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, *Nucleic Acids Res.* 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U.S.A.* 79: 6522-6; Nunberg et al., 1980, *Cell* 19: 355-64; Setzer et al., 1982, *J. Biol. Chem.* 257: 5143-7; McGrogan et al., 1985, *J. Biol. Chem.* 260: 2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, *Mol. Cell Biol.* 8: 466-72, Genbank Accession Number J02400) |
| 4299 to 4565 | A translational enhancer element from the HTLV-1 LTR domain (Seiki et al., 1983, *Proc. Natl. Acad. Sci. U.S.A.* 80: 3618-22, Genbank Accession Number J02029) |
| 4574 to 4730 | An intron from the SV40 16S, 19S splice donor/acceptor signals (Okayama and Berg, 1983. *Mol. Cell Biol.* 3: 280-9, Genbank Accession Number J02400) |
| 4755 to 6178 | The 3.10.1 heavy chain IgG1 cDNA between the XbaI and Sa/l sites |

Each of the ten purified heavy chain variable region sequences were separately ligated into a pDSRα20 mammalian expression vector along with sequences encoding the IgG2 constant region to create ten IgG2 expression vectors. Each of the ten resulting IgG2 expression vectors (designated pDSRα20:hIgG2:hybirdoma #) comprised sequences encoding the constant region of IgG2 and one of the ten heavy chain variable region sequences. The ten heavy chain variable region sequence inserts were sequenced to confirm that they comprised the same heavy chain variable region sequences that were identified in the cloned plasmids from the pCR4-TOPO clones. The pDSRα20:hIgG2 expression vector containing the heavy chain variable region ultimately derived from hybridoma 2.12.1 (pDSRα20:hIgG2:2.12.1) is summarized in Table 9.

TABLE 9

Expression Vector pDSRα20:IgG2:2.12.1

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, *Nucleic Acids Res.* 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U.S.A.* 79: 6522-6; Nunberg et al., 1980, *Cell* 19: 355-64; Setzer et al., 1982, *J. Biol. Chem.* 257: 5143-7; McGrogan et al., 1985, *J. Biol. Chem.* 260: 2307-14) |
| 2031 to 3947 | pBR322 sequences containing the ampicillin resistance marker gene and the origin for replication of the plasmid in *E. coli* (Genbank Accession Number J01749) |

TABLE 9-continued

Expression Vector pDSRα20:IgG2:2.12.1

Plasmid Base Pair Number:

| | |
|---|---|
| 3949 to 4292 | An SV40 early promoter, enhancer and origin of replication (Takebe et al., 1988, *Mol. Cell Biol.* 8: 466-72, Genbank Accession Number J02400) |
| 4299 to 4565 | A translational enhancer element from the HTLV-1 LTR domain (Seiki et al., 1983, *Proc. Natl. Acad. Sci. U.S.A.* 80: 3618-22, Genbank Accession Number J02029) |
| 4574 to 4730 | An intron from the SV40 16S, 19S splice donor/acceptor signals (Okayama and Berg, 1983. *Mol. Cell Biol.* 3: 280-9 Genbank Accession Number J02400) |
| 4755 to 6166 | The 2.12.1 heavy chain IgG2 cDNA between the XbaI and Sa/l sites |

The cDNA sequences for the kappa light chain variable regions (SEQ ID NOs.: 1, 3, 5, 7, 9, 11, 13, 15, 17, and 19), the kappa light chain constant region (SEQ ID NO: 21), the heavy chain variable regions (SEQ ID NOs.: 2, 4, 6, 8, 10, 12, 14, 16, 18, and 20), and the IgG1 and IgG2 heavy chain constant regions (SEQ ID NOs: 22 and 23) are shown in FIGS. 3A to 3E.

The polypeptide sequences predicted from each of those cDNA sequences were determined. The predicted polypeptide sequences for the kappa light chain variable regions (SEQ ID NOs: 24, 26, 28, 30, 32, 34, 36, 38, 40, and 42), the kappa light chain constant region (SEQ ID NO 44), the heavy chain variable regions (SEQ. ID NOs. 25, 27, 29, 31, 33, 35, 37, 39, 41, and 43), and the IgG1 and IgG2 heavy chain constant regions (SEQ ID NOs: 45 and 46) are shown in FIGS. 4A to 4C.

Figure 2A:
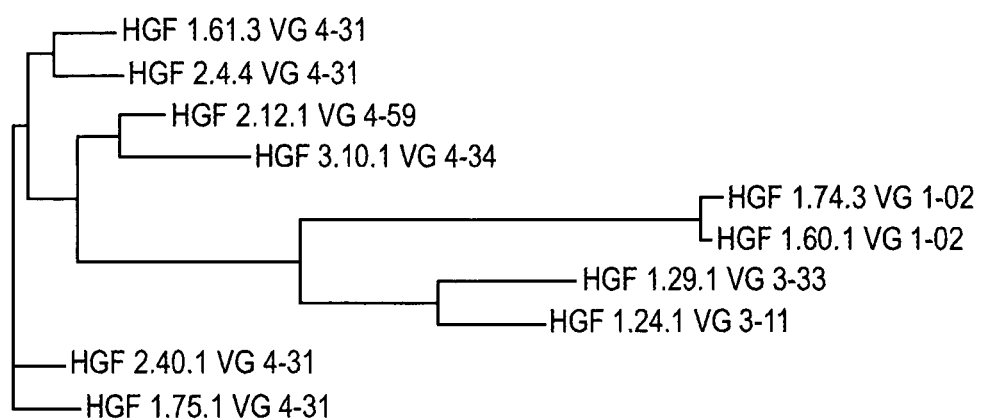

Based on the sequence data, the germline genes from which each heavy chain or light chain variable region was derived was determined. The identity of the germline genes are indicated next to the corresponding hybridoma line in FIGS. 1, 2, 3 and 4. Further analysis of the relatedness of the sequences (FIGS. 1B and 2B) led to the dendrograms displayed in FIG. 1A (kappa light chain variable regions) and FIG. 2A (heavy chain variable regions).

Example 4

Transient Expression in 293T Cells

In ten separate co-transfections, 293T cells were co-transfected with a pDSRα20 expression vector comprising a kappa light chain sequence described in Example 3A (light chain vector) and a pDSRα20 expression vector comprising a heavy chain sequence described in Example 3B (heavy chain vector). In those ten separate co-transfections, 293T cells were co-transfected with both the light chain vector and the heavy chain vector ultimately derived from one of the hybridomas discussed in Example 1. Specifically, for the co-transfection of the vector ultimately derived from hybridoma 3.10.1, the heavy chain vector comprising IgG1 (pDSRα20: hIgGC$_H$:3.10.1) was used. For the co-transfections of the vectors ultimately derived from the other nine hybridomas, the heavy chain comprising IgG2 (pDSRα20:hIgG2:hybridoma #) was used. The co-transfections were performed using either Fugene 6 or X-TremeGene RO-1539 (both from Roche Molecular Biochemicals, Indianapolis, Ind.) following the instructions provided by the manufacturer.

Co-transfections were first conducted using adherent 293T cells in standard roller bottles. The roller bottles were seeded with $4 \times 10^7$ to $5 \times 10^7$ cells per roller bottle in DMEM containing 5% Fetal Bovine Serum (FBS)(Hyclone, cat # SH 30070.03), 1× non-essential amino acids (Sigma, cat # M 7145), 1× penicillin/streptomycin (Sigma, cat # P7539 (10,000 U/ml penicillin/streptomycin)), and 1× sodium pyruvate (Invitrogen, Carlsbad, Calif.). When the cells reached 60-70% confluency, the heavy chain vector and light chain vector ultimately derived from a particular hybridoma were co-transfected into the cells for 24 hours, after which the media was changed to the same media lacking serum. The serum-free media was collected and replaced with fresh serum-free media two times, at 48 and 96 hours post-transfection, yielding a total volume of 1.25 L of collected serum-free media.

The ten separate co-transfections were repeated using serum-free adapted 293T cells in suspension in the same media discussed above lacking serum. The heavy chain vectors and light chain vectors corresponding to a particular hybridoma were co-transfected into the cells in a culture volume of 500 mL. The transfected cells were incubated for 7 days, after which the serum-free conditioned medium was collected.

Example 5

Antibody Expression and Cloning of CHO Cells

Chinese hamster ovary cells deficient in DHFR(CHOd$^-$) were used to generate stable expression of recombinant antibodies to HGF. In ten separate co-transfections, CHOd$^-$ cells were co-transfected with both the heavy chain vector and the light chain vector ultimately derived from one of the hybridomas discussed in Example 1, as discussed in Example 4. The co-transfections were achieved using a standard calcium phosphate method.

Transfected cells from each of the ten co-transfections were separately grown in selection media containing high glucose DMEM lacking hypoxanthine-thymidine (Gibco/BRL, Carlsbad, Calif. Cat #11965) with 5% dialyzed fetal bovine serum. Such media lacking hypoxanthine-thymidine selects for growth of cells expressing the recombinant DHFR enzyme. Media from each of the grown transfectants was screened using standard ELISA assays to detect the presence of the human antibodies.

Example 6

Expression of Antibodies to HGF in CHOd$^-$ Clones

Six samples of each of the ten different stable CHOd$^-$ clones described in Example 5, each different clone expressing one of the ten different antibodies to HGF, were separately grown in growth media. The growth media was DMEM with high glucose (Gibco/BRL, Carlsbad, Calif. Cat #11965), supplemented with 5% dialyzed FBS, non-essential amino acids and L-glutamine (Life Technologies, Carlsbad, Calif.). The cells were grown at 37° C. under 5% CO$_2$.

When the CHOd$^-$ clones reached the six-well stage of growth, 10 nM methotrexate was added to the growth media to amplify expression of the antibodies. After the cells became confluent, they were moved to 100 mm dishes. The methotrexate concentration was stepped up from 10 nM to 20 nM, to 50 nM, to 100 nM, to 250 nm, to 500 nM, to 1 µM, to 2 µM, to 4 µM, and finally to 10 µM. The cells were kept at each concentration for a minimum of one week and until they had sufficiently adapted to a given concentration of methotrexate, as determined visually.

Conditioned media from each of the clones was assayed at each methotrexate concentration to determine the expression level of each antibody to HGF. The media was assayed by standard ELISA and time-resolved fluorescence (TRF) sandwich assays to semi-quantitatively measure binding of the antibodies to HGF to human HGF-coated plates.

Methotreaxate amplified clones with the highest antibody expression levels were adapted to grow in serum free production medium as follows. Clones were trypsinized from the culture vessel, centrifuged and resuspended in 50 ml of serum free production medium at $4 \times 10^5$ cells/ml in a 250 ml solid cap shake flask. Cultures were incubated in a warm room at 37° C. and stirred at approximately 125 RPM. Every 34 days, the cells were spun down and diluted to $4 \times 10^5$ cells/ml with fresh serum free production medium. Fresh serum free production medium was added approximately ten times for each of the cultures to complete this adaptation phase.

Example 7

Antibody Purification from Recombinant Cell Conditioned Media

Media was collected from the hybridomas described in Example 1, from the transient expression 293 T cells described in Example 4, from the stable transfectants described in Example 5, and from the methotrexate amplified clones described in Example 6. Media from each of those sources was separately concentrated about 10-fold using a YM30 spiral wound cartridge (Milipore, Bedford, Mass. Cat #S10Y30) following instructions provided by the manufacturer. The concentration of antibody present in each concentrated media sample was estimated by High Performance Liquid Chromatography (HPLC).

Antibodies were purified from the concentrated media samples by affinity resin purification using recombinant Protein A Sepharose (rProA) (Amersham, Piscataway, N.J., Cat #17-1279-03). The rProA was first washed four times with phosphate buffered saline (PBS). Following the last wash, a slurry of washed rProA in PBS was made by mixing an equal volume of rProA and PBS. That rProA slurry was added to each concentrated media sample at an amount of approximately 1 μl of rProA slurry for each 5 μg of antibody in the media sample, but not less than 50 μl of rProA slurry for any media sample. The resulting media/slurry samples were incubated overnight at 4° C. with shaking. The media/slurry samples were then centrifuged to pellet the rProA. The supernatant fractions containing unbound proteins were discarded. The rProA pellets were separately resuspended in 0.5 ml PBS each. The resuspended rProA samples were then transferred to 0.45 μm Spin-X tubes (CoStar, Corning N.Y., Cat #8162) and spun to remove the PBS. The rProA in the Spin-X-tubes was then washed 3 times with 0.5 ml PBS per wash.

Antibody fractions were eluted from the rProA in the Spin-X tubes by adding 1.5 volumes of 0.1 M glycine, pH 2.7, and incubating for 10 minutes at room temperature. The Spin-X tubes were then centrifuged and the eluates from each Spin-X tube were separately collected. Elution was repeated and the two eluates from each Spin-X tube were pooled. The pH of the pooled eluates was neutralized with $\frac{1}{25}^{th}$ volume of 1.0 M Tris, pH 9.2. Each sample was then filtered through a new Spin-X tube to remove particulates.

The protein concentration of the final preparations was determined by Bradford assay using human IgG as the standard. To assess purity, samples of each of the final preparations were separately run on separate lanes of an SDS-PAGE gel, stained with coomassie and was inspected visually.

Example 8

Characterization of Binding of Antibodies to HGF
A. Affinity Measurements

Using a BIAcore®3000 (Biacore, Inc., Piscataway, N.J.) affinity analysis of six of the antibodies to HGF described in Example 6 (those ultimately derived from hybridomas 3.10.1, 2.4.4, 2.12.1, 1.29.1, 1.75.1, and 1.74.3) was performed according to the manufacturer's instructions. The running buffer for those analyses was PBS with 0.005% P20 surfactant (BIAcore, Inc. Piscataway, N.J.). Recombinant Protein G (Pierce, Rockford, Ill.) was immobilized to a research grade CM5 sensor chip (Biacore, Inc. Piscataway, N.J.) via primary amine groups using the Amine Coupling Kit (Biacore, Inc. Piscataway, N.J.), according to the manufacturer's instructions.

In six separate samples, about 200 resonance units (RU) of each of the six antibodies to HGF was separately attached to immobilized Protein G following the manufacturer's instructions. Samples comprising various concentrations (0-100 nM) of human HGF were injected over the bound antibody surface at a flow rate of 50 μl/min for 3 minutes. Antibody binding kinetic parameters including $k_a$ (association rate constant), $k_d$ (dissociation rate constant), and $K_D$ (dissociation equilibrium constant) were determined using the BIA evaluation 3.1 computer program (BIAcore, Inc. Piscataway, N.J.). Lower dissociation equilibrium constants indicate greater affinity of the antibody for HGF. Data are presented in FIG. 6A.

The $K_D$ values of each of four antibodies to HGF (those ultimately derived from hybridomas 2.4.4, 1.29.1, 1.74.2, and 2.12.1) were also measured using an equilibrium binding method. That method was performed with a BIAcore® 3000 (Biacore, Inc., Piscataway, N.J.) using PBS with 0.005% P20 surfactant (BIAcore, Inc. Piscataway, N.J.) as running buffer. The four antibodies to HGF were separately immobilized to research grade CM5 sensor chips (Biacore, Inc. Piscataway, N.J.) via primary amine groups using an Amine Coupling Kit (Biacore, Inc. Piscataway, N.J.) following the manufacturer's instructions.

In separate assays, each of the four antibodies to HGF, over a range of concentrations (from 0.01 nM to 50 nM) was separately incubated with each of two different concentrations (0.05 nM and 1 nM) of human HGF in PBS with 0.005% P-20 and 0.1 mg/mL BSA at room temperature for at least six hours. Each of those samples was then injected over a surface of a CM5 sensor chip onto which the same antibody to HGF had been immobilized. The binding signal obtained was proportional to the free HGF in solution. The dissociation equilibrium constant ($K_D$) was obtained from nonlinear regression analysis of the competition curves using a dual-curve one-site homogeneous binding model (KinExA software, Sapidyne Instruments Inc., Boise Id.). Those dissociation equilibrium constant values are presented in FIG. 6B.

B. Specificity of Binding of Antibodies to HGF

Human HGF was either expressed in CHO cells or purchased from R&D Systems (R & D Systems, Minneapolis Minn., Cat #294-HG-005). Recombinant mouse HGF was prepared using the sequence in Liu et al., *Molecular cloning and characterization of cDNA encoding mouse hepatocyte growth factor*, Biochim Biophys Acta. 16:1216(2):299-300 (1993). Recombinant mouse HGF was obtained either by expression in insect cells using a baculovirus vector, or by expression in 293T cells. In either event, mouse HGF was purified by heparin sulfate affinity chromatography.

Each of the preparations of human and mouse HGF was shown to be biologically active. Human HGF induced a dose-dependent human Met phosphorylation in human PC3 cells (ATCC Manassas, Va. # CRL 1435) and in mouse 4T1 cells (ATCC Manassas, Va. # CRL 2531). Mouse HGF induced Met phosphorylation in mouse 4T1 cells, but not human PC3 cells.

Human HGF and mouse HGF were run on separate lanes of SDS PAGE gels. Human HGF and mouse HGF were each separately run at 100 ng/lane and at 10 ng/lane. Some gels were run under non-reducing conditions and other separate gels were run under reducing conditions using beta-mercaptoethanol. The human HGF and mouse HGF in the SDS PAGE gels were transferred to nitrocellulose membranes. Those membranes were separately incubated with one of the ten antibodies to HGF described in Example 6. Each of the ten antibodies to HGF was separately incubated with nitrocellulose membranes from gels containing human HGF and mouse HGF under reducing and with nitrocellulose membranes from gels containing human HGF and mouse HGF under non-reducing conditions. The membranes were then incubated with a goat anti-human IgG antibody linked to HRP (Pierce, Rockford, Ill., Cat. #31412). Signal from that goat anti-human IgG antibody linked to HRP was detected by electrochemiluminescence (ECL™; Amersham Pharmacia Biotech, Piscataway, N.J., Cat. # RPN2106) following the manufacturer's instructions.

Figure 7A:
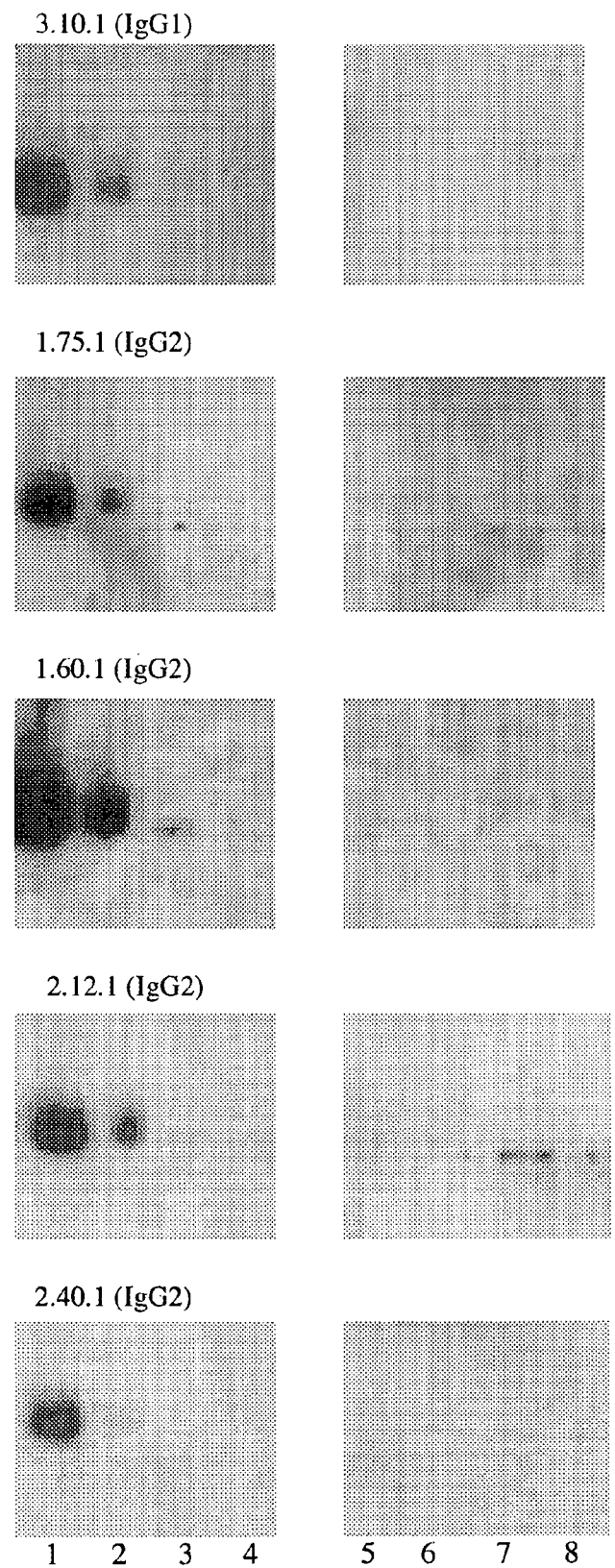

FIGS. 7A and 7B show pictures of gels testing each of the ten antibodies to HGF described in Example 6. The panels on the left show gels testing each antibody against 100 ng of human HGF (lane 1), 10 ng of human HGF (lane 2), 100 ng of mouse HGF, and 10 ng of mouse HGF (lane 4) under non-reducing conditions. The panels on the right show gels testing each antibody against 100 ng of human HGF (lane 5), 10 ng of human HGF (lane 6), 100 ng of mouse HGF (lane 7), and 10 ng of mouse HGF (lane 8) under reducing conditions. Each of the antibodies to HGF tested bound to human HGF under non-reducing conditions (lanes 1 and 2). None of the antibodies to HGF tested bound significantly to mouse HGF under non-reducing conditions (lanes 3 and 4), or to human HGF (lanes 5 and 6) or mouse HGF (lanes 7 and 8) under reducing conditions.

C. Epitope Mapping using Fusion Proteins

Figure 9A:
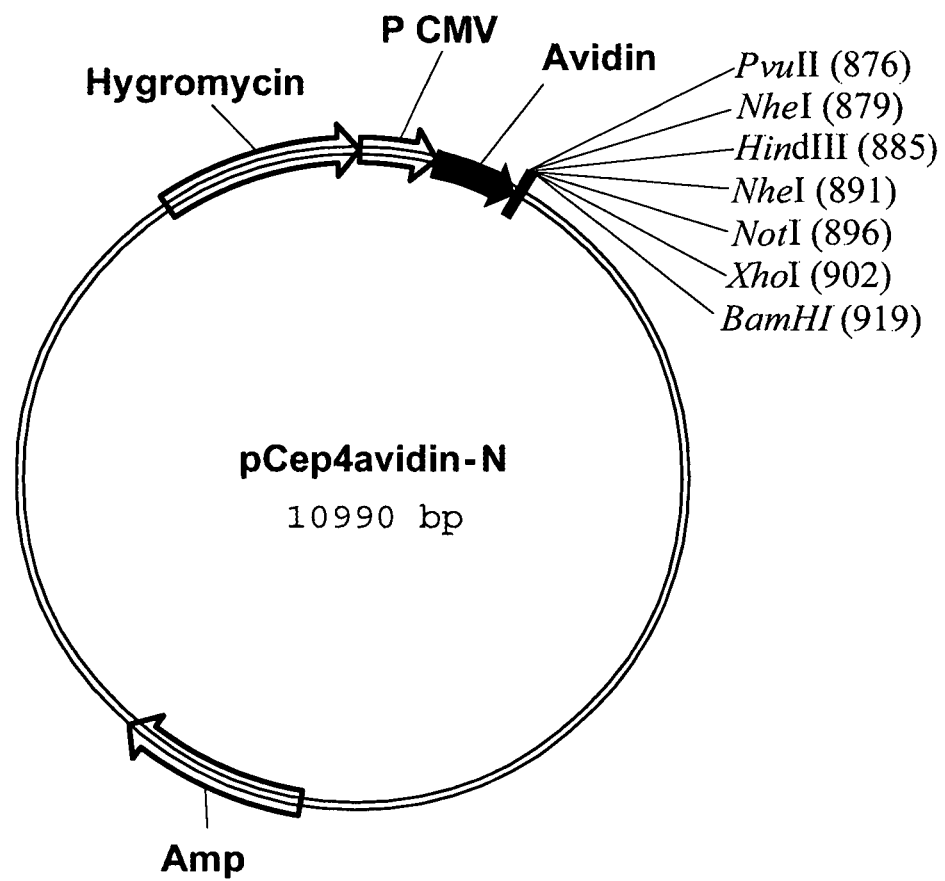

A mammalian expression vector comprising a cDNA sequence encoding chicken avidin adjacent to the multiple cloning site of vector pCEP4 (Invitrogen, Carlsbad, Calif., cat# V044-50) was constructed using standard molecular techniques (FIG. 9A). That vector included the chicken avidin signal sequence (FIG. 9B) to enable secretion of subsequently expressed fusion proteins. Expression vectors were constructed by inserting sequence encoding a particular target protein into the multiple cloning site of the fusion protein expression vector. The resulting fusion constructs each encoded an avidin protein at the N-terminus of a target protein.

Using this technique, fusion proteins comprising avidin fused to the following target proteins were prepared: full-length human HGF; d5 HGF, which is a naturally occurring splice variant of human HGF (Rubin, J. et al. PNAS 88:415-419 (1991)); full-length mouse HGF; chimera #1 comprising an N-terminal portion of human HGF (amino acids 32-505) and a C-terminal portion of mouse HGF (amino acids 508-728); chimera #2 comprising an N-terminal portion of mouse HGF (amino acids 33-506) and a C-terminal portion of human HGF (amino acids 506-728); and chimera #3 comprising an N-terminal portion of human HGF (amino acids 32-582) and a C-terminal portion of mouse HGF (amino acids 583-728).

A schematic representation of the fusion proteins is shown in FIG. 10. The N-terminal domain of HGF contains four kringle domains, represented by boxes labeled K1-K4. The C-terminal domain of HGF shares homology with serine proteases. That domain is represented by bars. Open boxes and solid bars indicate human HGF sequences. Shaded boxes and strippled bars indicate mouse sequences.

The individual fusion proteins were transiently expressed in 293T cells by separately transfecting cells with one of the individual fusion protein expression vectors using Lipofectamine (Gibco BRL, Carlsbad, Calif., Cat #18324) following the manufacturers instructions. Approximately 48 hours after transfection, conditioned media was collected and assayed.

In separate samples, five of the ten antibodies to HGF described in Example 6 (those ultimately derived from hybridomas 2.4.4, 1.74.1, 1.75.1, 3.10.1, and 2.12.1) were separately incubated with fusion proteins comprising each of the following target proteins: full-length human HGF, d5 HGF, and mouse HGF. After incubation, the fusion proteins in each sample were separately captured using biotin-coated beads (Spherotech Inc., Libertyville, Ill., Cat # TP-60-5). The resulting bead-protein complexes were labeled by adding FITC labeled anti-avidin antibody (Vector Lab, Burlingame, Calif., Cat. # SP-2040). The presence of antibodies to HGF was determined by adding phycoerythrin (PE) labeled goat anti-human F(ab')2 antibody (Southern Biotech Associates, Inc, Birmingham, Ala., Cat #2043-09).

Figure 8A:
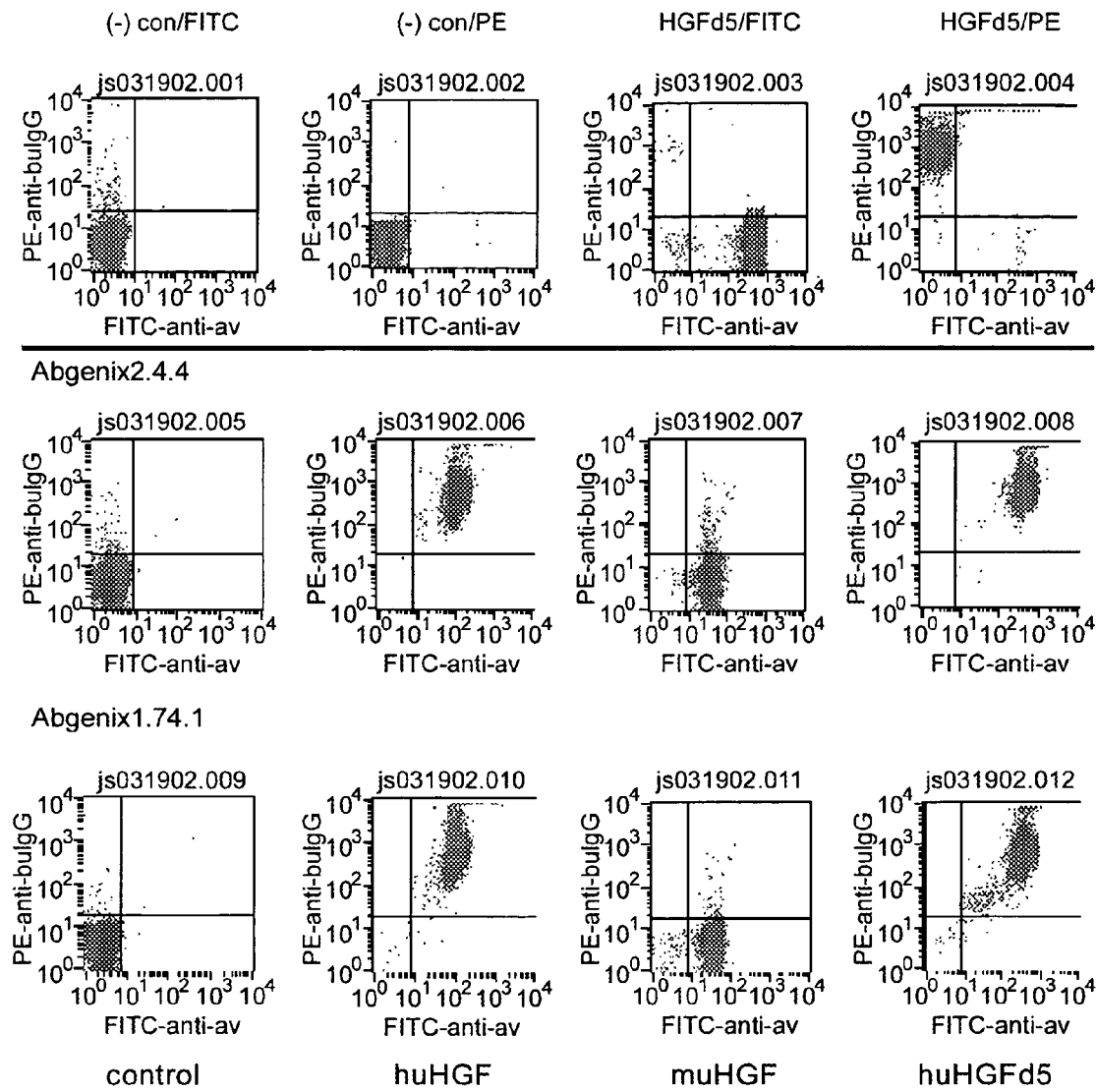

Those samples were then subjected to Fluorescence Activated Cell Sorter (FACS) analysis. Bead complexes labeled by FITC (which indicated the presence of avidin) and/or PE (which indicated the presence of antibody to HGF) were detected on a Becton Dickinson Bioscience FACScan (BD, Franklin Lakes, N.J.). FACS scatter plots for the five antibodies to HGF tested are presented in FIGS. 8A and 8B.

In separate samples, two of the ten antibodies to HGF described in Example 6 (those ultimately derived from hybridomas 2.12.1 and 2.4.4) were separately incubated with fusion proteins comprising each of the following target proteins: full-length human HGF, d5 HGF, and mouse HGF, chimera #1, chimera #2, and chimera #3. Those samples were subjected to FACS analysis as described above.

The results of those binding experiments are summarized in FIG. 10A, to the right of the schematic diagram. Neither antibody 2.12.1, nor 2.4.4 bound to the chimera #1. Both antibody 2.12.1 and antibody 2.4.4 bound to chimera #2 Antibody 2.4.4 bound to chimera #3. Antibody 2.12.1 did not bind to chimera #3.

D. Further Epitope Mapping Using Fusion Proteins

To provide additional information about the epitope(s) of HGF to which antibodies 2.4.4 and 2.12.1 bind, further human/mouse chimeras were constructed and assayed as described above in Example 8C (FIG. 10B). The primers used to generate the chimeras are shown in Table 10.

TABLE 10

Oligonucleotides Used to Generate Human/Mouse HGF Chimeras and
Point Mutants, Insertions and Deletions

| SEQ ID NO. | Oligo # | Sequence | n | Construct | Break points or mutation |
|---|---|---|---|---|---|
| 124 | 3201-76 | ATG CGT CTC CCT TGA TGA TGC TGG CTG CAT TTC | 33 | pt. mutant | hHGFR647Q |
| 125 | 3201-75 | ATG CGT CTC TCA AGG GAA GGT GAC TCT GAA TGA | 33 | pt. mutant | hHGFR647Q |
| 126 | 3201-72 | ATG CGT CTC TAA CTA GGT AAA TCA ATC GTA CTA ACA | 36 | pt. mutant | hHGFN601S |
| 127 | 3201-71 | ATG CGT CTC TAG TTA TGG ATG CAC AAT TCC TGA AA | 35 | pt. mutant | hHGFN601S |
| 128 | 3201-70 | ATG CGT CTC AAT TAT CCA GGA CAG CAG GCC TG | 32 | pt. mutant | hHGFD592N |
| 129 | 3201-69 | ATG CGT CTC ATA ATT TTG TTA GTA CGA TTG ATT TAC C | 37 | pt. mutant | hHGFD592N |
| 130 | 3201-68 | ATG CGT CTC GCG TTT CTC ATC TCC TCT TCC GT | 32 | pt. mutant | hHGFC561R |
| 131 | 3201-67 | ATG CGT CTC AAA CGC AAA CAG GTT CTC AAT GTT T | 34 | pt. mutant | hHGFC561R |
| 132 | 3201-66 | ATG CGT CTC CTT TCG TGG ACA TCA TGA ATT CCA A | 34 | pt. mutant | hHGFG555E |
| 133 | 3201-65 | ATG CGT CTC CGA AAG AGG AGA TGA GAA ATG CAA A | 34 | pt. mutant | hHGFG555E |
| 134 | 3201-64 | GAG CAG CTG CTA GCA AGC TTG CTA | 24 | restriction site | hHGF n-terminal + NotI |
| 135 | 3167-41 | ATG CGT CTC AGA GAC TTG AAA GAC TAT GAA GCT TG | 35 | deletion | mHGF DK deletion |
| 136 | 3167-42 | ATG CGT CTC GTC TCT GGC TGG AAA ACA TTG TCT T | 34 | deletion | mHGF DK deletion |
| 137 | 3167-44 | ATG CGT CTC AAC AAA GAC TTG AAA GAT TAT GAA GCT TG | 38 | insertion | hHGF DK insertion |
| 138 | 3167-43 | ATG CGT CTC TTT GTT TCG AGA AGG GAA ACA CTG TCG | 36 | Insertion | hHGF DK insertion |
| 139 | 3167-37 | ATG CGT CTC AAG CTT GCC AGG CCT GCT GT | 29 | chimera 9 | hHGF aa586-3' |
| 140 | 3167-40 | ATG CGT CTC AAG CTT GAG TAA AAC CAA GTC TGA | 33 | chimera 9 | mHGF 5'-aa585 |
| 141 | 3167-38 | ATG CGT CTC AAG CTT GCT CGA CCT GCA ATC | 30 | chimera 8 | mHGF aa586-3' |
| 142 | 3167-39 | ATG CGT CTC AAG CTT CAT TAA AAC CAG ATC TGA | 33 | chimera 8 | hHGF 5'-aa585 |
| 143 | 3167-37 | ATG CGT CTC AAG CTT GCC AGG CCT GCT GT | 29 | chimera 7 | hHGF aa586-3' |
| 144 | 3167-40 | ATG CGT CTC AAG CTT CAG TAA AAC CAA GTC TGA | 33 | chimera 7 | mHGF 5'-aa585 |
| 145 | 3167-38 | ATG CGT CTC AAG CTT GCT CGA CCT GCA ATC | 30 | chimera 3 | mHGF aa586-3' |
| 146 | 3167-39 | ATG CGT CTC AAG CTT CAT TAA AAC CAG ATC TGA | 33 | chimera 3 | hHGF 5'-aa585 |
| 147 | 3167-35 | ATG CGT CTC TAG GAT GGA TGG TTA GTT TGA GAT | 33 | chimera 2 | hHGF aa507-3' |

TABLE 10-continued

Oligonucleotides Used to Generate Human/Mouse HGF Chimeras and
Point Mutants, Insertions and Deletions

| SEQ ID NO. | Oligo # | Sequence | n | Construct | Break points or mutation |
|---|---|---|---|---|---|
| 148 | 3167-36 | ATG CGT CTC ATC CTA CTG TTG TTT GTG TTG GAA T | 34 | chimera 2 | mHGF 5'-aa506 |
| 149 | 3144-31 | ATG CGT CTC TAG GAT GGA TGG TTA GTT TGA AAT A | 34 | chimera 1 | mHGF aa507-3' |
| 150 | 3080-16 | ATG CGT CTC ATC CTA TGT TTG TTC GTG TTG G | 31 | chimera 1 | hHGF 5'-aa506 |
| 151 | 3080-04 | ATG CGT CTC ATG CAT CCA AGG TCA AGG AGA AG | 32 | chimera 6 | hHGF aa307-3' |
| 152 | 3144-28 | ATG CGT CTC ATG CAT TCA GTT GTT TCC ATA GG | 32 | chimera 6 | mHGF 5'-aa306 |
| 153 | 3079-84 | ATG CGT CTC ATG CAT GAC CTG CAA TGG GGA G | 31 | chimera 5 | hHGF aa213-3' |
| 154 | 3144-27 | ATG CGT CTC ATG CAT TCA ACT TCT GAA CAC TGA | 33 | chimera 5 | mHGF 5'-aa212 |
| 155 | 3079-77 | ATG CGT CTC ATG CAT CAT TGG TAA AGG ACG C | 31 | chimera 4 | hHGF aa129-3' |
| 156 | 3079-78 | ATG CGT CTC ATG CAG TTT CTA ATA TAG TCT TTG TTT TC | 38 | chimera 4 | mHGF 5'-aa128 |
| 157 | 3079-83 | ATG GGA TCC CTA TGA CTG TGG TAC CTT ATA TG | 32 | restriction site | hHGF c-terminal + BamHI |
| 158 | 2870-60 | ATG CGG CCG CAC AAA GGA AAA GAA GAA ATA CAA TTC | 36 | restriction site | hHGF n-terminal + NotI |
| 159 | 3013-96 | CGG GAT CCT TAC AAC TTG TAT GTC AAA ATT AC | 32 | restriction site | mHGF c-terminal + BamHI |
| 160 | 3013-95 | ATG ATG GCG GCC GCT CAG AAG AAA AGA AGA AAT ACA CTT C | 40 | restriction site | mHGF n-terminal + NotI |

FIG. 10B shows schematic drawings of the mouse and human HGF chimeric molecules created for the study, with the binding behavior of antibodies 2.12.1 and 2.4.4 to each chimera indicated on the right-hand side of the figure. Chimeras #1-3 in this study were identical to chimeras #1-3 described in Example 8C and FIG. 10A. Chimeras #4-6 incorporated increasing amounts of the N-terminus of mouse HGF into an otherwise entirely human HGF molecule. Chimera #7 utilized amino acids 507-585 of mouse HGF in an otherwise human HGF molecule, and chimera #8 utilized amino acids 507-585 of human HGF in an otherwise mouse HGF molecule. Chimera #9 was constructed from amino acids 1-585 of mouse HGF and amino acids 586-731 of human HGF.

Binding of antibodies 2.4.4 and 2.12.1 to the chimeric proteins was assayed as described in Example 8C. After incubation of either antibody 2.4.4 or antibody 2.12.1 with one of the fusion proteins, the fusion proteins in each sample were separately captured using biotin-coated beads (Spherotech Inc., Libertyville, Ill., Cat # TP-60-5). The resulting bead-protein complexes were labeled by adding FITC labeled anti-avidin antibody (Vector Lab, Burlingame, Calif., Cat. # SP-2040). The presence of antibodies to HGF was determined by adding phycoerythrin (PE) labeled goat anti-human F(ab')2 antibody (Southern Biotech Associates, Inc, Birmingham, Ala., Cat #2043-09). Those samples were then subjected to Fluorescence Activated Cell Sorter (FACS) analysis. Bead complexes labeled by FITC (which indicated the presence of avidin) and/or PE (which indicated the presence of antibody to HGF) were detected on a Becton Dickinson Bioscience FACScan (BD, Franklin Lakes, N.J.). In some cases, after expression normalization using FITC, single-color FACS analysis was performed following antibody binding by the PE label. This method increased the sensitivity of the assay and aided the measurement of binding with constructs that were not expressed at very high levels.

As shown in FIG. 10B, both antibodies 2.4.4 and 2.12.1 bound chimera #8 (FIG. 10B), which contains amino acids 507-585 of human HGF. Those results suggested that that region contains residues involved directly or indirectly in binding of antibody 2.4.4 and 2.12.1 to HGF. Chimeras that contained the mouse sequence in this same 507-585 region (chimeras 7 and 9) did not bind antibodies 2.12.1 or 2.4.4. Chimera 3 did not bind to antibody 2.12.1 but did bind to antibody 2.4.4, despite the presence of amino acids 507-585 of human HGF.

To obtain further information about amino acids 507-585 of human HGF (GWMVSLRYRNKHICGGSLIKESWVLTAR-QCFPSRDLKDYEAWLGIHDVHGRGDEKCKQVLNVSQLVYGPEGSDLVLM (SEQ ID NO: 123) (see FIG. 10D)), mutant HGF containing specific point mutations changing the human residue to the mouse residue within the region of amino acids 507-585 were created (FIG. 1C), using primers set forth in Table 10. Human HGF-avidin fusion proteins containing five single, non-conservative amino acid changes from the human HGF sequence to the mouse HGF sequence (Genbank Accession No. NM_000601 and NM_010427, respectively) were constructed. Two additional constructs were also created, one containing a two amino acid insertion into the human HGF sequence, and the other containing a two amino acid deletion from the mouse sequence (FIG. 10C).

These constructs were expressed and subjected to binding analysis as described in Examples 8C and 8D. After incubation of either antibody 2.4.4 or antibody 2.12.1 with one of the mutated proteins, the mutated proteins in each sample were separately captured using biotin-coated beads (Spherotech Inc., Libertyville, Ill., Cat # TP-60-5). The resulting bead-protein complexes were labeled by adding FITC labeled anti-avidin antibody (Vector Lab, Burlingame, Calif., Cat. # SP-2040). The presence of antibodies to HGF was determined by adding phycoerythrin (PE) labeled goat anti-human F(ab')2 antibody (Southern Biotech Associates, Inc, Birmingham, Ala., Cat #2043-09). Those samples were then subjected to Fluorescence Activated Cell Sorter (FACS) analysis. Bead complexes labeled by FITC (which indicated the presence of avidin) and/or PE (which indicated the presence of antibody to HGF) were detected on a Becton Dickinson Bioscience FACScan (BD, Franklin Lakes, N.J.). In some cases, after expression normalization using FITC, single-color FACS analysis was performed following antibody binding by the PE label. This method increased the sensitivity of the assay and aided the measurement of binding with constructs that were not expressed at very high levels.

It was found that mutations at amino acid 561, but not amino acids 592, 601, or 647, disrupted binding between the mutated human HGF and antibody 2.12.1 as well as between mutated human HGF and antibody 2.4.4. The mutation at amino acid 555 disrupted antibody 2.12.1 binding, but did not interfere with antibody 2.4.4 binding. Insertion of the two mouse amino acids 540N and 541K, not present in the human sequence (see FIG. 10D), disrupted binding to either antibody. The deletion of those two amino acids from the mouse HGF sequence, did not result in binding of either antibody to the mouse HGF.

E. Epitope Mapping by Protease Protection Assays

Complementary classical protease protection assays were also performed to identify the HGF epitopes bound by antibody 2.12.1. See Yi and Skalka, *Mapping Epitopes of Monoclonal Antibodies Against HIV-*1 *Integrase with Limited Proteolysis and Matrix-Assisted Laser Desorption Ionization Time-of-Flight Mass Spectrometry*, Biopolymers (Peptide Science) 55: 308-318 (2000). Human HGF (30 ug/10 ul) was mixed with antibody 2.12.1 (40 μg/4 ul) in 200 ul of 0.1 M Tris buffer, pH 7.5 and incubated on ice for 30 minutes. Digestion with trypsin (1 μg) was carried out at 37° C. for 1 hour. The digested material was subjected to reverse phase HPLC for peptide separation. A similar trypsin digest of human HGF alone, without antibody 2.12.1, was carried out in parallel. The HPLC column (Vydac C18, 2.1×150 mm, Vydac Inc., Hesperia Calif.) was run in 0.1% trifluoro aceticacid (TFA) with an elution gradient of 2-35% acetonitrile in 0.1% TFA. The UV trace of the eluting peptides was recorded by an HP 1090 HPLC device (Hewlett Packard, Palo Alto). The two HPLC maps were compared to investigate peptides that were protected by bound to antibody 2.12.1 (FIG. 11A).

Subsequent N-terminal sequencing and mass spectrometry was performed to identify the specific protected peptides. N-terminal peptide sequencing was performed by Edman degradation on an ABI-Procise protein sequencer (Applied Biosystems, Foster City, Calif.). The amino acids in each cycle were identified by the retention time on the coupled HPLC device and comparison to amino acid standards. Mass spectrometry of the protected fragments was performed on a Perceptive Voyager mass spectrometer (Applied Biosystems, Framingham, Mass.). Matrix assisted laser desorption ionization (MALDI) was performed using the matrix, 4-hydroxycyanocinnamic acid (HCCA) or sinapic acid. Molecular weights were determined by calibration relative to known standards (oxidized insulin beta chain and cytochrome c).

The α subunit of human HGF spans amino acids 32-494, and the β subunit spans amino acids 495-728 (see Swiss-Prot entry P14210 for human HGF). Antibody 2.12.1 binding to human HGF protected two peaks, T33 and T38.6. (FIG. 11A). Peak T38.6 contained two peptides, both corresponding to sequences at or near the beginning of the β subunit of mature HGF (see FIG. 10D, sequence beginning at the bold, underlined text (VVNGIPTRTN (SEQ ID NO: 172)) and FIG. 11C). T33 was derived from the α subunit (FIG. 11C). Based on mass spectrometry, the observed masses of the two peptides in peak T38.6 were measured to be 7165 and 6840 Daltons, respectively. Based on the possible trypsin cleavage sites present in the sequence of HGF (see, for example, the bold underlined arginine residue at amino acid 559 of human HGF in FIG. 10D), arginine residue number 559 is predicted to define the C-terminus of the protected peptides.

Another complementary experiment was also designed to investigate antibody-binding peptides. The mixture of HGF and antibody 2.12.1, as described above, was digested with trypsin for one hour and was then subjected to filtration by Microcon® 10 (Millipore Corp., Bedford, Mass.) to remove the unbound peptides. The bound peptides were expected to be captured by the membrane together with antibody 2.12.1. Intact human HGF (15 μg) was added to the peptide-antibody 2.12.1 mixture to elute the bound peptide(s) from the complex. The sample was incubated overnight at 4° C. and was again subjected to filtration by Microcon® 10 to separate the HGF-eluted peptides from the antibody and intact HGF. Both samples (bound and unbound peptides) were analyzed by reverse phase HPLC (FIG. 11B). Bound peptides were isolated by HPLC and subjected to N-terminal sequencing and mass spectrometry as described above.

When HGF was used to elute bound peptides, a large peptide peak (T48 in FIG. 11B) was observed to elute from the antibody-HGF complex and was identified by N-terminal peptide sequencing to contain the same two β subunit sequences found in T38.6, above. The size of the peptide(s) in peak T48 was heterogeneous based on the mass spectrometry and therefore a precise C-terminus could not be predicted from this data. Three other peaks (labeled # in FIG. 11B) either contained no peptide or a peptide of unknown origin, unrelated to HGF.

Together, these two experiments indicated that the N-terminal region of the beta subunit of HGF is part of the epitope for antibody 2.12.1. This data complements the data in Example 8D, where it was found that the epitopes involved in binding were located within amino acids 507-585 of human HGF. The mutational analysis and the molecular masses of the protected peptides show that the antibody-binding epitope of human HGF is located within amino acids 495-556 of human HGF.

F. Competition Binding of Antibodies Antibodies to HGF described in Example 6 ultimately derived from hybridoma 2.4.4 (antibody 2.4.4) and antibodies to HGF ultimately derived from hybridoma 2.12.1 (antibody 2.12.1) were FITC labeled for use in competition assays as follows. Antibodies 2.4.4 and 2.12.1 were separately dialyzed in PBS pH 8.5. FITC label ([6-fluorescein-5-(and -6)-carboxamido]hexanoic acid, succinimidyl ester (5(6)-SFX] mixed isomers) (Molecular Probes. Cat # F-2181) was added to each of the two dialyzed antibodies at a molar ratio 5:1 (label: antibody) from a stock solution of FITC label at 5 mg/ml in DMSO. Those mixtures were incubated at room temperature (20-22° C.) overnight in the dark. The mixtures were then each separately run through Pharmacia PD-10 columns (Amersham, Piscataway, N.J.) which had been equilibrated with PBS. The resulting preparations were read on a spectrophotometer at 280 nM and 495 nM. The antibody concentrations of those preparations were calculated using absorbance at 280 nm. The ratio of labeled antibody to unlabeled antibody was calculated using the following formula:

$$\frac{Ax}{E} \times \frac{\text{MW antibody}}{\text{mg antibody/ml}} = \frac{\text{mole labeled antibody}}{\text{mole unlabeled antibody}}$$

where Ax=label absorbency at 495 nm, and E=extinction coefficient of label=77500. Typically, antibody was labeled about 3:1 (FITC-labeled antibody:unlabeled antibody).

The ability of each of the two labeled antibodies to compete for binding with each of the other nine antibodies to HGF was assessed. Each of the two labeled antibody to HGF was separately incubated with HGF and each of the two labeled antibody to HGF was also separately incubated with HGF in the presence of a 50-fold molar excess of one of the other nine antibodies to HGF that had not been labeled. Thus, in nine separate samples, labeled antibody 2.4.4 was separately incubated with HGF along with each of the other nine antibodies to HGF that had not been labeled. Likewise, in nine separate samples, labeled antibody 2.12.1 was separately incubated HGF along with each of the other nine antibodies to HGF that had not been labeled. Each of these combinations was also repeated using the d5 splice variant of HGF instead of full-length HGF.

The positive competition control for these competition assays was to incubate each labeled antibody with a 50-fold molar excess of the same antibody that was not labeled. Thus, FITC labeled antibody 2.12.1 was incubated in the presence of, and separately in the absence of, a 50-fold molar excess of unlabeled antibody 2.12.1. Likewise, FITC labeled antibody 2.4.4 was incubated in the presence of, and in the absence of, a 50-fold molar excess of unlabeled antibody 2.4.4. As expected, the fluorescence signals from samples in the presence of a 50-fold molar excess of unlabeled antibodies were significantly lower than the fluorescence signals from samples in which unlabeled antibodies were not added.

Binding profiles are provided in FIG. 12. FIGS. 12A and 12B show experiments using labeled antibody 2.12.1. Key to curves in all panels of 12A and 12B: A: negative control (FITC-labeled antibody 2.12.1 without HGF); B: positive control (FITC labeled antibody 2.12.1 with HGF); C: antibody 1.74.1; D: antibody 1.75.1; E: antibody 1.29.1; F: antibody 3.10.1; G: antibody 1.61.3; H: antibody 1.24.1; I: antibody-1.60.1; J: antibody 2.40.1; K: antibody 2.12.1; L: antibody 2.4.4. FIG. 12A shows results from a competitive binding assay using fluorescent antibody 2.12.1 with the d5 HGF splice variant target protein. FIG. 12B shows results from a competitive binding assay using fluorescent antibody 2.12.1 with full length HGF target protein. FIGS. 12C and 12D show experiments using labeled antibody 2.4.4. Key to curves in all panels of 12C and 12D: A: negative control (FITC-labeled antibody 2.4.4 without HGF); B: positive control (FITC labeled antibody 2.4.4 with HGF); C: antibody 1.74.1; D: antibody 1.75.1; E: antibody 1.29.1; F: antibody 3.10.1; G: antibody 1.61.3; H: antibody 1.24.1; I: antibody 1.60.1; J: antibody 2.40.1; K: antibody 2.12.1; L: antibody 2.4.4. FIG. 12C shows results from a competitive binding assay using fluorescent antibody 2.4.4 with the d5 HGF splice variant target protein. FIG. 12D shows results from a competitive binding assay using fluorescent antibody 2.4.4 with full length HGF target protein.

The data indicate that each of the ten antibodies to HGF competes with each of the two labeled antibodies for binding to full length or d5 HGF. Some of the antibodies exhibited complete competition with the labeled antibody. (e.g. antibodies 2.12.1, 1.24.1 and 2.4.4 compete completely with FITC-labeled antibody 2.12.1, FIGS. 12A and 12B, peaks H, K and L, respectively). Other antibodies only partially competed for binding (e.g. antibodies 2.12.1, 2.40.1 and 1.61.3 partially compete with FITC-labeled 2.4.4, FIGS. 12C and 12D, peaks K, J and G, respectively).

Example 9

Neutralizing ELISA Assays

A neutralization ELISA assay was developed to assess whether the antibodies discussed in Example 6 could interrupt Met-HGF binding. Delphia 96-well plates (Cat#: AAAND-0001, Wallac Inc., Gaithersburg, Md.) were coated with HGF by adding 100 µl of HGF at 6.25 µg/ml per well. The plates were incubated at 37° C. for 1 hour or at 4° C. overnight. The plates were then blocked with 5% BSA (Cat#50-61-00, KPL, Gaithersburg, Md.) in PBS containing 0.1% Tween 20 for 1 hour at room temperature with shaking.

Test samples were prepared by separately mixing soluble Met (2 nM, 0.256 µg/ml) with different concentrations of a particular antibody to HGF being tested. The concentrations tested were: 667 nM, 223 nM, 74.1 nM, 24.7 nM, 8.2 nM, 2.7 nM, 0.91 nM, 0.30 nM, 0.10 nM, and 0.034 nM. A volume of 100 µl of a test sample was added to each well of the plates. The plates were then incubated at 4° C. overnight and then washed 4 times with PBS containing 0.1% Tween 20. Next, 100 µl per well of Biotinylated anti-cMetR antibody (Cat#: BAF358, R&D Systems Inc., Minneapolis, Minn.) at 2 µg/ml, was added. That antibody binds to the Met-HGF complexes on the plate, but does not bind to anti-HGF antibody bound to the HGF on the plate. The plates were then incubated for 2 hours with shaking, and were washed 4 times with PBS containing 0.1% Tween 20. Eu-streptavidin (1:1000 dilution in Assay buffer) (Cat#1244-360, Wallac Inc., Gaithersburg, Md.) was added and the plates were shaken at room temperature for 1 hour. The plates were then washed 4 times with PBS containing 0.1% Tween 20. Next, 100 µl of enhancement buffer (Wallac Inc., Cat#: 1244-105, Gaithersburg, Md.) was added. After at least for 5 minutes, the plates were read using Europium method on Victor 2 (1420 Multilabel Counter, Wallac Inc., Gaithersburg, Md.).

Percent inhibition of Met binding to HGF (i.e. neutralization) was calculated and $IC_{50}$ values were determined using the 4 parameter fit equation Excelfit, Version 2.0.6, (Microsoft Inc, Seattle, Wash.). In the presence of the antibodies to HGF discussed in Examples 6, Met binding to HGF was neutralized. Data for two experiments are shown in FIG. 13.

Example 10

Neutralization in Cells

A. Met Phosphorylation

HGF induces Met phosphorylation in PC-3 cells (ATCC, Manassas, Va. # CRL 1435). PC-3 cells were grown in 96-well Falcon tissue culture plates (VWR, San Diego, Calif., Cat.#62740-081) by adding 1×04 PC-3 cells per well in 100 µl RPMI 1640 (Invitrogen, Carlsbad, Calif., Cat. #11875-093) containing 5% Fetal Bovine Serum (Hyclone, Logan, Utah, Cat. # SH 30070.03) and 1× penicillin, streptomycin, glutamine (Invitrogen, Carlsbad, Calif., Cat. #10378-016). After 24 hours of growth at 37° C. under 5% $CO_2$, the cells were rinsed once with DMEM-low glucose (Invitrogen, Carlsbad, Calif., Cat. #11885-084) containing 0.1% bovine serum albumin (Sigma, Louis, Mo., Cat. #A-3156) and incubated for 18 to 20 hours with 100 µl DMEM-low glucose media containing 0.1% bovine serum albumin (Sigma, Louis, Mo., Cat. #A-3156).

Eight different dilutions of each of the ten antibodies to HGF from Example 6 were separately prepared by serial dilution in media (DMEM-low glucose with 0.1% bovine serum albumin) containing 200 ng/ml HGF. The concentrations of the antibodies to HGF in the separate dilutions were: 200 nM, 67 nM, 22 nM, 7 nM, 2.5 nM, 1 nM, 0.3 nM, and 0.1 nM of a particular antibody to HGF. Those antibody/HGF dilutions were incubated for 30 minutes at 37° C.

The PC-3 cells were rinsed once with 100 µl DMEM-low glucose containing 0.1% bovine serum albumin. Then 100 µl of each of the antibody/HGF dilutions was separately added to separate wells of PC-3 cells. After incubation for 10 minutes at 37° C. under 5% $CO_2$, the antibody/HGF dilutions were aspirated from the wells, and the plates were placed on ice for 1-2 minutes. The cells were rinsed once with 100 µl ice-cold PBS containing 0.3 mM sodium-ortho vanadate (Sigma, Louis, Mo., Cat. #S-6508). The washed cells were incubated for 15-30 minutes on ice in 60 µl lysis buffer containing 1% Triton X-100 (Pierce, Rockford, Ill., Cat.#28314), 50 mM Tris pH8, 100 mM NaCl, 0.3 mM sodium-ortho vanadate (Sigma, Louis, Mo., Cat. #S-6508) and 1× protease inhibitor cocktail (Sigma Cat. # P-8340).

Anti-Met antibody coated beads were prepared by incubating, Dynabeads M-280 Streptavidin (IGEN International, Gaithersburgh, Md., Cat. #110029) with 4 µg/ml of goat-anti Met-biotin (R&D Systems Inc., Minneapolis, Minn., Cat.# BAF 358) for 30 minutes at room temperature in PBS containing 1% bovine serum albumin (Sigma, St. Louis, Mo., Cat. # A-7888), 0.1% Tween 20 (Biorad, Hercules, Calif., Cat.#170-6531). A volume of 25 µl of anti-Met antibody coated beads per well was placed in 96-well Costar assay plates (Corning, N.Y., Cat. #3365).

A volume of 25 µl of each of the different PC-3 cell lysates was separately added to each well containing anti-Met antibody coated beads. The plates were incubated for 1 hour at room temperature with shaking. A volume of 12.5 µl of PBS containing 1% bovine serum albumin (Sigma, Louis, Mo., Cat. # A-7888), 0.1% Tween 20 (Biorad, Hercules, Calif., Cat.#170-6531) and 0.04 µg of the anti-Phosphotyrosine antibody 4G10 (Upstate Biotechnology, Lake Placid, N.Y., Cat. #05-321) was added per well and incubated for 1 hour at room temperature with shaking. A volume of 12.5 µl of PBS containing 1% bovine serum albumin, 0.1% Tween 20 and 8 µg/ml of anti-mouse ORI-TAG-label (IGEN International, Gaithersburgh, Md., Cat. #110087) was added and the plates were incubated for 30 minutes at room temperature with shaking. Signal (expressed in IGEN counts) was determined in IGEN M8 reader (IGEN International, Gaithersburgh, Md.). $IC_{50}$ values were calculated using the four parameter fit equation and the Excelfit software package, version 2.0.6, (Microsoft Inc., Seattle Wash.). Data for two experiments using the IGEN format is shown in FIG. 14. For each of the ten of the antibodies to HGF, $IC_{50}$ values were in the low nanamolar to sub-nanomolar range.

B. Neutralization of U-87 MG Growth/Survival

U-87 MG cells (ATCC # HTB-14) are a human glioblastoma line that expresses both Met and HGF. Growth/survival of those cells in culture is not enhanced by exogenous HGF. Endogenous Met, however, appears to be activated by endogenous HGF under growth conditions. Disruption of binding of the endogenous HGF to the endogenous Met may result in decreased growth and/or survival.

U-87 MG cells were grown in 96-well Costar assay plates (Corning, N.Y., Cat. #3365) by adding 800 cells per well in IMEM media (Gibco BRL, Rockville, Md., catalog #11125-028) containing 5% FBS. After approximately 24 hours, each of eleven different concentrations of each of the ten antibodies to HGF from Example 6 was added to separate wells of U-87 MG cells. The concentrations of the antibodies to HGF in the separate dilutions were: 100 µg/ml, 33.3 µg/ml, 11.1 µg/ml, 3.7 µg/ml, 1.2 µg/ml, 0.4 µg/ml, 0.14 µg/ml, 0.05 µg/ml, 0.015 µg/ml, 5.1 ng/ml, and 1.7 ng/ml of a particular antibody to HGF.

Seven days after the addition of the antibodies to HGF, the media was removed from the plates and the cells were fixed with 100 µl of 10% trichloroacetic acid (Sigma Inc., St Louis, Mo. Cat#: T-9159) per well and incubated at 4° C. for 1-2 hours. The wells were rinsed 5 times with tap water. The fixed cells were stained with 100 µl of 0.4% sulforhodamine B (Sigma, St Louis, Mo. Cat#: S-9012) in 1% acetic acid (Fisher, Pittsburgh, Pa. Cat#: UN2789) by a ten minute incubation at room temperature. Following the staining, the cells were washed 5 times with 1% acetic acid and air-dried. The optical density of the plates at 540 nm was read on a microtiter plate reader (SpectraMax PLUS, Molecular Devices, Sunnyvale, Calif.). The optical density is proportional to the total amount of protein present in the cell monolayer, and thus is a measure of cell survival/proliferation over the 7-day assay period. To calculate $IC_{50}$ values, the percent inhibition was calculated compared to cells incubated with an isotype control antibody, or with no antibody. The $IC_{50}$ values were calculated using the four 4 parameter fit equation and the Excelfit software package, version 2.0.6, (Microsoft Inc., Seattle Wash.).

Data for two experiments are shown in FIG. 15. All ten of the antibodies to HGF described in Example 6 inhibited the growth/survival of the U-87 MG cells. The $IC_{50}$ values of each of the antibodies were typically less than 100 nM.

Example 11

Neutralizing in Xenograft Tumors

A. U-87 MG Xenograft Minimal Residual Disease Model

U-87 MG cells were grown to near-confluency and then were suspended in serum-free medium at a concentration of $25×10^6$ cells/ml. The cells were visually assessed to be >98.5% viable, as determined by trypan blue exclusion. To test a single antibody to HGF, $5×10^6$ U-87 MG cells in serum free media were injected subcutaneously into the right flank of fifty female nude mice (CD1 Nu/Nu, Charles River Laboratories, Wilmington, Mass.). The fifty mice were placed into five groups of ten mice each.

Each mouse within a particular group of ten mice was treated by intra-peritoneal injection with the same dose of the same antibody to HGF discussed in Example 7, or with the IgG1 constant region (Isotype Control). The antibody doses tested were: 1 µg, 3 µg, 10 µg, and 30 µg per injection. The antibody injections were performed twice per week for four weeks, beginning on day 2 after injection of the U-87 MG cells. Tumor measurements and body weights were recorded twice per week for 30 days, and tumor volumes were calculated using the formula: length×width×height. Results were analyzed with the StatView® statistical program (SAS Institute, Inc., Cary, N.C.) using repeated measures ANOVA, followed by Scheffe's post hoc test.

Figure 16A:
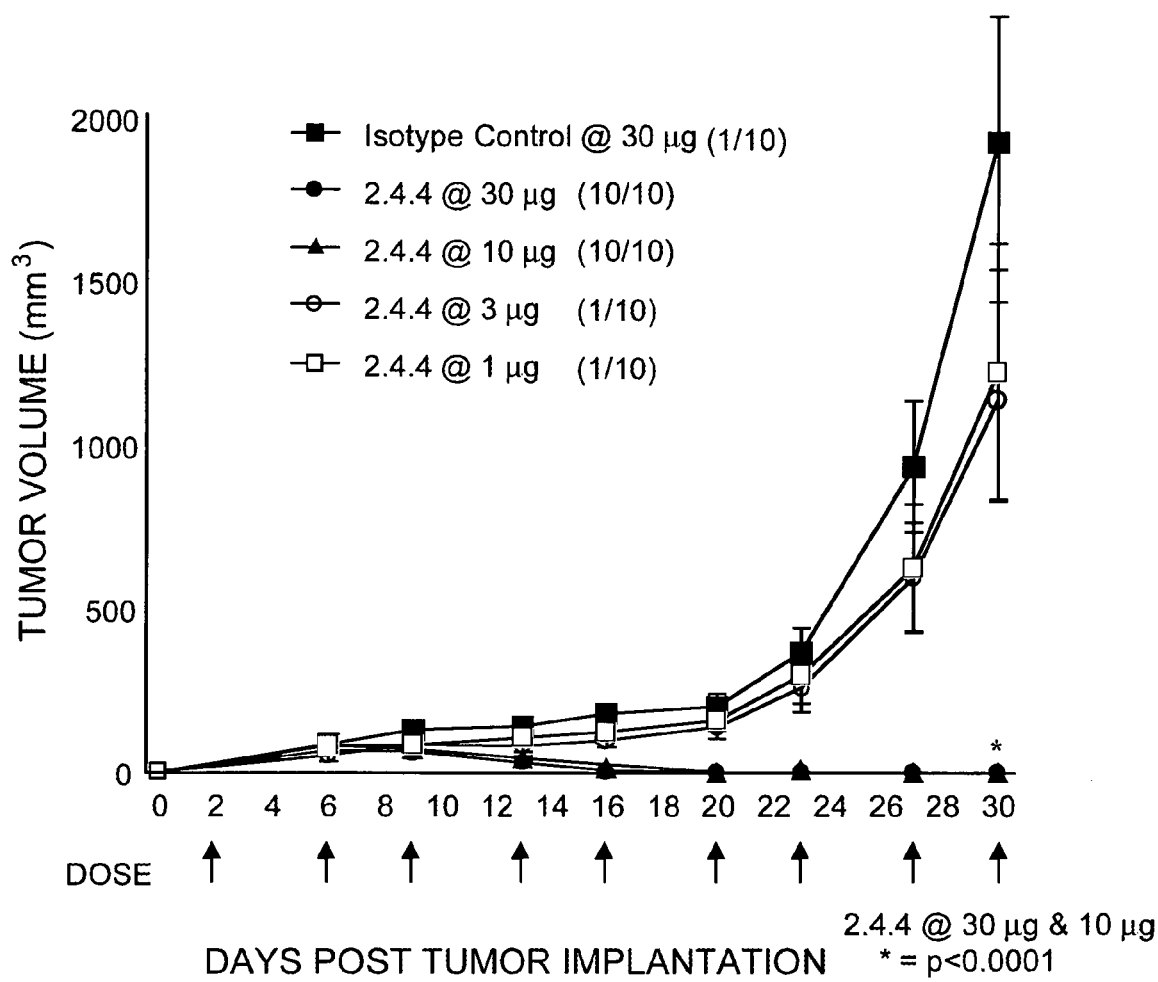
Figure 16B:
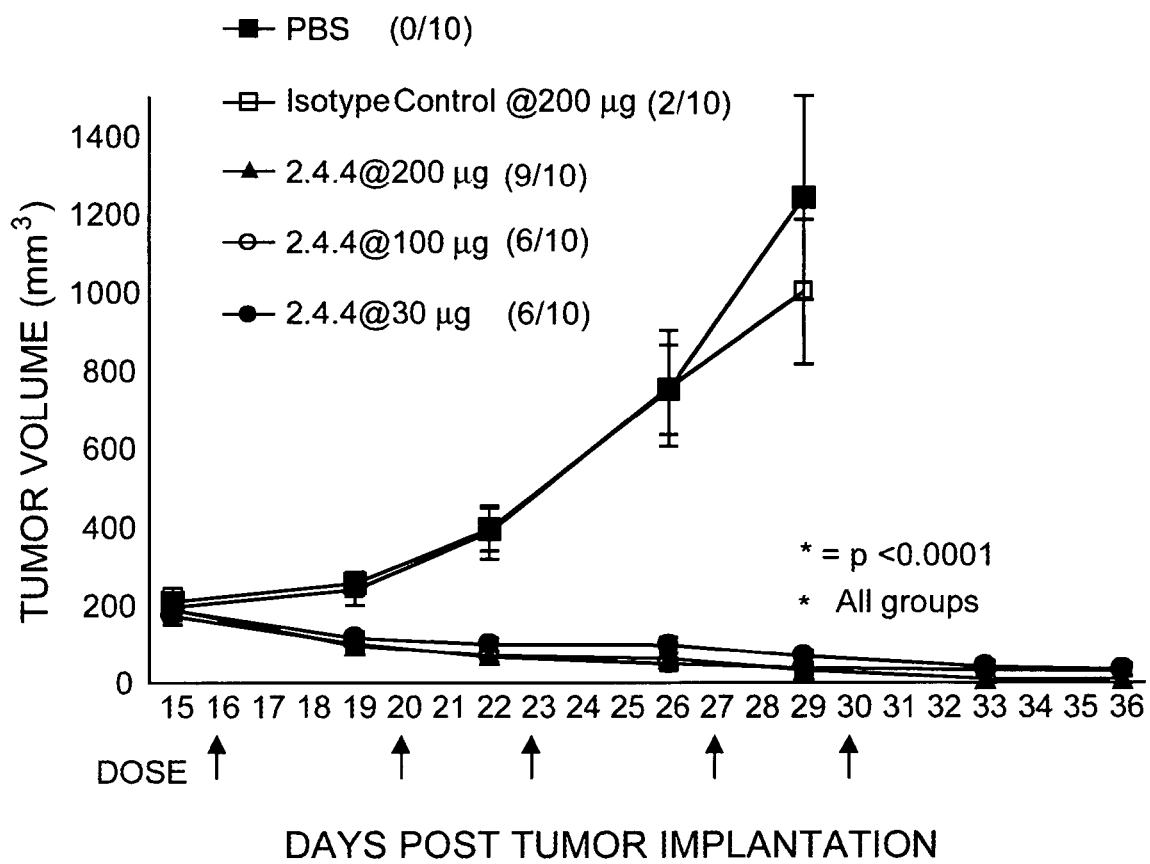

In separate experiments, each of the ten antibodies to HGF discussed in Example 6 was tested in this model. A dose-response experiment for antibody 2.4.4 is shown in FIG. 16A. Arrows indicate time of dosing, and the doses are shown in the legend. The number of animals at each dose (out of 10) with no measurable tumor is indicated in parenthesis. For the two highest doses tested, 10 µg administered twice per week and 30 µg administered twice per week, the inhibition of tumor growth was statistically significant when compared to control animals receiving the isotype control at 30 µg twice per week (human IgG2 #PK16.3.1, Abgenix Inc. Fremont, Calif.). Slight, but not statistically significant, growth inhibition was seen with the 2 lower doses (1 and 3 µg twice per week) of 2.4.4. Data are presented as the mean±standard error; n=10 animals per group and $p<0.05$ was considered statistically significant. Experiments testing the other nine antibodies to HGF from Example 6 showed similar complete inhibition of tumor growth at the higher doses.

B. U-87 MG Xenograft Established Disease Model

U-87 MG cells in serum-free media were injected into nude mice, following the procedure discussed above in Example 11A. Tumors were allowed to grow for approximately two weeks until they reached a volume of ~200 mm$^3$ before intra-peritoneal dosing with antibodies to HGF began. The mice were treated twice per week with antibody 2.4.4 at 200 µg, 100 µg, or 30 µg twice per week beginning on day 16, as indicated by the arrows in FIG. 16B. Tumor volume was measured and evaluated as described above. The number of animals (out of 10) with no measurable tumor on day 30 is indicated in parenthesis. Complete inhibition of U-87 MG tumor growth was observed at all doses. Statistically significant regression of the established tumors was achieved by day 29. In separate experiments, each of the ten antibodies to HGF discussed in Example 6 were tested in this model and complete inhibition was observed at the higher doses of each antibody.

C. Ranking Antibodies in the U-87 MG Minimal Residual Disease Model

Figure 16C:
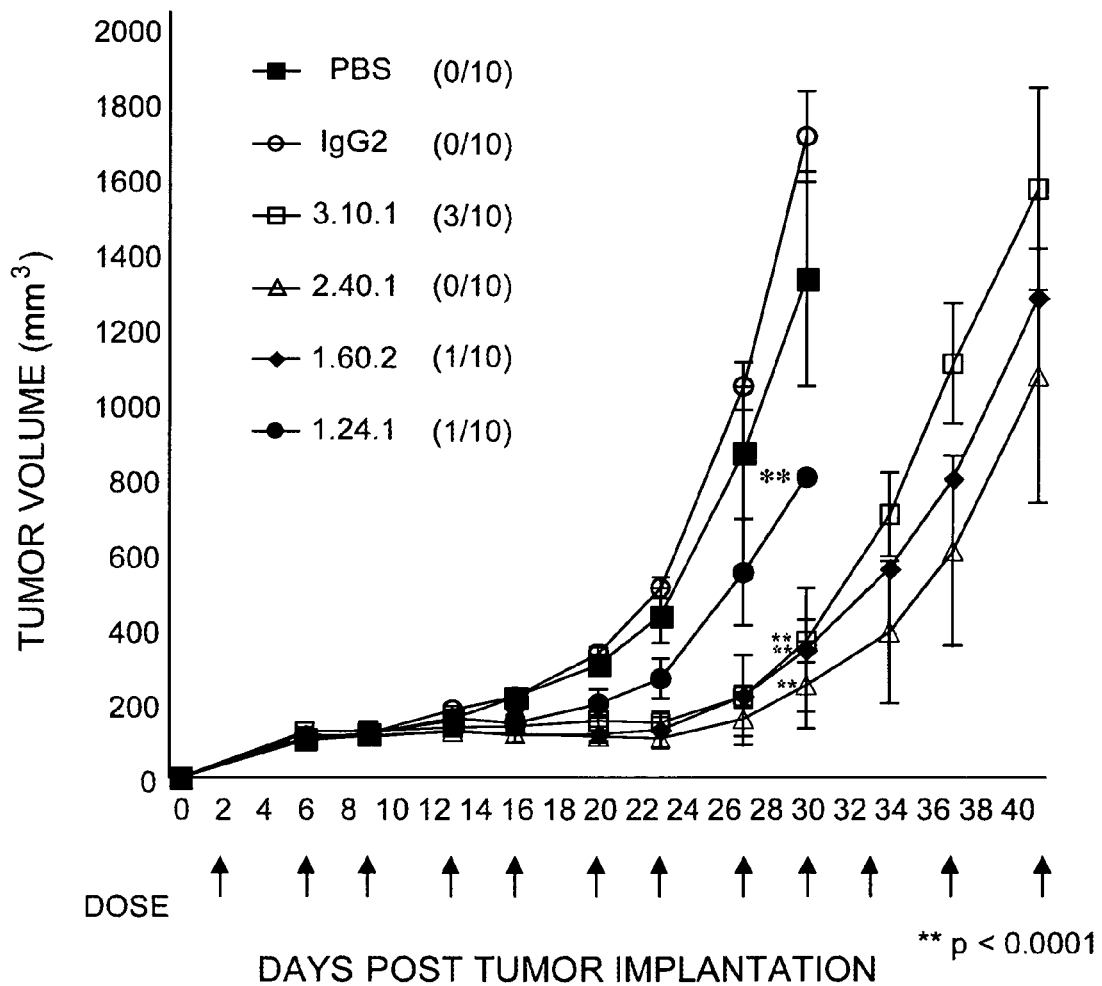
Figure 16D:
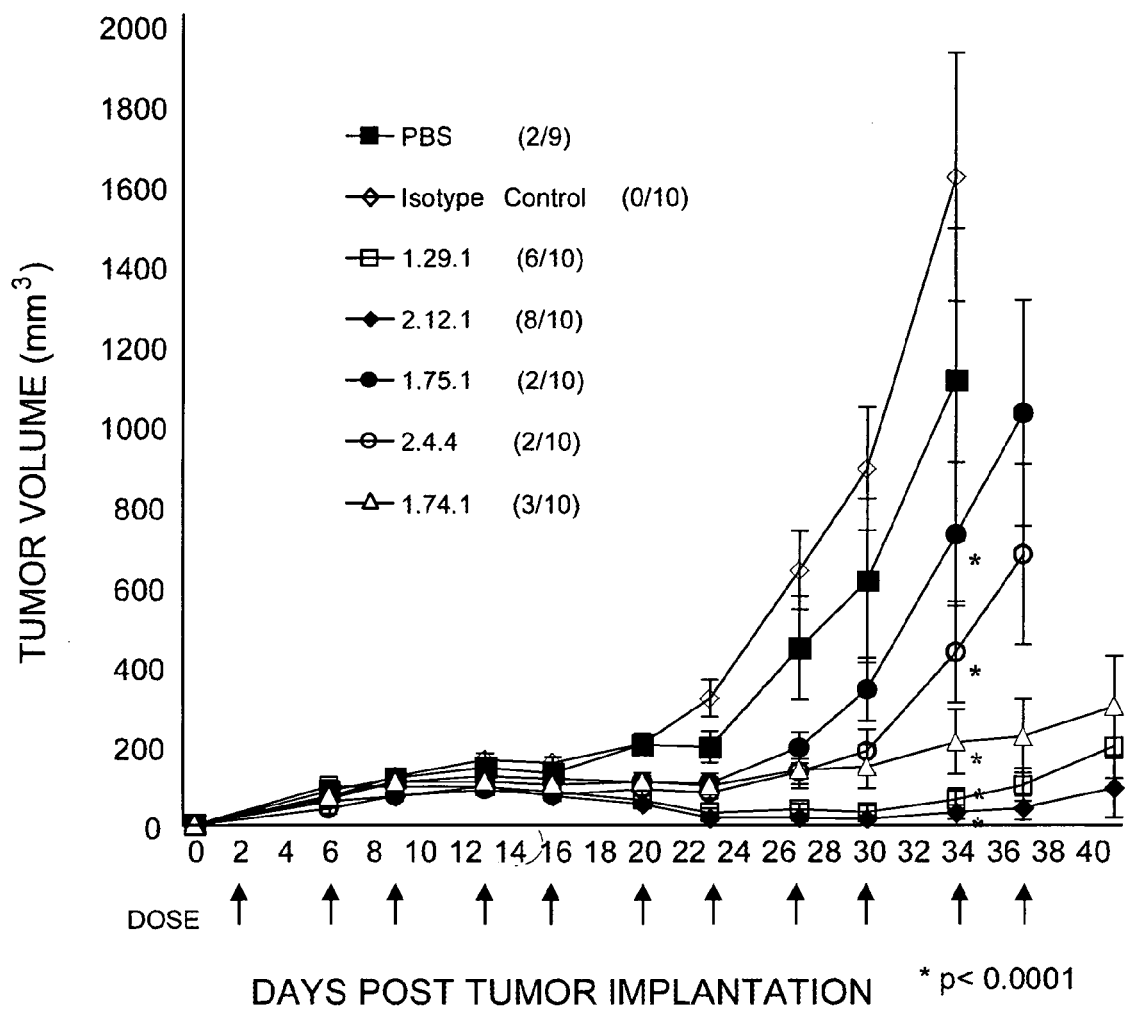

To determine the relative potency of the ten antibodies to HGF discussed in Example 6 in the U-87 MG tumor model discussed in Example 11A, a low dose that only partially inhibited tumor growth in the minimal residual disease model was chosen. Preliminary dose-response studies (FIG. 16A) suggested that 5 µg twice per week would give partial inhibition by the antibodies to HGF. A series of head-to-head experiments comparing up to 5 different antibodies to HGF were conducted. Results from two of these experiments are shown in FIGS. 16C and 16D. The ** indicates those antibodies to HGF that significantly inhibited tumor growth compared to the PBS and Isotype control IgG2 antibody ($p<0.0001$).

Figure 16E:
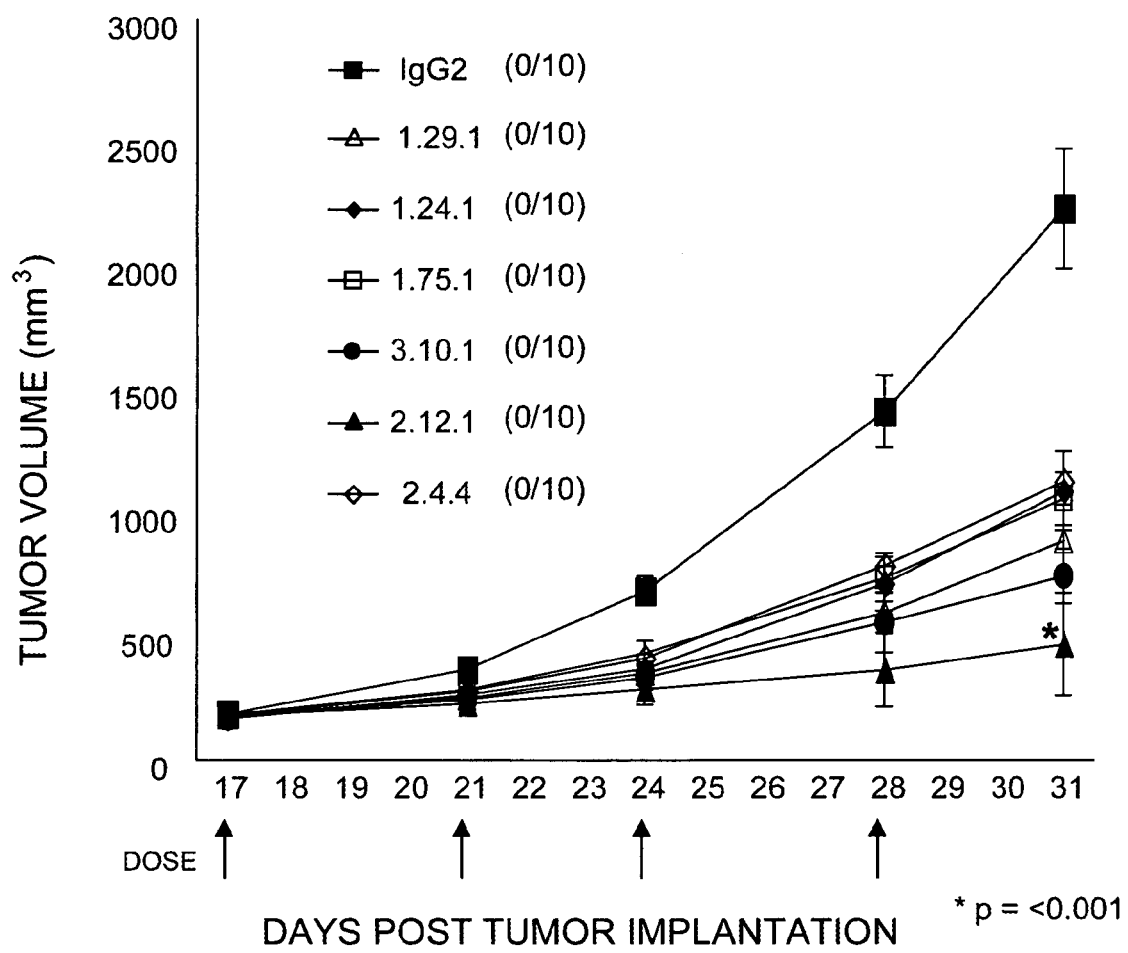
Figure 16F:
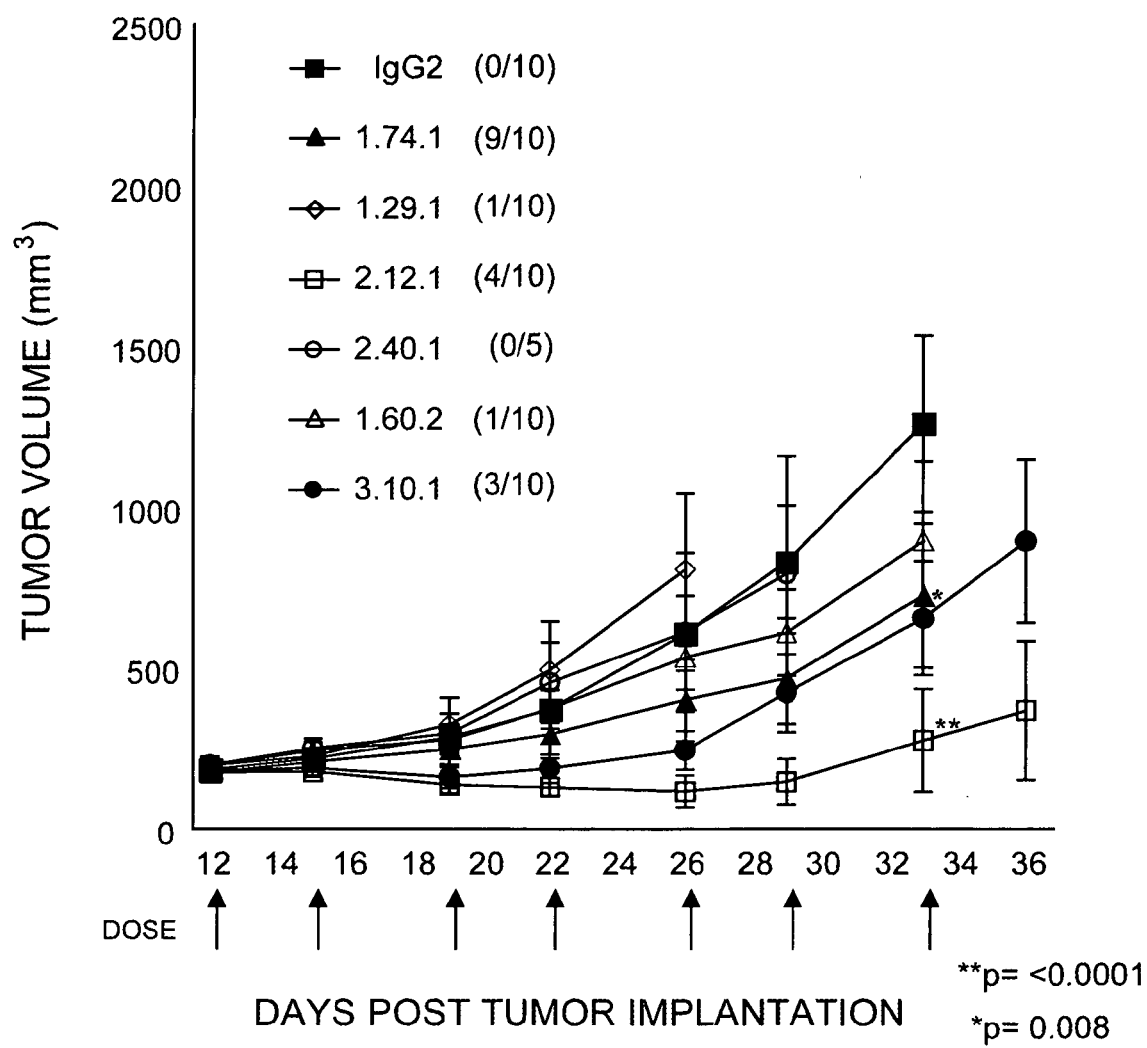

Similar rank ordering experiments were performed using the established U-87 disease model discussed in Example 11B. In those experiments, a dose of 10 µg, 2× per week was used. Results from two of these experiments are shown in FIGS. 16E and 16F.

We claim:

1. An isolated antibody that binds human hepatocyte growth factor (HGF), wherein the antibody is selected from the group consisting of:

an antibody comprising a light chain comprising the amino acid sequence of SEQ ID NO:24 from residue 23 to residue 129 and a heavy chain comprising the amino acid sequence of SEQ ID NO: 25 from residue 20 to residue 141;

an antibody comprising a light chain comprising the amino acid sequence of SEQ ID NO:26 from residue 21 to residue 133 and a heavy chain comprising the amino acid sequence of SEQ ID NO: 27 from residue 20 to residue 137;

an antibody comprising a light chain comprising the amino acid sequence of SEQ ID NO:28 from residue 23 to residue 129 and a heavy chain comprising the amino acid sequence of SEQ ID NO: 29 from residue 20 to residue 139;

an antibody comprising a light chain comprising the amino acid sequence of SEQ ID NO:30 from residue 23 to residue 129 and a heavy chain comprising the amino acid sequence of SEQ ID NO: 31 from residue 20 to residue 148;

an antibody comprising a light chain comprising the amino acid sequence of SEQ ID NO:32 from residue 23 to residue 129 and a heavy chain comprising the amino acid sequence of SEQ ID NO: 33 from residue 20 to residue 139;

an antibody comprising a light chain comprising the amino acid sequence of SEQ ID NO:34 from residue 23 to residue 129 and a heavy chain comprising the amino acid sequence of SEQ ID NO: 35 from residue 20 to residue 144;

an antibody comprising a light chain comprising the amino acid sequence of SEQ ID NO:36 from residue 21 to residue 133 and a heavy chain comprising the amino acid sequence of SEQ ID NO: 37 from residue 20 to residue 142;

an antibody comprising a light chain comprising the amino acid sequence of SEQ ID NO:38 from residue 21 to residue 128 and a heavy chain comprising the amino acid sequence of SEQ ID NO: 39 from residue 20 to residue 139;

an antibody comprising a light chain comprising the amino acid sequence of SEQ ID NO:40 from residue 23 to residue 129 and a heavy chain comprising the amino acid sequence of SEQ ID NO: 41 from residue 20 to residue 140; and an antibody comprising a light chain comprising the amino acid sequence of SEQ ID NO:42 from residue 21 to residue 128 and a heavy chain comprising the amino acid sequence of SEQ ID NO: 43 from residue 20 to residue 139.

2. The antibody of claim 1, wherein the antibody comprises a light chain comprising the amino acid sequence of SEQ ID NO: 24 from residue 23 to residue 129 and a heavy chain comprising the amino acid sequence of SEQ ID NO: 25 from residue 20 to residue 141.

3. The antibody of claim 1, wherein the antibody comprises a light chain comprising the amino acid sequence of SEQ ID NO: 26 from residue 21 to residue 133 and a heavy chain comprising the amino acid sequence of SEQ ID NO: 27 from residue 20 to residue 137.

4. The antibody of claim 1, wherein the antibody comprises a light chain comprising the amino acid sequence of SEQ ID NO: 28 from residue 23 to residue 129 and a heavy chain comprising the amino acid sequence of SEQ ID NO: 29 from residue 20 to residue 139.

5. The antibody of claim 1, wherein the antibody comprises a light chain comprising the amino acid sequence of SEQ ID NO: 30 from residue 23 to residue 129 and a heavy chain comprising the amino acid sequence of SEQ ID NO: 31 from residue 20 to residue 148.

6. The antibody of claim 1, wherein the antibody comprises a light chain comprising the amino acid sequence of SEQ ID NO: 32 from residue 23 to residue 129 and a heavy chain comprising the amino acid sequence of SEQ ID NO: 33 from residue 20 to residue 139.

7. The antibody of claim 1, wherein the antibody comprises a light chain comprising the amino acid sequence of SEQ ID NO: 34 from residue 23 to residue 129 and a heavy chain comprising the amino acid sequence of SEQ ID NO: 35 from residue 20 to residue 144.

8. The antibody of claim 1, wherein the antibody comprises a light chain comprising the amino acid sequence of SEQ ID NO: 36 from residue 21 to residue 133 and a heavy chain comprising the amino acid sequence of SEQ ID NO: 37 from residue 20 to residue 142.

9. The antibody of claim 1, wherein the antibody comprises a light chain comprising the amino acid sequence of SEQ ID NO: 38 from residue 21 to residue 128 and a heavy chain comprising the amino acid sequence of SEQ ID NO: 39 from residue 20 to residue 139.

10. The antibody of claim 1, wherein the antibody comprises a light chain comprising the amino acid sequence of SEQ ID NO: 40 from residue 23 to residue 129 and a heavy chain comprising the amino acid sequence of SEQ ID NO: 41 from residue 20 to residue 140.

11. The antibody of claim 1, wherein the antibody comprises a light chain comprising the amino acid sequence of SEQ ID NO: 42 from residue 21 to residue 128 and a heavy chain comprising the amino acid sequence of SEQ ID NO: 43 from residue 20 to residue 139.

12. An isolated antibody that binds human hepatocyte growth factor (HGF), wherein the antibody is selected from the group consisting of:
an antibody comprising a light chain comprising SEQ ID NOs: 60, 70, and 80, and a heavy chain comprising SEQ ID NOs: 90, 100, and 110;
an antibody comprising a light chain comprising SEQ ID NOs: 61, 71, and 81, and a heavy chain comprising SEQ ID NOs: 91, 101, and 111;
an antibody comprising a light chain comprising SEQ ID NOs: 62, 72, and 82, and a heavy chain comprising SEQ ID NOs: 92, 102, and 112;
an antibody comprising a light chain comprising SEQ ID NOs: 63, 73, and 83, and a heavy chain comprising SEQ ID NOs: 93, 103, and 113;
an antibody comprising a light chain comprising SEQ ID NOs: 64, 74, and 84, and a heavy chain comprising SEQ ID NOs: 94, 104, and 114;
an antibody comprising a light chain comprising SEQ ID NOs: 65, 75, and 85, and a heavy chain comprising SEQ ID NOs: 95, 105, and 115;
an antibody comprising a light chain comprising SEQ ID NOs: 66, 76, and 86, and a heavy chain comprising SEQ ID NOs: 96, 106, and 116;
an antibody comprising a light chain comprising SEQ ID NOs: 67, 77, and 87, and a heavy chain comprising SEQ ID NOs: 97, 107, and 117;
an antibody comprising a light chain comprising SEQ ID NOs: 68, 78, and 88, and a heavy chain comprising SEQ ID NOs: 98, 108, and 118; and
an antibody comprising a light chain comprising SEQ ID NOs: 69, 79, and 89, and a heavy chain comprising SEQ ID NOs: 99, 109, and 119.

13. The antibody of claim 12, wherein the antibody comprises a light chain comprising SEQ ID NOs: 60, 70, and 80, and a heavy chain comprising SEQ ID NOs: 90, 100, and 110.

14. The antibody of claim 12, wherein the antibody comprises a light chain comprising SEQ ID NOs: 61, 71, and 81, and a heavy chain comprising SEQ ID NOs: 91, 101, and 111.

15. The antibody of claim 12, wherein the antibody comprises a light chain comprising SEQ ID NOs: 62, 72, and 82, and a heavy chain comprising SEQ ID NOs: 92, 102, and 112.

16. The antibody of claim 12, wherein the antibody comprises a light chain comprising SEQ ID NOs: 63, 73, and 83, and a heavy chain comprising SEQ ID NOs: 93, 103, and 113.

17. The antibody of claim 12, wherein the antibody comprises a light chain comprising SEQ ID NOs: 64, 74, and 84, and a heavy chain comprising SEQ ID NOs: 94, 104, and 114.

18. The antibody of claim 12, wherein the antibody comprises a light chain comprising SEQ ID NOs: 65, 75, and 85, and a heavy chain comprising SEQ ID NOs: 95, 105, and 115.

19. The antibody of claim 12, wherein the antibody comprises a light chain comprising SEQ ID NOs: 66, 76, and 86, and a heavy chain comprising SEQ ID NOs: 96, 106, and 116.

20. The antibody of claim 12, wherein the antibody comprises a light chain comprising SEQ ID NOs: 67, 77, and 87, and a heavy chain comprising SEQ ID NOs: 97, 107, and 117.

21. The antibody of claim 12, wherein the antibody comprises a light chain comprising SEQ ID NOs: 68, 78, and 88, and a heavy chain comprising SEQ ID NOs: 98, 108, and 118.

22. The antibody of claim 12, wherein the antibody comprises a light chain comprising SEQ ID NOs: 69, 79, and 89, and a heavy chain comprising SEQ ID NOs: 99, 109, and 119.

23. The antibody of claim 9, wherein the light chain further comprises the amino acid sequence of SEQ ID NO: 44 and the heavy chain further comprises the amino acid sequence of SEQ ID NO: 46.

24. An isolated fully human antibody that binds human hepatocyte growth factor comprising a light chain and a heavy chain, wherein the light chain comprises SEQ ID NOs. 67, 77, and 87 and the heavy chain comprises SEQ ID NOs: 97, 107, and 117.

25. The antibody of claim 24, wherein the light chain further comprises the amino acid sequence of SEQ ID NO: 44 and the heavy chain further comprises the amino acid sequence of SEQ ID NO: 46.

26. An isolated fully human antibody that binds human hepatocyte growth factor (HGF) comprising a light chain and a heavy chain, wherein the light chain comprises the amino acid sequence of SEQ ID NO: 38 from residue 21 to residue 128 and the heavy chain comprises the amino acid sequence of SEQ ID NO: 39 from residue 20 to residue 139.

27. The antibody of claim 26, wherein the light chain further comprises the amino acid sequence of SEQ ID NO: 44 and the heavy chain further comprises the amino acid sequence of SEQ ID NO: 46.

28. A polypeptide consisting of at least one amino acid sequence selected from SEQ ID NO: 164 and 165.

29. An isolated antibody or antigen binding domain which is capable of binding at least one amino acid sequence consisting of SEQ ID NO: 164 or SEQ ID NO: 165, wherein the antibody or antigen binding domain is humanized or fully human.

30. A method of obtaining an antibody capable of binding hepatocyte growth factor (HGF) comprising administering at least one polypeptide consisting of SEQ ID NO: 164 or 165 to a non-human animal and obtaining the antibody from the animal.

31. A method of producing a humanized antibody capable of binding hepatocyte growth factor (HGF) comprising administering at least one polypeptide consisting of SEQ ID NO: 164 or 165 to a non-human animal, obtaining an antibody capable of binding HGF from the animal, designing a humanized antibody capable of binding HGF based on the antibody obtained from the animal, and producing the humanized antibody.

32. An antibody of any one of claim 1, 29, 12, or 20, wherein the antibody neutralizes binding of HGF to c-MET.

33. An antibody of any one of claim 1-11, or 12-22, wherein the antibody is an immunologically functional immunoglobulin fragment that binds human hepatocyte growth factor.

34. A composition comprising an antibody of any one of claim 1, 12, or 23 and a pharmaceutically acceptable carrier.

35. A composition comprising the antibody of claim 24 and a pharmaceutically acceptable carrier.

36. A composition comprising the antibody of claim 26 and a pharmaceutically acceptable carrier.

* * * * *

SEQUENCE LISTING

```
<160> NUMBER OF SEQ ID NOS: 194

<210> SEQ ID NO 1
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 1.24.1 Light chain V region (Vk, 1-L15)

<400> SEQUENCE: 1
atggacatga gggtgcccgc tcagctcctg gggctcctgc tgctctggtt cccaggttcc        60
agatgcgaca tccagatgac ccagtctcca tcttccgtgt ctgcatctgt aggagacaga       120
gtcaccatca cttgtcgggc gagtcagggt attagcagct ggttagcctg gtatcagcag       180
aaaccaggga aagcccctaa cctcctgatc tatgaagcat ccagtttgca aagtggggtc       240
ccatcaaggt tcggcggcag tggatctggg acagatttca ctctcaccat cagcagcctg       300
cagcctgaag attttgcaac ttactattgt caacaggcta cggtttccc gtggacgttc        360 ggccaaggga ccaaggtgga aatcaaa                                            387

<210> SEQ ID NO 2
<211> LENGTH: 423
<212> TYPE: DNA
<213> ORGANISM: Artificial Sequence
<220> FEATURE:
<223> OTHER INFORMATION: Description of Artificial Sequence: Synthetic
```

-continued

HGF 1.24.1 Heavy chain V region (Vh, H3-11)-huIgG2 C region)

<400> SEQUENCE: 2

```
atggagtttg ggctgagctg ggttttcctt gttgctatta taaaaggtgt ccagtgtcag      60
gtgcagctgg tggagtctgg gggaggcttg gtcaagcctg agggtccct gagactctcc     120
tgtgcagcct ctggattcac cttcagtgac tactacatga gctggatccg ccaggctcca    180
gggaaggggc tggagtgggt ttcatacatt agtagtagtg gtagtaccat atactacgca    240
gactctgtga agggccgatt caccatctcc aggacaacg ccaagaactc actgtatctg     300
caaatgaaca gcctgagagc cgaggacacg gccgtgtatt actgtgcgag agatgagtat    360
aacagtggct ggtacgtcct ctttgactac tggggccagg gaaccctggt caccgtctct    420
agt                                                                   423
```

<210> SEQ ID NO 3
<211> LENGTH: 399
<212> TYPE: DNA
<213> ORGANISM: Artificial Sequence
<220> FEATURE:
<223> OTHER INFORMATION: Description of Artificial Sequence: Synthetic
      HGF 1.29.1 Light chain V region (Vk, 4-B3)

<400> SEQUENCE: 3

```
atggtgttgc agacccaggt cttcatttct ctgttgctct ggatctctga tgcctacgga     60
gacatcgtga tgacccagtc tccagactcc ctggctgtgt ctctgggcga gagggccacc    120
atcaactgca gtccagcca gagtattttt tacagctcca ccaataagaa ctacttagct     180
tggtatcaga gaaaccggg acagcctcct aagctgctca tttactgggc atctacccgg     240
gaatccgggg tccctgaccg gttcagtggc agcgggtctg gacagattt cactctcacc     300
atcagcagcc tgcaggctga agatgtggca gtttattact gtcagcaata ttatagtact    360
ccgtggacgt tcggccaagg gaccaaggtg gaaatcaaa                            399
```

<210> SEQ ID NO 4
<211> LENGTH: 411
<212> TYPE: DNA
<213> ORGANISM: Artificial Sequence
<220> FEATURE:
<223> OTHER INFORMATION: Description of Artificial Sequence: Synthetic
      HGF 1.29.1 Heavy chain V region (Vh, 3-33)- huIgG2 C region

<400> SEQUENCE: 4

```
atggagtttg ggctgaactg ggttttcctc gttgctcttt taagaggtgt ccagtgtcag     60
gtgcagctgg tggagtctgg gggaggcgtg gtccagcctg gaggtccct gagactctcc    120
tgtgcagcgt ctggattcac cttcagtagc tatggcatgc actgggtccg ccaggctccg    180
ggcaagggac tggagtgggt ggcagttata tggtatgatg aagtgataa atactatgca    240
gactccgtga agggccgatt caccatctcc agagacaatt ccaagaacac gctgtatctg    300
caaatgaaca gcctgagagc cgaggacacg gctgtgtatt actgtgcgag agaggactac    360
ggcgagggtt ttgactactg gggccaggga accctggtca ccgtctctag t             411
```

<210> SEQ ID NO 5
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 1.60.1 Light chain V region (Vk, 1-A20)

<400> SEQUENCE: 5

```
atggacatga gggtgcccgc tcagctcctg ggactcctgc tgctctggct cccagatacc    60
agatgtgaca tccagatgac ccagtctcca tcctccctgt ctgtatctgt cggagacaga   120
gtcaccatca cttgccgggc gagtcagggc attagcagtt atttagcctg gtatcagcag   180
aaaccaggga agttcctaa gctcctgatc tatgttgcat ccactttgca atcaggggtc    240
ccgtctcggt tcagtggcag tggatctggg acagatttca ctctcaccat cagcagcctg   300
cagcctgaag atgttgcaac ttattactgt caaaactata acagtgaccc gctcactttc   360
ggcggcggga ccaaggtgga gatcaaa                                         387
```

```
<210> SEQ ID NO 6
<211> LENGTH: 417
<212> TYPE: DNA
<213> ORGANISM: Artificial Sequence
<220> FEATURE:
<223> OTHER INFORMATION: Description of Artificial Sequence: Synthetic
      HGF 1.60.1 Heavy chain V region (Vh, H1-02)- huIgG2 C region

<400> SEQUENCE: 6
```

```
atggactgga cctggaggat cctcttcttg gtggcagcag ccacaggagc ccactcccag    60
gtgcagctgg tgcagtctgg ggctgaggtg aagaagcctg ggcctcagt gaaggtctcc    120 tgcaaggctt ctggatacac cttcaccggc tactatataa actgggtgcg acaggcccct   180
ggacaagggc ttgagtggat gggatggatc aaccctaaca gtggtggcac aaactatgca   240
cagaagtttc agggcagggt caccatgacc agggacacgt ccatcaccac agcctacatg   300
gagctgagca ggctgagagc tgacgacacg gccgtgtact actgtgcgag agaactggaa   360
ctacgctact acggtatgga cgtctggggc caagggacca cggtcaccgt ctctagt      417
```

```
<210> SEQ ID NO 7
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 1.61.3 Light chain V region (Vk, 1-O18/O8)

<400> SEQUENCE: 7
```

```
atggacatga gggtgcccgc tcagctcctg gggctcctgc tgctctggct ctcaggtgcc    60
agatgtgaca tccagatgac ccagtctcca tcctccctgt ctgcatctgt aggagacaga   120
gtcaccatca cttgccaggc gagtcaggac attagcaact atttaaattg gtatcagcag   180
aaaccaggga cagcccctaa actcctgatc tacggtgcat ccgatttgga aacgggggtc   240
ccatcaaggt tcagtggaag tggatctggg acagatttta ctttcgccat cagcagcctg   300
cagcctgaag atattgcaac atattactgt caacagtatg ataatctccc gtacaatttt   360
ggccagggga ccaagctgga gatcaaa                                         387
```

```
<210> SEQ ID NO 8
<211> LENGTH: 444
<212> TYPE: DNA
<213> ORGANISM: Artificial Sequence
<220> FEATURE:
<223> OTHER INFORMATION: Description of Artificial Sequence: Synthetic
      HGF 1.61.3 Heavy chain V region (Vh, 4-31)- huIgG2 C region

<400> SEQUENCE: 8
```

```
atgaaacacc tgtggttctt cctcctgctg gtggcagctc ccagatgggt cctgtcccag    60
gtgcagctgc aggagtcggg cccaggactg gtgaagcctt cacagaccct gtccctcacc   120
```

```
tgcactgtct ctggtggctc catcagcagt gatggttact actggagctg atccgccag      180 cacccaggga agggcctgga gtggattggg tacatctatt acagtgggag cacctactac      240
aacccgtccc tcaagagtcg agtcaccata tcagtagaca cgtctaagaa ccagttctcc      300
ctgaagctga gctctgtgac tgccgcggac acggccgtct attactgtgc gagatcccac      360
cttcattact atgatagtag tggttattac tacggcggtg cttttgatat ctggggccaa      420
gggacaatgg tcaccgtctc tagt                                             444

<210> SEQ ID NO 9
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 1.74.3 Light chain V region (Vk, 1-012/02)

<400> SEQUENCE: 9
atggacatga gggtgcccgc tcagctcctg gggctcctgc tactctggct ccgaggtgcc       60
agatgtgaca tccagatgac ccagtctcca tcctccctgt ctgcatctgt aggagacaga      120
gtcaccatca cttgccgggc aagtcagagc attaacagcg atttaaattg gtatcagcag      180
aaaccaggga agtccctaa gctcctgatc tatgttgcat ccagtttgca aaatggggtc       240
ccatcaaggt tcagtggcag tggatctggg acagatttca ctctcaccat cagcagtctg      300
caacctgaag attttgcaac ttactactgt caacggagtt acagtacccc tcccactttc      360
ggccctggga ccaaagtgga tatcaaa                                          387

<210> SEQ ID NO 10
<211> LENGTH: 417
<212> TYPE: DNA
<213> ORGANISM: Artificial Sequence
<220> FEATURE:
<223> OTHER INFORMATION: Description of Artificial Sequence: Synthetic
      HGF 1.74.3 Heavy chain V region (Vh, VG1-02)- huIgG2 C region

<400> SEQUENCE: 10
atggactgga cctggaggat cctcttcttg gtggcagcag ccacaggagc ccactcccag       60
gtgcagctgg tgcagtctgg ggctgaggtg aagaagcctg ggcctcagt gaaggtctcc       120 tgcaaggctt ctggatacac cttcaccggc tactatatac actgggtgcg acaggccct       180 ggacaagggc ttgagtggat gggatggatc aaccctaaca gtggtggcac aaactatgca      240
cagaagtttc agggcagggt caccatgacc agggacacgt ccatcagcac agcctacatg      300
gagctgagca ggctgagatc tgacgacacg gccgtgtatt actgtgcgag agaactggaa      360
ctacgctact acggtatgga cgtctggggc caagggacca cggtcaccgt ctctagt         417

<210> SEQ ID NO 11
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 1.75.1 Light chain V region (Vk, 1-A30)

<400> SEQUENCE: 11
atggacatga gggtgcccgc tcagctcctg gggctcctgc tgctctggtt cccaggtgcc       60
aggtgtgaca tccagatgac ccagtctcca tcctccctgt ctgcatctgt aggagacaga      120
gtcaccatca cttgccgggc aagtcagggc attagaaatg atttaggctg gtttcagcag      180
aaaccaggga agcccctaa gcgcctgatc tatgctgcat ccagtttgca aagtggggtc       240
```

```
ccatcaaggt tcagcggcag tggatctggg acagaattca ctctcacaat cagcagcctg      300
cagcctgaag attttgcaac ttattactgt ctacagcatg atagttaccc gctcactttc      360
ggcggaggga ccaaggtgga gatcaaa                                          387
```

```
<210> SEQ ID NO 12
<211> LENGTH: 432
<212> TYPE: DNA
<213> ORGANISM: Artificial Sequence
<220> FEATURE:
<223> OTHER INFORMATION: Description of Artificial Sequence: Synthetic
      HGF 1.75.1 Heavy chain V region (Vh, VG4-31)- huIgG2 C region

<400> SEQUENCE: 12
atgaaacacc tgtggttctt cctcctgctg gtggcagctc ccagatgggt cctgtcccag      60
gtgcagctgc aggagtcggg cccaggactg gtgaagcctt cacagaccct gtccctcacc     120
tgcactgtct ctggtggctc catcagcagt ggtggttact actggagctg gatccgccag     180
cacccaggga agggcctgga gtggattggg tacatctatt acagtgggag cacctactac     240
aacccgtccc tcaagagtcg agttaccata tcagtagaca cgtctaagaa ccagttctcc     300
ctgaaggtga gctctgtgac tgccgcggac acggccgtgt attactgtgc gagagaccca     360
ctatggttcg gggagttcga ctactacggt atggacgtct ggggccaagg gaccacggtc     420
accgtctcta gt                                                         432
```

```
<210> SEQ ID NO 13
<211> LENGTH: 399
<212> TYPE: DNA
<213> ORGANISM: Artificial Sequence
<220> FEATURE:
<223> OTHER INFORMATION: Description of Artificial Sequence: Synthetic
      HGF 2.4.4 Light chain V region (Vk, 4-B3)

<400> SEQUENCE: 13
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gtccagccca gagtgtttta ttcagctcca acaataagaa ttacttagct     180
tggtatcagc agaaaccagg acagcctcct aagttgctca tttactgggc atctacccgg     240
gaatccgggg tccctgaccg attcagtggc agcgggtctg ggacagattt cactctcacc     300
atcagcagcc tgcaggctga agatgtggca gtttattact gtcagcaata ttttagtcct     360
ccgtggacgt tcggccaagg gaccaaggtg gaaatcaaa                            399
```

```
<210> SEQ ID NO 14
<211> LENGTH: 426
<212> TYPE: DNA
<213> ORGANISM: Artificial Sequence
<220> FEATURE:
<223> OTHER INFORMATION: Description of Artificial Sequence: Synthetic
      HGF 2.4.4 Heavy chain V region (Vh, VG 4-31)- huIgG2 C region

<400> SEQUENCE: 14
atgaaacacc tgtggttctt cctcctgctg gtggcagctc ccagatggat cctgtcccag      60
gtgcagctga aggagtcggg cccaggactg gtgaagcctt cacagaccct gtccctcacc     120
tgcactgtct ctggtggctc catcagcagt ggtgtttact actggagctg gatccgccag     180
cacccaggga agggcctgga gtggattggg tacttctatt atagtgggaa cacctaccac     240
aacccgtccc tcaagagtcg agtgaccata tcagtagaca cgtctaagaa ccagttctcc     300
```

```
ctgaagctga gctctgtgac tgccgcggac acggccgtgt attactgtgc gagagatcgt    360
agtggctacg atcaccctga tgcttttgat atctggggcc aagggacaat ggtcaccgtc    420
tctagt                                                               426

<210> SEQ ID NO 15
<211> LENGTH: 384
<212> TYPE: DNA
<213> ORGANISM: Artificial Sequence
<220> FEATURE:
<223> OTHER INFORMATION: Description of Artificial Sequence: Synthetic
      HGF 2.12.1 Light chain V region (Vk, 3-L2/L16)

<400> SEQUENCE: 15
atggaagccc cagctcagct tctcttcctc ctgctactct ggctcccaga taccactgga     60
gaaatagtga tgacgcagtc tccagccacc ctgtctgtgt ctccagggga aagagccacc    120
ctctcctgca gggccagtca gagtgttgac agcaacttag cctggtaccg gcagaaacct    180
ggccaggctc ccaggctcct catctatggt gcatccacca gggccactgg tatcccagcc    240
aggttcagtg gcagtgggtc tgggactgag ttcactctca ccatcagcag cctgcagtct    300
gaagattttg cagtttatta ctgtcagcag tatattaact ggcctccgat caccttcggc    360
caagggacac gactggagat taaa                                           384

<210> SEQ ID NO 16
<211> LENGTH: 417
<212> TYPE: DNA
<213> ORGANISM: Artificial Sequence
<220> FEATURE:
<223> OTHER INFORMATION: Description of Artificial Sequence: Synthetic
      HGF 2.12.1 Heavy chain V region (Vh4-59)- huIgG2 C region

<400> SEQUENCE: 16
atgaaacacc tgtggttctt ccttctcctg gtggcagctc ccagatgggt cctgtcccag     60
gtgcagctgc aggagtcggg cccaggactg gtgaagcctt cggagaccct gtccctcacc    120
tgcactgtct ctggtggctc catcagtatt tactactgga gctggatccg gcagccccca    180
gggaagggac tggagtggat tgggtatgtc tattacagtg ggagcaccaa ttacaacccc    240
tccctcaaga gtcgagtcac catatcagta gacacgtcca agaaccagtt ctccctgaag    300
ctgaactctg tgaccgctgc ggacacggcc gtgtattact gtgcgagagg gggatacgat    360
ttttggagtg gttattttga ctactggggc cagggaaccc tggtcaccgt ctctagt      417

<210> SEQ ID NO 17
<211> LENGTH: 387
<212> TYPE: DNA
<213> ORGANISM: Artificial Sequence
<220> FEATURE:
<223> OTHER INFORMATION: Description of Artificial Sequence: Synthetic
      HGF 2.40.1 Light chain V region (Vk, 1A20)

<400> SEQUENCE: 17
atggacatga gggtgcccgc tcagctcctg gggctcctgc tgctctggtt cccaggtgcc     60
aggtgtgaca tccagatgac ccagtctcca tcctccctgt ctgcatctgt aggagacaga    120
gtcaccatca cttgccgggc aagtcagggc attagaaatg atttaggctg gtatcagcag    180
aaaccaggga aagcccctaa gcgcctgatc tatgttgcat ccagtttgca aagtggggtc    240
ccatcaaggt tcagcggcag tggatctggg acagaattca ctctcacaat cagcagcctg    300
cagcctgaag attttgcaac ttattactgt ctacaacata tagttacccc gctcactttc    360
ggcggaggga ccaaggtgga gatcaaa                                        387
```

<210> SEQ ID NO 18
<211> LENGTH: 420
<212> TYPE: DNA
<213> ORGANISM: Artificial Sequence
<220> FEATURE:
<223> OTHER INFORMATION: Description of Artificial Sequence: Synthetic
      HGF 2.40.1 Heavy chain V region (Vh, VG 4-31)- huIgG2 C region

<400> SEQUENCE: 18

```
atgaaacacc tgtggttctt cctcctgctg gtggcagctc ccagatgggt cctgtcccag    60
gtgcagctgc aggagtcggg cccaggactg gtgaagcctt cacagaccct gtccctcacc   120
tgcactgtct ctggtggctc catcagcagt ggtggttact actggagctg gatccgtcag   180
cacccaggga agggcctgga gtggattggg aacatctatt acagtgggat cacctactac   240
aacccgtccc tcaagagtcg agttaccatg tcagtagaca cgtctaagaa ccagttctcc   300
ctgaagctga gttctgtgac tgccgcggac acggccgtgt attactgtgc gagagatccc   360
ctctacggtg actacgggtt cgaccccctgg ggccagggaa ccctggtcac cgtctctagt   420
```

<210> SEQ ID NO 19
<211> LENGTH: 384
<212> TYPE: DNA
<213> ORGANISM: Artificial Sequence
<220> FEATURE:
<223> OTHER INFORMATION: Description of Artificial Sequence: Synthetic
      HGF 3.10.1 Light chain V region (Vk, 3-L2/L16)

<400> SEQUENCE: 19

```
atggaagccc cagctcagct tctcttcctc ctgctactct ggctcccaga taccactgga    60
gaaatagtga tgacgcagtc tccagccacc ctgtctgtgt ctcctgggga agagccacc    120 ctctcctgca gggccagtca gagtgttagc agcaacttag cctggtacca gcagaaacct   180
ggccaggctc ccaggctcct catgtatggt gcatccacca gggccactgg tatcccagcc   240
aggttcagtg gcagtgggtc tgggacagag ttcactctca ccatcagcag cctgcagtct   300
gaagattttg cagtttatta ctgtcagcag tataataact ggcctccgat caccttcggc   360
caagggacac gactggagat taaa                                           384
```

<210> SEQ ID NO 20
<211> LENGTH: 417
<212> TYPE: DNA
<213> ORGANISM: Artificial Sequence
<220> FEATURE:
<223> OTHER INFORMATION: Description of Artificial Sequence: Synthetic
      HGF 3.10.1 Heavy chain V region (Vh, VG 4-34)- huIgG1 C region

<400> SEQUENCE: 20

```
atgaaacacc tgtggttctt cctcctcctg gtggcagctc ccagatgggt cctgtcccag    60
gtgcagctac agcagtgggg cgcaggactg ttgaagcctt cggagaccct gtccctcacc   120
tgcgctgtct atggtgggtc cttcagtact tactactgga gctggatccg ccagccccca   180
gggaaggggc tggagtggat tgggaaatc aatcatagtg gaagcaccaa ctacaacccg   240
tccctcaaga gtcgagtcac catatcagta gacacgtcca agaaccagtt ctccctgaag   300
ctgagctctg tgaccgccgc ggacacggct gtgtattact gtgcgagagg ggggtacgat   360
ttttggagtg gttattatga ctactggggc cagggaaccc tggtcaccgt ctctagt     417
```

<210> SEQ ID NO 21
<211> LENGTH: 324
<212> TYPE: DNA

```
<213> ORGANISM: Artificial Sequence
<220> FEATURE:
<223> OTHER INFORMATION: Description of Artificial Sequence: Synthetic
      Human Kappa Constant Region

<400> SEQUENCE: 21
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttga                                             324

<210> SEQ ID NO 22
<211> LENGTH: 993
<212> TYPE: DNA
<213> ORGANISM: Artificial Sequence
<220> FEATURE:
<223> OTHER INFORMATION: Description of Artificial Sequence: Synthetic
      Human IgG1 Constant Region

<400> SEQUENCE: 22
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggggagga gcagtacaac     540 agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                   993

<210> SEQ ID NO 23
<211> LENGTH: 981
<212> TYPE: DNA
<213> ORGANISM: Artificial Sequence
<220> FEATURE:
<223> OTHER INFORMATION: Description of Artificial Sequence: Synthetic
      Human IgG2 Constant Region

<400> SEQUENCE: 23
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
```

```
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctaccccg cgacatcgc cgtggagtgg    780 gagagcaatg ggcagccgga gaacaactac aagaccacac ctcccatgct ggactccgac    840
ggctccttct cctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaatg a                                              981
```

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 1.24.1 Light chain V region (Vk, 1-L15)

<400> SEQUENCE: 24

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Asn Leu Leu Ile Tyr Glu Ala Ser Ser Leu Gln Ser Gly Val
65                  70                  75                  80

Pro Ser Arg Phe Gly Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Gly Phe Pro Trp Thr Phe Gly Gln Gly Thr Lys Val Glu Ile
        115                 120                 125

Lys

<210> SEQ ID NO 25
<211> LENGTH: 141
<212> TYPE: PRT
<213> ORGANISM: Artificial Sequence
<220> FEATURE:
<223> OTHER INFORMATION: Description of Artificial Sequence: Synthetic
      HGF 1.24.1 Heavy chain V region (Vh, H3-11)-huIgG2 C region

<400> SEQUENCE: 25

Met Glu Phe Gly Leu Ser Trp Val Phe Leu Val Ala Ile Ile Lys Gly
1               5                   10                  15

```
Val Gln Cys Gln Val Gln Leu Val Glu Ser Gly Gly Leu Val Lys
            20                  25                  30

Pro Gly Gly Ser Leu Arg Leu Ser Cys Ala Ala Ser Gly Phe Thr Phe
            35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Thr Ala Val
            100                 105                 110

Tyr Tyr Cys Ala Arg Asp Glu Tyr Asn Ser Gly Trp Tyr Val Leu Phe
            115                 120                 125

Asp Tyr Trp Gly Gln Gly Thr Leu Val Thr Val Ser Ser
    130                 135                 140

<210> SEQ ID NO 26
<211> LENGTH: 133
<212> TYPE: PRT
<213> ORGANISM: Artificial Sequence
<220> FEATURE:
<223> OTHER INFORMATION: Description of Artificial Sequence: Synthetic
      HGF 1.29.1 Light chain V region (Vk, 4-B3)

<400> SEQUENCE: 26

Met Val Leu Gln Thr Gln Val Phe Ile Ser Leu Leu Leu Trp Ile Ser
 1               5                  10                  15

Asp Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
            35                  40                  45

Ile Phe Tyr Ser Ser Thr Asn Lys Asn Tyr Leu Ala Trp Tyr Gln Lys
    50                  55                  60

Lys Pro Gly Gln Pro Pro Lys Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Trp Thr Phe Gly Gln Gly Thr
            115                 120                 125

Lys Val Glu Ile Lys
    130

<210> SEQ ID NO 27
<211> LENGTH: 137
<212> TYPE: PRT
<213> ORGANISM: Artificial Sequence
<220> FEATURE:
<223> OTHER INFORMATION: Description of Artificial Sequence: Synthetic
      HGF 1.29.1 Heavy chain V region (Vh, 3-33)- huIgG2 C region

<400> SEQUENCE: 27

Met Glu Phe Gly Leu Asn Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
```

```
                     35                  40                  45
Ser Ser Tyr Gly Met His Trp Val Arg Gln Ala Pro Gly Lys Gly Leu
         50                  55                  60

Glu Trp Val Ala Val Ile Trp Tyr Asp Gly Ser Asp Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Arg Glu Asp Tyr Gly Glu Gly Phe Asp Tyr Trp Gly
         115                 120                 125

Gln Gly Thr Leu Val Thr Val Ser Ser
     130                 135

<210> SEQ ID NO 28
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 1.60.1 Light chain V region (Vk, 1-A20)

<400> SEQUENCE: 28

Met Asp Met Arg Val Pro Ala Gln Leu Leu Gly Leu Leu Leu Leu Trp
 1               5                  10                  15

Leu Pro Asp Thr Arg Cys Asp Ile Gln Met Thr Gln Ser Pro Ser Ser
                 20                  25                  30

Leu Ser Val Ser Val Gly Asp Arg Val Thr Ile Thr Cys Arg Ala Ser
             35                  40                  45

Gln Gly Ile Ser Ser Tyr Leu Ala Trp Tyr Gln Gln Lys Pro Gly Lys
         50                  55                  60

Val Pro Lys Leu Leu Ile Tyr Val Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Val Ala Thr Tyr Tyr Cys Gln Asn
             100                 105                 110

Tyr Asn Ser Asp Pro Leu Thr Phe Gly Gly Gly Thr Lys Val Glu Ile
         115                 120                 125

Lys

<210> SEQ ID NO 29
<211> LENGTH: 139
<212> TYPE: PRT
<213> ORGANISM: Artificial Sequence
<220> FEATURE:
<223> OTHER INFORMATION: Description of Artificial Sequence: Synthetic
      HGF 1.60.1 Heavy chain V region (Vh, H1-02)- huIgG2 C region

<400> SEQUENCE: 29

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Gly Tyr Tyr Ile Asn Trp Val Arg Gln Ala Pro Gly Gln Gly Leu
         50                  55                  60
```

-continued

```
Glu Trp Met Gly Trp Ile Asn Pro Asn Ser Gly Gly Thr Asn Tyr Ala
 65                  70                  75                  80

Gln Lys Phe Gln Gly Arg Val Thr Met Thr Arg Asp Thr Ser Ile Thr
                 85                  90                  95

Thr Ala Tyr Met Glu Leu Ser Arg Leu Arg Ala Asp Asp Thr Ala Val
            100                 105                 110

Tyr Tyr Cys Ala Arg Glu Leu Glu Leu Arg Tyr Tyr Gly Met Asp Val
        115                 120                 125

Trp Gly Gln Gly Thr Thr Val Thr Val Ser Ser
    130                 135
```

<210> SEQ ID NO 30
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 1.61.3 Light chain V region (Vk, 1-O18/O8)

<400> SEQUENCE: 30

```
Met Asp Met Arg Val Pro Ala Gln Leu Leu Gly Leu Leu Leu Leu Trp
 1               5                  10                  15

Leu Ser Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Gln Ala Ser
            35                  40                  45

Gln Asp Ile Ser Asn Tyr Leu Asn Trp Tyr Gln Gln Lys Pro Gly Thr
        50                  55                  60

Ala Pro Lys Leu Leu Ile Tyr Gly Ala Ser Asp Leu Glu Thr Gly Val
 65                  70                  75                  80

Pro Ser Arg Phe Ser Gly Ser Gly Ser Gly Thr Asp Phe Thr Phe Ala
                 85                  90                  95

Ile Ser Ser Leu Gln Pro Glu Asp Ile Ala Thr Tyr Tyr Cys Gln Gln
            100                 105                 110

Tyr Asp Asn Leu Pro Tyr Asn Phe Gly Gln Gly Thr Lys Leu Glu Ile
        115                 120                 125

Lys
```

<210> SEQ ID NO 31
<211> LENGTH: 148
<212> TYPE: PRT
<213> ORGANISM: Artificial Sequence
<220> FEATURE:
<223> OTHER INFORMATION: Description of Artificial Sequence: Synthetic
      HGF 1.61.3. Heavy chain V region (Vg, 4-31)- huIgG2 C region

<400> SEQUENCE: 31

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                 20                  25                  30

Pro Ser Gln Thr Leu Ser Leu Thr Cys Thr Val Ser Gly Gly Ser Ile
            35                  40                  45

Ser Ser Asp Gly Tyr Tyr Trp Ser Trp Ile Arg Gln His Pro Gly Lys
        50                  55                  60

Gly Leu Glu Trp Ile Gly Tyr Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95
```

Asn Gln Phe Ser Leu Lys Leu Ser Ser Val Thr Ala Ala Asp Thr Ala
                100                 105                 110

Val Tyr Tyr Cys Ala Arg Ser His Leu His Tyr Tyr Asp Ser Ser Gly
            115                 120                 125

Tyr Tyr Tyr Gly Gly Ala Phe Asp Ile Trp Gly Gln Gly Thr Met Val
    130                 135                 140

Thr Val Ser Ser
145

<210> SEQ ID NO 32
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 1.74.3 Light chain V region (Vk, 1-O12/02)

<400> SEQUENCE: 32

Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Ser Ile Asn Ser Asp Leu Asn Trp Tyr Gln Gln Lys Pro Gly Lys
        50                  55                  60

Val Pro Lys Leu Leu Ile Tyr Val Ala Ser Ser Leu Gln Asn Gly Val
 65                 70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Arg
                100                 105                 110

Ser Tyr Ser Thr Pro Pro Thr Phe Gly Pro Gly Thr Lys Val Asp Ile
            115                 120                 125

Lys

<210> SEQ ID NO 33
<211> LENGTH: 139
<212> TYPE: PRT
<213> ORGANISM: Artificial Sequence
<220> FEATURE:
<223> OTHER INFORMATION: Description of Artificial Sequence: Synthetic
      HGF 1.74.3 Heavy chain V region(Vh, VG1-02)-huIgG2 C region

<400> SEQUENCE: 33

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Ile His Trp Val Arg Gln Ala Pro Gly Gln Gly Leu
        50                  55                  60

Glu Trp Met Gly Trp Ile Asn Pro Asn Ser Gly Gly Thr Asn Tyr Ala
 65                 70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val

```
              100                 105                 110
Tyr Tyr Cys Ala Arg Glu Leu Glu Leu Arg Tyr Gly Met Asp Val
        115                 120                 125

Trp Gly Gln Gly Thr Thr Val Thr Val Ser Ser
        130                 135

<210> SEQ ID NO 34
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 1.75.1 Light chain V region (Vk, 1-A30)

<400> SEQUENCE: 34

Met Asp Met Arg Val Pro Ala Gln Leu Leu Gly Leu Leu Leu Trp
  1               5                  10                  15

Phe Pro Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Phe Gln Lys Pro Gly Lys
 50                  55                  60

Ala Pro Lys Arg Leu Ile Tyr Ala Ala Ser Ser Leu Gln Ser Gly Val
 65                  70                  75                  80

Pro Ser Arg Phe Ser Gly Ser Gly Ser Gly Thr Glu Phe Thr Leu Thr
                 85                  90                  95

Ile Ser Ser Leu Gln Pro Glu Asp Phe Ala Thr Tyr Tyr Cys Leu Gln
                100                 105                 110

His Asp Ser Tyr Pro Leu Thr Phe Gly Gly Gly Thr Lys Val Glu Ile
        115                 120                 125

Lys

<210> SEQ ID NO 35
<211> LENGTH: 144
<212> TYPE: PRT
<213> ORGANISM: Artificial Sequence
<220> FEATURE:
<223> OTHER INFORMATION: Description of Artificial Sequence: Synthetic
      HGF 1.75.1 Heavy chain V region (Vh, VG4-31)-huIgG2 C region

<400> SEQUENCE: 35

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
                 20                  25                  30

Pro Ser Gln Thr Leu Ser Leu Thr Cys Thr Val Ser Gly Gly Ser Ile
            35                  40                  45

Ser Ser Gly Gly Tyr Tyr Trp Ser Trp Ile Arg Gln His Pro Gly Lys
 50                  55                  60

Gly Leu Glu Trp Ile Gly Tyr Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Val Ser Ser Val Thr Ala Ala Asp Thr Ala
                100                 105                 110

Val Tyr Tyr Cys Ala Arg Asp Pro Leu Trp Phe Gly Glu Phe Asp Tyr
        115                 120                 125
```

```
Tyr Gly Met Asp Val Trp Gly Gln Gly Thr Thr Val Thr Val Ser Ser
        130                 135                 140
```

<210> SEQ ID NO 36
<211> LENGTH: 133
<212> TYPE: PRT
<213> ORGANISM: Artificial Sequence
<220> FEATURE:
<223> OTHER INFORMATION: Description of Artificial Sequence: Synthetic
      HGF 2.4.4 Light chain V region (Vk, 4-B3)

<400> SEQUENCE: 36

```
Met Val Leu Gln Thr Gln Val Phe Ile Ser Leu Leu Leu Trp Ile Ser
  1               5                  10                  15

Gly Ala Tyr Gly Asp Ile Val Met Thr Gln Ser Pro Asp Ser Leu Ala
                 20                  25                  30

Val Ser Leu Gly Glu Arg Ala Thr Ile Asn Cys Lys Ser Ser Gln Ser
             35                  40                  45

Val Leu Phe Ser Ser Asn Asn Lys Asn Tyr Leu Ala Trp Tyr Gln Gln
         50                  55                  60

Lys Pro Gly Gln Pro Pro Lys Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Tyr Cys Gln Gln Tyr Phe Ser Pro Pro Trp Thr Phe Gly Gln Gly Thr
            115                 120                 125

Lys Val Glu Ile Lys
            130
```

<210> SEQ ID NO 37
<211> LENGTH: 142
<212> TYPE: PRT
<213> ORGANISM: Artificial Sequence
<220> FEATURE:
<223> OTHER INFORMATION: Description of Artificial Sequence: Synthetic
      HGF 2.4.4 Heavy chain V region (Vh, VG 4-31)-huIgG2 C region

<400> SEQUENCE: 37

```
Met Lys His Leu Trp Phe Phe Leu Leu Leu Val Ala Ala Pro Arg Trp
  1               5                  10                  15

Ile Leu Ser Gln Val Gln Leu Lys Glu Ser Gly Pro Gly Leu Val Lys
                 20                  25                  30

Pro Ser Gln Thr Leu Ser Leu Thr Cys Thr Val Ser Gly Gly Ser Ile
             35                  40                  45

Ser Ser Gly Val Tyr Tyr Trp Ser Trp Ile Arg Gln His Pro Gly Lys
         50                  55                  60

Gly Leu Glu Trp Ile Gly Tyr Phe Tyr Tyr Ser Gly Asn Thr Tyr His
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg Asp Arg Ser Gly Tyr Asp His Pro Asp Ala
            115                 120                 125

Phe Asp Ile Trp Gly Gln Gly Thr Met Val Thr Val Ser Ser
            130                 135                 140
```

```
<210> SEQ ID NO 38
<211> LENGTH: 128
<212> TYPE: PRT
<213> ORGANISM: Artificial Sequence
<220> FEATURE:
<223> OTHER INFORMATION: Description of Artificial Sequence: Synthetic
      HGF 2.12.1 Light chain V region (Vk, 3-L2/L16)

<400> SEQUENCE: 38

Met Glu Ala Pro Ala Gln Leu Leu Phe Leu Leu Leu Trp Leu Pro
 1               5                  10                  15

Asp Thr Thr Gly Glu Ile Val Met Thr Gln Ser Pro Ala Thr Leu Ser
                20                  25                  30

Val Ser Pro Gly Glu Arg Ala Thr Leu Ser Cys Arg Ala Ser Gln Ser
            35                  40                  45

Val Asp Ser Asn Leu Ala Trp Tyr Arg Gln Lys Pro Gly Gln Ala Pro
 50                  55                  60

Arg Leu Leu Ile Tyr Gly Ala Ser Thr Arg Ala Thr Gly Ile Pro Ala
 65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Ile
                100                 105                 110

Asn Trp Pro Pro Ile Thr Phe Gly Gln Gly Thr Arg Leu Glu Ile Lys
            115                 120                 125

<210> SEQ ID NO 39
<211> LENGTH: 139
<212> TYPE: PRT
<213> ORGANISM: Artificial Sequence
<220> FEATURE:
<223> OTHER INFORMATION: Description of Artificial Sequence: Synthetic
      HGF 2.12.1 Heavy chain V region (Vg, 4-59)- huIgG2 C region

<400> SEQUENCE: 39

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Ser Ile Tyr Tyr Trp Ser Trp Ile Arg Gln Pro Pro Gly Lys Gly Leu
 50                  55                  60

Glu Trp Ile Gly Tyr Val Tyr Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
                100                 105                 110

Tyr Cys Ala Arg Gly Gly Tyr Asp Phe Trp Ser Gly Tyr Phe Asp Tyr
            115                 120                 125

Trp Gly Gln Gly Thr Leu Val Thr Val Ser Ser
            130                 135

<210> SEQ ID NO 40
<211> LENGTH: 129
<212> TYPE: PRT
<213> ORGANISM: Artificial Sequence
<220> FEATURE:
<223> OTHER INFORMATION: Description of Artificial Sequence: Synthetic
      HGF 2.40.1 Light chain V region (Vk, 1A20)
```

<400> SEQUENCE: 40

Met Asp Met Arg Val Pro Ala Gln Leu Leu Gly Leu Leu Leu Leu Trp
 1               5                  10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Gln Lys Pro Gly Lys
        50                  55                  60

Ala Pro Lys Arg Leu Ile Tyr Val Ala Ser Ser Leu Gln Ser Gly Val
 65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125

Lys

<210> SEQ ID NO 41
<211> LENGTH: 140
<212> TYPE: PRT
<213> ORGANISM: Artificial Sequence
<220> FEATURE:
<223> OTHER INFORMATION: Description of Artificial Sequence: Synthetic
      HGF 2.40.1 Heavy chain V region (Vh, VG 4-31)-huIgG2 C region

<400> SEQUENCE: 41

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
            35                  40                  45

Ser Ser Gly Gly Tyr Tyr Trp Ser Trp Ile Arg Gln His Pro Gly Lys
        50                  55                  60

Gly Leu Glu Trp Ile Gly Asn Ile Tyr Tyr Ser Gly Ile Thr Tyr Tyr
 65                  70                  75                  80

Asn Pro Ser Leu Lys Ser Arg Val Thr Met Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Asp Pro Leu Tyr Gly Asp Tyr Gly Phe Asp
        115                 120                 125

Pro Trp Gly Gln Gly Thr Leu Val Thr Val Ser Ser
130                 135                 140

<210> SEQ ID NO 42
<211> LENGTH: 128
<212> TYPE: PRT
<213> ORGANISM: Artificial Sequence
<220> FEATURE:
<223> OTHER INFORMATION: Description of Artificial Sequence: Synthetic
      HGF 3.10.1 Light chain V region (Vk, 3-L2/L16)

<400> SEQUENCE: 42

Met Glu Ala Pro Ala Gln Leu Leu Phe Leu Leu Leu Leu Trp Leu Pro
 1               5                  10                  15

```
Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Met Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Pro Ile Thr Phe Gly Gln Gly Thr Arg Leu Glu Ile Lys
        115                 120                 125

<210> SEQ ID NO 43
<211> LENGTH: 139
<212> TYPE: PRT
<213> ORGANISM: Artificial Sequence
<220> FEATURE:
<223> OTHER INFORMATION: Description of Artificial Sequence: Synthetic
      HGF 3.10.1 Heavy chain V region (Vh, VG 4-34)-huIgG1 C region

<400> SEQUENCE: 43

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Thr Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Gly Gly Tyr Asp Phe Trp Ser Gly Tyr Tyr Asp Tyr
        115                 120                 125

Trp Gly Gln Gly Thr Leu Val Thr Val Ser Ser
        130                 135

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      Human Kappa Constant Region

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 45
<211> LENGTH: 330
<212> TYPE: PRT
<213> ORGANISM: Artificial Sequence
<220> FEATURE:
<223> OTHER INFORMATION: Description of Artificial Sequence: Synthetic
      Human IgG1 Constant Region

<400> SEQUENCE: 45

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 326
<212> TYPE: PRT
<213> ORGANISM: Artificial Sequence
<220> FEATURE:
<223> OTHER INFORMATION: Description of Artificial Sequence: Synthetic
      Human IgG2 Constant Region

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325
```

-continued

```
<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      t-cell epitope peptide

<400> SEQUENCE: 47

Gln Tyr Ile Lys Ala Asn Ser Lys Phe Ile Gly Ile Thr Glu Leu Lys
  1               5                  10                  15

Lys Cys

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(23)
<223> OTHER INFORMATION: a, t, c or g

<400> SEQUENCE: 48
ggccggatag gcctccannn nnnt                                          24

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggacactgac atggactgaa ggagta                                        26

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggggtcaggc tggaactgag g                                             21

<210> SEQ ID NO 51
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acaacaaagc ttctagacca ccatggaagc cccagctcag cttctctt                48

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 52
cttgtcgact caacactctc ccctgttgaa gctc                                34

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggacactgac atggactgaa ggagta                                         26

<210> SEQ ID NO 54
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agcagaagct tctagaccac catgaaacac ctgtggttct tcctcctc                 48

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gtggaggcac tagagacggt gaccagggtt cc                                  32

<210> SEQ ID NO 56
<211> LENGTH: 1043
<212> TYPE: DNA
<213> ORGANISM: Artificial Sequence
<220> FEATURE:
<223> OTHER INFORMATION: Description of Artificial Sequence: Synthetic
      pI/hCh1 heavy chain nucleotide sequence

<400> SEQUENCE: 56
tctagaccac cgccatgggt gaaaattgaa tcgtctctag tgcctccacc aagggcccat    60
cggtcttccc cctggcaccc tcctccaaga gcacctctgg gggcacagcg gccctgggct   120
gcctggtcaa ggactacttc cccgaaccgg tgacggtgtc gtggaactca ggcgccctga   180
ccagcggcgt gcacaccttc ccggctgtcc tacagtcctc aggactctac tccctcagca   240
gcgtggtgac cgtgccctcc agcagcttgg gcacccagac ctacatctgc aacgtgaatc   300
acaagcccag caacaccaag gtggacaaga agttgagcc caaatcttgt gacaaaactc    360
acacatgccc accgtgccca gcacctgaac tcctgggggg accgtcagtc ttcctcttcc   420
ccccaaaacc caaggacacc ctcatgatct cccggacccc tgaggtcaca tgcgtggtgg   480
tggacgtgag ccacgaagac cctgaggtca agttcaactg gtacgtggac ggcgtggagg   540
tgcataatgc caagacaaag ccgcgggagg agcagtacaa cagcacgtac cgtgtggtca   600
gcgtcctcac cgtcctgcac caggactggc tgaatggcaa ggagtacaag tgcaaggtct   660
ccaacaaagc cctcccagcc cccatcgaga aaaccatctc caaagccaaa gggcagcccc   720
gagaaccaca ggtgtacacc ctgccccat cccgggatga gctgaccaag aaccaggtca   780

```
gcctgacctg cctggtcaaa ggcttctatc ccagcgacat cgccgtggag tgggagagca    840
atgggcagcc ggagaacaac tacaagacca cgcctcccgt gctggactcc gacggctcct    900
tcttcctcta tagcaagctc accgtggaca agagcaggtg gcagcagggg aacgtcttct    960
catgctccgt gatgcatgag gctctgcaca accactacac gcagaagagc ctctccctgt   1020
ctccgggtaa atgataagtc gac                                           1043

<210> SEQ ID NO 57
<211> LENGTH: 540
<212> TYPE: DNA
<213> ORGANISM: Gallus gallus
<220> FEATURE:
<221> NAME/KEY: CDS
<222> LOCATION: (2)..(520)

<400> SEQUENCE: 57 c ccc acc atg gtg cac gca acc tcc ccg ctg ctg ctg ctg ctg ctc         49
  Pro Thr Met Val His Ala Thr Ser Pro Leu Leu Leu Leu Leu Leu
   1               5                  10                  15 agc ctg gct ctg gtg gct ccc ggc ctc tct gcc aga aag tgc tcg ctg       97
Ser Leu Ala Leu Val Ala Pro Gly Leu Ser Ala Arg Lys Cys Ser Leu
             20                  25                  30 act ggg aaa tgg acc aac gat ctg ggc tcc aac atg acc atc ggg gct      145
Thr Gly Lys Trp Thr Asn Asp Leu Gly Ser Asn Met Thr Ile Gly Ala
         35                  40                  45 gtg aac agc aaa ggt gaa ttc aca ggc acc tac acc aca gcc gta aca      193
Val Asn Ser Lys Gly Glu Phe Thr Gly Thr Tyr Thr Thr Ala Val Thr
     50                  55                  60 gcc aca tca aat gag atc aaa gag tca cca ctg cat ggg aca caa aac      241
Ala Thr Ser Asn Glu Ile Lys Glu Ser Pro Leu His Gly Thr Gln Asn
 65                  70                  75                  80 acc atc aac aag agg acc cag ccc acc ttt ggc ttc act gtc aat tgg      289
Thr Ile Asn Lys Arg Thr Gln Pro Thr Phe Gly Phe Thr Val Asn Trp
                 85                  90                  95 aag ttt tca gag tcc acc act gtc ttc acg ggc cag tgc ttc ata gac      337
Lys Phe Ser Glu Ser Thr Thr Val Phe Thr Gly Gln Cys Phe Ile Asp
            100                 105                 110 agg aac ggg aag gag gtc ctg aag acc atg tgg ctg ctg cgg tca agt      385
Arg Asn Gly Lys Glu Val Leu Lys Thr Met Trp Leu Leu Arg Ser Ser
        115                 120                 125 gtt aat gac att ggt gat gac tgg aaa gct acc agg gtc ggc atc aac      433
Val Asn Asp Ile Gly Asp Asp Trp Lys Ala Thr Arg Val Gly Ile Asn
    130                 135                 140 atc ttc act cgc ctg cgc aca cag aag gag cag ctg cta gca agc ttg      481
Ile Phe Thr Arg Leu Arg Thr Gln Lys Glu Gln Leu Leu Ala Ser Leu
145                 150                 155                 160 cta gcg gcc gct cga ggc cgg caa ggc cgg atc cag aca tgataagata      530
Leu Ala Ala Ala Arg Gly Arg Gln Gly Arg Ile Gln Thr
                165                 170 cattgatgag                                                          540

<210> SEQ ID NO 58
<211> LENGTH: 540
<212> TYPE: DNA
<213> ORGANISM: Gallus gallus

<400> SEQUENCE: 58
ctcatcaatg tatcttatca tgtctggatc cggccttgcc ggcctcgagc ggccgctagc     60
aagcttgcta gcagctgctc cttctgtgtg cgcaggcgag tgaagatgtt gatgccgacc    120
```

```
ctggtagctt tccagtcatc accaatgtca ttaacacttg accgcagcag ccacatggtc    180
ttcaggacct ccttcccgtt cctgtctatg aagcactggc ccgtgaagac agtggtggac    240
tctgaaaact tccaattgac agtgaagcca aaggtgggct gggtcctctt gttgatggtg    300
ttttgtgtcc catgcagtgg tgactctttg atctcatttg atgtggctgt tacggctgtg    360
gtgtaggtgc ctgtgaattc acctttgctg ttcacagccc cgatggtcat gttggagccc    420
agatcgttgg tccatttccc agtcagcgag cactttctgg cagagaggcc gggagccacc    480
agagccaggc tgagcagcag cagcagcagc agcggggagg ttgcgtgcac catggtgggg    540
```

<210> SEQ ID NO 59
<211> LENGTH: 173
<212> TYPE: PRT
<213> ORGANISM: Gallus gallus

<400> SEQUENCE: 59

```
Pro Thr Met Val His Ala Thr Ser Pro Leu Leu Leu Leu Leu Leu Leu
 1               5                  10                  15

Ser Leu Ala Leu Val Ala Pro Gly Leu Ser Ala Arg Lys Cys Ser Leu
            20                  25                  30

Thr Gly Lys Trp Thr Asn Asp Leu Gly Ser Asn Met Thr Ile Gly Ala
        35                  40                  45

Val Asn Ser Lys Gly Glu Phe Thr Gly Thr Tyr Thr Thr Ala Val Thr
    50                  55                  60

Ala Thr Ser Asn Glu Ile Lys Glu Ser Pro Leu His Gly Thr Gln Asn
65                  70                  75                  80

Thr Ile Asn Lys Arg Thr Gln Pro Thr Phe Gly Phe Thr Val Asn Trp
                85                  90                  95

Lys Phe Ser Glu Ser Thr Thr Val Phe Thr Gly Gln Cys Phe Ile Asp
            100                 105                 110

Arg Asn Gly Lys Glu Val Leu Lys Thr Met Trp Leu Leu Arg Ser Ser
        115                 120                 125

Val Asn Asp Ile Gly Asp Asp Trp Lys Ala Thr Arg Val Gly Ile Asn
    130                 135                 140

Ile Phe Thr Arg Leu Arg Thr Gln Lys Glu Gln Leu Leu Ala Ser Leu
145                 150                 155                 160

Leu Ala Ala Ala Arg Gly Arg Gln Gly Arg Ile Gln Thr
                165                 170
```

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 60

```
Arg Ala Ser Gln Gly Ile Ser Ser Trp Leu Ala
 1               5                  10
```

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 61

```
Lys Ser Ser Gln Ser Ile Phe Tyr Ser Ser Thr Asn Lys Asn Tyr Leu
 1               5                   10                  15
Ala

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 62

Arg Ala Ser Gln Gly Ile Ser Ser Tyr Leu Ala
 1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 63

Gln Ala Ser Gln Asp Ile Ser Asn Tyr Leu Asn
 1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 64

Arg Ala Ser Gln Ser Ile Asn Ser Asp Leu Asn
 1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 65

Arg Ala Ser Gln Gly Ile Arg Asn Asp Leu Gly
 1               5                   10

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 66

Lys Ser Ser Gln Ser Val Leu Phe Ser Ser Asn Asn Lys Asn Tyr Leu
 1               5                   10                  15
Ala

<210> SEQ ID NO 67
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 67

Arg Ala Ser Gln Ser Val Asp Ser Asn Leu Ala
 1               5                  10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 68

Arg Ala Ser Gln Gly Ile Arg Asn Asp Leu Gly
 1               5                  10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 69

Arg Ala Ser Gln Ser Val Ser Ser Asn Leu Ala
 1               5                  10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 70

Glu Ala Ser Ser Leu Gln Ser
 1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 71

Trp Ala Ser Thr Arg Glu Ser
 1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 72

Val Ala Ser Thr Leu Gln Ser
 1               5
```

```
<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 73

Gly Ala Ser Asp Leu Glu Thr
 1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 74

Val Ala Ser Ser Leu Gln Asn
 1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 75

Ala Ala Ser Ser Leu Gln Ser
 1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 76

Trp Ala Ser Thr Arg Glu Ser
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 77

Gly Ala Ser Thr Arg Ala Thr
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide
```

```
<400> SEQUENCE: 78

Val Ala Ser Ser Leu Gln Ser
 1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 79

Gly Ala Ser Thr Arg Ala Thr
 1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 80

Gln Gln Ala Asn Gly Phe Pro Trp Thr
 1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 81

Gln Gln Tyr Tyr Ser Thr Pro Trp Thr
 1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 82

Gln Asn Tyr Asn Ser Asp Pro Leu Thr
 1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 83

Gln Gln Tyr Asp Asn Leu Pro Tyr Asn
 1               5

<210> SEQ ID NO 84
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      light chain variable region CDR peptide

<400> SEQUENCE: 84

Gln Arg Ser Tyr Ser Thr Pro Pro Thr
 1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 85

Leu Gln His Asp Ser Tyr Pro Leu Thr
 1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 86

Gln Gln Tyr Phe Ser Pro Pro Trp Thr
 1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 87

Gln Gln Tyr Ile Asn Trp Pro Pro Ile Thr
 1               5                  10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 88

Leu Gln His Asn Ser Tyr Pro Leu Thr
 1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain variable region CDR peptide

<400> SEQUENCE: 89

Gln Gln Tyr Asn Asn Trp Pro Pro Ile Thr
 1               5                  10
```

```
<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 90

Asp Tyr Tyr Met Ser
 1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 91

Ser Tyr Gly Met His
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 92

Gly Tyr Tyr Ile Asn
 1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 93

Ser Asp Gly Tyr Tyr Trp Ser
 1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 94

Gly Tyr Tyr Ile His
 1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 95
```

```
Ser Gly Gly Tyr Tyr Trp Ser
  1               5
```

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 96

```
Ser Gly Val Tyr Tyr Trp Ser
  1               5
```

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 97

```
Ile Tyr Tyr Trp Ser
  1               5
```

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 98

```
Ser Gly Gly Tyr Tyr Trp Ser
  1               5
```

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 99

```
Thr Tyr Tyr Trp Ser
  1               5
```

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 100

```
Tyr Ile Ser Ser Ser Gly Ser Thr Ile Tyr Tyr Ala Asp Ser Val Lys
  1               5                  10                  15

Gly
```

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 101

Val Ile Trp Tyr Asp Gly Ser Asp Lys Tyr Tyr Ala Asp Ser Val Lys
 1               5                  10                  15
Gly

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 102

Trp Ile Asn Pro Asn Ser Gly Gly Thr Asn Tyr Ala Gln Lys Phe Gln
 1               5                  10                  15
Gly

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 103

Tyr Ile Tyr Tyr Ser Gly Ser Thr Tyr Tyr Asn Pro Ser Leu Lys Ser
 1               5                  10                  15

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 104

Trp Ile Asn Pro Asn Ser Gly Gly Thr Asn Tyr Ala Gln Lys Phe Gln
 1               5                  10                  15
Gly

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 105

Tyr Ile Tyr Tyr Ser Gly Ser Thr Tyr Tyr Asn Pro Ser Leu Lys Ser
 1               5                  10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 106

Tyr Phe Tyr Tyr Ser Gly Asn Thr Tyr His Asn Pro Ser Leu Lys Ser
 1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 107

Tyr Val Tyr Tyr Ser Gly Ser Thr Asn Tyr Asn Pro Ser Leu Lys Ser
 1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 108

Asn Ile Tyr Tyr Ser Gly Ile Thr Tyr Tyr Asn Pro Ser Leu Lys Ser
 1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 109

Glu Ile Asn His Ser Gly Ser Thr Asn Tyr Asn Pro Ser Leu Lys Ser
 1               5                   10                  15

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 110

Asp Glu Tyr Asn Ser Gly Trp Tyr Val Leu Phe Asp Tyr
 1               5                   10

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 111

Glu Asp Tyr Gly Glu Gly Phe Asp Tyr
 1               5

<210> SEQ ID NO 112
<211> LENGTH: 11
<212> TYPE: PRT
<213> ORGANISM: Artificial Sequence

```
<220> FEATURE:
<223> OTHER INFORMATION: Description of Artificial Sequence: Synthetic
      heavy chain variable region CDR peptide

<400> SEQUENCE: 112

Glu Leu Glu Leu Arg Tyr Tyr Gly Met Asp Val
1               5                   10

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 113

Ser His Leu His Tyr Tyr Asp Ser Ser Gly Tyr Tyr Gly Gly Ala
1               5                   10                  15

Phe Asp Ile

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 114

Glu Leu Glu Leu Arg Tyr Tyr Gly Met Asp Val
1               5                   10

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 115

Asp Pro Leu Trp Phe Gly Glu Phe Asp Tyr Tyr Gly Met Asp Val
1               5                   10                  15

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 116

Asp Arg Ser Gly Tyr Asp His Pro Asp Ala Phe Asp Ile
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 117

Gly Gly Tyr Asp Phe Trp Ser Gly Tyr Phe Asp Tyr
1               5                   10
```

-continued

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 118

Asp Pro Leu Tyr Gly Asp Tyr Gly Phe Asp Pro
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain variable region CDR peptide

<400> SEQUENCE: 119

Gly Gly Tyr Asp Phe Trp Ser Gly Tyr Tyr Asp Tyr
1               5                   10

<210> SEQ ID NO 120
<211> LENGTH: 279
<212> TYPE: PRT
<213> ORGANISM: Homo sapiens

<400> SEQUENCE: 120

Pro Trp Cys Tyr Thr Gly Asn Pro Leu Ile Pro Trp Asp Tyr Cys Pro
1               5                   10                  15

Ile Ser Arg Cys Glu Gly Asp Thr Thr Pro Thr Ile Val Asn Leu Asp
            20                  25                  30

His Pro Val Ile Ser Cys Ala Lys Thr Lys Gln Leu Arg Val Val Asn
        35                  40                  45

Gly Ile Pro Thr Arg Thr Asn Ile Gly Trp Met Val Ser Leu Arg Tyr
    50                  55                  60

Arg Asn Lys His Ile Cys Gly Gly Ser Leu Ile Lys Glu Ser Trp Val
65                  70                  75                  80

Leu Thr Ala Arg Gln Cys Phe Pro Ser Arg Asp Leu Lys Asp Tyr Glu
                85                  90                  95

Ala Trp Leu Gly Ile His Asp Val His Gly Arg Gly Asp Glu Lys Cys
            100                 105                 110

Lys Gln Val Leu Asn Val Ser Gln Leu Val Tyr Gly Pro Glu Gly Ser
        115                 120                 125

Asp Leu Val Leu Met Lys Leu Ala Arg Pro Ala Val Leu Asp Asp Phe
    130                 135                 140

Val Ser Thr Ile Asp Leu Pro Asn Tyr Gly Cys Thr Ile Pro Glu Lys
145                 150                 155                 160

Thr Ser Cys Ser Val Tyr Gly Trp Gly Tyr Thr Gly Leu Ile Asn Tyr
                165                 170                 175

Asp Gly Leu Leu Arg Val Ala His Leu Tyr Ile Met Gly Asn Glu Lys
            180                 185                 190

Cys Ser Gln His His Arg Gly Lys Val Thr Leu Asn Glu Ser Glu Ile
        195                 200                 205

Cys Ala Gly Ala Glu Lys Ile Gly Ser Gly Pro Cys Glu Gly Asp Tyr
    210                 215                 220

Gly Gly Pro Leu Val Cys Glu Gln His Lys Met Arg Met Val Leu Gly

```
                225                 230                 235                 240
Val Ile Val Pro Gly Arg Gly Cys Ala Ile Pro Asn Arg Pro Gly Ile
                245                 250                 255

Phe Val Arg Val Ala Tyr Tyr Ala Lys Trp Ile His Lys Ile Ile Leu
                260                 265                 270

Thr Tyr Lys Val Pro Gln Ser
                275

<210> SEQ ID NO 121
<211> LENGTH: 278
<212> TYPE: PRT
<213> ORGANISM: Mus musculus

<400> SEQUENCE: 121

Pro Trp Cys Tyr Thr Gly Asn Pro Leu Ile Pro Trp Asp Tyr Cys Pro
  1               5                  10                  15

Ile Ser Arg Cys Glu Gly Asp Thr Thr Pro Thr Ile Val Asn Leu Asp
                 20                  25                  30

His Pro Val Ile Ser Cys Ala Lys Thr Lys Gln Leu Arg Val Val Asn
             35                  40                  45

Gly Ile Pro Thr Gln Thr Thr Val Gly Trp Met Val Ser Leu Lys Tyr
         50                  55                  60

Arg Asn Lys His Ile Cys Gly Gly Ser Leu Ile Lys Glu Ser Trp Val
 65                  70                  75                  80

Leu Thr Ala Arg Gln Cys Phe Pro Ala Arg Asn Lys Asp Leu Lys Asp
                 85                  90                  95

Tyr Glu Ala Trp Leu Gly Ile His Asp Val His Glu Arg Gly Glu Glu
            100                 105                 110

Lys Arg Lys Gln Ile Leu Asn Ile Ser Gln Leu Val Tyr Gly Pro Glu
        115                 120                 125

Gly Ser Asp Leu Val Leu Leu Lys Leu Ala Arg Pro Ala Ile Leu Asp
    130                 135                 140

Asn Phe Val Ser Thr Ile Asp Leu Pro Ser Tyr Gly Cys Thr Ile Pro
145                 150                 155                 160

Glu Lys Thr Thr Cys Ser Ile Tyr Gly Trp Gly Tyr Thr Gly Leu Ile
                165                 170                 175

Asn Ala Asp Gly Leu Leu Arg Val Ala His Leu Tyr Ile Met Gly Asn
            180                 185                 190

Glu Lys Cys Ser Gln His His Gln Gly Lys Val Thr Leu Asn Glu Ser
        195                 200                 205

Glu Leu Cys Ala Gly Ala Glu Lys Ile Gly Ser Gly Pro Cys Glu Gly
    210                 215                 220

Asp Tyr Gly Gly Pro Leu Ile Cys Glu Gln His Lys Met Arg Met Val
225                 230                 235                 240

Leu Gly Val Ile Val Pro Gly Arg Gly Cys Ala Ile Pro Asn Arg Pro
                245                 250                 255

Gly Ile Phe Val Arg Val Ala Tyr Tyr Ala Lys Trp Ile His Lys Val
            260                 265                 270

Ile Leu Thr Tyr Lys Leu
        275

<210> SEQ ID NO 122
<211> LENGTH: 278
<212> TYPE: PRT
<213> ORGANISM: Artificial Sequence
<220> FEATURE:
<223> OTHER INFORMATION: Description of Artificial Sequence: Consensus
``` sequence
<220> FEATURE:
<221> NAME/KEY: MOD_RES
<222> LOCATION: (53)..(53)
<223> OTHER INFORMATION: Undetermined consensus residue; variable amino
      acid
<220> FEATURE:
<221> NAME/KEY: MOD_RES
<222> LOCATION: (55)..(55)
<223> OTHER INFORMATION: Undetermined consensus residue; variable amino
      acid
<220> FEATURE:
<221> NAME/KEY: MOD_RES
<222> LOCATION: (91)..(92)
<223> OTHER INFORMATION: Undetermined consensus residue; variable amino
      acid
<220> FEATURE:
<221> NAME/KEY: MOD_RES
<222> LOCATION: (108)..(108)
<223> OTHER INFORMATION: Undetermined consensus residue; variable amino
      acid
<220> FEATURE:
<221> NAME/KEY: MOD_RES
<222> LOCATION: (114)..(114)
<223> OTHER INFORMATION: Undetermined consensus residue; variable amino
      acid
<220> FEATURE:
<221> NAME/KEY: MOD_RES
<222> LOCATION: (145)..(145)
<223> OTHER INFORMATION: Undetermined consensus residue; variable amino
      acid
<220> FEATURE:
<221> NAME/KEY: MOD_RES
<222> LOCATION: (154)..(154)
<223> OTHER INFORMATION: Undetermined consensus residue; variable amino
      acid
<220> FEATURE:
<221> NAME/KEY: MOD_RES
<222> LOCATION: (178)..(178)
<223> OTHER INFORMATION: Undetermined consensus residue; variable amino
      acid
<220> FEATURE:
<221> NAME/KEY: MOD_RES
<222> LOCATION: (200)..(200)
<223> OTHER INFORMATION: Undetermined consensus residue; variable amino
      acid

<400> SEQUENCE: 122

Pro Trp Cys Tyr Thr Gly Asn Pro Leu Ile Pro Trp Asp Tyr Cys Pro
 1               5                  10                  15

Ile Ser Arg Cys Glu Gly Asp Thr Thr Pro Thr Ile Val Asn Leu Asp
            20                  25                  30

His Pro Val Ile Ser Cys Ala Lys Thr Lys Gln Leu Arg Val Val Asn
        35                  40                  45

Gly Ile Pro Thr Xaa Thr Xaa Ile Gly Trp Met Val Ser Leu Lys Tyr
    50                  55                  60

Arg Asn Lys His Ile Cys Gly Gly Ser Leu Ile Lys Glu Ser Trp Val
65                  70                  75                  80

Leu Thr Ala Arg Gln Cys Phe Pro Ala Arg Xaa Xaa Asp Leu Lys Asp
                85                  90                  95

Tyr Glu Ala Trp Leu Gly Ile His Asp Val His Xaa Arg Gly Asp Glu
            100                 105                 110

Lys Xaa Lys Gln Ile Leu Asn Ile Ser Gln Leu Val Tyr Gly Pro Glu
        115                 120                 125

Gly Ser Asp Leu Val Leu Leu Lys Leu Ala Arg Pro Ala Ile Leu Asp
    130                 135                 140

Xaa Phe Val Ser Thr Ile Asp Leu Pro Xaa Tyr Gly Cys Thr Ile Pro
145                 150                 155                 160

Glu Lys Thr Ser Cys Ser Ile Tyr Gly Trp Gly Tyr Thr Gly Leu Ile

```
                   165                 170                 175
Asn Xaa Asp Gly Leu Leu Arg Val Ala His Leu Tyr Ile Met Gly Asn
            180                 185                 190

Glu Lys Cys Ser Gln His His Xaa Gly Lys Val Thr Leu Asn Glu Ser
        195                 200                 205

Glu Ile Cys Ala Gly Ala Glu Lys Ile Gly Ser Gly Pro Cys Glu Gly
    210                 215                 220

Asp Tyr Gly Gly Pro Leu Ile Cys Glu Gln His Lys Met Arg Met Val
225                 230                 235                 240

Leu Gly Val Ile Val Pro Gly Arg Gly Cys Ala Ile Pro Asn Arg Pro
                245                 250                 255

Gly Ile Phe Val Arg Val Ala Tyr Tyr Ala Lys Trp Ile His Lys Ile
            260                 265                 270

Ile Leu Thr Tyr Lys Leu
        275

<210> SEQ ID NO 123
<211> LENGTH: 77
<212> TYPE: PRT
<213> ORGANISM: Homo sapiens

<400> SEQUENCE: 123

Gly Trp Met Val Ser Leu Arg Tyr Arg Asn Lys His Ile Cys Gly Gly
1               5                   10                  15

Ser Leu Ile Lys Glu Ser Trp Val Leu Thr Ala Arg Gln Cys Phe Pro
            20                  25                  30

Ser Arg Asp Leu Lys Asp Tyr Glu Ala Trp Leu Gly Ile His Asp Val
        35                  40                  45

His Gly Arg Gly Asp Glu Lys Cys Lys Gln Val Leu Asn Val Ser Gln
    50                  55                  60

Leu Val Tyr Gly Pro Glu Gly Ser Asp Leu Val Leu Met
65                  70                  75

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<400> SEQUENCE: 124
atgcgtctcc cttgatgatg ctggctgcat ttc                             33

<210> SEQ ID NO 125
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<400> SEQUENCE: 125
atgcgtctct caagggaagg tgactctgaa tga                             33

<210> SEQ ID NO 126
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
```

```
atgcgtctct aactaggtaa atcaatcgta ctaaca                            36
```

<210> SEQ ID NO 127
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127

```
atgcgtctct agttatggat gcacaattcc tgaaa                             35
```

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128

```
atgcgtctca attatccagg acagcaggcc tg                                32
```

<210> SEQ ID NO 129
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

```
atgcgtctca taattttgtt agtacgattg atttacc                           37
```

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130

```
atgcgtctcg cgtttctcat ctcctcttcc gt                                32
```

<210> SEQ ID NO 131
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
atgcgtctca aacgcaaaca ggttctcaat gttt                              34
```

<210> SEQ ID NO 132
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
atgcgtctcc tttcgtggac atcatgaatt ccaa                              34
```

<210> SEQ ID NO 133
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
atgcgtctcc gaaagaggag atgagaaatg caaa                               34

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gagcagctgc tagcaagctt gcta                                          24

<210> SEQ ID NO 135
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atgcgtctca gagacttgaa agactatgaa gcttg                              35

<210> SEQ ID NO 136
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
atgcgtctcg tctctggctg gaaaacattg tctt                               34

<210> SEQ ID NO 137
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
atgcgtctca acaaagactt gaaagattat gaagcttg                           38

<210> SEQ ID NO 138
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
atgcgtctct tgtttcgag aagggaaaca ctgtcg                              36

```
<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atgcgtctca agcttgccag gcctgctgt                                              29

<210> SEQ ID NO 140
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
atgcgtctca agcttcagta aaaccaagtc tga                                         33

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atgcgtctca agcttgctcg acctgcaatc                                             30

<210> SEQ ID NO 142
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
atgcgtctca agcttcatta aaaccagatc tga                                         33

<210> SEQ ID NO 143
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
atgcgtctca agcttgccag gcctgctgt                                              29

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
atgcgtctca agcttcagta aaaccaagtc tga                                         33

<210> SEQ ID NO 145
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
atgcgtctca agcttgctcg acctgcaatc                                      30

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atgcgtctca agcttcatta aaaccagatc tga                                  33

<210> SEQ ID NO 147
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
atgcgtctct aggatggatg gttagtttga gat                                  33

<210> SEQ ID NO 148
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
atgcgtctca tcctactgtt gtttgtgttg gaat                                 34

<210> SEQ ID NO 149
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atgcgtctct aggatggatg gttagtttga aata                                 34

<210> SEQ ID NO 150
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
atgcgtctca tcctatgttt gttcgtgttg g                                    31

<210> SEQ ID NO 151
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 151
atgcgtctca tgcatccaag gtcaaggaga ag                                   32

<210> SEQ ID NO 152
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
atgcgtctca tgcattcagt tgtttccata gg                                   32

<210> SEQ ID NO 153
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
atgcgtctca tgcatgacct gcaatgggga g                                    31

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atgcgtctca tgcattcaac ttctgaacac tga                                  33

<210> SEQ ID NO 155
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atgcgtctca tgcatcattg gtaaaggacg c                                    31

<210> SEQ ID NO 156
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
atgcgtctca tgcagtttct aatatagtct ttgttttc                             38

<210> SEQ ID NO 157
<211> LENGTH: 32
<212> TYPE: DNA
<213> ORGANISM: Artificial Sequence
<220> FEATURE:
<223> OTHER INFORMATION: Description of Artificial Sequence: Synthetic
```

```
                               oligonucleotide

<400> SEQUENCE: 157
atgggatccc tatgactgtg gtaccttata tg                                32

<210> SEQ ID NO 158
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
atgcggccgc acaaaggaaa agaagaaata caattc                            36

<210> SEQ ID NO 159
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cgggatcctt acaacttgta tgtcaaaatt ac                                32

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
atgatggcgg ccgctcagaa gaaaagaaga aatacacttc                        40

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Val Asn Gly Ile Pro Thr Arg His Gly Arg
  1               5                  10

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Ile Pro Thr Arg Thr His Gly Arg
  1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 163

Val Asn Thr Leu Asp Gln
  1               5

<210> SEQ ID NO 164
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Val Val Asn Gly Ile Pro Thr Arg Thr Asn Ile Gly Trp Met Val Ser
  1               5                  10                  15

Leu Arg Tyr Arg Asn Lys His Ile Cys Gly Gly Ser Leu Ile Lys Glu
             20                  25                  30

Ser Trp Val Leu Thr Ala Arg Gln Cys Phe Pro Ser Arg Asp Leu Lys
         35                  40                  45

Asp Tyr Glu Ala Trp Leu Gly Ile His Asp Val His Gly Arg
     50                  55                  60

<210> SEQ ID NO 165
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ile Pro Thr Arg Thr Asn Ile Gly Trp Met Val Ser Leu Arg Tyr
  1               5                  10                  15

Arg Asn Lys His Ile Cys Gly Gly Ser Leu Ile Lys Glu Ser Trp Val
             20                  25                  30

Leu Thr Ala Arg Gln Cys Phe Pro Ser Arg Asp Leu Lys Asp Tyr Glu
         35                  40                  45

Ala Trp Leu Gly Ile His Asp Val His Gly Arg
     50                  55

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Light chain
      CDR1 consensus sequence (CDR1a)
<220> FEATURE:
<221> NAME/KEY: MOD_RES
<222> LOCATION: (1)
<223> OTHER INFORMATION: lysine, arginine, or glutamine
<220> FEATURE:
<221> NAME/KEY: MOD_RES
<222> LOCATION: (2)
<223> OTHER INFORMATION: serine or alanine
<220> FEATURE:
<221> NAME/KEY: MOD_RES
<222> LOCATION: (5)
<223> OTHER INFORMATION: serine, glycine, or aspartic acid
<220> FEATURE:
<221> NAME/KEY: MOD_RES
<222> LOCATION: (6)
<223> OTHER INFORMATION: valine or isoleucine or is not present
<220> FEATURE:
<221> NAME/KEY: MOD_RES
<222> LOCATION: (7)

-continued

```
<223> OTHER INFORMATION: leucine or phenylalanine or is not present
<220> FEATURE:
<221> NAME/KEY: MOD_RES
<222> LOCATION: (8)
<223> OTHER INFORMATION: phenylalanine, tyrosine or is not present
<220> FEATURE:
<221> NAME/KEY: MOD_RES
<222> LOCATION: (9)..(10)
<223> OTHER INFORMATION: serine or not present
<220> FEATURE:
<221> NAME/KEY: MOD_RES
<222> LOCATION: (11)
<223> OTHER INFORMATION: asparagine, threonine, or not present
<220> FEATURE:
<221> NAME/KEY: MOD_RES
<222> LOCATION: (12)
<223> OTHER INFORMATION: asparagine, isoleucine, or valine
<220> FEATURE:
<221> NAME/KEY: MOD_RES
<222> LOCATION: (13)
<223> OTHER INFORMATION: lysine, arginine, asparagine, or aspartic acid
<220> FEATURE:
<221> NAME/KEY: MOD_RES
<222> LOCATION: (14)
<223> OTHER INFORMATION: asparagine or serine
<220> FEATURE:
<221> NAME/KEY: MOD_RES
<222> LOCATION: (15)
<223> OTHER INFORMATION: tyrosine, aspartic acid, tryptophan, or
      asparagine
<220> FEATURE:
<221> NAME/KEY: MOD_RES
<222> LOCATION: (17)
<223> OTHER INFORMATION: alanine, glycine, or asparagine

<400> SEQUENCE: 166

Xaa Xaa Ser Gln Xaa Xaa Xaa Xaa Xaa Xaa Xaa Xaa Xaa Xaa Leu
 1               5                   10                  15

Xaa

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Light chain
      CDR2 consensus sequence (CDR2a)
<220> FEATURE:
<221> NAME/KEY: MOD_RES
<222> LOCATION: (1)
<223> OTHER INFORMATION: tryptophan, alanine, valine, glutamic acid, or
      glycine
<220> FEATURE:
<221> NAME/KEY: MOD_RES
<222> LOCATION: (4)
<223> OTHER INFORMATION: threonine, serine, or aspartic acid
<220> FEATURE:
<221> NAME/KEY: MOD_RES
<222> LOCATION: (5)
<223> OTHER INFORMATION: arginine or leucine
<220> FEATURE:
<221> NAME/KEY: MOD_RES
<222> LOCATION: (6)
<223> OTHER INFORMATION: glutamic acid, glutamine, or alanine
<220> FEATURE:
<221> NAME/KEY: MOD_RES
<222> LOCATION: (7)
<223> OTHER INFORMATION: serine, asparagine, or threonine

<400> SEQUENCE: 167

Xaa Xaa Xaa Xaa Xaa Xaa Xaa
 1               5

<210> SEQ ID NO 168
<211> LENGTH: 10
```

```
<212> TYPE: PRT
<213> ORGANISM: Artificial Sequence
<220> FEATURE:
<223> OTHER INFORMATION: Description of Artificial Sequence: Light chain
      CDR3 consensus sequence (CDR3a)
<220> FEATURE:
<221> NAME/KEY: MOD_RES
<222> LOCATION: (1)
<223> OTHER INFORMATION: glutamine or leucine
<220> FEATURE:
<221> NAME/KEY: MOD_RES
<222> LOCATION: (2)
<223> OTHER INFORMATION: glutamine, asparagine, or arginine
<220> FEATURE:
<221> NAME/KEY: MOD_RES
<222> LOCATION: (3)
<223> OTHER INFORMATION: tyrosine, histidine, alanine, or serine
<220> FEATURE:
<221> NAME/KEY: MOD_RES
<222> LOCATION: (4)
<223> OTHER INFORMATION: phenylalanine, tyrosine, aspartic acid,
      asparagine, or isoleucine
<220> FEATURE:
<221> NAME/KEY: MOD_RES
<222> LOCATION: (5)
<223> OTHER INFORMATION: serine, glycine, or asparagine
<220> FEATURE:
<221> NAME/KEY: MOD_RES
<222> LOCATION: (6)
<223> OTHER INFORMATION: proline, tyrosine, threonine, phenylalanine,
      aspartic acid, leucine, or tryptophan
<220> FEATURE:
<221> NAME/KEY: MOD_RES
<222> LOCATION: (8)
<223> OTHER INFORMATION: proline or is not present
<220> FEATURE:
<221> NAME/KEY: MOD_RES
<222> LOCATION: (9)
<223> OTHER INFORMATION: tryptophan, leucine, proline, tyrosine, or
      isoleucine
<220> FEATURE:
<221> NAME/KEY: MOD_RES
<222> LOCATION: (10)
<223> OTHER INFORMATION: threonine or asparagine

<400> SEQUENCE: 168

Xaa Xaa Xaa Xaa Xaa Xaa Pro Xaa Xaa Xaa
  1               5                  10

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Heavy chain
      CDR1 consensus sequence (CDR1b)
<220> FEATURE:
<221> NAME/KEY: MOD_RES
<222> LOCATION: (1)
<223> OTHER INFORMATION: serine or is not present
<220> FEATURE:
<221> NAME/KEY: MOD_RES
<222> LOCATION: (2)
<223> OTHER INFORMATION: aspartic acid or glycine, or is not present
<220> FEATURE:
<221> NAME/KEY: MOD_RES
<222> LOCATION: (3)
<223> OTHER INFORMATION: aspartic acid, glycine, serine, valine,
      threonine, or isoleucine
<220> FEATURE:
<221> NAME/KEY: MOD_RES
<222> LOCATION: (5)
<223> OTHER INFORMATION: tyrosine or glycine
<220> FEATURE:
<221> NAME/KEY: MOD_RES
<222> LOCATION: (6)
<223> OTHER INFORMATION: isoleucine, methionine, or tryptophan
<220> FEATURE:
```

-continued

```
<221> NAME/KEY: MOD_RES
<222> LOCATION: (7)
<223> OTHER INFORMATION: histidine, asparagine, or serine

<400> SEQUENCE: 169

Xaa Xaa Xaa Tyr Xaa Xaa Xaa
  1               5

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Heavy chain
      CDR2 consensus sequence (CDR2b)
<220> FEATURE:
<221> NAME/KEY: MOD_RES
<222> LOCATION: (1)
<223> OTHER INFORMATION: tryptophan, tyrosine, valine, asparagine, or
      glutamic acid
<220> FEATURE:
<221> NAME/KEY: MOD_RES
<222> LOCATION: (2)
<223> OTHER INFORMATION: isoleucine, phenylalanine, or valine
<220> FEATURE:
<221> NAME/KEY: MOD_RES
<222> LOCATION: (3)
<223> OTHER INFORMATION: asparagine, serine, tryptophan, or tyrosine
<220> FEATURE:
<221> NAME/KEY: MOD_RES
<222> LOCATION: (4)
<223> OTHER INFORMATION: proline, serine, tyrosine, or histidine
<220> FEATURE:
<221> NAME/KEY: MOD_RES
<222> LOCATION: (5)
<223> OTHER INFORMATION: asparagine, serine, or aspartic acid
<220> FEATURE:
<221> NAME/KEY: MOD_RES
<222> LOCATION: (6)
<223> OTHER INFORMATION: serine or glycine
<220> FEATURE:
<221> NAME/KEY: MOD_RES
<222> LOCATION: (7)
<223> OTHER INFORMATION: glycine or serine, or is not present
<220> FEATURE:
<221> NAME/KEY: MOD_RES
<222> LOCATION: (8)
<223> OTHER INFORMATION: glycine, threonine, aspartic acid, serine,
      isoleucine, or asparagine
<220> FEATURE:
<221> NAME/KEY: MOD_RES
<222> LOCATION: (9)
<223> OTHER INFORMATION: threonine, isoleucine, or lysine
<220> FEATURE:
<221> NAME/KEY: MOD_RES
<222> LOCATION: (10)
<223> OTHER INFORMATION: asparagine or tyrosine
<220> FEATURE:
<221> NAME/KEY: MOD_RES
<222> LOCATION: (11)
<223> OTHER INFORMATION: tyrosine or histidine
<220> FEATURE:
<221> NAME/KEY: MOD_RES
<222> LOCATION: (12)
<223> OTHER INFORMATION: alanine or asparagine
<220> FEATURE:
<221> NAME/KEY: MOD_RES
<222> LOCATION: (13)
<223> OTHER INFORMATION: glutamine, aspartic acid, or proline
<220> FEATURE:
<221> NAME/KEY: MOD_RES
<222> LOCATION: (14)
<223> OTHER INFORMATION: lysine or serine
<220> FEATURE:
<221> NAME/KEY: MOD_RES
<222> LOCATION: (15)
<223> OTHER INFORMATION: phenylalanine, valine, or leucine
<220> FEATURE:
```

```
<221> NAME/KEY: MOD_RES
<222> LOCATION: (16)
<223> OTHER INFORMATION: glutamine or lysine
<220> FEATURE:
<221> NAME/KEY: MOD_RES
<222> LOCATION: (17)
<223> OTHER INFORMATION: glycine or serine

<400> SEQUENCE: 170

Xaa Xaa Xaa Xaa Xaa Xaa Xaa Xaa Xaa Xaa Xaa Xaa Xaa Xaa Xaa Xaa
 1               5                  10                  15

Xaa

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Heavy chain
      CDR3 consensus sequence (CDR3b)
<220> FEATURE:
<221> NAME/KEY: MOD_RES
<222> LOCATION: (1)
<223> OTHER INFORMATION: glutamic acid, aspartic acid, serine, or
      glycine, or is not present
<220> FEATURE:
<221> NAME/KEY: MOD_RES
<222> LOCATION: (2)
<223> OTHER INFORMATION: leucine, glutamic acid, aspartic acid,
      histidine, proline, or glycine, or is not present
<220> FEATURE:
<221> NAME/KEY: MOD_RES
<222> LOCATION: (3)
<223> OTHER INFORMATION: glutamic acid, tyrosine, or leucine, or is not
      present
<220> FEATURE:
<221> NAME/KEY: MOD_RES
<222> LOCATION: (4)
<223> OTHER INFORMATION: leucine, asparagine, glycine, histidine,
      tyrosine, or tryptophan, or is not present
<220> FEATURE:
<221> NAME/KEY: MOD_RES
<222> LOCATION: (5)
<223> OTHER INFORMATION: arginine, serine, glutamic acid, tyrosine,
      glycine, or phenylalanine, or is not present
<220> FEATURE:
<221> NAME/KEY: MOD_RES
<222> LOCATION: (6)
<223> OTHER INFORMATION: glycine or is not present
<220> FEATURE:
<221> NAME/KEY: MOD_RES
<222> LOCATION: (7)
<223> OTHER INFORMATION: tryptophan or tyrosine, or is not present
<220> FEATURE:
<221> NAME/KEY: MOD_RES
<222> LOCATION: (8)
<223> OTHER INFORMATION: aspartic acid or is not present
<220> FEATURE:
<221> NAME/KEY: MOD_RES
<222> LOCATION: (9)
<223> OTHER INFORMATION: serine or arginine, or is not present
<220> FEATURE:
<221> NAME/KEY: MOD_RES
<222> LOCATION: (10)
<223> OTHER INFORMATION: serine or is not present
<220> FEATURE:
<221> NAME/KEY: MOD_RES
<222> LOCATION: (11)
<223> OTHER INFORMATION: glycine or tyrosine, or is not present
<220> FEATURE:
<221> NAME/KEY: MOD_RES
<222> LOCATION: (12)
<223> OTHER INFORMATION: tyrosine, glutamic acid, or aspartic acid, or
      is not present
<220> FEATURE:
<221> NAME/KEY: MOD_RES
<222> LOCATION: (13)
```

```
<223> OTHER INFORMATION: tyrosine, phenylalanine, or aspartic acid, or
      is not present
<220> FEATURE:
<221> NAME/KEY: MOD_RES
<222> LOCATION: (14)
<223> OTHER INFORMATION: tyrosine, aspartic acid, histidine, or
      tryptophan, or is not present
<220> FEATURE:
<221> NAME/KEY: MOD_RES
<222> LOCATION: (15)
<223> OTHER INFORMATION: tyrosine, glycine, aspartic acid, proline, or
      serine, or is not present
<220> FEATURE:
<221> NAME/KEY: MOD_RES
<222> LOCATION: (16)
<223> OTHER INFORMATION: glycine, valine, tyrosine, or aspartic acid, or
      is not present
<220> FEATURE:
<221> NAME/KEY: MOD_RES
<222> LOCATION: (17)
<223> OTHER INFORMATION: leucine, alanine, glycine, or tyrosine, or is
      not present
<220> FEATURE:
<221> NAME/KEY: MOD_RES
<222> LOCATION: (18)
<223> OTHER INFORMATION: methionine, phenylalanine, or tyrosine
<220> FEATURE:
<221> NAME/KEY: MOD_RES
<222> LOCATION: (20)
<223> OTHER INFORMATION: valine, tyrosine, isoleucine, or proline

<400> SEQUENCE: 171

Xaa Xaa Xaa Xaa Xaa Xaa Xaa Xaa Xaa Xaa Xaa Xaa Xaa Xaa Xaa Xaa
 1               5                   10                  15

Xaa Xaa Asp Xaa
            20

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Val Asn Gly Ile Pro Thr Arg Thr Asn
 1               5                   10

<210> SEQ ID NO 173
<211> LENGTH: 113
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 173

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

```
                    85                  90                  95
Tyr Phe Ser Pro Pro Trp Thr Phe Gly Gln Gly Thr Lys Val Glu Ile
                100                 105                 110
Lys

<210> SEQ ID NO 174
<211> LENGTH: 113
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 174

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Phe Tyr Ser
                20                  25                  30

Ser Thr Asn Lys Asn Tyr Leu Ala Trp Tyr Gln Lys Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
                100                 105                 110

Lys

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Tyr Pro Leu
                85                  90                  95

Thr Phe Gly Gly Gly Thr Lys Val Glu Ile Lys
                100                 105

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued kappa light chain protein sequence

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 177

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Glu Ala Ser Ser Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Trp
                85                  90                  95

Thr Phe Gly Gln Gly Thr Lys Val Glu Ile Lys
            100                 105

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 178

Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Lys Leu Leu Ile
        35                  40                  45

Tyr Val Ala Ser Thr Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Asn Tyr Asn Ser Asp Pro Leu
                 85                  90                  95

Thr Phe Gly Gly Gly Thr Lys Val Glu Ile Lys
            100                 105

<210> SEQ ID NO 179
<211> LENGTH: 107
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 179

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Ser Asp
                 20                  25                  30

Leu Asn Trp Tyr Gln Gln Lys Pro Gly Lys Val Pro Lys Leu Leu Ile
             35                  40                  45

Tyr Val Ala Ser Ser Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Arg Ser Tyr Ser Thr Pro Pro
                 85                  90                  95

Thr Phe Gly Pro Gly Thr Lys Val Asp Ile Lys
            100                 105

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 180

Asp Ile Gln Met Thr Gln Ser Pro Ser Ser Leu Ser Ala Ser Val Gly
 1               5                  10                  15

Asp Arg Val Thr Ile Thr Cys Gln Ala Ser Asp Gln Ile Ser Asn Tyr
                 20                  25                  30

Leu Asn Trp Tyr Gln Gln Lys Pro Gly Thr Ala Pro Lys Leu Leu Ile
             35                  40                  45

Tyr Gly Ala Ser Asp Leu Glu Thr Gly Val Pro Ser Arg Phe Ser Gly
 50                  55                  60

Ser Gly Ser Gly Thr Asp Phe Thr Phe Ala Ile Ser Ser Leu Gln Pro
 65                  70                  75                  80

Glu Asp Ile Ala Thr Tyr Tyr Cys Gln Gln Tyr Asp Asn Leu Pro Tyr
                 85                  90                  95

Asn Phe Gly Gln Gly Thr Lys Leu Glu Ile Lys
            100                 105

<210> SEQ ID NO 181
<211> LENGTH: 108
<212> TYPE: PRT
<213> ORGANISM: Artificial Sequence
<220> FEATURE:
<223> OTHER INFORMATION: Description of Artificial Sequence: Synthetic
``` kappa light chain protein sequence

<400> SEQUENCE: 181

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Asp Ser Asn
                 20                  25                  30

Leu Ala Trp Tyr Arg Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ile Asn Trp Pro Pro
                 85                  90                  95

Ile Thr Phe Gly Gln Gly Thr Arg Leu Glu Ile Lys
                100                 105
```

<210> SEQ ID NO 182
<211> LENGTH: 108
<212> TYPE: PRT
<213> ORGANISM: Artificial Sequence
<220> FEATURE:
<223> OTHER INFORMATION: Description of Artificial Sequence: Synthetic
      kappa light chain protein sequence

<400> SEQUENCE: 182

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Met
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Ile Thr Phe Gly Gln Gly Thr Arg Leu Glu Ile Lys
                100                 105
```

<210> SEQ ID NO 183
<211> LENGTH: 114
<212> TYPE: PRT
<213> ORGANISM: Artificial Sequence
<220> FEATURE:
<223> OTHER INFORMATION: Description of Artificial Sequence: Synthetic
      kappa light chain consensus sequence
<220> FEATURE:
<221> NAME/KEY: MOD_RES
<222> LOCATION: (13)..(13)
<223> OTHER INFORMATION: Undetermined consensus residue; variable amino
      acid
<220> FEATURE:
<221> NAME/KEY: MOD_RES
<222> LOCATION: (29)..(34)
<223> OTHER INFORMATION: Undetermined consensus residue; variable amino
      acid
<220> FEATURE:
<221> NAME/KEY: MOD_RES
<222> LOCATION: (36)..(38)
<223> OTHER INFORMATION: Undetermined consensus residue; variable amino
      acid

```
<220> FEATURE:
<221> NAME/KEY: MOD_RES
<222> LOCATION: (56)..(56)
<223> OTHER INFORMATION: Undetermined consensus residue; variable amino
      acid
<220> FEATURE:
<221> NAME/KEY: MOD_RES
<222> LOCATION: (98)..(98)
<223> OTHER INFORMATION: Undetermined consensus residue; variable amino
      acid
<220> FEATURE:
<221> NAME/KEY: MOD_RES
<222> LOCATION: (100)..(100)
<223> OTHER INFORMATION: Undetermined consensus residue; variable amino
      acid
<220> FEATURE:
<221> NAME/KEY: MOD_RES
<222> LOCATION: (102)..(103)
<223> OTHER INFORMATION: Undetermined consensus residue; variable amino
      acid

<400> SEQUENCE: 183

Asp Ile Gln Met Thr Gln Ser Pro Ser Ser Leu Ser Xaa Ser Val Gly
  1               5                  10                  15

Asp Arg Val Thr Ile Thr Cys Arg Ala Ser Gln Ser Xaa Xaa Xaa Xaa
             20                  25                  30

Xaa Xaa Ile Xaa Xaa Xaa Leu Ala Trp Tyr Gln Gln Lys Pro Gly Lys
         35                  40                  45

Ala Pro Lys Leu Leu Ile Tyr Xaa Ala Ser Thr Leu Gln Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Xaa Ser Xaa Pro Xaa Xaa Thr Phe Gly Gln Gly Thr Lys Val Glu
            100                 105                 110

Ile Lys

<210> SEQ ID NO 184
<211> LENGTH: 118
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 184

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Ile His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Leu Glu Leu Arg Tyr Tyr Gly Met Asp Val Trp Gly Gln
            100                 105                 110

Gly Thr Thr Val Thr Val
            115
```

-continued

```
<210> SEQ ID NO 185
<211> LENGTH: 118
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 185

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Ile Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Arg Ala Asp Asp Thr Ala Val Tyr Tyr Cys
                85                  90                  95

Ala Arg Glu Leu Glu Leu Arg Tyr Tyr Gly Met Asp Val Trp Gly Gln
            100                 105                 110

Gly Thr Thr Val Thr Val
        115

<210> SEQ ID NO 186
<211> LENGTH: 120
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 186

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Tyr Asn Ser Gly Trp Tyr Val Leu Phe Asp Tyr Trp
            100                 105                 110

Gly Gln Gly Thr Leu Val Thr Val
        115                 120

<210> SEQ ID NO 187
<211> LENGTH: 116
<212> TYPE: PRT
<213> ORGANISM: Artificial Sequence
<220> FEATURE:
<223> OTHER INFORMATION: Description of Artificial Sequence: Synthetic
      gamma heavy chain protein sequence
```

-continued

```
<400> SEQUENCE: 187

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Gly Gly Gly Phe Asp Tyr Trp Gly Gln Gly Thr
            100                 105                 110

Leu Val Thr Val
        115

<210> SEQ ID NO 188
<211> LENGTH: 127
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 188

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser His Leu His Tyr Tyr Asp Ser Ser Gly Tyr Tyr Tyr
            100                 105                 110

Gly Gly Ala Phe Asp Ile Trp Gly Gln Gly Thr Met Val Thr Val
        115                 120                 125

<210> SEQ ID NO 189
<211> LENGTH: 119
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 189

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45
```

Trp Ile Gly Asn Ile Tyr Tyr Ser Gly Ile Thr Tyr Tyr Asn Pro Ser
            50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Leu Tyr Gly Asp Tyr Gly Phe Asp Pro Trp Gly
            100                 105                 110

Gln Gly Thr Leu Val Thr Val
            115

<210> SEQ ID NO 190
<211> LENGTH: 123
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 190

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Asp Pro Leu Trp Phe Gly Glu Phe Asp Tyr Tyr Gly Met
            100                 105                 110

Asp Val Trp Gly Gln Gly Thr Thr Val Thr Val
            115                 120

<210> SEQ ID NO 191
<211> LENGTH: 121
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 191

Gln Val Gln Leu Lys Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Val Tyr Tyr Trp Ser Trp Ile Arg Gln His Pro Gly Lys Gly Leu Glu
        35                  40                  45

Trp Ile Gly Tyr Phe Tyr Tyr Ser Gly Asn Thr Tyr His Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

-continued

Cys Ala Arg Asp Arg Ser Gly Tyr Asp His Pro Asp Ala Phe Asp Ile
            100                 105                 110

Trp Gly Gln Gly Thr Met Val Thr Val
        115                 120

<210> SEQ ID NO 192
<211> LENGTH: 118
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 192

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Thr Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Asp Phe Trp Ser Gly Tyr Tyr Asp Tyr Trp Gly Gln
            100                 105                 110

Gly Thr Leu Val Thr Val
        115

<210> SEQ ID NO 193
<211> LENGTH: 116
<212> TYPE: PRT
<213> ORGANISM: Artificial Sequence
<220> FEATURE:
<223> OTHER INFORMATION: Description of Artificial Sequence: Synthetic
      gamma heavy chain protein sequence

<400> SEQUENCE: 193

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ile Tyr
             20                  25                  30

Tyr Trp Ser Trp Ile Arg Gln Pro Pro Gly Lys Gly Leu Glu Trp Ile
         35                  40                  45

Gly Tyr Val Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Gly Tyr Asp Phe Trp Ser Gly Tyr Phe Asp Tyr Trp Gly Gln
            100                 105                 110

Gly Thr Leu Val
        115

<210> SEQ ID NO 194
<211> LENGTH: 128
<212> TYPE: PRT

-continued

```
<213> ORGANISM: Artificial Sequence
<220> FEATURE:
<223> OTHER INFORMATION: Description of Artificial Sequence: Synthetic
      gamma heavy chain consensus sequence
<220> FEATURE:
<221> NAME/KEY: MOD_RES
<222> LOCATION: (16)..(16)
<223> OTHER INFORMATION: Undetermined consensus residue; variable amino
      acid
<220> FEATURE:
<221> NAME/KEY: MOD_RES
<222> LOCATION: (31)..(32)
<223> OTHER INFORMATION: Undetermined consensus residue; variable amino
      acid
<220> FEATURE:
<221> NAME/KEY: MOD_RES
<222> LOCATION: (42)..(42)
<223> OTHER INFORMATION: Undetermined consensus residue; variable amino
      acid
<220> FEATURE:
<221> NAME/KEY: MOD_RES
<222> LOCATION: (58)..(58)
<223> OTHER INFORMATION: Undetermined consensus residue; variable amino
      acid
<220> FEATURE:
<221> NAME/KEY: MOD_RES
<222> LOCATION: (102)..(112)
<223> OTHER INFORMATION: Undetermined consensus residue; variable amino
      acid
<220> FEATURE:
<221> NAME/KEY: MOD_RES
<222> LOCATION: (114)..(114)
<223> OTHER INFORMATION: Undetermined consensus residue; variable amino
      acid
<220> FEATURE:
<221> NAME/KEY: MOD_RES
<222> LOCATION: (116)..(116)
<223> OTHER INFORMATION: Undetermined consensus residue; variable amino
      acid

<400> SEQUENCE: 194

Gln Val Gln Leu Gln Glu Ser Gly Pro Gly Leu Val Lys Pro Ser Xaa
  1               5                  10                  15

Thr Leu Ser Leu Thr Cys Thr Val Ser Gly Gly Ser Ile Ser Xaa Xaa
             20                  25                  30

Gly Tyr Tyr Trp Ser Trp Ile Arg Gln Xaa Pro Gly Lys Gly Leu Glu
         35                  40                  45

Trp Ile Gly Tyr Ile Tyr Tyr Ser Gly Xaa Ser Thr Tyr Tyr Asn Pro
     50                  55                  60

Ser Leu Lys Ser Arg Val Thr Ile Ser Val Asp Thr Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Arg Asp Xaa Xaa Xaa Xaa Xaa Xaa Xaa Xaa Xaa Xaa Xaa
            100                 105                 110

Tyr Xaa Gly Xaa Phe Asp Val Trp Gly Gln Gly Thr Leu Val Thr Val
        115                 120                 125
```